US012503666B2

(12) United States Patent
Rogers-Simpson et al.

(10) Patent No.: US 12,503,666 B2
(45) Date of Patent: Dec. 23, 2025

(54) MULTIPURPOSE OXYPYRIDINONES AND THEIR FUNCTIONAL USE-2

(71) Applicant: INFINEUM INTERNATIONAL LIMITED, Linden, NJ (US)

(72) Inventors: Nicola J. Rogers-Simpson, Birmingham (GB); Hualong Song, Beijing (CN); Peter Scott, Kenilworth (GB); Alastair A. Cant, Didcot (GB); Peter M. Wright, Whitney (GB); Daniel J. Phillips, Warwickshire (GB); David R. Coultas, Oxford (GB); Joanne Tory, Didcot (GB); Abby Casey, Oxford (GB)

(73) Assignee: INFINEUM INTERNATIONAL LIMITED, Linden, NJ (US)

( * ) Notice: Subject to any disclaimer, the term of this patent is extended or adjusted under 35 U.S.C. 154(b) by 0 days.

(21) Appl. No.: 18/431,260

(22) Filed: Feb. 2, 2024

(65) Prior Publication Data

US 2024/0294840 A1 Sep. 5, 2024

(30) Foreign Application Priority Data

Feb. 17, 2023 (EP) .................................... 23157262

(51) Int. Cl.

| | |
|---|---|
| ***C10M 133/40*** | (2006.01) |
| ***C07D 213/69*** | (2006.01) |
| ***C10M 129/10*** | (2006.01) |
| ***C10M 133/12*** | (2006.01) |
| ***C10M 169/04*** | (2006.01) |
| ***C10N 30/06*** | (2006.01) |
| ***C10N 30/10*** | (2006.01) |

(52) U.S. Cl.

CPC ......... *C10M 133/40* (2013.01); *C07D 213/69* (2013.01); *C10M 129/10* (2013.01); *C10M 133/12* (2013.01); *C10M 169/04* (2013.01); *C10M 2201/02* (2013.01); *C10M 2207/023* (2013.01); *C10M 2215/064* (2013.01); *C10M 2215/221* (2013.01); *C10M 2215/30* (2013.01); *C10M 2223/045* (2013.01); *C10N 2030/06* (2013.01); *C10N 2030/10* (2013.01)

(58) Field of Classification Search

CPC .. C07D 213/69; C10N 129/10; C10N 133/12; C10N 133/40; C10N 169/04; C10N 2201/02; C10N 2207/023; C10N 2215/064; C10N 2215/221; C10N 2215/30; C10N 2223/045; C10N 2030/06; C10N 2030/10

See application file for complete search history.

(56) References Cited

U.S. PATENT DOCUMENTS

| | | | |
|---|---|---|---|
| 2,100,993 | A | 11/1937 | Bruson |
| 2,719,125 | A | 9/1955 | Roberts |
| 2,719,126 | A | 9/1955 | Fields et al. |
| 2,760,933 | A | 8/1956 | Fields et al. |
| 2,836,564 | A | 5/1958 | Roberts et al. |
| 3,087,937 | A | 4/1963 | Tesi et al. |
| 3,254,025 | A | 5/1966 | Suer |
| 3,502,677 | A | 3/1970 | Suer |
| 3,663,561 | A | 5/1972 | Blaha |
| 3,697,574 | A | 10/1972 | Piasek et al. |
| 3,703,536 | A | 11/1972 | Piasek et al. |
| 3,704,308 | A | 11/1972 | Piasek et al. |
| 3,751,365 | A | 8/1973 | Piasek et al. |
| 3,756,953 | A | 9/1973 | Piasek et al. |
| 3,798,165 | A | 3/1974 | Piasek et al. |
| 3,803,039 | A | 4/1974 | Piasek et al. |
| 3,843,536 | A | 10/1974 | Johnston |
| 4,231,759 | A | 11/1980 | Udelhofen et al. |
| 4,259,194 | A | 3/1981 | deVries et al. |
| 4,259,195 | A | 3/1981 | King et al. |
| 4,261,843 | A | 4/1981 | King et al. |

(Continued)

FOREIGN PATENT DOCUMENTS

| | | |
|---|---|---|
| EP | 4417672 A1 | 8/2024 |
| EP | 4417673 A1 | 8/2024 |

(Continued)

OTHER PUBLICATIONS

EP Form 1507W for related EP Application No. 24157623.0 dated 18.06.2024.
EP Form 1507W for related EP Application No. 24157621.4 dated 18.06.2024.
EP Form 1507W for related EP Application No. 24157627.1 dated 18.06.2024.
EP Form 1507W for related EP Application No. 24157626.3 dated 18.06.2024.

(Continued)

*Primary Examiner* — James C Goloboy
(74) *Attorney, Agent, or Firm* — Robert A. Migliorini

(57) ABSTRACT

A composition is provided to comprise a non-aqueous medium and a 3,4-oxypyridinone compound of structure (I):

(I)

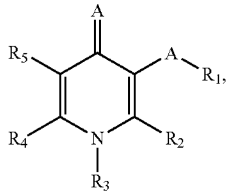

with each A being oxygen and/or sulfur, and with a variety of substituents at $R_1$-$R_5$ to enable a solution or an at least semi-stable emulsion to be formed in the non-aqueous medium. Methods of use are included herein, which may be focused on situations where the composition can be used as a lubricant and/or coolant.

22 Claims, No Drawings

(56) References Cited

U.S. PATENT DOCUMENTS

| | | | | |
|---|---|---|---|---|
| 4,263,152 | A | 4/1981 | King et al. | |
| 4,265,773 | A | 5/1981 | deVries et al. | |
| 4,272,387 | A | 6/1981 | King et al. | |
| 4,283,295 | A | 8/1981 | deVries et al. | |
| 4,285,822 | A | 8/1981 | deVries et al. | |
| 4,767,551 | A | 8/1988 | Hunt et al. | |
| 4,798,684 | A | 1/1989 | Salomon | |
| 4,857,214 | A | 8/1989 | Papay et al. | |
| 5,084,197 | A | 1/1992 | Galic et al. | |
| 5,242,612 | A | 9/1993 | Ryer et al. | |
| 5,326,487 | A | 7/1994 | Ryer et al. | |
| 5,534,170 | A | 7/1996 | Watts | |
| 5,840,663 | A | 11/1998 | Nibert et al. | |
| 6,323,164 | B1 | 11/2001 | Liesen et al. | |
| 6,432,313 | B2 | 8/2002 | Bruening et al. | |
| 7,491,248 | B2 | 2/2009 | Colucci et al. | |
| 8,048,833 | B2 | 11/2011 | Habeeb et al. | |
| 8,815,789 | B2 | 8/2014 | Tetard et al. | |
| 8,943,910 | B2 | 2/2015 | Addleman et al. | |
| 9,439,984 | B2 | 9/2016 | Raymond et al. | |
| 9,617,541 | B2 | 4/2017 | Mirkin et al. | |
| 9,677,075 | B2 | 6/2017 | Mirkin et al. | |
| 9,683,195 | B2 | 6/2017 | Nakada et al. | |
| 9,938,479 | B2 | 4/2018 | Lange et al. | |
| 10,731,101 | B2 | 8/2020 | Delamore et al. | |
| 10,899,986 | B2 | 1/2021 | Smith et al. | |
| 11,059,785 | B2 * | 7/2021 | Holbein ............... | C07D 213/69 |
| 2009/0005277 | A1 | 1/2009 | Watts et al. | |
| 2019/0270946 | A1 * | 9/2019 | Hogendoorn ........ | C10M 143/04 |
| 2020/0354647 | A1 | 11/2020 | Schwaebisch et al. | |
| 2024/0294840 | A1 | 9/2024 | Rogers-Simpson et al. | |

FOREIGN PATENT DOCUMENTS

| | | | | |
|---|---|---|---|---|
| EP | 4417674 | A1 | 8/2024 | |
| EP | 4417675 | A1 | 8/2024 | |
| GB | 2468750 | A * | 9/2010 | .......... C10M 133/38 |
| WO | 94/06897 | A1 | 3/1994 | |
| WO | 01/17497 | A1 | 3/2001 | |
| WO | 01/42399 | A1 | 6/2001 | |

OTHER PUBLICATIONS

Hider, Robert C. et al., "The potential application of iron chelators for the treatment of neurodegenerative diseases", Metallomics, 2011, vol. 3, pp. 239-249.

Campbell, Barbara K. et al., "Studies on [gamma]-Pyrones. II. Synthesis of 4-Piperidinols from Pyrones", The Journal of Organic Chemistry, 1952, vol. 15, No. 2, pp. 331-342.

Zhang, Guangling et al., "Direct C3-alkenylation of pyridin-4(1H)-one via oxidative Heck coupling", Tetrahedron, 2013, vol. 69, pp. 1115-1119.

Gagnon, M. Karen J. et al., "Synthesis and Hydroboration of Lipophilic Hydroxy-pyridinones and Their Complexes with Molybdenum (VI)", Australian Journal of Chemistry, 2000, vol. 53, No. 8, pp. 693-697.

Gumbau-Brisa, R. et al., "Enhanced Fe3+ binding through cooperativity of 3-hydroxypyridin-4-one groups within a linear co-polymer: wrapping effect leading to superior antimicrobial activity", Biometals, 2020, vol. 33, No. 6, pp. 339-351.

American Petroleum Institute, "Engine Oil Licensing and Certification System", Industry Services Department, API 1509, 1996 Fourteenth Edition, 1998 Addendum 1.

Smalheer, C.V. et al., "Lubricant Additives", 1967, pp. 1-11.

Crisponi, Guido et al., "Iron chelating agents for the treatment of iron overload", Coordination Chemistry Reviews, 2008, vol. 252, pp. 1225-1240.

Santos, M. Amelia, "Recent developments on 3-hydroxy-4-pyridinones with respect to their clinical applications Mono and combined ligand approaches", Coordination Chemistry Reviews, 2008, vol. 252, pp. 1213-1224.

Santos, M. Amelia, "Hydroxypyridinone complexes with aluminium. In vitro/vivo studies and perspectives", Coordination Chemistry Reviews, 2002, vol. 228, pp. 187-203.

Crumbliss, Alvin L et al., "Iron sequestration by small molecules: thermodynamic and kinetic studies of natural siderophores and synthetic model compounds", Advances in Inorganic Chemistry, 2009, vol. 61, p. 179.

Liu, Zu D. et al., "Design of iron chelators with therapeutic application", Coordination Chemistry Reviews, 2002, vol. 232, pp. 151-171.

* cited by examiner

MULTIPURPOSE OXYPYRIDINONES AND THEIR FUNCTIONAL USE-2

CROSS REFERENCE TO RELATED PATENT APPLICATIONS

This patent application relates to concurrently filed application U.S. Ser. No. 18/431,222, entitled Multipurpose Oxypyridinones and Their Functional Use-1.

This patent application relates to concurrently filed application U.S. Ser. No. 18/431,289, entitled Multipurpose Oxypyridinones and Their Functional Use-3.

This patent application relates to concurrently filed application U.S. Ser. No. 18/431,334, entitled Multipurpose Oxypyridinones and Their Functional Use-4.

PRIORITY CLAIM

This application claims priority to European Patent Office application EP 23157262.9, filed Feb. 17, 2023.

FIELD

This disclosure relates to compositions containing 3,4-oxypyridinone compounds in non-aqueous media and methods of using them for a variety of functions, such as lubrication and/or cooling, e.g., of drivetrain components and/or electronic components of vehicle engines.

BACKGROUND

The present disclosure is based on the multipurpose nature of hydroxypyrid(in)ones (abbreviated HOPOs). HOPOs have been studied as antioxidant drugs capable of silencing redox-active metals in applications such as neurodegenerative diseases and metal ion overload where oxidative damage is critical to the development of the pathology. One such HOPO family member is 1,2-dimethyl-3-hydroxy-4-pyridinone (a.k.a. Deferiprone, has been tested clinically in vivo in Europe), which is known to have iron chelating capability.

These HOPO chelators have been used in aqueous media to help reduce or prevent autoxidation of lipids and other biological molecules due to their inhibition of the formation of reactive oxygen species from normal dioxygen metabolism. See, inter alia, R. C. Hider; S. Roy; Y. M. Ma; X. Le Kong; and J. Preston, *Metallomics* 2011, 3, 239; G. Crisponi and M. Remelli, *Coord Chem. Rev.* 2008, 252, 1225; M. A. Santos, *Coord Chem. Rev.* 2008, 252, 1213; and M. A. Santos, *Coord Chem. Rev.* 2002, 228, 187-203.

The antioxidant action of HOPOs is believed to be primarily centered around the inhibition of $Fe^{3+}$ redox chemistry and the stability of the complex with Fe(III). For illustration, the stability constant log $\beta_{130}$ of 1,2-dimethyl-3-hydroxy-4-pyridinone for a few biologically relevant metal cations are: $Fe^{3+}$: 37.2; $Fe^{2+}$: 12.1; $Cu^{2+}$: 21.7. See, e.g., A. L. Crumbliss and J. M. Harrington, *Adv. Inorg. Chem.* 2009, 61, 179. Further, chelation of $Fe^{3+}$ ions with the hard donor HOPO ligand stabilizes the higher oxidation state and can ensure the reduction reaction to Fe(II) is out of reach of biological reductants (e.g., NADPH, $O_2^-$). See, e.g., Z. D. Liu and R. C. Hider, *Coord Chem. Rev.* 2002, 232, 151, or a Haber-Weiss process. In summary, once coordinated to HOPO ligands, Fe ions are bound in a highly stable and redox-inactive form.

In biological (aqueous) systems, 3,4-HOPO tends to be a more powerful iron chelator than 3,2-HOPO, which is turn more powerful than 1,2-HOPO.

However, because known 3,4-HOPO variants have only been studied in biological/aqueous environments, and have only been known to be synthesized by means capable of allowing aqueous end-uses, there was no inkling whether their metal (iron) chelation ability would extend to non-aqueous media, whether they could be easily synthesized to be compatible with non-aqueous media such as lubricant oil basestocks, nor whether they could have any utility in non-aqueous media for non-biological applications such as lubricants/coolants.

Other examples of publications of compounds containing chemistries and/or functionalities potentially analogous to HOPOs include, but are not necessarily limited to, U.S. Pat. Nos. 6,432,313, 8,815,789, 8,943,910, 9,617,541, 9,677,075, 9,439,984.

SUMMARY

Accordingly, the present disclosure provides a composition comprising a non-aqueous medium and a 3,4-oxypyridinone compound of structure (I):

(I)

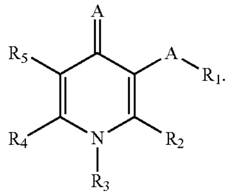

In structure (I), each A may individually be an oxygen or sulfur atom (e.g., at least some, perhaps all, A atoms may be oxygen atoms).

In structure (I), $R_1$ may be hydrogen; an ammonium ion; a $C_1$-$C_6$ monoalkylammonium ion; a $C_1$-$C_6$ dialkylammonium ion; a $C_1$-$C_6$ trialkylammonium ion; a $C_1$-$C_6$ tetraalkylammonium ion; a $C_1$-$C_6$ monoalkylsilyl moiety; a $C_1$-$C_6$ dialkylsilyl moiety; a $C_1$-$C_6$ trialkylsilyl moiety; an optionally substituted aryl, alkyl, alkaryl, or aralkyl sulfonyl moiety; a linear, branched, and/or cyclic $C_1$-$C_{20}$ hydrocarbyl sulfide; a linear, branched, and/or cyclic $C_1$-$C_{20}$ hydrocarbyl moiety; an at least partially halogenated linear, branched, and/or cyclic $C_1$-$C_{20}$ moiety; an ether-containing linear, branched, and/or cyclic $C_1$-$C_{20}$ moiety; a thioether-containing linear, branched, and/or cyclic $C_1$-$C_{20}$ moiety; an ester-containing linear, branched, and/or cyclic $C_1$-$C_{20}$ moiety; a thioester-containing linear, branched, and/or cyclic $C_1$-$C_{20}$ moiety; a linear, branched, and/or cyclic $C_1$-$C_{20}$ acyl moiety; a linear, branched, and/or cyclic $C_1$-$C_{20}$ thioacyl moiety; a linear, branched, and/or cyclic $C_1$-$C_{20}$ hydrocarbyloxyacyl moiety; a linear, branched, and/or cyclic $C_1$-$C_{20}$ hydrocarbyloxythioacyl moiety; a linear, branched, and/or cyclic $C_1$-$C_{20}$ hydrocarbylthiocarbonyl moiety; a linear, branched, and/or cyclic $C_1$-$C_{20}$ hydrocarbylthio-thioacyl moiety; an amide-containing linear, branched, and/or cyclic $C_1$-$C_{20}$ moiety; a thioamide-containing linear, branched, and/or cyclic $C_1$-$C_{20}$ moiety; a ketone-containing linear, branched, and/or cyclic $C_1$-$C_{20}$ moiety; a thioketone-containing linear, branched, and/or cyclic $C_1$-$C_{20}$ moiety; an aldehyde-containing linear, branched, and/or cyclic $C_1$-$C_{20}$ moiety; a thioaldehyde-containing linear, branched, and/or cyclic $C_1$-$C_{20}$ moiety; a mercaptan-containing linear, branched, and/or cyclic $C_1$-$C_{20}$ moiety; a hydroxyl-containing linear, branched, and/or cyclic $C_1$-$C_{20}$ moiety; a nonionic linear, branched, and/or (hetero)cyclic moiety containing 1 to 20 carbon atoms at least one nitrogen atom, and optionally at least one sulfur and/or oxygen atom; another 3,4-oxypyridinone connected as an ether or thioether at a meta position to the ring nitrogen thereof; or a combination thereof (e.g., hydrogen; a linear, branched, and/or cyclic $C_1$-$C_{12}$ hydrocarbyl moiety; an ether-containing linear, branched, and/or cyclic $C_1$-$C_{12}$ moiety; another 3,4-oxypyridinone connected as an ether at a meta position to the ring nitrogen thereof; or a combination thereof). Additionally or alternatively, in structure (I), $R_1$ may be an oligomeric and/or polymeric moiety pendant to one or more repeat units, optionally with a spacer, having a number average molecular weight from 400 g/mol (Daltons; "D") to 300 kg/mol (kiloDaltons; "kD"), e.g., from 700 D to 8000 D, from 700 D to 30 kD, from 7500 D to 300 kD, or from 5000 D to 100 kD; or a combination thereof In structure (I), $R_2$ may be hydrogen; a halogen; a linear, branched, and/or cyclic $C_1$-$C_{12}$ hydrocarbyl moiety; an at least partially halogenated linear, branched, and/or cyclic $C_1$-$C_{12}$ moiety; an amine-containing linear, branched, and/or cyclic $C_1$-$C_{20}$ moiety; an ether-containing linear, branched, and/or cyclic $C_1$-$C_{20}$ moiety; a hydroxyl-containing linear, branched, and/or cyclic $C_1$-$C_{12}$ moiety; an aldehyde-containing linear, branched, and/or cyclic $C_1$-$C_{20}$ moiety; a nitrile-containing linear, branched, and/or cyclic $C_1$-$C_{20}$ moiety; or a combination thereof (e.g., hydrogen; a linear, branched, and/or cyclic $C_1$-$C_{12}$ hydrocarbyl moiety; an ether-containing linear, branched, and/or cyclic $C_1$-$C_{12}$ moiety; an aldehyde-containing linear, branched, and/or cyclic $C_1$-$C_{12}$ moiety; a nitrile-containing linear, branched, and/or cyclic $C_1$-$C_{12}$ moiety; or a combination thereof).

In structure (I), $R_3$ may be hydrogen, a halogen; a linear, branched, and/or cyclic $C_6$-$C_{24}$ hydrocarbyl moiety; or a combination thereof (e.g., a linear, branched, and/or cyclic $C_8$-$C_{20}$ hydrocarbyl moiety). Additionally or alternatively, in structure (I), $R_3$ may be an oligomeric and/or polymeric moiety (i.e., greater than 30 carbons, preferably greater than 36 carbons, at least 60 carbons, and/or at least 80 carbons) containing repeat units (typically formed by addition reaction, such as comprising reacted olefins, hydrogenated dienes, or combinations thereof, but alternatively formed by condensation reaction), at least one of which repeat units is attached to the ring nitrogen, optionally with a spacer, a number average molecular weight of which oligomeric and/or polymeric moiety can be from 400 D to 300 kD, e.g., from 600 D to 8 kD, from 700 D to 30 kD, from 8 kD to 300 kD, or from 5 kD to 100 kD; or a combination thereof.

In structure (I), $R_4$ may be hydrogen; a halogen; a linear, branched, and/or cyclic $C_1$-$C_{12}$ hydrocarbyl moiety; an at least partially halogenated linear, branched, and/or cyclic $C_1$-$C_{12}$ moiety; an amine-containing linear, branched, and/or cyclic $C_1$-$C_{20}$ moiety; an ether-containing linear, branched, and/or cyclic $C_1$-$C_{20}$ moiety; a hydroxyl-containing linear, branched, and/or cyclic $C_1$-$C_{12}$ moiety; an aldehyde-containing linear, branched, and/or cyclic $C_1$-$C_{20}$ moiety; a nitrile-containing linear, branched, and/or cyclic $C_1$-$C_{20}$ moiety; or a combination thereof (e.g., hydrogen; a linear, branched, and/or cyclic $C_1$-$C_{12}$ hydrocarbyl moiety; an ether-containing linear, branched, and/or cyclic $C_1$-$C_{12}$ moiety; an aldehyde-containing linear, branched, and/or cyclic $C_1$-$C_{12}$ moiety; a nitrile-containing linear, branched, and/or cyclic $C_1$-$C_{12}$ moiety; or a combination thereof).

In structure (I), $R_5$ may be hydrogen; a halogen; a linear, branched, and/or cyclic $C_1$-$C_{12}$ hydrocarbyl moiety; an at least partially halogenated linear, branched, and/or cyclic $C_1$-$C_{12}$ moiety; a hydroxylated linear, branched, and/or cyclic $C_1$-$C_6$ moiety; an $R_1$-A- moiety; or a combination thereof (e.g., hydrogen; an $R_1$-A- moiety; or a combination thereof).

Alternatively, in structure (I), one or more of $R_1$ and $R_2$, $R_2$ and $R_3$, $R_3$ and $R_4$, and $R_4$ and $R_5$ may together form one or more (hetero)cyclic rings (e.g., $R_4$ and $R_5$ together may comprise from 3 to 12 carbons and form a (hetero)cyclic ring structure).

In a preferred embodiment of structure (I), both $R_1$ and $R_3$ are not simultaneously hydrogen.

Particularly when the non-aqueous medium comprises a Group I, Group II, Group III, Group IV, and/or Group V lubricating oil basestock, the composition can be considered a lubricant and/or (battery) coolant composition.

The present disclosure also provides methods of (a) inhibiting and/or mitigating viscosity increase in, and (b) improving oxidative stability and/or mitigating impact of oxidative degradation of, a lubricant and/or coolant composition comprising addition of an amount of a 3,4-oxypyridinone compound of structure (I), or formation of a complex or reaction product thereof, that is effective in disrupting oxidation catalysis through iron chelation. These can alternately be expressed as uses of a 3,4-oxypyridinone compound of structure (I), or formation of a complex or reaction product thereof, to (a) inhibit and/or mitigate viscosity increase in, and (b) to improve oxidative stability and/or mitigate impact of oxidative degradation of, a lubricant and/or coolant composition by disrupting oxidation catalysis through iron chelation.

The present disclosure also provides methods of (c) reducing friction and/or wear on a powertrain surface, and (d) improving fuel economy of a powertrain, exposed to a composition, the methods comprising incorporation of an amount of a 3,4-oxypyridinone compound of structure (I), or via formation of an effective complex or reaction product thereof, to attain a composition according to the disclosure for exposure at the powertrain surface. These can alternately be expressed as uses of a 3,4-oxypyridinone compound of structure (I), or formation of a complex or reaction product thereof, to (c) reduce friction and/or wear on a powertrain surface, and (d) to improve fuel economy of a powertrain exposed to said composition.

The present disclosure also provides methods of (e) inhibiting and/or mitigating copper and/or lead corrosion on a powertrain surface exposed to a composition, the method comprising incorporation of an amount of a 3,4-oxypyridinone compound of structure (I), or via formation of an effective complex or reaction product thereof, to attain the composition according to the disclosure for exposure at the powertrain surface. This can alternately be expressed as a use of a 3,4-oxypyridinone compound of structure (I), or formation of a complex or reaction product thereof, to (e) inhibit and/or mitigate copper and/or lead corrosion on a powertrain surface exposed to said composition.

The present disclosure also provides methods of (f) inhibiting and/or mitigating total acid number (TAN) increase over a time period, with substantially no change in total base number (TBN) over the same time period, in a composition according to the disclosure, the method comprising incorporation of an amount of a 3,4-oxypyridinone compound of structure (I) to the composition, or formation of an effective complex or reaction product thereof in the composition. This can alternately be expressed as a use of a 3,4-oxypyridinone compound of structure (I), or formation of a complex or reaction product thereof, to (f) inhibit and/or mitigate total acid number (TAN) increase over a time period, with substantially no change in total base number (TBN).

Other aspects of the present disclosure may become apparent from the Detailed Description and Examples sections hereinbelow.

DETAILED DESCRIPTION

Non-aqueous compositions according to the present disclosure can contain a non-aqueous medium and a 3,4-oxypyridinone according to structure (I).

(I)

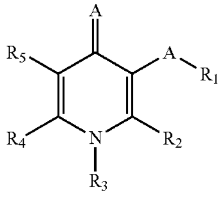

However, although structure (I) describes a relatively equilibrium (lower energy) conformation, it should be understood that structure (I) may be represented many different ways to represent an approximately identical isomer/resonance form/non-equilibrium structure. For example, structure (I) can rearrange to exhibit aromatic character in zwitterionic form, as shown below.

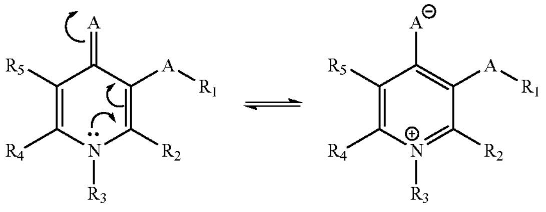

In the right side/zwitterionic form, a side reaction may include rearrangement of the $R_1$ group from the A atom meta- to the ring nitrogen to the A atom para- to the ring nitrogen, as shown below.

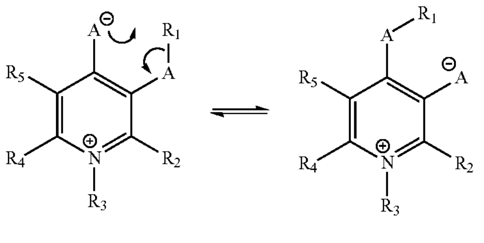

Although the zwitterionic left side of this tautomerization reaction may easily reorganize back into a nonionic 3,4-oxypyridinone, as above, the right side zwitterion may not so easily reorganize. Nevertheless, if $R_1$ is a sufficiently stable leaving group or becomes stabilized/complexed by some other component and/or the non-aqueous medium, then a particularly active iron chelating ligand can be created (whether through internal rearrangement or as "catalyzed" by the presence of a metal atom/ion, such as iron), as shown below.

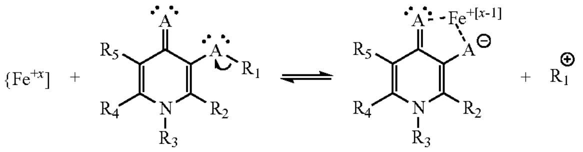

In structure (I), each A may individually be an oxygen atom, a sulfur atom, a oxymethyl (—$CH_2$—O—) moiety, or a thiomethyl (—$CH_2$—S—) moiety—in particular, at least some, perhaps all, A's may be oxygen atoms and/or oxymethyl moieties. For clarification, when A is or comprises a oxymethyl or thiomethyl moiety, the heteroatom should be understood to be oriented with the methyl(ene) group toward the ring and the oxy/thio portion toward $R_1$ (if it were meant to be oriented the other way around, it would have been stated as a methoxy or methylthio moiety).

In structure (I), $R_1$ may be hydrogen; an ammonium ion; a $C_1$-$C_6$ monoalkylammonium ion; a $C_1$-$C_6$ dialkylammonium ion; a $C_1$-$C_6$ trialkylammonium ion; a $C_1$-$C_6$ tetraalkylammonium ion; a $C_1$-$C_6$ monoalkylsilyl moiety; a $C_1$-$C_6$ dialkylsilyl moiety; a $C_1$-$C_6$ trialkylsilyl moiety; an optionally substituted aryl, alkyl, alkaryl, or aralkyl sulfonyl moiety; a linear, branched, and/or cyclic $C_1$-$C_{20}$ hydrocarbyl sulfide; a linear, branched, and/or cyclic $C_1$-$C_{20}$ hydrocarbyl moiety; an at least partially halogenated linear, branched, and/or cyclic $C_1$-$C_{20}$ moiety; an ether-containing linear, branched, and/or cyclic $C_1$-$C_{20}$ moiety; a thioether-containing linear, branched, and/or cyclic $C_1$-$C_{20}$ moiety; an ester-containing linear, branched, and/or cyclic $C_1$-$C_{20}$ moiety; a thioester-containing linear, branched, and/or cyclic $C_1$-$C_{20}$ moiety; a linear, branched, and/or cyclic $C_1$-$C_{20}$ acyl moiety; a linear, branched, and/or cyclic $C_1$-$C_{20}$ thioacyl moiety; a linear, branched, and/or cyclic $C_1$-$C_{20}$ hydrocarbyloxyacyl moiety; a linear, branched, and/or cyclic $C_1$-$C_{20}$ hydrocarbyloxythioacyl moiety; a linear, branched, and/or cyclic $C_1$-$C_{20}$ hydrocarbylthiocarbonyl moiety; a linear, branched, and/or cyclic $C_1$-$C_{20}$ hydrocarbylthio-thioacyl moiety; an amide-containing linear, branched, and/or cyclic $C_1$-$C_{20}$ moiety; a thioamide-containing linear, branched, and/or cyclic $C_1$-$C_{20}$ moiety; a ketone-containing linear, branched, and/or cyclic $C_1$-$C_{20}$ moiety; a thioketone-containing linear, branched, and/or cyclic $C_1$-$C_{20}$ moiety; an aldehyde-containing linear, branched, and/or cyclic $C_1$-$C_{20}$ moiety; a thioaldehyde-containing linear, branched, and/or cyclic $C_1$-$C_{20}$ moiety; a mercaptan-containing linear, branched, and/or cyclic $C_1$-$C_{20}$ moiety; a hydroxyl-containing linear, branched, and/or cyclic $C_1$-$C_{20}$ moiety; a nonionic linear, branched, and/or (hetero)cyclic moiety containing 1 to 20 carbon atoms at least one nitrogen atom, and optionally at least one sulfur and/or oxygen atom; another 3,4-oxypyridinone connected as an ether or thioether at a meta position to the ring nitrogen thereof, an oligomeric and/or polymeric moiety pendant to one or more repeat units, optionally with a spacer, having a number average molecular weight from 400 g/mol (Daltons; "D") to 300 kg/mol (kiloDaltons; "kD"), e.g., from 700 D to 8000 D, from 700 D to 30 kD, from 7500 D to 300 kD, or from 5000 D to 100 kD; or a combination thereof—in particular, hydrogen; a linear, branched, and/or cyclic $C_1$-$C_{12}$ hydrocarbyl moiety; an ether-containing linear, branched, and/or cyclic $C_1$-$C_{12}$ moiety; another 3,4-oxypyridinone connected as an ether at a meta position to the ring nitrogen thereof; or a combination thereof.

In structure (I), $R_2$ may be hydrogen; a halogen; a linear, branched, and/or cyclic $C_1$-$C_{12}$ hydrocarbyl moiety; an at least partially halogenated linear, branched, and/or cyclic $C_1$-$C_{12}$ moiety; an amine-containing linear, branched, and/or cyclic $C_1$-$C_{20}$ moiety; an ether-containing linear, branched, and/or cyclic $C_1$-$C_{20}$ moiety; a hydroxyl-containing linear, branched, and/or cyclic $C_1$-$C_{12}$ moiety; an aldehyde-containing linear, branched, and/or cyclic $C_1$-$C_{20}$ moiety; a nitrile-containing linear, branched, and/or cyclic $C_1$-$C_{20}$ moiety; or a combination thereof—in particular, hydrogen; a linear, branched, and/or cyclic $C_1$-$C_{12}$ hydrocarbyl moiety; an ether-containing linear, branched, and/or cyclic $C_1$-$C_{12}$ moiety; an aldehyde-containing linear, branched, and/or cyclic $C_1$-$C_{12}$ moiety; a nitrile-containing linear, branched, and/or cyclic $C_1$-$C_{12}$ moiety; or a combination thereof.

In structure (I), $R_3$ may be hydrogen; a halogen; a linear, branched, and/or cyclic $C_6$-$C_{24}$ hydrocarbyl moiety; an oligomeric and/or polymeric moiety (i.e., greater than 30 carbons, preferably greater than 36 carbons, at least 60 carbons, and/or at least 80 carbons) containing repeat units (typically formed by addition reaction, such as comprising reacted olefins, hydrogenated dienes, or combinations thereof, but alternatively formed by condensation reaction), at least one of which repeat units is attached to the ring nitrogen, optionally with a spacer, a number average molecular weight of which oligomeric and/or polymeric moiety can be from 400 D to 300 kD, e.g., from 600 D to 8 kD, from 700 D to 30 kD, from 8 kD to 300 kD, or from 5 kD to 100 kD; or a combination thereof—in particular, a linear, branched, and/or cyclic $C_8$-$C_{20}$ hydrocarbyl moiety; an oligomeric and/or polymeric moiety; or a combination thereof.

In structure (I), $R_4$ may be hydrogen; a halogen; a linear, branched, and/or cyclic $C_1$-$C_{12}$ hydrocarbyl moiety; an at least partially halogenated linear, branched, and/or cyclic $C_1$-$C_{12}$ moiety; an amine-containing linear, branched, and/or cyclic $C_1$-$C_{20}$ moiety; an ether-containing linear, branched, and/or cyclic $C_1$-$C_{20}$ moiety; a hydroxyl-containing linear, branched, and/or cyclic $C_1$-$C_{12}$ moiety; an aldehyde-containing linear, branched, and/or cyclic $C_1$-$C_{20}$ moiety; a nitrile-containing linear, branched, and/or cyclic $C_1$-$C_{20}$ moiety; or a combination thereof (e.g., hydrogen; a linear, branched, and/or cyclic $C_1$-$C_{12}$ hydrocarbyl moiety; an ether-containing linear, branched, and/or cyclic $C_1$-$C_{12}$ moiety; an aldehyde-containing linear, branched, and/or cyclic $C_1$-$C_{12}$ moiety; a nitrile-containing linear, branched, and/or cyclic $C_1$-$C_{12}$ moiety; or a combination thereof).

In structure (I), $R_5$ may be hydrogen; a halogen; a linear, branched, and/or cyclic $C_1$-$C_{12}$ hydrocarbyl moiety; an at least partially halogenated linear, branched, and/or cyclic $C_1$-$C_{12}$ moiety; a hydroxylated linear, branched, and/or cyclic $C_1$-$C_6$ moiety; an $R_1$-A- moiety; or a combination thereof—in particular, hydrogen; an $R_1$-A- moiety; or a combination thereof.

Alternatively, in structure (I), one or more of $R_1$ and $R_2$, $R_2$ and $R_3$, $R_3$ and $R_4$, and $R_4$ and $R_5$ may together form one or more (hetero)cyclic rings—in particular, at least $R_4$ and $R_5$ together may comprise from 3 to 15 carbons (e.g., from 4 to 13 carbons, from 5 to 11 carbons, or from 6 to 10 carbons) and form a (hetero)cyclic ring structure.

In particular embodiments of structure (I), it may be desired that $R_1$ and $R_3$ are not both simultaneously hydrogen.

In particular embodiments of structure (I), it may be desired that $R_2$, $R_4$, or both comprise neither a carboxylic acid nor an amide moiety, and optionally also not a carboxylic acid ester moiety, so as to exclude compounds such as disclosed in U.S. Pat. No. 6,432,313, the relevant disclosure of which is incorporated herein by reference.

In particular embodiments of structure (I), it may be desired that $R_3$ comprises no azide moiety, so as to exclude compounds such as disclosed in U.S. Pat. No. 9,617,541, the relevant disclosure of which is incorporated herein by reference.

In particular embodiments of structure (I), it may be desired that $R_3$ comprises neither a thiazolidinyl moiety nor a phosphorus-containing moiety, and optionally also not oligo- and/or poly-nucleotides, so as to exclude compounds such as disclosed in U.S. Pat. Nos. 9,677,075 and/or 9,439,984, the relevant disclosures of which are incorporated herein by reference.

In particular embodiments, the non-aqueous 3,4-oxypyridinone composition is not a bleach catalyst composition, so as to exclude compounds such as disclosed in U.S. Pat. No. 8,815,789, the relevant disclosure of which is incorporated herein by reference.

In particular embodiments, the 3,4-oxypyridinone compound is soluble and/or dispersible in the non-aqueous medium and may thus be not covalently attached to a surface such as that of a substrate, particle, fiber, bead, or the like, so as to exclude compositions of matter such as disclosed in U.S. Pat. No. 8,943,910, the relevant disclosure of which is incorporated herein by reference.

Examples of the 3,4-oxypyridinone according to the present disclosure may comprises, consist essentially of, or be, but are by no means limited to, N-hydrogenated tallow-3-hydroxypyridin-4-one, N-hydrogenated tallow-2-methyl-3-hydroxypyridin-4-one, N-hydrogenated tallow-2-ethyl-3-hydroxypyridin-4-one, N-hydrogenated tallow-2-formyl-3-hydroxypyridin-4-one, N-hydrogenated tallow-2-acetyl-3-hydroxypyridin-4-one, N-hydrogenated tallow-2-cyano-3-hydroxypyridin-4-one, N-hydrogenated tallow-2-methyl-3-hydroxymethyl-pyridin-4-one, N-hydrogenated tallow-2,3-dihydroxypyridin-4-one, N-hydrogenated tallow-3,6-dihydroxypyridin-4-one, N-hydrogenated tallow-2-methyl-3,6-dihydroxypyridin-4-one, N-hydrogenated tallow-2-ethyl-3,6-dihydroxypyridin-4-one, N-hydrogenated tallow-2-formyl-3,6-dihydroxypyridin-4-one, N-hydrogenated tallow-2-acetyl-3,6-dihydroxypyridin-4-one, N-hydrogenated tallow-2-cyano-3,6-dihydroxypyridin-4-one, N-hydrogenated tallow-3,5-dihydroxypyridin-4-one, N-hydrogenated tallow-2-methyl-3,5-dihydroxypyridin-4-one, N-hydrogenated tallow-2-ethyl-3,5-dihydroxypyridin-4-one, N-hydrogenated tallow-2-formyl-3,5-dihydroxypyridin-4-one, N-hydrogenated tallow-2-acetyl-3,5-dihydroxypyridin-4-one, N-hydrogenated tallow-2-cyano-3,5-dihydroxypyridin-4-one, N-hydrogenated tallow-3-methoxypyridin-4-one, N-hydrogenated tallow-2-methyl-3-methoxypyridin-4-one, N-hydrogenated tallow-2-ethyl-3-methoxypyridin-4-one, N-hydrogenated tallow-2-formyl-3-methoxypyridin-4-one, N-hydrogenated tallow-2-acetyl-3-methoxypyridin-4-one, N-hydrogenated tallow-2-cyano-3-methoxypyridin-4-one, N-hydrogenated tallow-2,3-dimethoxypyridin-4-one, N-hydrogenated tallow-3,6-dimethoxypyridin-4-one, N-hydrogenated tallow-2-methyl-3,6-dimethoxypyridin-4-one, N-hydrogenated tallow-2-ethyl-3,6-dimethoxypyridin-4-one, N-hydrogenated tallow-2-formyl-3,6-dimethoxypyridin-4-one, N-hydrogenated tallow-2-acetyl-3,6-dimethoxypyridin-4-one, N-hydrogenated tallow-2-cyano-3,6-dimethoxypyridin-4-one, N-hydrogenated tallow-3,5-dimethoxypyridin-4-one, N-hydrogenated tallow-2-methyl-3,5-dimethoxypyridin-4-one, N-hydrogenated tallow-2-ethyl-3,5-dimethoxypyridin-4-one, N-hydrogenated tallow-2-formyl-3,5-dimethoxypyridin-4-one, N-hydrogenated tallow-2-acetyl-3,5-dimethoxy-pyridin-4-one, N-hydrogenated tallow-2-cyano-3,5-dimethoxypyridin-4-one, N-hydrogenated tallow-3-ethoxypyridin-4-one, N-hydrogenated tallow-2-methyl-3-ethoxypyridin-4-one, N-hydrogenated tallow-2-ethyl-3-ethoxypyridin-4-one, N-hydrogenated tallow-2-formyl-3-ethoxypyridin-4-one, N-hydrogenated tallow-2-acetyl-3-ethoxypyridin-4-one, N-hydrogenated tallow-2-cyano-3-ethoxypyridin-4-one, N-hydrogenated tallow-2,3-diethoxypyridin-4-one, N-hydrogenated tallow-3,6-diethoxypyridin-4-one, N-hydrogenated tallow-2-methyl-3,6-diethoxypyridin-4-one, N-hydrogenated tallow-2-ethyl-3,6-diethoxypyridin-4-one, N-hydrogenated tallow-2-formyl-3,6-diethoxypyridin-4-one, N-hydrogenated tallow-2-acetyl-3,6-diethoxypyridin-4-one, N-hydrogenated tallow-2-cyano-3,6-diethoxypyridin-4-one, N-hydrogenated tallow-3,5-diethoxypyridin-4-one, N-hydrogenated tallow-2-methyl-3,5-diethoxypyridin-4-one, N-hydrogenated tallow-2-ethyl-3,5-diethoxypyridin-4-one, N-hydrogenated tallow-2-formyl-3,5-diethoxypyridin-4-one, N-hydrogenated tallow-2-acetyl-3,5-diethoxypyridin-4-one, N-hydrogenated tallow-2-cyano-3,5-diethoxypyridin-4-one, N-hydrogenated tallow-3-t-butylcarbonyloxy-pyridin-4-one, N-hydrogenated tallow-2-methyl-3-t-butylcarbonyloxy-pyridin-4-one, N-hydrogenated tallow-2-ethyl-3-t-butylcarbonyloxy-pyridin-4-one, N-hydrogenated tallow-2-formyl-3-t-butylcarbonyloxy-pyridin-4-one, N-hydrogenated tallow-2-acetyl-3-t-butylcarbonyloxy-pyridin-4-one, N-hydrogenated tallow-2-cyano-3-t-butylcarbonyloxy-pyridin-4-one, N-hydrogenated tallow-3-benzyloxypyridin-4-one, N-hydrogenated tallow-2-methyl-3-benzyloxypyridin-4-one, N-hydrogenated tallow-2-ethyl-3-benzyloxypyridin-4-one, N-hydrogenated tallow-2-formyl-3-benzyloxypyridin-4-one, N-hydrogenated tallow-2-acetyl-3-benzyloxypyridin-4-one, N-hydrogenated tallow-2-cyano-3-benzyloxypyridin-4-one, N-hydrogenated tallow-3-tetrahydropyranyloxypyridin-4-one, N-hydrogenated tallow-2-methyl-3-tetrahydropyranyloxypyridin-4-one, N-hydrogenated tallow-2-ethyl-3-tetrahydropyranyloxy-pyridin-4-one, N-hydrogenated tallow-2-formyl-3-tetrahydropyranyloxypyridin-4-one, N-hydrogenated tallow-2-acetyl-3-tetrahydropyranyloxypyridin-4-one, N-hydrogenated tallow-2-cyano-3-tetrahydropyranyloxypyridin-4-one, N-hydrogenated tallow-3-(4-hydroxybenzyloxy)-pyridin-4-one, N-hydrogenated tallow-2-methyl-3-(4-hydroxybenzyloxy)-pyridin-4-one, N-hydrogenated tallow-2-ethyl-3-(4-hydroxybenzyloxy)-pyridin-4-one, N-hydrogenated tallow-2-formyl-3-(4-hydroxybenzyloxy)-pyridin-4-one, N-hydrogenated tallow-2-acetyl-3-(4-hydroxybenzyloxy)-pyridin-4-one, N-hydrogenated tallow-2-cyano-3-(4-hydroxybenzyloxy)-pyridin-4-one, N-hydrogenated tallow-3-(4-methoxybenzyloxy)-pyridin-4-one, N-hydrogenated tallow-2-methyl-3-(4-methoxybenzyloxy)-pyridin-4-one, N-hydrogenated tallow-2-ethyl-3-(4-methoxybenzyloxy)-pyridin-4-one, N-hydrogenated tallow-2-formyl-3-(4-methoxybenzyloxy)-pyridin-4-one, N-hydrogenated tallow-2-acetyl-3-(4-methoxybenzyloxy)-pyridin-4-one, N-hydrogenated tallow-2-cyano-3-(4-methoxybenzyloxy)-pyridin-4-one, N-hydrogenated tallow-3-(2-propenyl-1-oxy)-pyridin-4-one, N-hydrogenated tallow-2-methyl-3-(2-propenyl-1-oxy)-pyridin-4-one, N-hydrogenated tallow-2-ethyl-3-(2-propenyl-1-oxy)-pyridin-4-one, N-hydrogenated tallow-2-formyl-3-(2-propenyl-1-oxy)-pyridin-4-one, N-hydrogenated tallow-2-acetyl-3-(2-propenyl-1-oxy)-pyridin-4-one, N-hydrogenated tallow-2-cyano-3-(2-propenyl-1-oxy)-pyridin-4-one, N-hydrogenated tallow-3-(2-ethylhexyl-1-oxy)-pyridin-4-one, N-hydrogenated tallow-2-methyl-3-(2-ethylhexyl-1-oxy)-pyridin-4-one, N-hydrogenated tallow-2-ethyl-3-(2-ethylhexyl-1-oxy)-pyridin-4-one, N-hydrogenated tallow-2-formyl-3-(2-ethylhexyl-1-oxy)-pyridin-4-one, N-hydrogenated tallow-2-acetyl-3-(2-ethylhexyl-1-oxy)-pyridin-4-one, N-hydrogenated tallow-2-cyano-3-(2-ethylhexyl-1-oxy)-pyridin-4-one, N-(2-ethylhexyl)-3-hydroxypyridin-4-one, N-(2-ethylhexyl)-2-methyl-3-hydroxypyridin-4-one, N-(2-ethylhexyl)-2-ethyl-3-hydroxypyridin-4-one, N-(2-ethylhexyl)-2-formyl-3-hydroxypyridin-4-one, N-(2-ethylhexyl)-2-acetyl-3-hydroxypyridin-4-one, N-(2-ethylhexyl)-2-cyano-3-hydroxypyridin-4-one, N-(2-ethylhexyl)-2-methyl-3-hydroxymethyl-pyridin-4-one N-(2-ethylhexyl)-2,3-dihydroxypyridin-4-one, N-(2-ethylhexyl)-3,6-dihydroxypyridin-4-one, N-(2-ethylhexyl)-2-methyl-3,6-dihydroxypyridin-4-one, N-(2-ethylhexyl)-2-ethyl-3,6-dihydroxypyridin-4-one, N-(2-ethylhexyl)-2-formyl-3,6-dihydroxypyridin-4-one, N-(2-ethylhexyl)-2-acetyl-3,6-dihydroxypyridin-4-one, N-(2-ethylhexyl)-2-cyano-3,6-dihydroxypyridin-4-one, N-(2-ethylhexyl)-3,5-dihydroxypyridin-4-one, N-(2-ethylhexyl)-2-methyl-3,5-dihydroxypyridin-4-one, N-(2-ethylhexyl)-2-ethyl-3,5-dihydroxypyridin-4-one, N-(2-ethylhexyl)-2-formyl-3,5-dihydroxypyridin-4-one, N-(2-ethylhexyl)-2-acetyl-3,5-dihydroxypyridin-4-one, N-(2-ethylhexyl)-2-cyano-3,5-dihydroxypyridin-4-one, N-(2-ethylhexyl)-3-t-butylcarbonyloxy-pyridin-4-one, N-(2-ethylhexyl)-2-methyl-3-t-butylcarbonyloxy-pyridin-4-one, N-(2-ethylhexyl)-2-ethyl-3-t-butylcarbonyloxy-pyridin-4-one, N-(2-ethylhexyl)-2-formyl-3-t-butylcarbonyloxy-pyridin-4-one, N-(2-ethylhexyl)-2-acetyl-3-t-butylcarbonyloxy-pyridin-4-one, N-(2-ethylhexyl)-2-cyano-3-t-butylcarbonyloxy-pyridin-4-one, N-(2-ethylhexyl)-3-benzyloxypyridin-4-one, N-tetradecyl-2-methyl-3-benzyloxypyridin-4-one, N-(2-ethylhexyl)-2-ethyl-3-benzyloxypyridin-4-one, N-(2-ethylhexyl)-2-formyl-3-benzyloxypyridin-4-one, N-(2-ethylhexyl)-2-acetyl-3-benzyloxypyridin-4-one, N-(2-ethylhexyl)-2-cyano-3-benzyloxypyridin-4-one, N-(2-ethylhexyl)-3-tetrahydropyranyloxypyridin-4-one, N-(2-ethylhexyl)-2-methyl-3-tetrahydropyranyloxypyridin-4-one, N-(2-ethylhexyl)-2-ethyl-3-tetrahydropyranyloxypyridin-4-one, N-(2-ethylhexyl)-2-formyl-3-tetrahydropyranyloxypyridin-4-one, N-(2-ethylhexyl)-2-acetyl-3-tetrahydropyranyloxypyridin-4-one, N-(2-ethylhexyl)-2-cyano-3-tetrahydropyranyloxypyridin-4-one, N-(2-ethylhexyl)-3-(4-hydroxybenzyloxy)-pyridin-4-one, N-(2-ethylhexyl)-2-methyl-3-(4-hydroxybenzyloxy)-pyridin-4-one, N-(2-ethylhexyl)-2-ethyl-3-(4-hydroxybenzyloxy)-pyridin-4-one, N-(2-ethylhexyl)-2-formyl-3-(4-hydroxybenzyloxy)-pyridin-4-one, N-(2-ethylhexyl)-2-acetyl-3-(4-hydroxybenzyloxy)-pyridin-4-one, N-(2-ethylhexyl)-2-cyano-3-(4-hydroxybenzyloxy)-pyridin-4-one, N-(2-ethylhexyl)-3-(4-methoxybenzyloxy)-pyridin-4-one, N-(2-ethylhexyl)-2-methyl-3-(4-methoxybenzyloxy)-pyridin-4-one, N-(2-ethylhexyl)-2-ethyl-3-(4-methoxybenzyloxy)-pyridin-4-one, N-(2-ethylhexyl)-2-formyl-3-(4-methoxybenzyloxy)-pyridin-4-one, N-(2-ethylhexyl)-2-acetyl-3-(4-methoxybenzyloxy)-pyridin-4-one, N-(2-ethylhexyl)-2-cyano-3-(4-methoxybenzyloxy)-pyridin-4-one, N-(2-ethylhexyl)-3-(2-propenyl-1-oxy)-pyridin-4-one, N-(2-ethylhexyl)-2-methyl-3-(2-propenyl-1-oxy)-pyridin-4-one, N-(2-ethylhexyl)-2-ethyl-3-(2-propenyl-1-oxy)-pyridin-4-one, N-(2-ethylhexyl)-2-formyl-3-(2-propenyl-1-oxy)-pyridin-4-one, N-(2-ethylhexyl)-2-acetyl-3-(2-propenyl-1-oxy)-pyridin-4-one, N-(2-ethylhexyl)-2-cyano-3-(2-propenyl-1-oxy)-pyridin-4-one, N-(2-ethylhexyl)-3-(2-ethylhexyl-1-oxy)-pyridin-4-one, N-(2-ethylhexyl)-2-methyl-3-(2-ethylhexyl-1-oxy)-pyridin-4-one, N-(2-ethylhexyl)-2-ethyl-3-(2-ethylhexyl-1-oxy)-pyridin-4-one, N-(2-ethylhexyl)-2-formyl-3-(2-ethylhexyl-1-oxy)-pyridin-4-one, N-(2-ethylhexyl)-2-acetyl-3-(2-ethylhexyl-1-oxy)-pyridin-4-one, N-(2-ethylhexyl)-2-cyano-3-(2-ethylhexyl-1-oxy)-pyridin-4-one, N-tetradecyl-3-hydroxypyridin-4-one, N-tetradecyl-2-methyl-3-hydroxypyridin-4-one, N-tetradecyl-2-ethyl-3-hydroxypyridin-4-one, N-tetradecyl-2-formyl-3-hydroxypyridin-4-one, N-tetradecyl-2-acetyl-3-hydroxypyridin-4-one, N-tetradecyl-2-cyano-3-hydroxypyridin-4-one, N-tetradecyl-2-methyl-3-hydroxymethyl-pyridin-4-one, N-tetradecyl-2,3-dihydroxypyridin-4-one, N-tetradecyl-3,6-dihydroxypyridin-4-one, N-tetradecyl-2-methyl-3,6-dihydroxypyridin-4-one, N-tetradecyl-2-ethyl-3,6-dihydroxypyridin-4-one, N-tetradecyl-2-formyl-3,6-dihydroxypyridin-4-one, N-tetradecyl-2-acetyl-3,6-dihydroxypyridin-4-one, N-tetradecyl-2-cyano-3,6-dihydroxypyridin-4-one, N-tetradecyl-3,5-dihydroxypyridin-4-one, N-tetradecyl-2-methyl-3,5-dihydroxypyridin-4-one, N-tetradecyl-2-ethyl-3,5-dihydroxypyridin-4-one, N-tetradecyl-2-formyl-3,5-dihydroxypyridin-4-one, N-tetradecyl-2-acetyl-3,5-dihydroxypyridin-4-one, N-tetradecyl-2-cyano-3,5-dihydroxypyridin-4-one, N-tetradecyl-3-t-butylcarbonyloxy-pyridin-4-one, N-tetradecyl-2-methyl-3-t-butylcarbonyloxy-pyridin-4-one, N-tetradecyl-2-ethyl-3-t-butylcarbonyloxy-pyridin-4-one, N-tetradecyl-2-formyl-3-t-butylcarbonyloxy-pyridin-4-one, N-tetradecyl-2-acetyl-3-t-butylcarbonyloxy-pyridin-4-one, N-tetradecyl-2-cyano-3-t-butylcarbonyloxy-pyridin-4-one, N-tetradecyl-3-benzyloxypyridin-4-one, N-tetradecyl-2-methyl-3-benzyloxypyridin-4-one, N-tetradecyl-2-ethyl-3-benzyloxypyridin-4-one, N-tetradecyl-2-formyl-3-benzyloxypyridin-4-one, N-tetradecyl-2-acetyl-3-benzyloxypyridin-4-one, N-tetradecyl-2-cyano-3-benzyloxypyridin-4-one, N-tetradecyl-3-tetrahydropyranyloxypyridin-4-one, N-tetradecyl-2-methyl-3-tetrahydropyranyloxypyridin-4-one, N-tetradecyl-2-ethyl-3-tetrahydropyranyloxypyridin-4-one, N-tetradecyl-2-formyl-3-tetrahydropyranyloxypyridin-4-one, N-tetradecyl-2-acetyl-3-tetrahydropyranyloxypyridin-4-one, N-tetradecyl-2-cyano-3-tetrahydropyranyloxypyridin-4-one, N-tetradecyl-3-(4-hydroxybenzyloxy)-pyridin-4-one, N-tetradecyl-2-methyl-3-(4-hydroxybenzyloxy)-pyridin-4-one, N-tetradecyl-2-ethyl-3-(4-hydroxybenzyloxy)-pyridin-4-one, N-tetradecyl-2-formyl-3-(4-hydroxybenzyloxy)-pyridin-4-one, N-tetradecyl-2-acetyl-3-(4-hydroxybenzyloxy)-pyridin-4-one, N-tetradecyl-2-cyano-3-(4-hydroxybenzyloxy)-pyridin-4-one, N-tetradecyl-3-(4-methoxybenzyloxy)-pyridin-4-one, N-tetradecyl-2-methyl-3-(4-methoxybenzyloxy)-pyridin-4-one, N-tetradecyl-2-ethyl-3-(4-methoxybenzyloxy)-pyridin-4-one, N-tetradecyl-2-formyl-3-(4-methoxybenzyloxy)-pyridin-4-one, N-tetradecyl-2-acetyl-3-(4-methoxybenzyloxy)-pyridin-4-one, N-tetradecyl-2-cyano-3-(4-methoxybenzyloxy)-pyridin-4-one, N-tetradecyl-3-(2-propenyl-1-oxy)-pyridin-4-one, N-tetradecyl-2-methyl-3-(2-propenyl-1-oxy)-pyridin-4-one, N-tetradecyl-2-ethyl-3-(2-propenyl-1-oxy)-pyridin-4-one, N-tetradecyl-2-formyl-3-(2-propenyl-1-oxy)-pyridin-4-one, N-tetradecyl-2-acetyl-3-(2-propenyl-1-oxy)-pyridin-4-one, N-tetradecyl-2-cyano-3-(2-propenyl-1-oxy)-pyridin-4-one, N-tetradecyl-3-(2-ethylhexyl-1-oxy)-pyridin-4-one, N-tetradecyl-2-methyl-3-(2-ethylhexyl-1-oxy)-pyridin-4-one, N-tetradecyl-2-ethyl-3-(2-ethylhexyl-1-oxy)-pyridin-4-one, N-tetradecyl-2-formyl-3-(2-ethylhexyl-1-oxy)-pyridin-4-one, N-tetradecyl-2-acetyl-3-(2-ethylhexyl-1-oxy)-pyridin-4-one, N-tetradecyl-2-cyano-3-(2-ethylhexyl-1-oxy)-pyridin-4-one, N-hexadecyl-3-hydroxypyridin-4-one, N-hexadecyl-2-methyl-3-hydroxypyridin-4-one, N-hexadecyl-2-ethyl-3-hydroxypyridin-4-one, N-hexadecyl-2-formyl-3-hydroxypyridin-4-one, N-hexadecyl-2-acetyl-3-hydroxypyridin-4-one, N-hexadecyl-2-cyano-3-hydroxypyridin-4-one, N-hexadecyl-2-methyl-3-hydroxymethyl-pyridin-4-one, N-hexadecyl-2,3-dihydroxypyridin-4-one, N-hexadecyl-3,6-dihydroxypyridin-4-one, N-hexadecyl-2-methyl-3,6-dihydroxypyridin-4-one, N-hexadecyl-2-ethyl-3,6-dihydroxypyridin-4-one, N-hexadecyl-2-formyl-3,6-dihydroxypyridin-4-one, N-hexadecyl-2-acetyl-3,6-dihydroxypyridin-4-one, N-hexadecyl-2-cyano-3,6-dihydroxypyridin-4-one, N-hexadecyl-3,5-dihydroxypyridin-4-one, N-hexadecyl-2-methyl-3,5-dihydroxypyridin-4-one, N-hexadecyl-2-ethyl-3,5-dihydroxypyridin-4-one, N-hexadecyl-2-formyl-3,5-dihydroxypyridin-4-one, N-hexadecyl-2-acetyl-3,5-dihydroxypyridin-4-one, N-hexadecyl-2-cyano-3,5-dihydroxypyridin-4-one, N-hexadecyl-3-t-butylcarbonyloxy-pyridin-4-one, N-hexadecyl-2-methyl-3-t-butylcarbonyloxy-pyridin-4-one, N-hexadecyl-2-ethyl-3-t-butylcarbonyloxy-pyridin-4-one, N-hexadecyl-2-formyl-3-t-butylcarbonyloxy-pyridin-4-one, N-hexadecyl-2-acetyl-3-t-butylcarbonyloxy-pyridin-4-one, N-hexadecyl-2-cyano-3-t-butylcarbonyloxy-pyridin-4-one, N-hexadecyl-3-benzyloxypyridin-4-one, N-hexadecyl-2-methyl-3-benzyloxypyridin-4-one, N-hexadecyl-2-ethyl-3-benzyloxypyridin-4-one, N-hexadecyl-2-formyl-3-benzyloxypyridin-4-one, N-hexadecyl-2-acetyl-3-benzyloxypyridin-4-one, N-hexadecyl-2-cyano-3-benzyloxypyridin-4-one, N-hexadecyl-3-tetrahydropyranyloxypyridin-4-one, N-hexadecyl-2-methyl-3-tetrahydropyranyloxypyridin-4-one, N-hexadecyl-2-ethyl-3-tetrahydropyranyloxypyridin-4-one, N-hexadecyl-2-formyl-3-tetrahydropyranyloxypyridin-4-one, N-hexadecyl-2-acetyl-3-tetrahydropyranyloxypyridin-4-one, N-hexadecyl-2-cyano-3-tetrahydropyranyloxypyridin-4-one, N-hexadecyl-3-(4-hydroxybenzyloxy)-pyridin-4-one, N-hexadecyl-2-methyl-3-(4-hydroxybenzyloxy)-pyridin-4-one, N-hexadecyl-2-ethyl-3-(4-hydroxybenzyloxy)-pyridin-4-one, N-hexadecyl-2-formyl-3-(4-hydroxybenzyloxy)-pyridin-4-one, N-hexadecyl-2-acetyl-3-(4-hydroxybenzyloxy)-pyridin-4-one, N-hexadecyl-2-cyano-3-(4-hydroxybenzyloxy)-pyridin-4-one, N-hexadecyl-3-(4-methoxybenzyloxy)-pyridin-4-one, N-hexadecyl-2-methyl-3-(4-methoxybenzyloxy)-pyridin-4-one, N-hexadecyl-2-ethyl-3-(4-methoxybenzyloxy)-pyridin-4-one, N-hexadecyl-2-formyl-3-(4-methoxybenzyloxy)-pyridin-4-one, N-hexadecyl-2-acetyl-3-(4-methoxybenzyloxy)-pyridin-4-one, N-hexadecyl-2-cyano-3-(4-methoxybenzyloxy)-pyridin-4-one, N-hexadecyl-3-(2-propenyl-1-oxy)-pyridin-4-one, N-hexadecyl-2-methyl-3-(2-propenyl-1-oxy)-pyridin-4-one, N-hexadecyl-2-ethyl-3-(2-propenyl-1-oxy)-pyridin-4-one, N-hexadecyl-2-formyl-3-(2-propenyl-1-oxy)-pyridin-4-one, N-hexadecyl-2-acetyl-3-(2-propenyl-1-oxy)-pyridin-4-one, N-hexadecyl-2-cyano-3-(2-propenyl-1-oxy)-pyridin-4-one, N-hexadecyl-3-(2-ethylhexyl-1-oxy)-pyridin-4-one, N-hexadecyl-2-methyl-3-(2-ethylhexyl-1-oxy)-pyridin-4-one, N-hexadecyl-2-ethyl-3-(2-ethylhexyl-1-oxy)-pyridin-4-one, N-hexadecyl-2-formyl-3-(2-ethylhexyl-1-oxy)-pyridin-4-one, N-hexadecyl-2-acetyl-3-(2-ethylhexyl-1-oxy)-pyridin-4-one, N-hexadecyl-2-cyano-3-(2-ethylhexyl-1-oxy)-pyridin-4-one, N-octadecyl-3-hydroxypyridin-4-one, N-octadecyl-2-methyl-3-hydroxypyridin-4-one, N-octadecyl-2-ethyl-3-hydroxypyridin-4-one, N-octadecyl-2-formyl-3-hydroxy-pyridin-4-one, N-octadecyl-2-acetyl-3-hydroxypyridin-4-one, N-octadecyl-2-cyano-3-hydroxypyridin-4-one, N-octadecyl-2-methyl-3-hydroxymethyl-pyridin-4-one, N-octadecyl-2,3-dihydroxypyridin-4-one, N-octadecyl-3,6-dihydroxypyridin-4-one, N-octadecyl-2-methyl-3,6-dihydroxypyridin-4-one, N-octadecyl-2-ethyl-3,6-dihydroxy-pyridin-4-one, N-octadecyl-2-formyl-3,6-dihydroxypyridin-4-one, N-octadecyl-2-acetyl-3,6-dihydroxypyridin-4-one, N-octadecyl-2-cyano-3,6-dihydroxypyridin-4-one, N-octadecyl-3,5-dihydroxypyridin-4-one, N-octadecyl-2-methyl-3,5-dihydroxypyridin-4-one, N-octadecyl-2-ethyl-3,5-dihydroxypyridin-4-one, N-octadecyl-2-formyl-3,5-dihydroxypyridin-4-one, N-octadecyl-2-acetyl-3,5-dihydroxypyridin-4-one, N-octadecyl-2-cyano-3,5-dihydroxypyridin-4-one, N-octadecyl-3-t-butylcarbonyloxy-pyridin-4-one, N-octadecyl-2-methyl-3-t-butylcarbonyloxy-pyridin-4-one, N-octadecyl-2-ethyl-3-t-butylcarbonyloxy-pyridin-4-one, N-octadecyl-2-formyl-3-t-butylcarbonyloxy-pyridin-4-one, N-octadecyl-2-acetyl-3-t-butylcarbonyloxy-pyridin-4-one, N-octadecyl-2-cyano-3-t-butylcarbonyloxy-pyridin-4-one, N-octadecyl-3-benzyloxypyridin-4-one, N-octadecyl-2-methyl-3-benzyloxypyridin-4-one, N-octadecyl-2-ethyl-3-benzyloxypyridin-4-one, N-octadecyl-2-formyl-3-benzyloxypyridin-4-one, N-octadecyl-2-acetyl-3-benzyloxypyridin-4-one, N-octadecyl-2-cyano-3-benzyloxypyridin-4-one, N-octadecyl-3-tetrahydropyranyloxypyridin-4-one, N-octadecyl-2-methyl-3-tetrahydropyranyloxypyridin-4-one, N-octadecyl-2-ethyl-3-tetrahydropyranyloxypyridin-4-one, N-octadecyl-2-formyl-3-tetrahydropyranyloxypyridin-4-one, N-octadecyl-2-acetyl-3-tetrahydropyranyloxypyridin-4-one, N-octadecyl-2-cyano-3-tetrahydropyranyloxypyridin-4-one, N-octadecyl-3-(4-hydroxybenzyloxy)-pyridin-4-one, N-octadecyl-2-methyl-3-(4-hydroxybenzyloxy)-pyridin-4-one, N-octadecyl-2-ethyl-3-(4-hydroxybenzyloxy)-pyridin-4-one, N-octadecyl-2-formyl-3-(4-hydroxybenzyloxy)-pyridin-4-one, N-octadecyl-2-acetyl-3-(4-hydroxybenzyloxy)-pyridin-4-one, N-octadecyl-2-cyano-3-(4-hydroxy-benzyloxy)-pyridin-4-one, N-octadecyl-3-(4-methoxybenzyloxy)-pyridin-4-one, N-octadecyl-2-methyl-3-(4-methoxybenzyloxy)-pyridin-4-one, N-octadecyl-2-ethyl-3-(4-methoxybenzyloxy)-pyridin-4-one, N-octadecyl-2-formyl-3-(4-methoxybenzyloxy)-pyridin-4-one, N-octadecyl-2-acetyl-3-(4-methoxybenzyloxy)-pyridin-4-one, N-octadecyl-2-cyano-3-(4-methoxybenzyloxy)-pyridin-4-one, N-octadecyl-3-(2-propenyl-1-oxy)-pyridin-4-one, N-octadecyl-2-methyl-3-(2-propenyl-1-oxy)-pyridin-4-one, N-octadecyl-2-ethyl-3-(2-propenyl-1-oxy)-pyridin-4-one, N-octadecyl-2-formyl-3-(2-propenyl-1-oxy)-pyridin-4-one, N-octadecyl-2-acetyl-3-(2-propenyl-1-oxy)-pyridin-4-one, N-octadecyl-2-cyano-3-(2-propenyl-1-oxy)-pyridin-4-one, N-octadecyl-3-(2-ethylhexyl-1-oxy)-pyridin-4-one, N-octadecyl-2-methyl-3-(2-ethylhexyl-1-oxy)-pyridin-4-one, N-octadecyl-2-ethyl-3-(2-ethylhexyl-1-oxy)-pyridin-4-one, N-octadecyl-2-formyl-3-(2-ethylhexyl-1-oxy)-pyridin-4-one, N-octadecyl-2-acetyl-3-(2-ethylhexyl-1-oxy)-pyridin-4-one, N-octadecyl-2-cyano-3-(2-ethylhexyl-1-oxy)-pyridin-4-one, N-octadecenyl-3-hydroxypyridin-4-one, N-octadecenyl-2-methyl-3-hydroxypyridin-4-one, N-octadecenyl-2-ethyl-3-hydroxypyridin-4-one, N-octadecenyl-2-formyl-3-hydroxypyridin-4-one, N-octadecenyl-2-acetyl-3-hydroxypyridin-4-one, N-octadecenyl-2-cyano-3-hydroxypyridin-4-one, N-octadecenyl-2-methyl-3-hydroxymethyl-pyridin-4-one, N-octadecenyl-2,3-dihydroxypyridin-4-one, N-octadecenyl-3,6-dihydroxypyridin-4-one, N-octadecenyl-2-methyl-3,6-dihydroxypyridin-4-one, N-octadecenyl-2-ethyl-3,6-dihydroxypyridin-4-one, N-octadecenyl-2-formyl-3,6-dihydroxypyridin-4-one, N-octadecenyl-2-acetyl-3,6-dihydroxypyridin-4-one, N-octadecenyl-2-cyano-3,6-dihydroxypyridin-4-one, N-octadecenyl-3,5-dihydroxypyridin-4-one, N-octadecenyl-2-methyl-3,5-dihydroxypyridin-4-one, N-octadecenyl-2-ethyl-3,5-dihydroxypyridin-4-one, N-octadecenyl-2-formyl-3,5-dihydroxypyridin-4-one, N-octadecenyl-2-acetyl-3,5-dihydroxypyridin-4-one, N-octadecenyl-2-cyano-3,5-dihydroxypyridin-4-one, N-octadecenyl-3-t-butylcarbonyloxy-pyridin-4-one, N-octadecenyl-2-methyl-3-t-butylcarbonyloxy-pyridin-4-one, N-octadecenyl-2-ethyl-3-t-butylcarbonyloxy-pyridin-4-one, N-octadecenyl-2-formyl-3-t-butylcarbonyloxy-pyridin-4-one, N-octadecenyl-2-acetyl-3-t-butylcarbonyloxy-pyridin-4-one, N-octadecenyl-2-cyano-3-t-butylcarbonyloxy-pyridin-4-one, N-octadecenyl-3-benzyloxypyridin-4-one, N-octadecenyl-2-methyl-3-benzyloxypyridin-4-one, N-octadecenyl-2-ethyl-3-benzyloxypyridin-4-one, N-octadecenyl-2-formyl-3-benzyloxypyridin-4-one, N-octadecenyl-2-acetyl-3-benzyloxypyridin-4-one, N-octadecenyl-2-cyano-3-benzyloxypyridin-4-one, N-octadecenyl-3-tetrahydropyranyloxypyridin-4-one, N-octadecenyl-2-methyl-3-tetrahydropyranyloxypyridin-4-one, N-octadecenyl-2-ethyl-3-tetrahydropyranyloxypyridin-4-one, N-octadecenyl-2-formyl-3-tetrahydropyranyloxypyridin-4-one, N-octadecenyl-2-acetyl-3-tetrahydropyranyloxypyridin-4-one, N-octadecenyl-2-cyano-3-tetrahydropyranyloxy-pyridin-4-one, N-octadecenyl-3-(4-hydroxybenzyloxy)-pyridin-4-one, N-octadecenyl-2-methyl-3-(4-hydroxybenzyloxy)-pyridin-4-one, N-octadecenyl-2-ethyl-3-(4-hydroxybenzyloxy)-pyridin-4-one, N-octadecenyl-2-formyl-3-(4-hydroxybenzyloxy)-pyridin-4-one, N-octadecenyl-2-acetyl-3-(4-hydroxybenzyloxy)-pyridin-4-one, N-octadecenyl-2-cyano-3-(4-hydroxybenzyloxy)-pyridin-4-one, N-octadecenyl-3-(4-methoxybenzyloxy)-pyridin-4-one, N-octadecenyl-2-methyl-3-(4-methoxybenzyloxy)-pyridin-4-one, N-octadecenyl-2-ethyl-3-(4-methoxybenzyloxy)-pyridin-4-one, N-octadecenyl-2-formyl-3-(4-methoxybenzyloxy)-pyridin-4-one, N-octadecenyl-2-acetyl-3-(4-methoxybenzyloxy)-pyridin-4-one, N-octadecenyl-2-cyano-3-(4-methoxybenzyloxy)-pyridin-4-one, N-octadecenyl-3-(2-propenyl-1-oxy)-pyridin-4-one, N-octadecenyl-2-methyl-3-(2-propenyl-1-oxy)-pyridin-4-one, N-octadecenyl-2-ethyl-3-(2-propenyl-1-oxy)-pyridin-4-one, N-octadecenyl-2-formyl-3-(2-propenyl-1-oxy)-pyridin-4-one, N-octadecenyl-2-acetyl-3-(2-propenyl-1-oxy)-pyridin-4-one, N-octadecenyl-2-cyano-3-(2-propenyl-1-oxy)-pyridin-4-one, N-octadecenyl-3-(2-ethylhexyl-1-oxy)-pyridin-4-one, N-octadecenyl-2-methyl-3-(2-ethylhexyl-1-oxy)-pyridin-4-one, N-octadecenyl-2-ethyl-3-(2-ethylhexyl-1-oxy)-pyridin-4-one, N-octadecenyl-2-formyl-3-(2-ethylhexyl-1-oxy)-pyridin-4-one, N-octadecenyl-2-acetyl-3-(2-ethylhexyl-1-oxy)-pyridin-4-one, N-octadecenyl-2-cyano-3-(2-ethylhexyl-1-oxy)-pyridin-4-one, 3,3'-oxybis(N-hydrogenated tallow-pyridin-4-one), 5,5'-oxybis(N-hydrogenated tallow-2-methyl-pyridin-4-one), 5,5'-oxybis(N-hydrogenated tallow-2-ethyl-pyridin-4-one), 5,5'-oxybis(N-hydrogenated tallow-2-formyl-pyridin-4-one), 5,5'-oxybis(N-hydrogenated tallow-2-acetyl-pyridin-4-one), 5,5'-oxybis(N-hydrogenated tallow-2-cyano-pyridin-4-one), 3,3'-oxybis(N-(2-ethylhexyl)-pyridin-4-one), 5,5'-oxybis(N-(2-ethylhexyl)-2-methyl-pyridin-4-one), 5,5'-oxybis(N-(2-ethylhexyl)-2-ethyl-pyridin-4-one), 5,5'-oxybis(N-(2-ethyl-hexyl)-2-formyl-pyridin-4-one), 5,5'-oxybis(N-(2-ethylhexyl)-2-acetyl-pyridin-4-one), 5,5'-oxybis(N-(2-ethylhexyl)-2-cyano-pyridin-4-one), 3,3'-oxybis(N-tetradecyl-pyridin-4-one), 5,5'-oxybis(N-tetradecyl-2-methyl-pyridin-4-one), 5,5'-oxybis(N-tetradecyl-2-ethyl-pyridin-4-one), 5,5'-oxybis(N-tetradecyl-2-formyl-pyridin-4-one), 5,5'-oxybis(N-tetradecyl-2-acetyl-pyridin-4-one), 5,5'-oxybis(N-tetradecyl-2-cyano-pyridin-4-one), 3,3'-oxybis(N-hexadecyl-pyridin-4-one), 5,5'-oxybis(N-hexadecyl-2-methyl-pyridin-4-one), 5,5'-oxybis(N-hexadecyl-2-ethyl-pyridin-4-one), 5,5'-oxybis(N-hexadecyl-2-formyl-pyridin-4-one), 5,5'-oxybis(N-hexadecyl-2-acetyl-pyridin-4-one), 5,5'-oxybis(N-hexadecyl-2-cyano-pyridin-4-one), 3,3'-oxybis(N-octadecyl-pyridin-4-one), 5,5'-oxybis(N-octadecyl-2-methyl-pyridin-4-one), 5,5'-oxybis(N-octadecyl-2-ethyl-pyridin-4-one), 5,5'-oxybis(N-octadecyl-2-formyl-pyridin-4-one), 5,5'-oxybis(N-octadecyl-2-acetyl-pyridin-4-one), 5,5'-oxybis(N-octadecyl-2-cyano-pyridin-4-one), 3,3'-oxybis(N-octadecenyl-pyridin-4-one), 5,5'-oxybis(N-octadecenyl-2-methyl-pyridin-4-one), 5,5'-oxybis(N-octadecenyl-2-ethyl-pyridin-4-one), 5,5'-oxybis(N-octadecenyl-2-formyl-pyridin-4-one), 5,5'-oxybis(N-octadecenyl-2-acetyl-pyridin-4-one), 5,5'-oxybis(N-octadecenyl-2-cyano-pyridin-4-one), 5,5'-oxybis(N-hydrogenated tallow-3-hydroxypyridin-4-one), 5,5'-oxybis(N-hydrogenated tallow-2-methyl-3-hydroxypyridin-4-one), 5,5'-oxybis(N-hydrogenated tallow-2-ethyl-3-hydroxypyridin-4-one), 5,5'-oxybis(N-hydrogenated tallow-2-formyl-3-hydroxypyridin-4-one), 5,5'-oxybis(N-hydrogenated tallow-2-acetyl-3-hydroxypyridin-4-one), 5,5'-oxybis(N-hydrogenated tallow-2-cyano-3-hydroxypyridin-4-one), 5,5'-oxybis(N-(2-ethylhexyl)-3-hydroxypyridin-4-one), 5,5'-oxybis(N-(2-ethylhexyl)-2-methyl-3-hydroxypyridin-4-one), 5,5'-oxybis(N-(2-ethylhexyl)-2-ethyl-3-hydroxypyridin-4-one), 5,5'-oxybis(N-(2-ethylhexyl)-2-formyl-3-hydroxypyridin-4-one), 5,5'-oxybis(N-(2-ethylhexyl)-2-acetyl-3-hydroxypyridin-4-one), 5,5'-oxybis(N-(2-ethylhexyl)-2-cyano-3-hydroxypyridin-4-one), 5,5'-oxybis(N-tetradecyl-3-hydroxypyridin-4-one), 5,5'-oxybis(N-tetradecyl-2-methyl-3-hydroxypyridin-4-one), 5,5'-oxybis(N-tetradecyl-2-ethyl-3-hydroxypyridin-4-one), 5,5'-oxybis(N-tetradecyl-2-formyl-3-hydroxypyridin-4-one), 5,5'-oxybis(N-tetradecyl-2-acetyl-3-hydroxypyridin-4-one), 5,5'-oxybis(N-tetradecyl-2-cyano-3-hydroxypyridin-4-one), 5,5'-oxybis(N-hexadecyl-3-hydroxypyridin-4-one), 5,5'-oxybis(N-hexadecyl-2-methyl-3-hydroxypyridin-4-one), 5,5'-oxybis(N-hexadecyl-2-ethyl-3-hydroxypyridin-4-one), 5,5'-oxybis(N-hexadecyl-2-formyl-3-hydroxypyridin-4-one), 5,5'-oxybis(N-hexadecyl-2-acetyl-3-hydroxypyridin-4-one), 5,5'-oxybis(N-hexadecyl-2-cyano-3-hydroxypyridin-4-one), 5,5'-oxybis(N-octadecyl-3-hydroxypyridin-4-one), 5,5'-oxybis(N-octadecyl-2-methyl-3-hydroxypyridin-4-one), 5,5'-oxybis(N-octadecyl-2-ethyl-3-hydroxypyridin-4-one), 5,5'-oxybis(N-octadecyl-2-formyl-3-hydroxypyridin-4-one), 5,5'-oxybis(N-octadecyl-2-acetyl-3-hydroxypyridin-4-one), 5,5'-oxybis(N-octadecyl-2-cyano-3-hydroxypyridin-4-one), 5,5'-oxybis(N-octadecenyl-3-hydroxypyridin-4-one), 5,5'-oxybis(N-octadecenyl-2-methyl-3-hydroxypyridin-4-one), 5,5'-oxybis(N-octadecenyl-2-ethyl-3-hydroxypyridin-4-one), 5,5'-oxybis(N-octadecenyl-2-formyl-3-hydroxypyridin-4-one), 5,5'-oxybis(N-octadecenyl-2-acetyl-3-hydroxypyridin-4-one), 5,5'-oxybis(N-octadecenyl-2-cyano-3-hydroxypyridin-4-one), N-hydrogenated tallow-2-phenyl-3-hydroxyquinolin-4-one, N-hydrogenated tallow-2-phenyl-3-methoxyquinolin-4-one, N-hydrogenated tallow-2-phenyl-3-ethoxyquinolin-4-one, N-hydrogenated tallow-2-phenyl-3-t-butylcarbonyloxy-quinolin-4-one, N-hydrogenated tallow-2-phenyl-3-benzyloxy-quinolin-4-one, N-hydrogenated tallow-2-phenyl-3-tetrahydropyranyloxy-quinolin-4-one, N-hydrogenated tallow-2-phenyl-3-(4-hydroxybenzyloxy)-quinolin-4-one, N-hydrogenated tallow-2-phenyl-3-(4-methoxybenzyloxy)-quinolin-4-one, N-hydrogenated tallow-2-phenyl-3-(2-propenyl-1-oxy)-quinolin-4-one, N-hydrogenated tallow-2-phenyl-3-(2-ethylhexyl-1-oxy)-quinolin-4-one, N-(2-ethylhexyl)-2-phenyl-3-hydroxyquinolin-4-one, N-(2-ethylhexyl)-2-phenyl-3-methoxyquinolin-4-one, N-(2-ethylhexyl)-2-phenyl-3-ethoxyquinolin-4-one, N-(2-ethylhexyl)-2-phenyl-3-t-butylcarbonyloxy-quinolin-4-one, N-(2-ethylhexyl)-2-phenyl-3-benzyloxy-quinolin-4-one, N-(2-ethylhexyl)-2-phenyl-3-tetrahydropyranyloxy-quinolin-4-one, N-(2-ethylhexyl)-2-phenyl-3-(4-hydroxybenzyloxy)-quinolin-4-one, N-(2-ethylhexyl)-2-phenyl-3-(4-methoxybenzyloxy)-quinolin-4-one, N-(2-ethylhexyl)-2-phenyl-3-(2-propenyl-1-oxy)-quinolin-4-one, N-(2-ethylhexyl)-2-phenyl-3-(2-ethylhexyl-1-oxy)-quinolin-4-one, N-tetradecyl-2-phenyl-3-hydroxyquinolin-4-one, N-tetradecyl-2-phenyl-3-methoxyquinolin-4-one, N-tetradecyl-2-phenyl-3-ethoxyquinolin-4-one, N-tetradecyl-2-phenyl-3-t-butylcarbonyloxy-quinolin-4-one, N-tetradecyl-2-phenyl-3-benzyloxy-quinolin-4-one, N-tetradecyl-2-phenyl-3-tetrahydropyranyloxy-quinolin-4-one, N-tetradecyl-2-phenyl-3-(4-hydroxybenzyloxy)-quinolin-4-one, N-tetradecyl-2-phenyl-3-(4-methoxybenzyloxy)-quinolin-4-one, N-tetradecyl-2-phenyl-3-(2-propenyl-1-oxy)-quinolin-4-one, N-tetradecyl-2-phenyl-3-(2-ethylhexyl-1-oxy)-quinolin-4-one, N-hexadecyl-2-phenyl-3-hydroxyquinolin-4-one, N-hexadecyl-2-phenyl-3-methoxyquinolin-4-one, N-hexadecyl-2-phenyl-3-ethoxyquinolin-4-one, N-hexadecyl-2-phenyl-3-t-butylcarbonyloxy-quinolin-4-one, N-hexadecyl-2-phenyl-3-benzyloxy-quinolin-4-one, N-hexadecyl-2-phenyl-3-tetrahydropyranyloxy-quinolin-4-one, N-hexadecyl-2-phenyl-3-(4-hydroxybenzyloxy)-quinolin-4-one, N-hexadecyl-2-phenyl-3-(4-methoxybenzyloxy)-quinolin-4-one, N-hexadecyl-2-phenyl-3-(2-propenyl-1-oxy)-quinolin-4-one, N-hexadecyl-2-phenyl-3-(2-ethylhexyl-1-oxy)-quinolin-4-one, N-octadecyl-2-phenyl-3-hydroxyquinolin-4-one, N-octadecyl-2-phenyl-3-methoxyquinolin-4-one, N-octadecyl-2-phenyl-3-ethoxyquinolin-4-one, N-octadecyl-2-phenyl-3-t-butylcarbonyloxy-quinolin-4-one, N-octadecyl-2-phenyl-3-benzyloxy-quinolin-4-one, N-octadecyl-2-phenyl-3-tetrahydropyranyloxy-quinolin-4-one, N-octadecyl-2-phenyl-3-(4-hydroxybenzyloxy)-quinolin-4-one, N-octadecyl-2-phenyl-3-(4-methoxybenzyloxy)-quinolin-4-one, N-octadecyl-2-phenyl-3-(2-propenyl-1-oxy)-quinolin-4-one, N-octadecyl-2-phenyl-3-(2-ethylhexyl-1-oxy)-quinolin-4-one, N-octadecenyl-2-phenyl-3-hydroxyquinolin-4-one, N-octadecenyl-2-phenyl-3-methoxyquinolin-4-one, N-octadecenyl-2-phenyl-3-ethoxyquinolin-4-one, N-octadecenyl-2-phenyl-3-t-butylcarbonyloxy-quinolin-4-one, N-octadecenyl-2-phenyl-3-benzyloxy-quinolin-4-one, N-octadecenyl-2-phenyl-3-tetrahydropyranyloxy-quinolin-4-one, N-octadecenyl-2-phenyl-3-(4-hydroxybenzyloxy)-quinolin-4-one, N-octadecenyl-2-phenyl-3-(4-methoxybenzyloxy)-quinolin-4-one, N-octadecenyl-2-phenyl-3-(2-propenyl-1-oxy)-quinolin-4-one, N-octadecenyl-2-phenyl-3-(2-ethylhexyl-1-oxy)-quinolin-4-one, N-hydrogenated tallow-2-(3,4-dihydroxyphenyl)-3,5,7-trihydroxyquinolin-4-one, N-hydrogenated tallow-2-(3,4-dimethoxyphenyl)-3,5,7-trimethoxyquinolin-4-one, N-hydrogenated tallow-2-(3,4-diethoxyphenyl)-3,5,7-triethoxyquinolin-4-one, N-hydrogenated tallow-2-(3,4-di-t-butylcarbonyloxy-phenyl)-3,5,7-tri-t-butylcarbonyloxy-quinolin-4-one, N-hydrogenated tallow-2-(3,4-dibenzyloxy-phenyl)-3,5,7-tribenzyloxy-quinolin-4-one, N-hydrogenated tallow-2-(3,4-ditetrahydropyranyloxyphenyl)-3,5,7-tritetrahydropyranyloxyquinolin-4-one, N-hydrogenated tallow-2-(3,4-di-(2-propenyl-1-oxy)-phenyl)-3,5,7-tri-(2-propenyl-1-oxy)-quinolin-4-one, N-hydrogenated tallow-2-(3,4-di-(2-ethylhexyl-1-oxy)-phenyl)-3,5,7-tri-(2-ethylhexyl-1-oxy)-quinolin-4-one, N-(2-ethylhexyl)-2-(3,4-dihydroxyphenyl)-3,5,7-trihydroxyquinolin-4-one, N-(2-ethylhexyl)-2-(3,4-dimethoxyphenyl)-3,5,7-trimethoxyquinolin-4-one, N-(2-ethylhexyl)-2-(3,4-diethoxyphenyl)-3,5,7-triethoxyquinolin-4-one, N-(2-ethylhexyl)-2-(3,4-di-t-butylcarbonyloxy-phenyl)-3,5,7-tri-t-butylcarbonyloxy-quinolin-4-one, N-(2-ethylhexyl)-2-(3,4-dibenzyloxy-phenyl)-3,5,7-tribenzyloxy-quinolin-4-one, N-(2-ethylhexyl)-2-(3,4-ditetrahydropyranyloxyphenyl)-3,5,7-tritetrahydropyranyloxyquinolin-4-one, N-(2-ethylhexyl)-2-(3,4-di-(2-propenyl-1-oxy)-phenyl)-3,5,7-tri-(2-propenyl-1-oxy)-quinolin-4-one, N-(2-ethylhexyl)-2-(3,4-di-(2-ethylhexyl-1-oxy)-phenyl)-3,5,7-tri-(2-ethylhexyl-1-oxy)-quinolin-4-one, N-tetradecyl-2-(3,4-dihydroxyphenyl)-3,5,7-trihydroxyquinolin-4-one, N-tetradecyl-2-(3,4-dimethoxyphenyl)-3,5,7-trimethoxyquinolin-4-one, N-tetradecyl-2-(3,4-diethoxyphenyl)-3,5,7-triethoxyquinolin-4-one, N-tetradecyl-2-(3,4-di-t-butylcarbonyloxy-phenyl)-3,5,7-tri-t-butylcarbonyloxy-quinolin-4-one, N-tetradecyl-2-(3,4-dibenzyloxy-phenyl)-3,5,7-tribenzyloxy-quinolin-4-one, N-tetradecyl-2-(3,4-ditetrahydropyranyloxyphenyl)-3,5,7-tritetrahydropyranyloxyquinolin-4-one, N-tetradecyl-2-(3,4-di-(2-propenyl-1-oxy)-phenyl)-3,5,7-tri-(2-propenyl-1-oxy)-quinolin-4-one, N-tetradecyl-2-(3,4-di-(2-ethylhexyl-1-oxy)-phenyl)-3,5,7-tri-(2-ethylhexyl-1-oxy)-quinolin-4-one, N-hexadecyl-2-(3,4-dihydroxyphenyl)-3,5,7-trihydroxyquinolin-4-one, N-hexadecyl-2-(3,4-dimethoxyphenyl)-3,5,7-trimethoxyquinolin-4-one, N-hexadecyl-2-(3,4-diethoxyphenyl)-3,5,7-triethoxyquinolin-4-one, N-hexadecyl-2-(3,4-di-t-butylcarbonyloxy-phenyl)-3,5,7-tri-t-butylcarbonyloxy-quinolin-4-one, N-hexadecyl-2-(3,4-dibenzyloxy-phenyl)-3,5,7-tribenzyloxy-quinolin-4-one, N-hexadecyl-2-(3,4-ditetrahydropyranyloxyphenyl)-3,5,7-tritetrahydropyranyloxyquinolin-4-one, N-hexadecyl-2-(3,4-di-(2-propenyl-1-oxy)-phenyl)-3,5,7-tri-(2-propenyl-1-oxy)-quinolin-4-one, N-hexadecyl-2-(3,4-di-(2-ethylhexyl-1-oxy)-phenyl)-3,5,7-tri-(2-ethylhexyl-1-oxy)-quinolin-4-one, N-octadecyl-2-(3,4-dihydroxyphenyl)-3,5,7-trihydroxyquinolin-4-one, N-octadecyl-2-(3,4-dimethoxyphenyl)-3,5,7-trimethoxyquinolin-4-one, N-octadecyl-2-(3,4-diethoxyphenyl)-3,5,7-triethoxyquinolin-4-one, N-octadecyl-2-(3,4-di-t-butylcarbonyloxy-phenyl)-3,5,7-tri-t-butylcarbonyloxy-quinolin-4-one, N-octadecyl-2-(3,4-dibenzyloxy-phenyl)-3,5,7-tribenzyloxy-quinolin-4-one, N-octadecyl-2-(3,4-ditetrahydropyranyloxyphenyl)-3,5,7-tritetrahydropyranyloxyquinolin-4-one, N-octadecyl-2-(3,4-di-(2-propenyl-1-oxy)-phenyl)-3,5,7-tri-(2-propenyl-1-oxy)-quinolin-4-one, N-octadecyl-2-(3,4-di-(2-ethylhexyl-1-oxy)-phenyl)-3,5,7-tri-(2-ethylhexyl-1-oxy)-quinolin-4-one, N-octadecenyl-2-(3,4-dihydroxyphenyl)-3,5,7-trihydroxyquinolin-4-one, N-octadecenyl-2-(3,4-dimethoxyphenyl)-3,5,7-trimethoxyquinolin-4-one, N-octadecenyl-2-(3,4-diethoxyphenyl)-3,5,7-triethoxyquinolin-4-one, N-octadecenyl-2-(3,4-di-t-butylcarbonyloxy-phenyl)-3,5,7-tri-t-butylcarbonyloxy-quinolin-4-one, N-octadecenyl-2-(3,4-dibenzyloxy-phenyl)-3,5,7-tribenzyloxy-quinolin-4-one, N-octadecenyl-2-(3,4-ditetrahydropyranyloxyphenyl)-3,5,7-tritetrahydropyranyloxyquinolin-4-one, N-octadecenyl-2-(3,4-di-(2-propenyl-1-oxy)-phenyl)-3,5,7-tri-(2-propenyl-1-oxy)-quinolin-4-one, N-octadecenyl-2-(3,4-di-(2-ethylhexyl-1-oxy)-phenyl)-3,5,7-tri-(2-ethylhexyl-1-oxy)-quinolin-4-one, N-hydrogenated tallow-2-(4-hydroxyphenyl)-3,5,7-trihydroxyquinolin-4-one, N-hydrogenated tallow-2-(4-methoxyphenyl)-3,5,7-trimethoxyquinolin-4-one, N-hydrogenated tallow-2-(4-ethoxyphenyl)-3,5,7-triethoxyquinolin-4-one, N-hydrogenated tallow-2-(4-t-butylcarbonyloxy-phenyl)-3,5,7-tri-t-butylcarbonyloxy-quinolin-4-one, N-hydrogenated tallow-2-(4-benzyloxyphenyl)-3,5,7-tribenzyloxyquinolin-4-one, N-hydrogenated tallow-2-(4-tetrahydropyranyloxyphenyl)-3,5,7-tritetrahydropyranyloxyquinolin-4-one, N-hydrogenated tallow-2-(4-(2-propenyl-1-oxy)phenyl)-3,5,7-tri-(2-propenyl-1-oxy)-quinolin-4-one, N-hydrogenated tallow-2-(4-(2-ethylhexyl-1-oxy)-phenyl)-3,5,7-trihydroxyquinolin-4-one, N-(2-ethylhexyl)-2-(4-hydroxyphenyl)-3,5,7-trihydroxyquinolin-4-one, N-(2-ethylhexyl)-2-(4-methoxyphenyl)-3,5,7-trimethoxyquinolin-4-one, N-(2-ethylhexyl)-2-(4-ethoxyphenyl)-3,5,7-triethoxyquinolin-4-one, N-(2-ethylhexyl)-2-(4-t-butylcarbonyloxy-phenyl)-3,5,7-tri-t-butylcarbonyloxy-quinolin-4-one, N-(2-ethylhexyl)-2-(4-benzyloxyphenyl)-3,5,7-tribenzyloxyquinolin-4-one, N-(2-ethylhexyl)-2-(4-tetrahydropyranyloxyphenyl)-3,5,7-tritetrahydropyranyloxyquinolin-4-one, N-(2-ethylhexyl)-2-(4-(2-propenyl-1-oxy)phenyl)-3,5,7-tri-(2-propenyl-1-oxy)-quinolin-4-one, N-(2-ethylhexyl)-2-(4-(2-ethylhexyl-1-oxy)-phenyl)-3,5,7-trihydroxyquinolin-4-one, N-tetradecyl-2-(4-hydroxyphenyl)-3,5,7-trihydroxyquinolin-4-one, N-tetradecyl-2-(4-methoxyphenyl)-3,5,7-trimethoxyquinolin-4-one, N-tetradecyl-2-(4-ethoxyphenyl)-3,5,7-triethoxyquinolin-4-one, N-tetradecyl-2-(4-t-butylcarbonyloxy-phenyl)-3,5,7-tri-t-butylcarbonyloxy-quinolin-4-one, N-tetradecyl-2-(4-benzyloxyphenyl)-3,5,7-tribenzyloxyquinolin-4-one, N-tetradecyl-2-(4-tetrahydropyranyloxyphenyl)-3,5,7-tritetrahydropyranyloxyquinolin-4-one, N-tetradecyl-2-(4-(2-propenyl-1-oxy)phenyl)-3,5,7-tri-(2-propenyl-1-oxy)-quinolin-4-one, N-tetradecyl-2-(4-(2-ethylhexyl-1-oxy)-phenyl)-3,5,7-trihydroxyquinolin-4-one, N-hexadecyl-2-(4-hydroxyphenyl)-3,5,7-trihydroxyquinolin-4-one, N-hexadecyl-2-(4-methoxyphenyl)-3,5,7-trimethoxyquinolin-4-one, N-hexadecyl-2-(4-ethoxyphenyl)-3,5,7-triethoxyquinolin-4-one, N-hexadecyl-2-(4-t-butylcarbonyloxy-phenyl)-3,5,7-tri-t-butylcarbonyloxy-quinolin-4-one, N-hexadecyl-2-(4-benzyloxyphenyl)-3,5,7-tribenzyloxyquinolin-4-one, N-hexadecyl-2-(4-tetrahydropyranyloxyphenyl)-3,5,7-tritetrahydropyranyloxyquinolin-4-one, N-hexadecyl-2-(4-(2-propenyl-1-oxy)phenyl)-3,5,7-tri-(2-propenyl-1-oxy)-quinolin-4-one, N-hexadecyl-2-(4-(2-ethylhexyl-1-oxy)-phenyl)-3,5,7-trihydroxyquinolin-4-one, N-octadecyl-2-(4-hydroxyphenyl)-3,5,7-trihydroxyquinolin-4-one, N-octadecyl-2-(4-methoxyphenyl)-3,5,7-trimethoxyquinolin-4-one, N-octadecyl-2-(4-ethoxyphenyl)-3,5,7-triethoxyquinolin-4-one, N-octadecyl-2-(4-t-butylcarbonyloxy-phenyl)-3,5,7-tri-t-butylcarbonyloxy-quinolin-4-one, N-octadecyl-2-(4-benzyloxyphenyl)-3,5,7-tribenzyloxyquinolin-4-one, N-octadecyl-2-(4-tetrahydropyranyloxyphenyl)-3,5,7-tritetrahydropyranyloxyquinolin-4-one, N-octadecyl-2-(4-(2-propenyl-1-oxy)phenyl)-3,5,7-tri-(2-propenyl-1-oxy)-quinolin-4-one, N-octadecyl-2-(4-(2-ethylhexyl-1-oxy)-phenyl)-3,5,7-trihydroxyquinolin-4-one, N-octadecenyl-2-(4-hydroxyphenyl)-3,5,7-trihydroxyquinolin-4-one, N-octadecenyl-2-(4-methoxyphenyl)-3,5,7-trimethoxyquinolin-4-one, N-octadecenyl-2-(4-ethoxyphenyl)-3,5,7-triethoxyquinolin-4-one, N-octadecenyl-2-(4-t-butylcarbonyloxy-phenyl)-3,5,7-tri-t-butylcarbonyloxy-quinolin-4-one, N-octadecenyl-2-(4-benzyloxyphenyl)-3,5,7-tribenzyloxyquinolin-4-one, N-octadecenyl-2-(4-tetrahydropyranyloxyphenyl)-3,5,7-tritetrahydropyranyloxyquinolin-4-one, N-octadecenyl-2-(4-(2-propenyl-1-oxy)phenyl)-3,5,7-tri-(2-propenyl-1-oxy)-quinolin-4-one, N-octadecenyl-2-(4-(2-ethylhexyl-1-oxy)-phenyl)-3,5,7-trihydroxyquinolin-4-one, N-hydrogenated tallow-2-(3,4,5-trihydroxyphenyl)-3,5,7-trihydroxyquinolin-4-one, N-hydrogenated tallow-2-(3,4,5-trimethoxyphenyl)-3,5,7-trimethoxyquinolin-4-one, N-hydrogenated tallow-2-(3,4,5-triethoxyphenyl)-3,5,7-triethoxyquinolin-4-one, N-hydrogenated tallow-2-(3,4,5-tri-(t-butylcarbonyloxy)-phenyl)-3,5,7-tri-(t-butylcarbonyloxy)-quinolin-4-one, N-hydrogenated tallow-2-(3,4,5-tribenzyloxyphenyl)-3,5,7-tribenzyloxyquinolin-4-one, N-hydrogenated tallow-2-(3,4,5-tritetrahydropyranyloxy-phenyl)-3,5,7-tritetrahydropyranyloxyquinolin-4-one, N-hydrogenated tallow-2-(3,4,5-tri-(2-propenyl-1-oxy)-phenyl)-3,5,7-tri-(2-propenyl-1-oxy)-quinolin-4-one, N-hydrogenated tallow-2-(3,4,5-tri-(2-ethylhexyl-1-oxy)-phenyl)-3,5,7-tri-(2-ethylhexyl-1-oxy)-quinolin-4-one, N-(2-ethylhexyl)-2-(3,4,5-trihydroxyphenyl)-3,5,7-trihydroxyquinolin-4-one, N-(2-ethylhexyl)-2-(3,4,5-trimethoxy-phenyl)-3,5,7-trimethoxyquinolin-4-one, N-(2-ethylhexyl)-2-(3,4,5-triethoxyphenyl)-3,5,7-triethoxyquinolin-4-one, N-(2-ethylhexyl)-2-(3,4,5-tri-(t-butylcarbonyloxy)-phenyl)-3,5,7-tri-(t-butylcarbonyloxy)-quinolin-4-one, N-(2-ethylhexyl)-2-(3,4,5-tribenzyloxyphenyl)-3,5,7-tribenzyloxyquinolin-4-one, N-(2-ethylhexyl)-2-(3,4,5-tritetrahydropyranyloxyphenyl)-3,5,7-tritetrahydropyranyloxyquinolin-4-one, N-(2-ethylhexyl)-2-(3,4,5-tri-(2-propenyl-1-oxy)-phenyl)-3,5,7-tri-(2-propenyl-1-oxy)-quinolin-4-one, N-(2-ethylhexyl)-2-(3,4,5-tri-(2-ethylhexyl-1-oxy)-phenyl)-3,5,7-tri-(2-ethylhexyl-1-oxy)-quinolin-4-one, N-tetradecyl-2-(3,4,5-trihydroxyphenyl)-3,5,7-trihydroxyquinolin-4-one, N-tetradecyl-2-(3,4,5-trimethoxyphenyl)-3,5,7-trimethoxy-quinolin-4-one, N-tetradecyl-2-(3,4,5-triethoxyphenyl)-3,5,7-triethoxyquinolin-4-one, N-tetradecyl-2-(3,4,5-tri-(t-butylcarbonyloxy)-phenyl)-3,5,7-tri-(t-butylcarbonyloxy)-quinolin-4-one, N-tetradecyl-2-(3,4,5-tribenzyloxyphenyl)-3,5,7-tribenzyloxyquinolin-4-one, N-tetradecyl-2-(3,4,5-tritetrahydropyranyloxyphenyl)-3,5,7-tritetrahydro-pyranyloxyquinolin-4-one, N-tetradecyl-2-(3,4,5-tri-(2-propenyl-1-oxy)-phenyl)-3,5,7-tri-(2-propenyl-1-oxy)-quinolin-4-one, N-tetradecyl-2-(3,4,5-tri-(2-ethylhexyl-1-oxy)-phenyl)-3,5,7-tri-(2-ethylhexyl-1-oxy)-quinolin-4-one, N-hexadecyl-2-(3,4,5-trihydroxyphenyl)-3,5,7-trihydroxy-quinolin-4-one, N-hexadecyl-2-(3,4,5-trimethoxyphenyl)-3,5,7-trimethoxyquinolin-4-one, N-hexadecyl-2-(3,4,5-triethoxyphenyl)-3,5,7-triethoxyquinolin-4-one, N-hexadecyl-2-(3,4,5-tri-(t-butylcarbonyloxy)-phenyl)-3,5,7-tri-(t-butylcarbonyloxy)-quinolin-4-one, N-hexadecyl-2-(3,4,5-tribenzyloxyphenyl)-3,5,7-tribenzyloxyquinolin-4-one, N-hexadecyl-2-(3,4,5-tritetrahydropyranyloxyphenyl)-3,5,7-tritetrahydropyranyloxyquinolin-4-one, N-hexadecyl-2-(3,4,5-tri-(2-propenyl-1-oxy)-phenyl)-3,5,7-tri-(2-propenyl-1-oxy)-quinolin-4-one, N-hexadecyl-2-(3,4,5-tri-(2-ethylhexyl-1-oxy)-phenyl)-3,5,7-tri-(2-ethylhexyl-1-oxy)-quinolin-4-one, N-octadecyl-2-(3,4,5-trihydroxyphenyl)-3,5,7-trihydroxyquinolin-4-one, N-octadecyl-2-(3,4,5-trimethoxyphenyl)-3,5,7-trimethoxyquinolin-4-one, N-octadecyl-2-(3,4,5-triethoxyphenyl)-3,5,7-triethoxyquinolin-4-one, N-octadecyl-2-(3,4,5-tri-(t-butylcarbonyloxy)-phenyl)-3,5,7-tri-(t-butylcarbonyloxy)-quinolin-4-one, N-octadecyl-2-(3,4,5-tribenzyloxyphenyl)-3,5,7-tribenzyloxyquinolin-4-one, N-octadecyl-2-(3,4,5-tritetrahydropyranyloxyphenyl)-3,5,7-tritetrahydropyranyloxyquinolin-4-one, N-octadecyl-2-(3,4,5-tri-(2-propenyl-1-oxy)-phenyl)-3,5,7-tri-(2-propenyl-1-oxy)-quinolin-4-one, N-octadecyl-2-(3,4,5-tri-(2-ethylhexyl-1-oxy)-phenyl)-3,5,7-tri-(2-ethylhexyl-1-oxy)-quinolin-4-one, N-octadecenyl-2-(3,4,5-trihydroxyphenyl)-3,5,7-trihydroxyquinolin-4-one, N-octadecenyl-2-(3,4,5-trimethoxyphenyl)-3,5,7-trimethoxyquinolin-4-one, N-octadecenyl-2-(3,4,5-triethoxyphenyl)-3,5,7-triethoxyquinolin-4-one, N-octadecenyl-2-(3,4,5-tri-(t-butylcarbonyloxy)-phenyl)-3,5,7-tri-(t-butylcarbonyloxy)-quinolin-4-one, N-octadecenyl-2-(3,4,5-tribenzyloxyphenyl)-3,5,7-tribenzyloxyquinolin-4-one, N-octadecenyl-2-(3,4,5-tritetrahydropyranyloxyphenyl)-3,5,7-tritetrahydropyranyloxyquinolin-4-one, N-octadecenyl-2-(3,4,5-tri-(2-propenyl-1-oxy)-phenyl)-3,5,7-tri-(2-propenyl-1-oxy)-quinolin-4-one, N-octadecenyl-2-(3,4,5-tri-(2-ethylhexyl-1-oxy)-phenyl)-3,5,7-tri-(2-ethylhexyl-1-oxy)-quinolin-4-one, N-hydrogenated tallow-2-(3,4-dihydroxyphenyl)-3,7-dihydroxyquinolin-4-one, N-hydrogenated tallow-2-(3,4-dimethoxyphenyl)-3,7-dimethoxy-quinolin-4-one, N-hydrogenated tallow-2-(3,4-diethoxyphenyl)-3,7-diethoxyquinolin-4-one, N-hydrogenated tallow-2-(3,4-di-(t-butylcarbonyloxy)-phenyl)-3,7-di-(t-butylcarbonyloxy)-quinolin-4-one, N-hydrogenated tallow-2-(3,4-dibenzyloxyphenyl)-3,7-dibenzyloxyquinolin-4-one, N-hydrogenated tallow-2-(3,4-ditetrahydropyranyloxyphenyl)-3,7-ditetrahydropyranyloxyquinolin-4-one, N-hydrogenated tallow-2-(3,4-di-(2-propenyl-1-oxy)-phenyl)-3,7-di-(2-propenyl-1-oxy)-quinolin-4-one, N-hydrogenated tallow-2-(3,4-di-(2-ethylhexyl-1-oxy)-phenyl)-3,7-di-(2-ethylhexyl-1-oxy)-quinolin-4-one, N-(2-ethylhexyl)-2-(3,4-dihydroxyphenyl)-3,7-dihydroxyquinolin-4-one, N-(2-ethylhexyl)-2-(3,4-dimethoxyphenyl)-3,7-dimethoxyquinolin-4-one, N-(2-ethylhexyl)-2-(3,4-diethoxyphenyl)-3,7-diethoxyquinolin-4-one, N-(2-ethylhexyl)-2-(3,4-di-(t-butylcarbonyloxy)-phenyl)-3,7-di-(t-butylcarbonyloxy)-quinolin-4-one, N-(2-ethylhexyl)-2-(3,4-dibenzyloxyphenyl)-3,7-dibenzyloxyquinolin-4-one, N-(2-ethylhexyl)-2-(3,4-ditetrahydropyranyloxyphenyl)-3,7-ditetrahydropyranyloxyquinolin-4-one, N-(2-ethylhexyl)-2-(3,4-di-(2-propenyl-1-oxy)-phenyl)-3,7-di-(2-propenyl-1-oxy)-quinolin-4-one, N-(2-ethylhexyl)-2-(3,4-di-(2-ethylhexyl-1-oxy)-phenyl)-3,7-di-(2-ethylhexyl-1-oxy)-quinolin-4-one, N-tetradecyl-2-(3,4-dihydroxyphenyl)-3,7-dihydroxyquinolin-4-one, N-tetradecyl-2-(3,4-dimethoxyphenyl)-3,7-dimethoxyquinolin-4-one, N-tetradecyl-2-(3,4-diethoxyphenyl)-3,7-diethoxyquinolin-4-one, N-tetradecyl-2-(3,4-di-(t-butylcarbonyloxy)-phenyl)-3,7-di-(t-butylcarbonyloxy)-quinolin-4-one, N-tetradecyl-2-(3,4-dibenzyloxyphenyl)-3,7-dibenzyloxyquinolin-4-one, N-tetradecyl-2-(3,4-ditetrahydropyranyloxyphenyl)-3,7-ditetrahydropyranyloxyquinolin-4-one, N-tetradecyl-2-(3,4-di-(2-propenyl-1-oxy)-phenyl)-3,7-di-(2-propenyl-1-oxy)-quinolin-4-one, N-tetradecyl-2-(3,4-di-(2-ethylhexyl-1-oxy)-phenyl)-3,7-di-(2-ethylhexyl-1-oxy)-quinolin-4-one, N-hexadecyl-2-(3,4-dihydroxyphenyl)-3,7-dihydroxyquinolin-4-one, N-hexadecyl-2-(3,4-dimethoxyphenyl)-3,7-dimethoxyquinolin-4-one, N-hexadecyl-2-(3,4-diethoxyphenyl)-3,7-diethoxyquinolin-4-one, N-hexadecyl-2-(3,4-di-(t-butylcarbonyloxy)-phenyl)-3,7-di-(t-butylcarbonyloxy)-quinolin-4-one, N-hexadecyl-2-(3,4-dibenzyloxyphenyl)-3,7-dibenzyloxyquinolin-4-one, N-hexadecyl-2-(3,4-ditetrahydropyranyloxyphenyl)-3,7-ditetrahydropyranyloxyquinolin-4-one, N-hexadecyl-2-(3,4-di-(2-propenyl-1-oxy)-phenyl)-3,7-di-(2-propenyl-1-oxy)-quinolin-4-one, N-hexadecyl-2-(3,4-di-(2-ethylhexyl-1-oxy)-phenyl)-3,7-di-(2-ethylhexyl-1-oxy)-quinolin-4-one, N-octadecyl-2-(3,4-dihydroxyphenyl)-3,7-dihydroxyquinolin-4-one, N-octadecyl-2-(3,4-dimethoxyphenyl)-3,7-dimethoxyquinolin-4-one, N-octadecyl-2-(3,4-diethoxyphenyl)-3,7-diethoxyquinolin-4-one, N-octadecyl-2-(3,4-di-(t-butylcarbonyloxy)- phenyl)-3,7-di-(t-butylcarbonyloxy)-quinolin-4-one, N-octadecyl-2-(3,4-dibenzyloxyphenyl)-3,7-dibenzyloxyquinolin-4-one, N-octadecyl-2-(3,4-ditetrahydropyranyloxyphenyl)-3,7-ditetrahydropyranyloxyquinolin-4-one, N-octadecyl-2-(3,4-di-(2-propenyl-1-oxy)-phenyl)-3,7-di-(2-propenyl-1-oxy)-quinolin-4-one, N-octadecyl-2-(3,4-di-(2-ethylhexyl-1-oxy)-phenyl)-3,7-di-(2-ethylhexyl-1-oxy)-quinolin-4-one, N-octadecenyl-2-(3,4-dihydroxyphenyl)-3,7-dihydroxyquinolin-4-one, N-octadecenyl-2-(3,4-dimethoxyphenyl)-3,7-dimethoxyquinolin-4-one, N-octadecenyl-2-(3,4-diethoxyphenyl)-3,7-diethoxyquinolin-4-one, N-octadecenyl-2-(3,4-di-(t-butylcarbonyloxy)-phenyl)-3,7-di-(t-butylcarbonyloxy)-quinolin-4-one, N-octadecenyl-2-(3,4-dibenzyloxyphenyl)-3,7-dibenzyloxyquinolin-4-one, N-octadecenyl-2-(3,4-ditetrahydropyranyloxyphenyl)-3,7-ditetrahydropyranyloxyquinolin-4-one, N-octadecenyl-2-(3,4-di-(2-propenyl-1-oxy)-phenyl)-3,7-di-(2-propenyl-1-oxy)-quinolin-4-one, N-octadecenyl-2-(3,4-di-(2-ethylhexyl-1-oxy)-phenyl)-3,7-di-(2-ethylhexyl-1-oxy)-quinolin-4-one, N-hydrogenated tallow-2-phenyl-3,5,7-trihydroxyquinolin-4-one, N-hydrogenated tallow-2-phenyl-3,5,7-trimethoxyquinolin-4-one, N-hydrogenated tallow-2-phenyl-3,5,7-triethoxyquinolin-4-one, N-hydrogenated tallow-2-phenyl-3,5,7-tri-(t-butylcarbonyloxy)-quinolin-4-one, N-hydrogenated tallow-2-phenyl-3,5,7-tribenzyloxyquinolin-4-one, N-hydrogenated tallow-2-phenyl-3,5,7-tritetrahydropyranyloxyquinolin-4-one, N-hydrogenated tallow-2-phenyl-3,5,7-tri-(2-propenyl-1-oxy)-quinolin-4-one, N-hydrogenated tallow-2-phenyl-3,5,7-tri-(2-ethylhexyl-1-oxy)-quinolin-4-one, N-(2-ethylhexyl)-2-phenyl-3,5,7-trihydroxyquinolin-4-one, N-(2-ethylhexyl)-2-phenyl-3,5,7-trimethoxyquinolin-4-one, N-(2-ethylhexyl)-2-phenyl-3,5,7-triethoxyquinolin-4-one, N-(2-ethylhexyl)-2-phenyl-3,5,7-tri-(t-butylcarbonyloxy)-quinolin-4-one, N-(2-ethylhexyl)-2-phenyl-3,5,7-tribenzyloxyquinolin-4-one, N-(2-ethylhexyl)-2-phenyl-3,5,7-tritetrahydropyranyloxyquinolin-4-one, N-(2-ethylhexyl)-2-phenyl-3,5,7-tri-(2-propenyl-1-oxy)-quinolin-4-one, N-(2-ethylhexyl)-2-phenyl-3,5,7-tri-(2-ethylhexyl-1-oxy)-quinolin-4-one, N-tetradecyl-2-phenyl-3,5,7-trihydroxyquinolin-4-one, N-tetradecyl-2-phenyl-3,5,7-trimethoxyquinolin-4-one, N-tetradecyl-2-phenyl-3,5,7-triethoxyquinolin-4-one, N-tetradecyl-2-phenyl-3,5,7-tri-(t-butylcarbonyloxy)-quinolin-4-one, N-tetradecyl-2-phenyl-3,5,7-tribenzyloxyquinolin-4-one, N-tetradecyl-2-phenyl-3,5,7-tritetrahydropyranyloxyquinolin-4-one, N-tetradecyl-2-phenyl-3,5,7-tri-(2-propenyl-1-oxy)-quinolin-4-one, N-tetradecyl-2-phenyl-3,5,7-tri-(2-ethylhexyl-1-oxy)-quinolin-4-one, N-hexadecyl-2-phenyl-3,5,7-trihydroxyquinolin-4-one, N-hexadecyl-2-phenyl-3,5,7-trimethoxyquinolin-4-one, N-hexadecyl-2-phenyl-3,5,7-triethoxyquinolin-4-one, N-hexadecyl-2-phenyl-3,5,7-tri-(t-butylcarbonyloxy)-quinolin-4-one, N-hexadecyl-2-phenyl-3,5,7-tribenzyloxyquinolin-4-one, N-hexadecyl-2-phenyl-3,5,7-tritetrahydropyranyloxyquinolin-4-one, N-hexadecyl-2-phenyl-3,5,7-tri-(2-propenyl-1-oxy)-quinolin-4-one, N-hexadecyl-2-phenyl-3,5,7-tri-(2-ethylhexyl-1-oxy)-quinolin-4-one, N-octadecyl-2-phenyl-3,5,7-trihydroxyquinolin-4-one, N-octadecyl-2-phenyl-3,5,7-trimethoxyquinolin-4-one, N-octadecyl-2-phenyl-3,5,7-triethoxyquinolin-4-one, N-octadecyl-2-phenyl-3,5,7-tri-(t-butylcarbonyloxy)-quinolin-4-one, N-octadecyl-2-phenyl-3,5,7-tribenzyloxyquinolin-4-one, N-octadecyl-2-phenyl-3,5,7-tritetrahydropyranyloxyquinolin-4-one, N-octadecyl-2-phenyl-3,5,7-tri-(2-propenyl-1-oxy)-quinolin-4-one, N-octadecyl-2-phenyl-3,5,7-tri-(2-ethylhexyl-1-oxy)-quinolin-4-one, N-octadecenyl-2-phenyl-3,5,7-trihydroxyquinolin-4-one, N-octadecenyl-2-phenyl-3,5,7-trimethoxyquinolin-4-one, N-octadecenyl-2-phenyl-3,5,7-triethoxyquinolin-4-one, N-octadecenyl-2-phenyl-3,5,7-tri-(t-butylcarbonyloxy)-quinolin-4-one, N-octadecenyl-2-phenyl-3,5,7-tribenzyloxyquinolin-4-one, N-octadecenyl-2-phenyl-3,5,7-tritetrahydropyranyloxyquinolin-4-one, N-octadecenyl-2-phenyl-3,5,7-tri-(2-propenyl-1-oxy)-quinolin-4-one, N-octadecenyl-2-phenyl-3,5,7-tri-(2-ethylhexyl-1-oxy)-quinolin-4-one, N-hydrogenated tallow-2-(3-methoxy-4-hydroxyphenyl)-3,5,7-trihydroxyquinolin-4-one, N-hydrogenated tallow-2-(3-methoxy-4-ethoxyphenyl)-3,5,7-triethoxyquinolin-4-one, N-hydrogenated tallow-2-(3-methoxy-4-(t-butylcarbonyloxy)-phenyl)-3,5,7-tri-(t-butylcarbonyloxy)-quinolin-4-one, N-hydrogenated tallow-2-(3-methoxy-4-benzyloxyphenyl)-3,5,7-tribenzyloxyquinolin-4-one, N-hydrogenated tallow-2-(3-methoxy-4-tetrahydropyranyloxyphenyl)-3,5,7-tritetrahydropyranyloxyquinolin-4-one, N-hydrogenated tallow-2-(3-methoxy-4-(2-propenyl-1-oxy)-phenyl)-3,5,7-tri-(2-propenyl-1-oxy)-quinolin-4-one, N-hydrogenated tallow-2-(3-methoxy-4-(2-ethylhexyl-1-oxy)-phenyl)-3,5,7-tri-(2-ethylhexyl-1-oxy)-quinolin-4-one, N-(2-ethylhexyl)-2-(3-methoxy-4-hydroxyphenyl)-3,5,7-trihydroxyquinolin-4-one, N-(2-ethylhexyl)-2-(3-methoxy-4-ethoxyphenyl)-3,5,7-triethoxyquinolin-4-one, N-(2-ethylhexyl)-2-(3-methoxy-4-(t-butylcarbonyloxy)-phenyl)-3,5,7-tri-(t-butylcarbonyloxy)-quinolin-4-one, N-(2-ethylhexyl)-2-(3-methoxy-4-benzyloxyphenyl)-3,5,7-tribenzyloxyquinolin-4-one, N-(2-ethylhexyl)-2-(3-methoxy-4-tetrahydropyranyloxyphenyl)-3,5,7-tritetrahydropyranyloxyquinolin-4-one, N-(2-ethylhexyl)-2-(3-methoxy-4-(2-propenyl-1-oxy)-phenyl)-3,5,7-tri-(2-propenyl-1-oxy)-quinolin-4-one, N-(2-ethylhexyl)-2-(3-methoxy-4-(2-ethylhexyl-1-oxy)-phenyl)-3,5,7-tri-(2-ethylhexyl-1-oxy)-quinolin-4-one, N-tetradecyl-2-(3-methoxy-4-hydroxyphenyl)-3,5,7-trihydroxyquinolin-4-one, N-tetradecyl-2-(3-methoxy-4-ethoxyphenyl)-3,5,7-triethoxyquinolin-4-one, N-tetradecyl-2-(3-methoxy-4-(t-butylcarbonyloxy)-phenyl)-3,5,7-tri-(t-butylcarbonyloxy)-quinolin-4-one, N-tetradecyl-2-(3-methoxy-4-benzyloxyphenyl)-3,5,7-tribenzyloxyquinolin-4-one, N-tetradecyl-2-(3-methoxy-4-tetrahydropyranyloxyphenyl)-3,5,7-tritetrahydropyranyloxyquinolin-4-one, N-tetradecyl-2-(3-methoxy-4-(2-propenyl-1-oxy)-phenyl)-3,5,7-tri-(2-propenyl-1-oxy)-quinolin-4-one, N-tetradecyl-2-(3-methoxy-4-(2-ethylhexyl-1-oxy)-phenyl)-3,5,7-tri-(2-ethylhexyl-1-oxy)-quinolin-4-one, N-hexadecyl-2-(3-methoxy-4-hydroxyphenyl)-3,5,7-trihydroxyquinolin-4-one, N-hexadecyl-2-(3-methoxy-4-ethoxyphenyl)-3,5,7-triethoxyquinolin-4-one, N-hexadecyl-2-(3-methoxy-4-(t-butylcarbonyloxy)-phenyl)-3,5,7-tri-(t-butylcarbonyloxy)-quinolin-4-one, N-hexadecyl-2-(3-methoxy-4-benzyloxyphenyl)-3,5,7-tribenzyloxyquinolin-4-one, N-hexadecyl-2-(3-methoxy-4-tetrahydropyranyloxyphenyl)-3,5,7-tritetrahydropyranyloxyquinolin-4-one, N-hexadecyl-2-(3-methoxy-4-(2-propenyl-1-oxy)-phenyl)-3,5,7-tri-(2-propenyl-1-oxy)-quinolin-4-one, N-hexadecyl-2-(3-methoxy-4-(2-ethylhexyl-1-oxy)-phenyl)-3,5,7-tri-(2-ethylhexyl-1-oxy)-quinolin-4-one, N-octadecyl-2-(3-methoxy-4-hydroxyphenyl)-3,5,7-trihydroxyquinolin-4-one, N-octadecyl-2-(3-methoxy-4-ethoxyphenyl)-3,5,7-triethoxyquinolin-4-one, N-octadecyl-2-(3-methoxy-4-(t-butylcarbonyloxy)-phenyl)-3,5,7-tri-(t-butylcarbonyloxy)-quinolin-4-one, N-octadecyl-2-(3-methoxy-4-benzyloxyphenyl)-3,5,7-tribenzyloxyquinolin-4-one, N-octadecyl-2-(3-methoxy-4-tetrahydropyranyloxyphenyl)-3,5,7-tritetrahydropyranyloxyquinolin-4-one, N-octadecyl-2-(3-methoxy-4-(2-propenyl-1-oxy)-phenyl)-3,5,7-tri-(2-propenyl-1-oxy)-quinolin-4-one, N-octadecyl-2-(3-methoxy-4-(2-ethylhexyl-1-oxy)-phenyl)-3,5,7-tri-(2-ethylhexyl-1-oxy)-quinolin-4-one, N-octadecenyl-2-(3-methoxy-4-hydroxyphenyl)-3,5,7-trihydroxyquinolin-4-one, N-octadecenyl-2-(3-methoxy-4-ethoxyphenyl)-3,5,7-triethoxyquinolin-4-one, N-octadecenyl-2-(3-methoxy-4-(t-butylcarbonyloxy)-phenyl)-3,5,7-tri-(t-butylcarbonyloxy)-quinolin-4-one, N-octadecenyl-2-(3-methoxy-4-benzyloxyphenyl)-3,5,7-tribenzyloxyquinolin-4-one, N-octadecenyl-2-(3-methoxy-4-tetrahydropyranyloxyphenyl)-3,5,7-tritetrahydropyranyloxyquinolin-4-one, N-octadecenyl-2-(3-methoxy-4-(2-propenyl-1-oxy)-phenyl)-3,5,7-tri-(2-propenyl-1-oxy)-quinolin-4-one, N-octadecenyl-2-(3-methoxy-4-(2-ethylhexyl-1-oxy)-phenyl)-3,5,7-tri-(2-ethylhexyl-1-oxy)-quinolin-4-one, N-hydrogenated tallow-2-(3-methoxy-4-hydroxyphenyl)-3,7-dimethoxy-5-hydroxyquinolin-4-one, N-(2-ethylhexyl)-2-(3-methoxy-4-hydroxyphenyl)-3,7-dimethoxy-5-hydroxyquinolin-4-one, N-tetradecyl-2-(3-methoxy-4-hydroxyphenyl)-3,7-dimethoxy-5-hydroxyquinolin-4-one, N-hexadecyl-2-(3-methoxy-4-hydroxyphenyl)-3,7-dimethoxy-5-hydroxyquinolin-4-one, N-octadecyl-2-(3-methoxy-4-hydroxyphenyl)-3,7-dimethoxy-5-hydroxyquinolin-4-one, N-octadecenyl-2-(3-methoxy-4-hydroxyphenyl)-3,7-dimethoxy-5-hydroxyquinolin-4-one, N-hydrogenated tallow-2-(3-methoxy-4-hydroxyphenyl)-7-methoxy-3,5-dihydroxyquinolin-4-one, N-hydrogenated tallow-2-(3-methoxy-4-ethoxyphenyl)-7-methoxy-3,5-diethoxyquinolin-4-one, N-hydrogenated tallow-2-(3-methoxy-4-(t-butylcarbonyloxy)-phenyl)-7-methoxy-3,5-di-(t-butylcarbonyloxy)-quinolin-4-one, N-hydrogenated tallow-2-(3-methoxy-4-benzyloxyphenyl)-7-methoxy-3,5-dibenzyloxyquinolin-4-one, N-hydrogenated tallow-2-(3-methoxy-4-tetrahydropyranyloxyphenyl)-7-methoxy-3,5-ditetrahydropyranyloxyquinolin-4-one, N-hydrogenated tallow-2-(3-methoxy-4-(2-propenyl-1-oxy)-phenyl)-7-methoxy-3,5-di-(2-propenyl-1-oxy)-quinolin-4-one, N-hydrogenated tallow-2-(3-methoxy-4-(2-ethylhexyl-1-oxy)-phenyl)-7-methoxy-3,5-di-(2-ethylhexyl-1-oxy)-quinolin-4-one, N-(2-ethylhexyl)-2-(3-methoxy-4-hydroxyphenyl)-7-methoxy-3,5-dihydroxyquinolin-4-one, N-(2-ethylhexyl)-2-(3-methoxy-4-ethoxyphenyl)-7-methoxy-3,5-diethoxyquinolin-4-one, N-(2-ethylhexyl)-2-(3-methoxy-4-(t-butylcarbonyloxy)-phenyl)-7-methoxy-3,5-di-(t-butylcarbonyloxy)-quinolin-4-one, N-(2-ethylhexyl)-2-(3-methoxy-4-benzyloxyphenyl)-7-methoxy-3,5-dibenzyloxyquinolin-4-one, N-(2-ethylhexyl)-2-(3-methoxy-4-tetrahydropyranyloxyphenyl)-7-methoxy-3,5-ditetrahydropyranyloxyquinolin-4-one, N-(2-ethylhexyl)-2-(3-methoxy-4-(2-propenyl-1-oxy)-phenyl)-7-methoxy-3,5-di-(2-propenyl-1-oxy)-quinolin-4-one, N-(2-ethylhexyl)-2-(3-methoxy-4-(2-ethylhexyl-1-oxy)-phenyl)-7-methoxy-3,5-di-(2-ethylhexyl-1-oxy)-quinolin-4-one, N-tetradecyl-2-(3-methoxy-4-hydroxyphenyl)-7-methoxy-3,5-dihydroxyquinolin-4-one, N-tetradecyl-2-(3-methoxy-4-ethoxyphenyl)-7-methoxy-3,5-diethoxyquinolin-4-one, N-tetradecyl-2-(3-methoxy-4-(t-butylcarbonyloxy)-phenyl)-7-methoxy-3,5-di-(t-butylcarbonyloxy)-quinolin-4-one, N-tetradecyl-2-(3-methoxy-4-benzyloxyphenyl)-7-methoxy-3,5-dibenzyloxyquinolin-4-one, N-tetradecyl-2-(3-methoxy-4-tetrahydropyranyloxyphenyl)-7-methoxy-3,5-ditetrahydropyranyloxyquinolin-4-one, N-tetradecyl-2-(3-methoxy-4-(2-propenyl-1-oxy)-phenyl)-7-methoxy-3,5-di-(2-propenyl-1-oxy)-quinolin-4-one, N-tetradecyl-2-(3-methoxy-4-(2-ethylhexyl-1-oxy)-phenyl)-7-methoxy-3,5-di-(2-ethylhexyl-1-oxy)-quinolin-4-one, N-hexadecyl-2-(3-methoxy-4-hydroxyphenyl)-7-methoxy-3,5-dihydroxyquinolin-4-one, N-hexadecyl-2-(3-methoxy-4-ethoxyphenyl)-7-methoxy-3,5-diethoxyquinolin-4-one, N-hexadecyl-2-(3-methoxy-4-(t-butylcarbonyloxy)-phenyl)-7-methoxy-3,5-di-(t-butylcarbonyloxy)-quinolin-4-one, N-hexadecyl-2-(3-methoxy-4-benzyloxyphenyl)-7-methoxy-3,5-dibenzyloxyquinolin-4-one, N-hexadecyl-2-(3-methoxy-4-tetrahydropyranyloxyphenyl)-7-methoxy-3,5-ditetrahydropyranyloxyquinolin-4-one, N-hexadecyl-2-(3-methoxy-4-(2-propenyl-1-oxy)-phenyl)-7-methoxy-3,5-di-(2-propenyl-1-oxy)-quinolin-4-one, N-hexadecyl-2-(3-methoxy-4-(2-ethylhexyl-1-oxy)-phenyl)-7-methoxy-3,5-di-(2-ethylhexyl-1-oxy)-quinolin-4-one, N-octadecyl-2-(3-methoxy-4-hydroxyphenyl)-7-methoxy-3,5-dihydroxyquinolin-4-one, N-octadecyl-2-(3-methoxy-4-ethoxyphenyl)-7-methoxy-3,5-diethoxyquinolin-4-one, N-octadecyl-2-(3-methoxy-4-(t-butylcarbonyloxy)-phenyl)-7-methoxy-3,5-di-(t-butylcarbonyloxy)-quinolin-4-one, N-octadecyl-2-(3-methoxy-4-benzyloxyphenyl)-7-methoxy-3,5-dibenzyloxyquinolin-4-one, N-octadecyl-2-(3-methoxy-4-tetrahydropyranyloxyphenyl)-7-methoxy-3,5-ditetrahydropyranyloxyquinolin-4-one, N-octadecyl-2-(3-methoxy-4-(2-propenyl-1-oxy)-phenyl)-7-methoxy-3,5-di-(2-propenyl-1-oxy)-quinolin-4-one, N-octadecyl-2-(3-methoxy-4-(2-ethylhexyl-1-oxy)-phenyl)-7-methoxy-3,5-di-(2-ethylhexyl-1-oxy)-quinolin-4-one, N-octadecenyl-2-(3-methoxy-4-hydroxyphenyl)-7-methoxy-3,5-dihydroxyquinolin-4-one, N-octadecenyl-2-(3-methoxy-4-ethoxyphenyl)-7-methoxy-3,5-diethoxyquinolin-4-one, N-octadecenyl-2-(3-methoxy-4-(t-butylcarbonyloxy)-phenyl)-7-methoxy-3,5-di-(t-butylcarbonyloxy)-quinolin-4-one, N-octadecenyl-2-(3-methoxy-4-benzyloxyphenyl)-7-methoxy-3,5-dibenzyloxyquinolin-4-one, N-octadecenyl-2-(3-methoxy-4-tetrahydropyranyloxyphenyl)-7-methoxy-3,5-ditetrahydropyranyloxyquinolin-4-one, N-octadecenyl-2-(3-methoxy-4-(2-propenyl-1-oxy)-phenyl)-7-methoxy-3,5-di-(2-propenyl-1-oxy)-quinolin-4-one, N-octadecenyl-2-(3-methoxy-4-(2-ethylhexyl-1-oxy)-phenyl)-7-methoxy-3,5-di-(2-ethylhexyl-1-oxy)-quinolin-4-one, N-hydrogenated tallow-8-phenyl-7-methoxy-furo[3,2-h]quinolin-6-one, N,N-di-hydrogenated tallow-8-phenyl-7-methoxy-pyrrolo[3,2-h]quinolin-6-one, N-(2-ethylhexyl)-8-phenyl-7-methoxy-furo[3,2-h]quinolin-6-one, N,N-di-(2-ethylhexyl)-8-phenyl-7-methoxy-pyrrolo[3,2-h]quinolin-6-one, N-tetradecyl-8-phenyl-7-methoxy-furo[3,2-h]quinolin-6-one, N,N-di-tetradecyl-8-phenyl-7-methoxy-pyrrolo[3,2-h]quinolin-6-one, N-hexadecyl-8-phenyl-7-methoxy-furo[3,2-h]quinolin-6-one, N,N-di-hexadecyl-8-phenyl-7-methoxy-pyrrolo[3,2-h]quinolin-6-one, N-octadecyl-8-phenyl-7-methoxy-furo[3,2-h]quinolin-6-one, N,N-di-octadecyl-8-phenyl-7-methoxy-pyrrolo[3,2-h]quinolin-6-one, N-octadecenyl-8-phenyl-7-methoxy-furo[3,2-h]quinolin-6-one, N,N-di-octadecenyl-8-phenyl-7-methoxy-pyrrolo[3,2-h]quinolin-6-one, N-hydrogenated tallow-9-phenyl-8-methoxy-2,2-dimethyl-pyrano[3,2-h]quinolin-6-one, N,N-di-hydrogenated tallow-2-phenyl-3-methoxy-9,9-dimethyl-1,10-phenanthrolin-4-one, N-(2-ethylhexyl)-9-phenyl-8-methoxy-2,2-dimethyl-pyrano[3,2-h]quinolin-6-one, N,N-di-(2-ethylhexyl)-2-phenyl-3-methoxy-9,9-dimethyl-1,10-phenanthrolin-4-one, N-tetradecyl-9-phenyl-8-methoxy-2,2-dimethyl-pyrano[3,2-h]quinolin-6-one, N,N-di-tetradecyl-2-phenyl-3-methoxy-9,9-dimethyl-1,10-phenanthrolin-4-one, N-hexadecyl-9-phenyl-8-methoxy-2,2-dimethyl-pyrano[3,2-h]quinolin-6-one, N,N-di-hexadecyl-2-phenyl-3-methoxy-9,9-dimethyl-1,10-phenanthrolin-4-one, N-octadecyl-9-phenyl-8-methoxy-2,2-dimethyl-pyrano[3,2-h]quinolin-6-one, N,N-di-octadecyl-2-phenyl-3-methoxy-9,9-dimethyl-1,10-phenanthrolin-4-one, N-octadecenyl-9-phenyl-8-methoxy-2,2-dimethyl-pyrano

[3,2-h]quinolin-6-one, N,N-di-octadecenyl-2-phenyl-3-methoxy-9,9-dimethyl-1,10-phenanthrolin-4-one, or a combination thereof.

Additionally or alternatively, the 3,4-oxypyridinone according to the present disclosure may comprise, consist essentially of, or be an oligomeric and/or polymeric moiety containing repeat units, at least one of which repeat units is attached to the ring nitrogen, optionally with a spacer. With the ring nitrogen being a secondary nitrogen and somewhat constrained sterically, appending a relatively reactive spacer to the nitrogen can enable facile attachment to the oligomer/polymer, which can make a spacer preferred in some embodiments.

In some embodiments, particularly those in which the 3,4-oxypyridinone can be synthesized from a cyclic analog having an oxygen in the ring nitrogen position, the oligomeric and/or polymeric moieties may be polymerized from monomers that may include a functional group for attachment directly to the 3,4-oxypyridinone (e.g., via a pendant primary amine, for reaction/displacement of the ring oxygen), may include a functional group for attachment to the 3,4-oxypyridinone indirectly via a spacer (e.g., if the spacer is a diamine, then the functional group may be a pendant anhydride, a pendant carboxylic acid, a pendant carboxylate ion, a pendant carboxylate (hydrocarbyl) ester, and/or some other pendant moiety capable of forming a linear or cyclic amide/imide therewith, either before or after the reaction/displacement of the ring oxygen by the diamine spacer), may be polymerized from monomers that may include a polymerizable functional group attached to the 3,4-oxypyridinone directly with or without an intervening spacer (e.g., if the polymerizable functional group is a vinyl or vinylidene moiety, the ring nitrogen may connect directly to that moiety or may connect indirectly to that moiety via an optionally heteroatom-containing spacer between the ring nitrogen and the moiety, which vinyl or vinylidene moiety may thereafter be polymerized/oligomerized, such as via an addition reaction optionally with one or more olefinic comonomers), may be post-oligomerization/post-polymerization reacted to include a functional group for attachment directly to the 3,4-oxypyridinone (e.g., via a pendant primary amine, for reaction/displacement of the ring oxygen), may be post-oligomerization/post-polymerization reacted to include a functional group for attachment to the 3,4-oxypyridinone indirectly via a spacer (e.g., if the spacer is a diamine, then the functional group may be an anhydride such as a pendant succinic anhydride, a pendant carboxylic acid, a pendant carboxylate ion, a pendant carboxylate (hydrocarbyl) ester, and/or some other pendant moiety capable of forming a linear or cyclic amide/imide therewith, either before or after the reaction/displacement of the ring oxygen by the diamine spacer), may be functionalized at oligomerization/polymerization termination to exhibit a functional group for attachment directly to the 3,4-oxypyridinone (e.g., via a pendant primary amine, for reaction/displacement of the ring oxygen), and/or may be functionalized at oligomerization/polymerization termination to exhibit a functional group for attachment to the 3,4-oxypyridinone indirectly via a spacer (e.g., if the spacer is a diamine, then the functional group may be an anhydride such as a pendant succinic anhydride, a pendant carboxylic acid, a pendant carboxylate ion, a pendant carboxylate (hydrocarbyl) ester, and/or some other pendant moiety capable of forming a linear or cyclic amide/imide therewith, either before or after the reaction/displacement of the ring oxygen by the diamine spacer). Although, in some embodiments, there can be approximately one oligomeric and/or polymeric moiety attached to one 3,4-oxypyridinone, it is contemplated that approximately one oligomeric and/or polymeric moiety may include two attachment points to two separate 3,4-oxypyridinones (or, in some embodiments less preferably, to three or more separate 3,4-oxypyridinones) —some such circumstances may arise from relatively low percentage (e.g., 10% or less, or 5% or less, on a molar basis) "side reaction" deviations from otherwise stoichiometric reactions, although it is contemplated that deliberate functionalization other than mono- and/or di-functional might be seen as desirable in some embodiments.

Further additionally or alternatively, the 3,4-oxypyridinone according to the present disclosure may comprise, consist essentially of, or be an oligomeric and/or polymeric moiety containing repeat units, at least one of which repeat units is attached to the heteroatom (oxygen or sulfur) attached to the 3-position of the ring (the 3-alpha heteroatom), optionally with a spacer. With the proximity of the heteroatoms attached to the 3- and 4-positions of the ring causing bonding to the 3-alpha heteroatom to be somewhat constrained sterically, appending a relatively reactive spacer to the 3-alpha heteroatom can enable facile attachment to the oligomer/polymer, which can make a spacer preferred in some embodiments.

In some embodiments, the oligomeric and/or polymeric moieties may be polymerized from monomers that may include a polymerizable functional group attached to the 3,4-oxypyridinone directly with or without an intervening spacer (e.g., if the polymerizable functional group is a vinyl or vinylidene moiety, the 3-alpha heteroatom may connect directly to that moiety or may connect indirectly to that moiety via an optionally heteroatom-containing spacer between the 3-alpha heteroatom and the moiety, which vinyl or vinylidene moiety may thereafter be polymerized/oligomerized, such as via an addition reaction optionally with one or more olefinic comonomers), that may include a functional group for attachment to the 3,4-oxypyridinone indirectly via a spacer (e.g., if the spacer is an etheramine, then the functional group may be a pendant anhydride, a pendant carboxylic acid, a pendant carboxylate ion, a pendant carboxylate (hydrocarbyl) ester, and/or some other pendant moiety capable of forming a linear or cyclic amide/imide therewith), may be post-oligomerization/post-polymerization reacted to include a functional group for attachment directly to the 3,4-oxypyridinone (e.g., via a pendant carboxylic acid, carboxylate (hydrocarbyl) ester, carboxylate ion, and/or some other moiety, such as that pendant from a polymerized/oligomerized (meth)acrylate/(meth)acrylic acid, capable of reacting with a hydroxyl/mercaptyl group including the 3-alpha heteroatom), may be post-oligomerization/post-polymerization reacted to include a functional group for attachment to the 3,4-oxypyridinone indirectly via a spacer (e.g., if the spacer is an etheramine, then the functional group may be a pendant anhydride, a pendant carboxylic acid, a pendant carboxylate ion, a pendant carboxylate ester, and/or some other pendant moiety capable of forming a linear or cyclic amide/imide therewith), may be functionalized at oligomerization/polymerization termination to exhibit a functional group for attachment directly to the 3,4-oxypyridinone (e.g., via a pendant primary amine, for reaction/displacement of the ring oxygen), and/or may be functionalized at oligomerization/polymerization termination to exhibit a functional group for attachment to the 3,4-oxypyridinone indirectly via a spacer (e.g., if the spacer is an etheramine, then the functional group may be an anhydride such as a pendant succinic anhydride, a pendant carboxylic acid, a pendant carboxylate ion, a pendant carboxylate (hydrocarbyl) ester, and/or some other pendant moiety capable of forming a linear or cyclic amide/imide therewith). Although, in some embodiments, there can be approximately one oligomeric and/or polymeric moiety attached to one 3,4-oxypyridinone, it is contemplated that approximately one oligomeric and/or polymeric moiety may include two attachment points to two separate 3,4-oxypyridinones (or, in some embodiments less preferably, to three or more separate 3,4-oxypyridinones) —some such circumstances may arise from relatively low percentage (e.g., 10% or less, or 5% or less, on a molar basis) "side reaction" deviations from otherwise stoichiometric reactions, although it is contemplated that deliberate functionalization other than mono- and/or di-functional might be seen as desirable in some embodiments.

In embodiments where the 3,4-oxypyrid(in)one ring is attached to an oligomeric and/or polymeric moiety (e.g., via $R_1$ and/or $R_3$, optionally via a spacer), because functionality is believed to center upon the >C=A and/or >C-A-$R_1$ moieties at the 4- and 3-positions on the ring, respectively (perhaps in tandem with the aromatic nitrogen-containing ring), any reference to masses and/or molar quantities of "the 3,4-oxypyridinones of structure (I)" or "the 3,4-oxypyridinone groups of structure (I)" (or anything similar) should be understood by an ordinary skilled artisan to refer only to the nitrogen-containing ring (including the groups pendant to that ring, even if ionically bonded) and its optional spacer, as effectively pendant to the oligomer/polymer, but not to the backbone or other pendant moieties of the oligomeric and/or polymeric moiety itself. For example, in the case of 2-ethyl-3-benzyloxypyridin-4-one with a hexamethylene diamine spacer (resulting in the group connected to the ring nitrogen being an aminohexyl moiety, when reacted) connected to a polyisobutylene backbone of ~2,300 g/mol number average molecular weight and having at least one pendant succinic anhydride (such as formed by post-polymerization reaction with maleic anhydride), the molecular mass of the 3,4-oxypyridinone "portion"/ligand/group would be ~326.2 g/mol, which ignores includes all but the two hydrogens of the amine spacer that are consumed during the reaction (condensed with the anhydride oxygen) that creates an oligomeric/polymeric succinimide. Indeed, it is contemplated herein that one oligomeric and/or polymeric moiety may have 2 or more pendant 3,4-oxypyridinone ligands, each of which must be considered separately/independently, particularly when molar amounts, equivalents, balances, and/or ratios are involved.

The oligomeric and/or polymeric moiety attached to the 3,4-oxypyridinone may simply provide additional oil solubility/dispersibility or it may additionally impart one or more other functions, such as viscosity modification (viscosity index improvement), pour point depression, antifoaming capability, demulsification, dispersancy, detergency, frictional improvement, antiwear capability, stability to degradation/deactivation, and the like. Non-limiting examples of the oligomeric and/or polymeric moiety may include olefin (co)polymers, at least partially (e.g., substantially) hydrogenated conjugated diene (co)polymers, pendant ester addition (co)polymers, pendant anhydride addition (co)polymers, pendant acrylamide addition (co) polymers, dihydrocarbyl-siloxane (co)polymers, styrenic (co)polymers, $C_2$-$C_6$ alkylene oxide (co)polymers, 2-hydrocarbyl-2-oxazoline (co)polymers, or the like, or combinations thereof.

Examples of olefin (co)polymers may include, but are not necessarily limited to, polyisobutylene, metallocene-catalyzed poly(alpha-olefin)s (mPAOs, such as those having repeat units made from monomers consisting essentially of 1-octene, 1-decene, and 1-dodecene), ethylene-propylene (EP) copolymers, copolymers of ethylene and a $C_4$-$C_{20}$ olefin (e.g., an alpha-olefin) such as ethylene-butene (EB) copolymers, ethylene-hexene copolymers, ethylene-octene copolymers, or ethylene-decene copolymers, and the like, as well as combinations and random/alternating/block/comb/gradient and/or atactic/isotactic/syndiotactic copolymers thereof.

Examples of at least partially hydrogenated conjugated diene copolymers may include, but are not necessarily limited to, (at least partially) hydrogenated polyisoprene (co)polymers, (at least partially) hydrogenated polybutadiene (co)polymers, and the like, as well as combinations and random/alternating/block/comb/gradient and/or atactic/isotactic/syndiotactic copolymers thereof.

Examples of pendant ester addition (co)polymers may include, but are not necessarily limited to, hydrocarbyl ($C_1$-$C_2$ alk)acrylate (co)polymers such as hydrocarbyl (meth)acrylate (co)polymers including one or more monomers such as methyl (meth)acrylate, ethyl (meth)acrylate, butyl (meth)acrylate, hexyl (meth)acrylate, 2-ethylhexyl (meth)acrylate, decyl (meth)acrylate, lauryl (meth)acrylate, myristyl (meth)acrylate, palmityl (meth)acrylate, stearyl (meth)acrylate, eicosyl (meth)acrylate, docosyl (meth)acrylate, oleyl (meth)acrylate linoleyl (meth)acrylate, linolenyl (meth)acrylate, benzyl (meth)acrylate, phenyl (meth)acrylate, and naphthyl (meth)acrylate, alkylene oxide (meth) acrylate copolymers such as ethylene oxide and/or propylene oxide (meth)acrylate copolymers having pendant hydroxyl and/or pendant hydrocarbyl ether/ester moieties, dihydrocarbyl maleate (co)polymers, dihydrocarbyl itaconate (co)polymers, dihydrocarbyl muconate (co)polymers, $C_{12}$-$C_{30}$ dihydrocarbyl fumarate (co)polymers, vinyl alcohol (co)polymers post-reacted with $C_2$-$C_{25}$ monocarboxylic acids to form vinyl acylate (co)polymers, vinyl formate (i.e., $C_1$ vinyl acylate) (co)polymers, vinyl acetate (co)polymers, vinyl propionate (co)polymers, vinyl butyrate (co)polymers, vinyl valerate (co)polymers, vinyl benzoate (co)polymers, (co)polymers made using the monomer of formula (1) in U.S. Pat. No. 9,683,195 (the relevant disclosure of which is incorporated herein by reference) in which $X^1$ is not —NH— (inter alia), (co)polymers made using the monomer of formula (2) in U.S. Pat. No. 9,683,195 in which $X^2$ is not —NH— (inter alia), (co)polymers made using the monomer of formula (3) in U.S. Pat. No. 9,683,195 in which $X^3$ is not —NH— (inter alia), and the like, as well as combinations and random/alternating/block/comb/gradient and/or atactic/isotactic/syndiotactic copolymers thereof.

Examples of pendant anhydride addition (co)polymers may include, but are not limited to, maleic anhydride (co)polymers and the like.

Examples of pendant acrylamide addition (co)polymers may include, but are not limited to vinylpyrrolidone (co) polymers, hydrocarbyl (meth)acrylamide (co)polymers, aminohydrocarbyl (meth)acrylamide (co)polymers, N,N-dihydrocarbylaminohydrocarbyl (meth)acrylamide (co)polymers, (co)polymers made using the monomer of formula (1) in U.S. Pat. No. 9,683,195 in which $X^1$ is —NH— (inter alia), (co)polymers made using the monomer of formula (2) in U.S. Pat. No. 9,683,195 in which $X^2$ is —NH— (inter alia), (co)polymers made using the monomer of formula (3) in U.S. Pat. No. 9,683,195 in which $X^3$ is —NH— (inter alia), and the like, as well as combinations and random/alternating/block/comb/gradient and/or atactic/isotactic/syndiotactic copolymers thereof.

Examples of dihydrocarbyl-siloxane (co)polymers may include, but are not necessarily limited to, dialkylsiloxane (co)polymers such as polydimethylsiloxane or silicone (co) polymers, diarylsiloxane (co)polymers, diaralkylsiloxane (co)polymers, dialkarylsiloxane (co)polymers, monoalkyl-monoaryl siloxane (co)polymers, and the like, as well as combinations and random/alternating/block/comb/gradient and/or atactic/isotactic/syndiotactic copolymers thereof.

Examples of styrenic (co)polymers may include, but are not necessarily limited to, styrene (co)polymers, vinylpyridine (co)polymers, vinylnaphthalene (co)polymers, vinylcarbazole (co)polymers, vinylpyrimidine (co)polymers, vinylphenol (co)polymers, alkylstyrene (co)polymers such as alpha-methyl styrene (co)polymers, alkyl vinylpyridine (co)polymers such as methyl vinylpyridine (co)polymers, styrene sulfonate (co)polymers, and the like, as well as combinations and random/alternating/block/comb/gradient and/or atactic/isotactic/syndiotactic copolymers thereof.

Examples of $C_2$-$C_6$ alkylene oxide (co)polymers may include, but are not necessarily limited to, ethylene oxide (EO) (co)polymers, propylene oxide (PO) (co)polymers, butylene oxide (BO) (co)polymers, hexylene oxide (co) polymers, EO-PO diblock copolymers, EO-PO-EO triblock copolymers, PO-EO-PO triblock copolymers, and the like, as well as combinations and random/alternating/block/comb/gradient and/or atactic/isotactic/syndiotactic copolymers thereof.

Non-limiting examples of the oligomeric and/or polymeric moieties may include polyisobutylene, (at least partially) hydrogenated polyisoprene, (at least partially) hydrogenated polybutadienes, metallocene-catalyzed poly(alpha-olefin)s (mPAOs), olefin copolymers (OCPs) such as ethylene-propylene (EP) copolymers, polyalkyl (meth)acrylate homopolymers and/or copolymers (PAMAs/PAAs), poly(meth)acrylamides, alpha olefin-maleic anhydride copolymers, polyarenes such as polystyrene, polyacrylonitrile, poly($C_1$-$C_6$ alkylene oxide)s, and mixtures, reaction products, and (di-/multi-)block, random, comb, gradient, multi-armed star, alternating, and/or statistical copolymers thereof.

With or without the optional spacer(s) and/or the (pendant) 3,4-hydroxypyridinone moiety(ies), the oligomeric and/or polymeric moieties can have a number average molecular weight from 400 D to 300 kD, e.g., from 400 D to 250 kD, from 400 D to 200 kD, from 400 D to 150 kD, from 400 D to 100 kD, from 400 D to 80 kD, from 400 D to 60 kD, from 400 D to 40 kD, from 400 D to 30 kD, from 400 D to 20 kD, from 400 D to 10 kD, from 400 D to 8000 D, from 400 D to 6000 D, from 400 D to 5000 D, from 400 D to 4000 D, from 400 D to 3000 D, from 400 D to 2500 D, from 400 D to 2000 D, from 400 D to 1500 D, from 400 D to 1000 D, from 700 D to 300 kD, from 700 D to 250 kD, from 700 D to 200 kD, from 700 D to 150 kD, from 700 D to 100 kD, from 700 D to 80 kD, from 700 D to 60 kD, from 700 D to 40 kD, from 700 D to 30 kD, from 700 D to 20 kD, from 700 D to 10 kD, from 700 D to 8000 D, from 700 D to 6000 D, from 700 D to 5000 D, from 700 D to 4000 D, from 700 D to 3000 D, from 700 D to 2500 D, from 700 D to 2000 D, from 700 D to 1500 D, from 700 D to 1000 D, from 800 D to 300 kD, from 800 D to 250 kD, from 800 D to 200 kD, from 800 D to 150 kD, from 800 D to 100 kD, from 800 D to 80 kD, from 800 D to 60 kD, from 800 D to 40 kD, from 800 D to 30 kD, from 800 D to 20 kD, from 800 D to 10 kD, from 800 D to 8000 D, from 800 D to 6000 D, from 800 D to 5000 D, from 800 D to 4000 D, from 800 D to 3000 D, from 800 D to 2500 D, from 800 D to 2000 D, from 800 D to 1500 D, from 800 D to 1000 D, from 900 D to 300 kD, from 900 D to 250 kD, from 900 D to 200 kD, from 900 D to 150 kD, from 900 D to 100 kD, from 900 D to 80 kD, from 900 D to 60 kD, from 900 D to 40 kD, from 900 D to 30 kD, from 900 D to 20 kD, from 900 D to 10 kD, from 900 D to 8000 D, from 900 D to 6000 D, from 900 D to 5000 D, from 900 D to 4000 D, from 900 D to 3000 D, from 900 D to 2500 D, from 900 D to 2000 D, from 900 D to 1500 D, from 1200 D to 300 kD, from 1200 D to 250 kD, from 1200 D to 200 kD, from 1200 D to 150 kD, from 1200 D to 100 kD, from 1200 D to 80 kD, from 1200 D to 60 kD, from 1200 D to 40 kD, from 1200 D to 30 kD, from 1200 D to 20 kD, from 1200 D to 10 kD, from 1200 D to 8000 D, from 1200 D to 6000 D, from 1200 D to 5000 D, from 1200 D to 4000 D, from 1200 D to 3000 D, from 1200 D to 2500 D, from 1200 D to 2000 D, from 1200 D to 1500 D, from 1500 D to 300 kD, from 1500 D to 250 kD, from 1500 D to 200 kD, from 1500 D to 150 kD, from 1500 D to 100 kD, from 1500 D to 80 kD, from 1500 D to 60 kD, from 1500 D to 40 kD, from 1500 D to 30 kD, from 1500 D to 20 kD, from 1500 D to 10 kD, from 1500 D to 8000 D, from 1500 D to 6000 D, from 1500 D to 5000 D, from 1500 D to 4000 D, from 1500 D to 3000 D, from 1500 D to 2500 D, from 1500 D to 2000 D, from 1800 D to 300 kD, from 1800 D to 250 kD, from 1800 D to 200 kD, from 1800 D to 150 kD, from 1800 D to 100 kD, from 1800 D to 80 kD, from 1800 D to 60 kD, from 1800 D to 40 kD, from 1800 D to 30 kD, from 1800 D to 20 kD, from 1800 D to 10 kD, from 600 D to 8000 D, from 600 D to 6000 D, from 1800 D to 5000 D, from 1800 D to 4000 D, from 1800 D to 3000 D, from 1800 D to 2500 D, from 2100 D to 300 kD, from 2100 D to 250 kD, from 2100 D to 200 kD, from 2100 D to 150 kD, from 2100 D to 100 kD, from 2100 D to 80 kD, from 2100 D to 60 kD, from 2100 D to 40 kD, from 2100 D to 30 kD, from 2100 D to 20 kD, from 2100 D to 10 kD, from 2100 D to 8000 D, from 2100 D to 6000 D, from 2100 D to 5000 D, from 2100 D to 4000 D, from 2100 D to 3000 D, from 2500 D to 300 kD, from 2500 D to 250 kD, from 2100 D to 200 kD, from 2500 D to 150 kD, from 2500 D to 100 kD, from 2500 D to 80 kD, from 2500 D to 60 kD, from 2500 D to 40 kD, from 2500 D to 30 kD, from 2500 D to 20 kD, from 2500 D to 10 kD, from 2500 D to 8000 D, from 2500 D to 6000 D, from 2500 D to 5000 D, from 2500 D to 4000 D, from 2500 D to 3000 D, from 5000 D to 300 kD, from 5000 D to 250 kD, from 5000 D to 200 kD, from 5000 D to 150 kD, from 5000 D to 100 kD, from 5000 D to 80 kD, from 5000 D to 60 kD, from 5000 D to 40 kD, from 5000 D to 30 kD, from 5000 D to 20 kD, from 5000 D to 10 kD, from 5000 D to 8000 D, from 7500 D to 300 kD, from 7500 D to 250 kD, from 7500 D to 200 kD, from 7500 D to 150 kD, from 7500 D to 100 kD, from 7500 D to 80 kD, from 7500 D to 60 kD, from 7500 D to 40 kD, from 7500 D to 30 kD, from 7500 D to 20 kD, from 7500 D to 10 kD, from 10 kD to 300 kD, from 10 kD to 250 kD, from 10 kD to 200 kD, from 10 kD to 150 kD, from 10 kD to 100 kD, from 10 kD to 80 kD, from 10 kD to 60 kD, from 10 kD to 40 kD, from 10 kD to 30 kD, from 10 kD to 20 kD, from 20 kD to 300 kD, from 20 kD to 250 kD, from 20 kD to 200 kD, from 20 kD to 150 kD, from 20 kD to 100 kD, from 20 kD to 80 kD, from 20 kD to 60 kD, from 20 kD to 40 kD, from 20 kD to 30 kD, from 30 kD to 300 kD, from 30 kD to 250 kD, from 30 kD to 200 kD, from 30 kD to 150 kD, from 30 kD to 100 kD, from 30 kD to 80 kD, from 30 kD to 60 kD, from 50 kD to 300 kD, from 50 kD to 250 kD, from 50 kD to 200 kD, from 50 kD to 150 kD, from 50 kD to 100 kD, from 50 kD to 80 kD; in particular, from 400 D to 300 kD, from 700 D to 8000 D, from 700 D to 30 kD, or from 7500 D to 300 kD.

The non-aqueous medium in the compositions according to the present disclosure may generally include any fluid and/or viscoelastic medium (or phase, in a phase separated mixed medium) that does not have a substantial (e.g., about 5 wt % or less, about 2 wt % or less, about 1 wt % or less, about 0.5 wt % or less, about 0.1 wt % or less, about 500 wppm or less, or about 200 wppm or less) or purposeful water content. Non-limiting examples of such media may include organic solvents, inorganic solvents, (co)polymer melts, crosslinked (co)polymers/gels, supercritical fluids (such as supercritical $CO_2$), lubricating oil basestocks, lubricant fluids, dewaxing lube oils, (bio)fuels, transmission fluids, greases, gear oils, refrigerant oils, battery coolant fluids, metal working/cutting fluids, hydraulic fluids, electro-rheological fluids, lubricant/fuel additives, crude oil transportation additives, explosives (e.g., emulsion explosives), coatings formulations, and mixtures and combinations thereof.

Organic solvents, inorganic solvents, and supercritical fluids can be media used in a variety of specific applications and/or with a variety of functions. For example, paints/emulsions may have one or more non-aqueous phases that coexist with one or more aqueous phases—in such an example, one or more of the non-aqueous phases may contain the 3,4-oxypyridinone according to the present disclosure. Non-limiting examples of organic solvents may include a pentane, a hexane, a heptane, an octane, a nonane, a decane, a dodecane, a tetradecane, a hexadecane, an octadecane, Exxsol™ (dearomatized hydrocarbon) fluids, Isopar™ (paraffinic hydrocarbon) fluids, a cyclohexane, a cyclooctane, a decahydronaphthalene, benzene, toluene, a xylene, a mesitylene, naphthalene, Solvesso™ (aromatic hydrocarbon) fluids, carbon tetrachloride, carbon tetrabromide, bromoform, chloroform, iodoform, methylene chloride, methylene bromide, methylene iodide, chloromethane, iodomethane, chlorobutane, a trichloroethane, trichlorotrifluoroethane, tetrachloroethylene, a trifluoroethanol, chlorobenzene, a dichlorobenzene, liquid (supercritical) carbon dioxide, methanol, ethanol, isopropanol, n-propanol, a butanol, a pentanol, a hexanol, a heptanol, an octanol, a nonanol, a decanol, a dodecanol, a tetradecanol, a hexadecanol, an octadecanol, cyclohexanol, cyclooctanol, phenol, a catechol, naphthol, ethylene glycol, propylene glycol, diethylene glycol, dipropylene glycol, a butanediol, a pentanediol, a hexanediol, a heptanediol, an octanediol, a nonanediol, a decanediol, a dodecanediol, a tetradecanediol, a hexadecanediol, an octadecanediol, diethyl ether, diethylene glycol dimethyl ether, ethoxyethyl ether, tetrahydrofuran, tetrahydropyran, a dioxane, petroleum ether, acetone, methyl ethyl ketone, methyl isobutyl ketone, diethyl ketone, cyclohexanone, isophorone, acetylacetone, a cyclohexanedione, benzoquinone, ethyl acetate, butyl acetate, butyrolactone, caprolactone, a lactide, formic acid, acetic acid, propionic acid, butyric acid, isobutyric acid, valeric acid, isovaleric acid, pivalic acid, caproic acid, caprylic acid, capric acid, lauric acid, myristic acid, palmitic acid, stearic acid, isostearic acid, oleic acid, linoleic acid, benzoic acid, salicylic acid, oxalic acid, malonic acid, succinic acid, adipic acid, sebacic acid, glycolic acid, lactic acid, tartaric acid, malic acid, phthalic acid, isophthalic acid, terephthalic acid, citric acid, ascorbic acid, acetic anhydride, ethylene carbonate, propylene carbonate, triethylamine, diethylamine, acetonitrile, pyridine, N-methylpyrrolid(in)one, N,N-dimethylacetamide, dimethylformamide, dimethylacetamide, ethylenediaminetetraacetic acid, nitromethane, nitrobenzene, carbon disulfide, dimethylsulfoxide, methanesulfonic acid, trifluoromethanesulfonic acid, trifluoroethylsulfonic acid, benzenesulfonic acid, toluenesulfonic acid, naphthalenesulfonic acid, tetramethyl orthosilicate, tetraethyl orthosilicate, and the like, and combinations thereof. Non-limiting examples of inorganic solvents may include nitric acid, hydrochloric acid, hydrofluoric acid, sulfuric acid, phosphoric acid, aqua regia, boron trifluoride, boron trichloride, titanium trichloride, titanium tetrachloride, sodium hydroxide, lithium hydroxide, potassium hydroxide, calcium hydroxide, magnesium hydroxide, sodium perchlorate, potassium perchlorate, potassium permanganate, Lubricating oil basestocks are well known in the art. Both natural and synthetic lubricating oil basestocks may be suitable. Natural lubricating oils may include animal oils, vegetable oils (e.g., castor oil and lard oil), petroleum oils, mineral oils, oils derived from coal or shale, and combinations thereof. One particular natural lubricating oil includes or is mineral oil.

Suitable mineral oils may include all common mineral oil basestocks, including oils that are naphthenic or paraffinic in chemical structure. Suitable oils may be refined by conventional methodology using acid, alkali, and clay, or other agents such as aluminum chloride, or they may be extracted oils produced, for example, by solvent extraction with solvents such as phenol, sulfur dioxide, furfural, dichlorodiethyl ether, etc., or combinations thereof. They may be hydrotreated or hydrofined, dewaxed by chilling or catalytic dewaxing processes, hydrocracked, or some combination thereof. Suitable mineral oils may be produced from natural crude sources or may be composed of isomerized wax materials, or residues of other refining processes.

Synthetic lubricating oil basestocks may include hydrocarbon oils and halo-substituted hydrocarbon oils such as oligomerized, polymerized, and interpolymerized olefins (e.g., polybutylenes, polypropylenes, propylene, isobutylene copolymers, chlorinated polylactenes, poly(1-hexenes), poly (1-octenes), poly-(1-decenes), etc., and mixtures thereof); alkylbenzenes (e.g., dodecyl-benzenes, tetradecylbenzenes, dinonyl-benzenes, di(2-ethylhexyl)benzene, etc.); polyphenyls (e.g., biphenyls, terphenyls, alkylated polyphenyls, etc.); alkylated diphenyl ethers, alkylated diphenyl sulfides, as well as their derivatives, analogs, and homologs thereof, and the like; and combinations and/or reaction products thereof.

In some embodiments, oils from this class of synthetic oil basestocks may comprise or be polyalphaolefins (PAO), including hydrogenated oligomers of an alpha-olefin, particularly oligomers of 1-decene, such as those produced by free radical processes, Ziegler catalysis, or cationic catalysis. They may, for example, be oligomers of branched or straight chain alpha-olefins having from 2 to 16 carbon atoms, specific non-limiting examples including polypropylenes, polyisobutenes, poly-1-butenes, poly-1-hexenes, poly-1-octenes, poly-1-decene, poly-1-dodecene, and mixtures and/or interpolymers/copolymers thereof.

Synthetic lubricating oil basestocks may additionally or alternatively include alkylene oxide polymers, interpolymers, copolymers, and derivatives thereof, in which any (most) terminal hydroxyl groups have been modified by esterification, etherification, etc. This class of synthetic oils may be exemplified by: polyoxyalkylene polymers prepared by polymerization of ethylene oxide or propylene oxide; the alkyl and aryl ethers of these polyoxyalkylene polymers (e.g., methyl-polyisopropylene glycol ether having an average Mn of ~1000 Daltons, diphenyl ether of polypropylene glycol having an average Mn from about 1000 to about 1500 Daltons); and mono- and poly-carboxylic esters thereof (e.g., acetic acid ester(s), mixed $C_3$-$C_8$ fatty acid esters, $C_{12}$ oxo acid diester(s) of tetraethylene glycol, or the like, or combinations thereof).

Another suitable class of synthetic lubricating oil basestocks may comprise the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkylmalonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoethers, propylene glycol, etc.). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, a complex ester formed by reacting one mole of sebacic acid with two moles of tetraethylene glycol and two moles of 2-ethyl-hexanoic acid, and the like, and combinations thereof. A preferred type of oil from this class of synthetic oils may include adipates of $C_4$ to $C_{12}$ alcohols.

Esters useful as synthetic lubricating oil basestocks may additionally or alternatively include those made from $C_5$-$C_{12}$ monocarboxylic acids, polyols, and/or polyol ethers, e.g., such as neopentyl glycol, trimethylolpropane pentaerythritol, dipentaerythritol, tripentaerythritol, and the like, as well as combinations thereof.

The lubricating oil basestocks may be derived from unrefined oils, refined oils, re-refined oils, or mixtures thereof. Unrefined oils are obtained directly from a natural source or synthetic source (e.g., coal, shale, or tar sands bitumen) without further purification or treatment. Examples of unrefined oils may include a shale oil obtained directly from a retorting operation, a petroleum oil obtained directly from distillation, or an ester oil obtained directly from an esterification process, each or a combination of which may then be used without further treatment. Refined oils are similar to the unrefined oils, except that refined oils have typically been treated in one or more purification steps to change chemical structure and/or to improve one or more properties. Suitable purification techniques may include distillation, hydrotreating, dewaxing, solvent extraction, acid or base extraction, filtration, and percolation, all of which are known to those skilled in the art. Re-refined oils may be obtained by treating used and/or refined oils in processes similar to those used to obtain refined oils in the first place. Such re-refined oils may be known as reclaimed or reprocessed oils and may often additionally be processed by techniques for removal of spent additives and oil breakdown products.

Another additional or alternative class of suitable lubricating oil basestocks may include those basestocks produced from oligomerization of natural gas feed stocks or isomerization of waxes. These basestocks can be referred to in any number of ways but commonly they are known as Gas-to-Liquid (GTL) or Fischer-Tropsch basestocks.

The lubricating oil basestock according to the present disclosure may be a blend of one or more of the oils/basestocks described herein, whether of a similar or different type, and a blend of natural and synthetic lubricating oils (i.e., partially synthetic) is expressly contemplated for this disclosure.

Lubricating oils can be classified as set out in the American Petroleum Institute (API) publication "Engine Oil Licensing and Certification System", Industry Services Department, Fourteenth Edition, December 1996, Addendum 1, December 1998, in which oils are categorized as follows:

a) Group I basestocks contain less than 90 percent saturates and/or greater than 0.03 weight percent sulfur and have a viscosity index greater than or equal to 80 and less than 120;
b) Group II basestocks contain greater than or equal to 90 percent saturates and less than or equal to 0.03 weight percent sulfur and have a viscosity index greater than or equal to 80 and less than 120;
c) Group III basestocks contain greater than or equal to 90 percent saturates and less than or equal to 0.03 weight percent sulfur and have a viscosity index greater than or equal to 120;
d) Group IV basestocks are polyalphaolefins (PAO); and,
e) Group V basestocks include all other basestock oils not included in Groups I, II, III, or IV.

In an embodiment of the present disclosure, when the non-aqueous medium comprises a lubricating oil basestock, it may comprise or be a mineral oil or a mixture of mineral oils, in particular mineral oils of Group II and/or Group III (of the API classification). Additionally or alternatively, the lubricating oil basestock may comprise or be a synthetic oil such as a polyalphaolefin (Group IV) and/or an oil of Group V.

In embodiments in which the non-aqueous medium comprises or is a lubricating oil basestock or a mixture of lubricating oil basestocks, optionally including another non-aqueous co-medium, the lubricating oil basestock(s) (individually or collectively) may exhibit a kinematic viscosity at 100° C. (KV100), as measured by ASTM D445, of from 1.0 cSt to 10 cSt (e.g., from 1.0 cSt to 8.1 cSt, from 1.0 cSt to 7.2 cSt, from 1.0 cSt to 6.5 cSt, from 1.0 cSt to 6.0 cSt, from 1.0 cSt to 5.5 cSt, from 1.0 cSt to 5.0 cSt, from 1.0 cSt to 4.5 cSt, from 1.0 cSt to 4.0 cSt, from 1.0 cSt to 3.5 cSt, from 1.5 cSt to 3.3 cSt, from 1.0 cSt to 3.0 cSt, from 1.0 cSt to 2.5 cSt, from 1.0 cSt to 2.0 cSt, from 1.5 cSt to 10 cSt, from 1.5 cSt to 8.1 cSt, from 1.5 cSt to 7.2 cSt, from 1.5 cSt to 6.5 cSt, from 1.5 cSt to 6.0 cSt, from 1.5 cSt to 5.5 cSt, from 1.5 cSt to 5.0 cSt, from 1.5 cSt to 4.5 cSt, from 1.5 cSt to 4.0 cSt, from 1.5 cSt to 3.5 cSt, from 1.5 cSt to 3.3 cSt, from 1.5 cSt to 3.0 cSt, from 1.5 cSt to 2.5 cSt, from 2.0 cSt to 10 cSt, from 2.0 cSt to 8.1 cSt, from 2.0 cSt to 7.2 cSt, from 2.0 cSt to 6.5 cSt, from 2.0 cSt to 6.0 cSt, from 2.0 cSt to 5.5 cSt, from 2.0 cSt to 5.0 cSt, from 2.0 cSt to 4.5 cSt, from 2.0 cSt to 4.0 cSt, from 2.0 cSt to 3.5 cSt, from 2.0 cSt to 3.0 cSt, from 2.0 cSt to 2.5 cSt, from 2.5 cSt to 10 cSt, from 2.5 cSt to 8.1 cSt, from 2.5 cSt to 7.2 cSt, from 2.5 cSt to 6.5 cSt, from 2.5 cSt to 6.0 cSt, from 2.5 cSt to 5.5 cSt, from 2.5 cSt to 5.0 cSt, from 2.5 cSt to 4.5 cSt, from 2.5 cSt to 4.0 cSt, from 2.5 cSt to 3.5 cSt, from 2.5 cSt to 3.0 cSt, from 2.7 cSt to 10 cSt, from 2.7 cSt to 8.1 cSt, from 2.7 cSt to 7.2 cSt, from 2.7 cSt to 6.5 cSt, from 2.7 cSt to 6.0 cSt, from 2.7 cSt to 5.5 cSt, from 2.7 cSt to 5.0 cSt, from 2.7 cSt to 4.5 cSt, from 2.7 cSt to 4.0 cSt, from 2.7 cSt to 3.5 cSt, from 2.7 cSt to 3.0 cSt, from 3.0 cSt to 10 cSt, from 3.0 cSt to 8.1 cSt, from 3.0 cSt to 7.2 cSt, from 3.0 cSt to 6.5 cSt, from 3.0 cSt to 6.0 cSt, from 3.0 cSt to 5.5 cSt, from 3.0 cSt to 5.0 cSt, from 3.0 cSt to 4.5 cSt, from 3.0 cSt to 4.0 cSt, from 3.0 cSt to 3.5 cSt, from 3.5 cSt to 10 cSt, from 3.5 cSt to 8.1 cSt, from 3.5 cSt to 7.2 cSt, from 3.5 cSt to 6.5 cSt, from 3.5 cSt to 6.0 cSt, from 3.5 cSt to 5.5 cSt, from 3.5 cSt to 5.0 cSt, from 3.5 cSt to 4.5 cSt, from 3.5 cSt to 4.0 cSt, from 4.0 cSt to 10 cSt, from 4.0 cSt to 8.1 cSt, from 4.0 cSt to 7.2 cSt, from 4.0 cSt to 6.5 cSt, from 4.0 cSt to 6.0 cSt, from 4.0 cSt to 5.5 cSt, from 4 cSt to 5.0 cSt, or from 4.0 cSt to 4.5 cSt), in particular from 1.0 cSt to 10 cSt, from 1.5 cSt to 3.3 cSt, from 2.7 cSt to 8.1 cSt, from 3.0 cSt to 7.2 cSt, or from 2.5 cSt to 6.5 cSt.

When the non-aqueous medium (e.g., lubricating oil basestock(s)) is used to make a concentrate, it may advantageously be present in a concentrate-forming amount to give a concentrate containing, e.g., from 5 wt % to 95 wt % (such as from 5 wt % to 80 wt %, from 5 wt % to 70 wt %, from 5 wt % to 60 wt %, from 5 wt % to 50 wt %, from 5 wt % to 40 wt %, from 5 wt % to 30 wt %, from 5 wt % to 25 wt %, from 5 wt % to 20 wt %, from 5 wt % to 15 wt %, from 10 wt % to 95 wt %, from 10 wt % to 80 wt %, from 10 wt % to 70 wt %, from 10 wt % to 60 wt %, from 10 wt % to 50 wt %, from 10 wt % to 40 wt %, from 10 wt % to 30 wt %, from 10 wt % to 25 wt %, from 10 wt % to 20 wt %, from 20 wt % to 95 wt %, from 20 wt % to 80 wt %, from 20 wt % to 70 wt %, from 20 wt % to 60 wt %, from 20 wt % to 50 wt %, from 20 wt % to 40 wt %, from 30 wt % to 95 wt %, from 30 wt % to 80 wt %, from 30 wt % to 70 wt %, from 30 wt % to 60 wt %, from 30 wt % to 50 wt %, from 30 wt % to 40 wt %, from 40 wt % to 95 wt %, from 40 wt % to 80 wt %, from 40 wt % to 70 wt %, from 40 wt % to 60 wt %, from 50 wt % to 95 wt %, from 50 wt % to 80 wt %, or from 50 wt % to 70 wt %; in particular, from 5 wt % to 80 wt %, from 10 wt % to 70 wt %, or from 5 wt % to 50 wt %) of an active ingredient (e.g., the 3,4-oxypryidinone) or a combination of active ingredients collectively (e.g., the 3,4-oxypyridinone plus optionally one or more co-additives). When 3,4-oxypyridinone-containing concentrates are used to make lubricants and/or coolants according to the present disclosure, 100 parts of a 3,4-oxypyridinone-containing concentrate may be further diluted, for example with from 101 parts to 2400 parts by weight (e.g., from 101 parts to 2000 parts, from 101 parts to 1600 parts, from 101 parts to 1200 parts, from 101 parts to 1000 parts, from 101 parts to 800 parts, from 101 parts to 600 parts, from 101 parts to 400 parts, from 250 parts to 2400 parts, from 250 parts to 2000 parts, from 250 parts to 1600 parts, from 250 parts to 1200 parts, from 250 parts to 1000 parts, from 250 parts to 800 parts, from 250 parts to 600 parts, from 400 parts to 2400 parts, from 400 parts to 2000 parts, from 400 parts to 1600 parts, from 400 parts to 1200 parts, from 400 parts to 1000 parts, from 400 parts to 800 parts, from 600 parts to 2400 parts, from 600 parts to 2000 parts, from 600 parts to 1600 parts, from 600 parts to 1200 parts, or from 600 parts to 1000 parts), of lubricating oil basestock(s) (optionally plus one or more additional co-additives).

In some cases, depending upon the circumstances, it may be desirable for the 3,4-oxypyridinone-containing compositions to contain substantially none of one, some, or all additional co-additives.

Lubricant/Coolant Co-Additives

Co-additives commonly found in (engine, transmission, gear oil, drivetrain, powertrain) lubricants and/or (electric/electronic component/battery) coolants may optionally be added to the non-aqueous 3,4-oxypyridinone compositions of the present disclosure. Some or all of such co-additives may additionally or alternatively be found in compositions suitable for other applications, which may include but are not necessarily limited to fuels, functional/hydraulic fluids, metalworking/metal cutting fluids, fluids for rheological and/or electrical applications, greases, compressor fluids, coatings, polymer manufacturing/processing, explosives (e.g., emulsion explosives), and the like and combinations thereof. Suitable co-additives will be known to those skilled in the relevant art. Some non-limiting examples are described herein.

The 3,4-oxypyridinone and any additional components may be added separately from one another to the non-aqueous medium to form the compositions (e.g., the lubricant and/or coolant compositions) according to the present disclosure or, more conveniently, at least one co-additive and the 3,4-oxypyridinone may be dissolved or dispersed in the non-aqueous medium to form a functional additive package, which may be further diluted at a later time. Particularly for lubricant and/or coolant compositions, such an additive package may optionally further contain, or functional compositions separate from the additive package may contain (for later combination together), one or more co-additives as defined hereinbelow.

Dispersants

Dispersants help keep certain compounds, such as insoluble oxidation byproducts, in solution, thus diminishing their deposition on substrate (typically metal) surfaces. Dispersants used/useful in the compositions herein may be ashless and/or ash-forming in nature (preferably ashless). So-called ashless dispersants are organic materials that form substantially no ash upon combustion. For example, non-metal-containing and/or boron-containing metal-free dispersants are considered ashless. In contrast, metal-containing detergents tend form ash upon combustion.

Dispersants useful herein typically contain a polar group attached to a relatively high molecular weight hydrocarbon chain. The polar group typically contains at least one element of nitrogen, oxygen, or phosphorus. Typical hydrocarbon chains contain 40 to 500 carbon atoms, such as 50 to 400 carbon atoms.

Basic nitrogen-containing ashless dispersants may advantageously comprise, consist essentially of, or be a compound of structure (II), as follows:

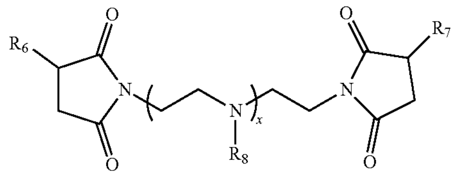

(II)

wherein: $R_6$ and $R_7$ are each independently a hydrocarbyl group having greater than 36 carbons, e.g., greater than 40 carbon atoms, and capable of providing a primary dispersancy function; and each $R_8$ is independently hydrogen, an acetyl moiety, or a moiety formed by reaction between ethylene carbonate and $>N—R_8$; and x is from 1 to 10 and is the same for all molecules of structure (II) or is an average of all molecules of structure (II) in a mixture of molecules of structure (II). Although some viscosity modifier additives may also have a dispersancy function, their molecular weight is so high (typically a number average molecular weight (Mn) of 10000-20000 Daltons or more) that the viscosity modification function becomes primary and the dispersancy secondary.

In some embodiments, one or each of $R_6$ and $R_7$ may comprise, consist essentially of, or be an oligomeric/polymeric polkyalkenyl (e.g., polyisobutenyl, at least partially hydrogenated polybutadienyl, and/or at least partially hydrogenated polyisoprenyl) moiety having a number average molecular weight (Mn) from 500 to 5000 Daltons or from 750 to 2500 Daltons, as determined by GPC with reference to linear polystyrene standards. Non-limiting examples of such ashless dispersants may include polyisobutenyl succinimides, polyisobutenyl succinamides, mixed ester/amides of polyisobutenyl-substituted succinic acid, hydroxyesters of polyisobutenyl-substituted succinic acid, and reaction products and mixtures thereof.

Additionally or alternatively, one or each of $R_6$ and $R_7$ may comprise, consist essentially of, or be moieties made by the metallocene-catalyzed polymerization of an α-olefin feedstock comprising 1-butene, 1-pentene, 1-hexene, 1-heptene, 1-octene, 1-nonene, 1-decene, 1-undecene, 1-dodecene, 1-tetradecene, 1-octadecene, or mixtures thereof (in particular, comprising, consisting essentially of, or being 1-octene, 1-decene, 1-dodecene, or mixtures thereof), such that the dispersant arms or endcaps of $R_6$ and $R_7$ are each metallocene-catalyzed poly(alpha-olefins), or mPAOs. In these mPAO embodiments, one or each of the mPAO endcaps or arms ($R_6$ and $R_7$ moieties) may independently exhibit a number average molecular weight (Mn) from 300 to 20000 Daltons, as determined by GPC with reference to linear polystyrene standards, e.g., from 400 to 15000 Daltons, from 450 to 10000 Daltons, from 500 to 8000 Daltons, from 650 to 6500 Daltons, from 800 to 5000 Daltons, or from 900 to 3000 Daltons; in particular from 300 to 20000 Daltons, from 500 to 8000 Daltons, or from 800 to 5000 Daltons. Non-limiting examples of such additional ashless dispersants may include mPAO-based succinimides, mPAO-based succinamides, mixed ester/amides of mPAO-substituted succinic acid (mPAOSA), and hydroxyesters of mPAO-substituted succinic acid, as well as reaction products and mixtures thereof.

Although typically less preferred in lubricant and/or coolant compositions, dispersants may alternatively be based on poly(meth)acrylate derivatives, such as including nitrogen-containing repeat units and repeat units derived from $C_5$-$C_{25}$ (meth)acrylate esters. Representative examples are disclosed in U.S. Pat. Nos. 2,100,993 and 6,323,164, inter alia, the relevant disclosures of which are incorporated herein by reference.

Also typically less preferred dispersants may be based on Mannich condensation products of optionally hydrocarbyl-substituted (e.g., alkyl-substituted) phenols, an aldehyde such as formaldehyde, and a (poly)amine component. Representative examples are disclosed in U.S. Pat. Nos. 4,767, 551 and 10,899,986, inter alia, the relevant disclosures of which are incorporated herein by reference. Process aids and catalysts, such as oleic acid and sulfonic acids, may optionally also be part of the reaction mixture. Representative examples are shown in U.S. Pat. Nos. 3,697,574; 3,703,536, 3,704,308, 3,751,365; 3,756,953, 3,798,165, 3,803,039, 4,231,759, 9,938,479, 7,491,248, and 10,899,986, as well as PCT Publication No. WO 01/42399, the relevant disclosures of which are incorporated herein by reference.

When used, an ashless dispersant may be present in an amount of from 0.01 wt % to 15 wt %, based on the weight of the non-aqueous 3,4-oxypyridinone composition, e.g., from 0.05 wt % to 12 wt %, from 0.1 wt % to 10 wt %, or from 0.5 to 8 wt %. In some embodiments, 3,4-oxypyridinone-containing compositions may contain substantially no (e.g., 0.03 wt % or less, 0.01 wt % or less, no intentionally added, and/or absolutely no) dispersant and/or ashless dispersant.

In some embodiments, these dispersants, similarly to other dispersants known in the art, may be further treated (e.g., with a secondary nitrogen-capping agent such as acetic anhydride and/or ethylene carbonate, with a borating/boronating agent, and/or with an inorganic acid of phosphorus). Suitable examples of post-treated dispersants may generally be found, e.g., in U.S. Pat. Nos. 3,254,025, 3,502,677, and 4,857,214, the relevant disclosures of which are incorporated herein by reference. In such embodiments according to the present disclosure in which co-additives such as dispersants are borated/boronated, the compositions may advantageously comprise less than 250 parts per million by weight (wppm) of boron, based on the total weight of the composition, e.g., less than 200 wppm boron, less than 150 wppm boron, less than 100 wppm boron, less than 70 wppm boron, or less than 50 wppm boron.

Detergents

Although detergents may generally include ashless varieties, most detergents tend to contain metals. Detergents generally comprise one or more relatively polar/ionic head groups, with one or more relatively long (and typically hydrophobic) tail groups. In lubricant and/or coolant compositions, metal detergents may function as acid neutralizers/rust inhibitors, as well as reducing and/or removing deposits, thereby resulting in less likelihood and/or severity of wear/corrosion and hopefully extending substrate (engine, transmission, electronic/battery component) life.

When the non-aqueous 3,4-oxypyridinone composition comprises a metal containing detergent, it may contain at least one alkali and/or alkaline earth metal. Useful detergents are typically sufficiently oil-soluble and/or oil-dispersible such as to remain dissolved or dispersed in the non-aqueous medium in order to be transportable to their intended site of action, which is typically a solid substrate, such as a powertrain part, e.g., an engine part and/or a transmission part. In lubricant and/or coolant embodiments, when a detergent is present, it is preferably an alkaline earth metal detergent, such as a calcium detergent and/or a magnesium detergent. Such detergents are well known in the lubricant art and can include neutral and/or overbased alkaline earth metal salts with acidic substances such as alkyl sulfonic acids, aryl sulfonic acids, alkaryl sulfonic acids, alkyl phenols, sulfurized alkyl phenols, alkyl phenates, sulfurized alkyl phenates, alkyl salicylates, sulfurized alkyl salicylates, alkyl naphthenates, alkyl thiophosphonates, other oil-soluble/oil-dispersible aryl and/or alkaryl carboxylic acids, and mixtures or hybrids of these substances.

Examples of metal detergents that may be used/useful in the compositions of the present disclosure may include, but are not necessarily limited to, neutral and/or overbased metal salts of salicylates (e.g., wherein each aromatic group has one or more aliphatic groups to impart hydrocarbon solubility); sulfurized salicylates (e.g., wherein each aromatic group has one or more aliphatic groups to impart hydrocarbon solubility); phenates (e.g., wherein each aromatic group may have one or more aliphatic groups to impart hydrocarbon solubility); sulfurized phenates (e.g., wherein each aromatic group may have one or more aliphatic groups to impart hydrocarbon solubility); sulfonates (e.g., wherein each sulfonic acid moiety is attached to an aromatic nucleus, which in turn may contain one or more aliphatic and/or aromatic substituents to impart hydrocarbon solubility); hydrolyzed phosphosulfurized olefins (e.g., having 10 to 2000 carbon atoms), hydrolyzed phosphosulfurized alcohols, and/or aliphatic-substituted phenolic compounds (e.g., having 10 to 2000 carbon atoms); aliphatic carboxylic acids and/or aliphatic substituted cycloaliphatic carboxylic acids; and combinations and/or reaction products thereof; as well as many other similar salts of oil-soluble organic acids. Mixtures of neutral and/or overbased salts of two or more different detergents can be used, if desired (e.g., one or more overbased calcium sulfonates with one or more overbased magnesium sulfonates, or alternatively one or more overbased calcium salicylates with one or more overbased calcium sulfonates).

Methods for the production of oil-soluble neutral and overbased alkaline earth metal detergents are well known to those skilled in the art and are extensively reported in the patent literature. Alkaline earth metal-containing detergents may optionally be post-treated, e.g., to include boron (such as by boration or boronation). Methods for preparing borated detergents are well known to those skilled in the art and are extensively reported in the patent literature.

Neutral detergents are generally those that contain approximately stoichiometrically equivalent amounts of calcium in relation to the amount of (Lewis) acidic moieties present in the detergent. Thus, in general, neutral detergents can typically have a relatively low basicity, when compared to their overbased counterparts.

The term "overbased," for example in connection with alkaline earth metal detergents, is used to designate the fact that the alkaline earth metal (e.g., calcium and/or magnesium) component is present in stoichiometrically larger amounts than the corresponding (Lewis) acid component. The commonly employed methods for preparing the overbased salts involve heating a mineral oil solution of an acid with a stoichiometric excess of a neutralizing agent at an appropriate temperature (in this case, a calcium and/or magnesium neutralizing agent, such as an oxide, hydroxide, carbonate, bicarbonate, sulfide, or combination thereof, at a temperature of about 50° C.) and filtering the resultant product. The use of a "promoter" in the neutralization step to aid the incorporation of a large excess of salt/base likewise is known. Examples of compounds useful as a promoter may include, but are not necessarily limited to, phenolic substances such as phenol, naphthol, alkyl phenol, thiophenol, sulfurized alkylphenol, and condensation products of formaldehyde with a phenolic substance; alcohols such as methanol, 2-propanol, octanol, Cellosolve™ alcohol, Carbitol™ alcohol, ethylene glycol, stearyl alcohol, and cyclohexyl alcohol; amines such as aniline, phenylene diamine, phenothiazine, phenyl-beta-naphthylamine, and dodecylamine; and combinations thereof. A particularly effective method for preparing the basic salts comprises mixing an acidic substance with an excess of alkaline earth metal neutralizing agent and at least one alcohol promoter, and carbonating the mixture at an elevated temperature, such as from 60 to 200° C.

Sulfonate detergents may be prepared from sulfonic acids, which may typically be obtained by the sulfonation of alkyl substituted aromatic hydrocarbons such as those obtained from the fractionation of petroleum or by the alkylation of aromatic hydrocarbons. Examples included those obtained by alkylating benzene, toluene, xylene, naphthalene, diphenyl, or their halogen derivatives such as chlorobenzene, chlorotoluene and chloronaphthalene. The alkylation may be carried out in the presence of a catalyst with alkylating agents having from 3 to more than 70 carbon atoms. Alkaryl sulfonates in lubricants can usually contain from 9 to 80 or more carbon atoms, such as from 16 to 60 carbon atoms per alkyl substituted aromatic moiety. The oil-soluble/oil-dispersible sulfonates or alkaryl sulfonic acids may be neutralized with oxides, hydroxides, alkoxides, carbonates, carboxylate, sulfides, hydrosulfides, nitrates, borates, and/or ethers of the metal. The amount of metal compound can be chosen with regard to a desired TBN of the final product but may typically range from about 100 wt % to about 220 wt % (preferably at least 125 wt %) of that stoichiometrically required.

Metal salts of phenols and sulfurized phenols may be prepared by reaction with an appropriate metal compound such as an oxide or hydroxide, and neutral and/or overbased products may be obtained by methods well known in the art. Sulfurized phenols may be prepared by reacting a phenol with sulfur or a sulfur containing compound such as hydrogen sulfide, sulfur monohalide, or sulfur dihalide, to form products that are generally mixtures of compounds in which two or more phenols may be bridged by sulfur containing bridges.

Carboxylate detergents (including salicylates) can be prepared by reacting an aromatic carboxylic acid with an appropriate metal compound such as an oxide or hydroxide, and neutral or overbased products may be obtained by methods well known in the art. The aromatic moiety of the aromatic carboxylic acid can contain heteroatoms, such as nitrogen and oxygen. Preferably, the moiety may contain only carbon atoms, e.g., six or more carbon atoms; for example, benzene is one preferred aromatic moiety. The aromatic carboxylic acid may contain one or more aromatic moieties, such as one or more benzene rings, either fused or connected via alkylene bridges.

Preferred substituents in oil-soluble/oil-dispersible salicylic acids can include or be alkyl substituents. In alkyl-substituted salicylic acids, the alkyl groups may advantageously contain from 5 to 100 (e.g., from 9 to 30 or from 14 to 20) carbon atoms. Where more than one alkyl group is present, the average number of carbon atoms in all of the alkyl groups may advantageously be at least 9 carbons, to ensure adequate solubility/dispersibility in the non-aqueous medium.

When present, the composition may comprise one or more alkaline earth metal detergents in an individual and/or collective amount from 0.05 wt % to 20.0 wt %, based on the total weight of the composition, e.g., from 0.07 wt % to 10.0 wt %, from 0.1 wt % to 7.0 wt %, or from 0.5 wt % to 5.0 wt %. Additionally or alternatively, the alkaline earth metal detergent, when present, may sufficiently provide the composition with from 50 to 8000 parts per million by weight (wppm) of alkaline earth metal (e.g., calcium and/or magnesium), based on the mass of the composition, e.g., from 60 to 6000 wppm, from 75 to 4000 wppm, or from 100 to 3500 ppm. When amounts at or above 1000-1200 wppm alkaline earth metal are present in the composition, typically the alkaline earth metal of the detergent(s) will comprise both calcium and magnesium. Calcium and magnesium content can be measured in accordance with ASTM D5185. In some embodiments, 3,4-oxypyridinone-containing compositions may contain substantially no (e.g., 0.03 wt % or less, 0.01 wt % or less, no intentionally added, and/or absolutely no) neutral detergents, overbased detergents, calcium detergents, magnesium detergents, phenate detergents, naphthenate detergents, sulfonate detergents, salicylate detergents, carboxylate detergents, combinations thereof, and/or all detergents.

Antioxidants

Antioxidants are sometimes referred to as oxidation inhibitors and may increase the resistance (or decrease the susceptibility) of the non-aqueous 3,4-oxypyridinone compositions to oxidation, as well as of the substrates/compositions of matter to which they're exposed. They may work by combining with and modifying oxidative agents, such as peroxides and other free radical-forming compounds, to render them harmless, e.g., by decomposing them or by rendering inert a catalyst or facilitator of oxidation. Oxidative deterioration can be evidenced by various means, such as by appearance of sludge in the fluid with increased use, by varnish-like deposits on metal surfaces, by viscosity increase, or the like, or by combinations thereof.

A wide variety of oxidation inhibitors that are useful in lubricating oil compositions. See, e.g., Lubricants and Related Products, Klamann, Wiley VCH, 1984; and U.S. Pat. Nos. 4,798,684 and 5,084,197, inter alia, the relevant disclosures of which are incorporated herein by reference. Examples of suitable antioxidants may include, but are not limited to, copper-containing antioxidants, catalytic antioxidants, sulfur-containing antioxidants, aromatic amine-containing and/or amide-containing antioxidants, hindered phenolic antioxidants, dithiophosphates and derivatives, and the like, as well as combinations and certain reaction products thereof. Some antioxidants may be ashless (i.e., may contain few, if any, metal atoms other than trace or contaminants). In preferred embodiments, one or more antioxidants is present in a lubricant and/or coolant composition according to the present disclosure.

Hindered phenolic antioxidants may be ashless (metal-free) phenolic compounds or neutral or basic metal salts of certain phenolic compounds. Typical hindered phenolic antioxidant compounds contain a sterically hindered hydroxyl group, and these include those derivatives of dihydroxy aryl compounds in which the hydroxyl groups are in the ortho- and/or para-position to each other. Typical phenolic antioxidants include the hindered phenols substituted with groups containing at least 6 carbons (e.g., alkyl or hydrocarbyl with optional heteroatoms, such as oxygen, sulfur, and/or the like) and the alkylene coupled derivatives of these hindered phenols. Examples of phenolic materials of this type include, but are not necessarily limited to, 2-t-butyl-4-heptyl phenol, 2-t-butyl-4-octyl phenol, 2-t-butyl-4-dodecyl phenol, 2,6-di-t-butyl-4-heptyl phenol, 2,6-di-t-butyl-4-dodecyl phenol, 2,6-di-t-butyl-4-substituted phenol where the substitution is a C8-C14 moiety containing an ester/thioester or ether/thioether, 2-methyl-6-t-butyl-4-heptyl phenol, 2-methyl-6-t-butyl-4-dodecyl phenol, and combinations thereof. Other useful hindered mono-phenolic antioxidants may include, for example, hindered 2,6-di-alkyl-phenolic propionic ester derivatives. Bis-phenolic antioxidants may additionally or alternatively be used herein. Non-limiting examples of ortho-coupled phenols include 2,2'-bis(4-heptyl-6-t-butyl-phenol), 2,2'-bis(4-octyl-6-t-butyl-phenol), 2,2'-bis(4-dodecyl-6-t-butyl-phenol), and the like. Non-limiting examples of para-coupled bisphenols include 4,4'-bis(2,6-di-t-butyl phenol), 4,4'-methylene-bis(2,6-di-t-butyl phenol), and the like. Combinations across or within any of these groupings are also contemplated.

Effective amounts of one or more catalytic antioxidants may also be used. The catalytic antioxidants may comprise an effective amount of a) one or more oil soluble polymetal organic compounds, as well as effective amounts of b) one or more substituted N,N'-diaryl-o-phenylenediamine compounds, c) one or more hindered phenol compounds, or a combination of both b) and c). Catalytic antioxidants are more fully described in U.S. Pat. No. 8,048,833, the relevant disclosure of which is incorporated herein by reference.

Non-limiting examples of non-phenolic antioxidants may include alkylated and non-alkylated aromatic amines such as aromatic monoamines of the formula $R^9R^{10}R^{11}N$, where $R^9$ is an aliphatic, aromatic, or substituted aromatic group, $R^{10}$ is an aromatic or a substituted aromatic group, and $R^{11}$ is H, alkyl, aryl, or $—R^{12}S(O)_xR^{13}$ where $R^{12}$ is an alkylene, alkenylene, or aralkylene group, $R^{13}$ is an alkyl, alkenyl, aryl, or alkaryl group, and x is 0, 1, or 2. When $R^9$ is an aliphatic group, it may contain from 1 to about 20 carbon atoms (preferably from about 6 to 12 carbon atoms) and is typically saturated. Preferably, both $R^9$ and $R^{10}$ can be aromatic or substituted aromatic groups, and the aromatic group may be a fused ring aromatic group such as naphthyl. When both are aromatic, groups $R^9$ and $R^{10}$ may be joined together with moieties such as —S—.

Non-limiting examples of aromatic amines antioxidants may typically have alkyl substituent groups of at least about 6 carbon atoms (e.g., hexyl, heptyl, octyl, nonyl, and/or decyl). Generally, the aliphatic groups may contain about 14 carbon atoms or less. Diphenylamines, phenyl naphthylamines, phenothiazines, imidodibenzyls and/or diphenyl phenylene diamines are each/all potentially useful aromatic amine antioxidants. Mixtures of two or more aromatic amines may also be useful. Polymeric amine antioxidants can additionally or alternatively be used. Particular examples of aromatic amine antioxidants useful in the present disclosure may include p,p'-dioctyldiphenylamine, t-octylphenyl-alpha-naphthylamine, phenyl-alphanaphthylamine, p-octylphenyl-alpha-naphthylamine, and the like, as well as combinations thereof.

Sulfur-containing antioxidants may be additionally or alternatively useful herein. For example, sulfurized alkyl phenols and alkali or alkaline earth metal salts thereof may be useful antioxidants herein. When present, the one or more sulfur containing antioxidant(s) may provide compositions according to the present disclosure with from 0.02 wt % to 0.2 wt %, e.g., from 0.02 wt % to 0.15 wt %, from 0.02 wt % to 0.1 wt %, or from 0.04 wt % to 0.1 wt % sulfur, based on the total weight of the composition. Optionally, when present, the oil-soluble or oil-dispersible sulfur-containing antioxidant(s) may be selected from sulfurized $C_4$ to $C_{25}$ olefin(s), sulfurized aliphatic ($C_7$ to $C_{29}$) hydrocarbyl fatty acid ester(s), ashless sulfurized phenolic antioxidant(s), and combinations thereof. For further information, on sulfurized materials useful as antioxidants, see U.S. Pat. No. 10,731,101 (e.g., at column 15, line 55 to column 22, line 12), the relevant disclosure of which is incorporated herein by reference. In some embodiments, 3,4-oxypyridinone-containing compositions may contain substantially no (e.g., 0.01 wt % or less, 0.005 wt % or less, no intentionally added, and/or absolutely no) copper-containing antioxidants, catalytic antioxidants, sulfur-containing antioxidants, aromatic amine-containing and/or amide-containing antioxidants, hindered phenolic antioxidants, dithiophosphate antioxidants, combinations thereof, or all antioxidants.

Corrosion Inhibitors

Corrosion inhibitors may be used to reduce the corrosion of metals and are often alternatively referred to as metal deactivators or metal passivators. Some corrosion inhibitors may alternatively be characterized as antioxidants.

Suitable corrosion inhibitors may include nitrogen and/or sulfur containing heterocyclic compounds such as triazoles (e.g., benzotriazoles), substituted thiadiazoles, imidazoles, thiazoles, tetrazoles, hydroxyquinolines, oxazolines, imidazolines, thiophenes, indoles, indazoles, quinolines, benzoxazines, dithiols, oxazoles, oxatriazoles, pyridines, piperazines, triazines and derivatives of any one or more thereof. A particular corrosion inhibitor is an optionally substituted triazole, such as Irgamet® 30, which is commercially available from BASF of Ludwigshafen, Germany. Another particular corrosion inhibitor is a benzotriazole represented by the structure:

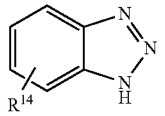

wherein $R^{14}$ is absent (hydrogen) or is a $C_1$ to $C_{20}$ hydrocarbyl or substituted hydrocarbyl group which may be linear or branched, saturated or unsaturated. It may contain ring structures that are alkyl or aromatic in nature and/or contain heteroatoms such as N, O, or S. Examples of suitable compounds may include benzotriazole, alkyl-substituted benzotriazoles (e.g., tolyltriazole, ethylbenzotriazole, hexylbenzotriazole, octylbenzotriazole, etc.), aryl substituted benzotriazole, alkaryl- or aralkyl-substituted benzotriazoles, and the like, as well as combinations thereof. For instance, the triazole may comprise or be a benzotriazole and/or an alkylbenzotriazole in which the alkyl group contains from 1 to about 20 carbon atoms or from 1 to about 8 carbon atoms. Non-limiting examples of such corrosion inhibitors may comprise or be benzotriazole, tolyltriazole, and/or optionally substituted benzotriazoles such as Irgamet® 39, which is commercially available from BASF of Ludwigshafen, Germany.

Additionally or alternatively, the corrosion inhibitor may include a substituted thiadiazoles represented by the structure:

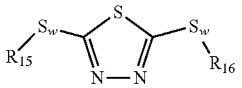

wherein $R^{15}$ and $R^{16}$ are independently hydrogen or a hydrocarbon group, which group may be aliphatic or aromatic, including cyclic, alicyclic, aralkyl, aryl and alkaryl, and wherein each w is independently 1-6 (preferably 2-4, in particular 2). These substituted thiadiazoles are derived from the 2,5-dimercapto-1,3,4-thiadiazole (DMTD) molecule. Many derivatives of DMTD have been described in the art, and any such compounds may be included in the compositions according to the present disclosure. For example, U.S. Pat. Nos. 2,719,125, 2,719,126, and 3,087,937 describe the preparation of various 2,5-bis-(hydrocarbon dithio)-1,3,4-thiadiazoles.

Further additionally or alternatively, the corrosion inhibitor may include one or more other derivatives of DMTD, such as a carboxylic ester in which $R^{15}$ and $R^{16}$ may be joined to the sulfide sulfur atom through a carbonyl group. Preparation of these thioester containing DMTD derivatives is described, for example, in U.S. Pat. No. 2,760,933. DMTD derivatives produced by condensation of DMTD with alpha-halogenated aliphatic monocarboxylic carboxylic acids having at least 10 carbon atoms are described, for example, in U.S. Pat. No. 2,836,564. This process produces DMTD derivatives wherein $R^{15}$ and $R^{16}$ are HOOC—CH($R^{17}$)— ($R^{17}$ being a hydrocarbyl group). DMTD derivatives further produced by amidation or esterification of these terminal carboxylic acid groups may also be useful.

The preparation of 2-hydrocarbyldithio-5-mercapto-1,3,4-thiadiazoles is described, for example, in U.S. Pat. No. 3,663,561.

A class of DMTD derivatives may include mixtures of a 2-hydrocarbyldithio-5-mercapto-1,3,4-thiadiazole and a 2,5-bis-hydrocarbyldithio-1,3,4-thiadiazole. Such mixtures may be sold under the tradename HiTEC® 4313 and are commercially available from Afton Chemical.

Still further additionally or alternatively, the corrosion inhibitor may include a trifunctional borate having the structure, $B(OR^{46})_3$, in which each $R^{46}$ may be the same or different. As the borate may typically be desirably compatible with the non-aqueous medium of the composition, each $R^{46}$ may in particular comprise or be a hydrocarbyl $C_1$-$C_8$ moiety. For compositions in which the non-aqueous medium comprises or is a lubricating oil basestock, for example, better compatibility can typically be achieved when the hydrocarbyl moieties are each at least $C_4$. Non-limiting examples of such corrosion inhibitors thus include, but are not limited to, triethylborate, tripropylborates such as triisopropylborate, tributylborates such as tri-tert-butylborate, tripentylborates, trihexylborates, trioctylborates such as tri-(2-ethylhexyl)borate, monohexyl dibutylborate, and the like, as well as combinations thereof.

When used, a corrosion inhibitor may comprise a substituted thiadiazole, a substituted benzotriazole, a substituted triazole, a trisubstituted borate, or a combination thereof.

When desired, corrosion inhibitors can be used in any effective amount, but, when used, may typically be used in amounts from about 0.001 wt % to 5.0 wt %, based on the weight of the composition, e.g., from 0.005 wt % to 3.0 wt % or from 0.01 wt % to 1.0 wt %. In some embodiments, 3,4-oxypyridinone-containing compositions may contain substantially no (e.g., less than 0.001 wt %, 0.0005 wt % or less, no intentionally added, and/or absolutely no) triazoles, benzotriazoles, substituted thiadiazoles, imidazoles, thiazoles, tetrazoles, hydroxyquinolines, oxazolines, imidazolines, thiophenes, indoles, indazoles, quinolines, benzoxazines, dithiols, oxazoles, oxatriazoles, pyridines, piperazines, triazines, derivatives thereof, combinations thereof, or all corrosion inhibitors.

Antiwear Compounds

Antiwear compounds typically prevent/mitigate, and/or work in tandem with one or more other additives in collectively helping to prevent/mitigate, wear of parts/substrates that may move and/or undergo physical (e.g., mechanical/frictional) interaction with other parts/substrates. In lubricant and/or coolant compositions, antiwear components may typically contain phosphorus, potentially as well as other functionalities, and may contribute to at least partial formation of a surface tribofilm on parts/substrates susceptible to wear damage. Antiwear compounds may be ashless (e.g., metal-free) and/or may contain one or more metals such as zinc, molybdenum, and the like.

Examples of ashless antiwear compounds may include a sulfur- and phosphorus-containing reaction product comprising both components (i) and (ii). Non-limiting examples of such reaction products are disclosed, e.g., in U.S. Pat. Nos. 5,242,612, 5,326,487, and 5,534,170, as well as U.S. Patent Application Publication No. 2020/0354647, inter alia. Antiwear component (i) may advantageously comprise a mixture of two or more compounds of the structures (III):

(III)

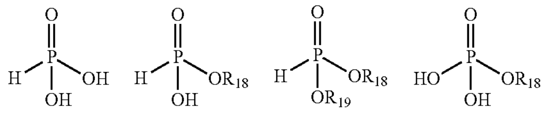

-continued

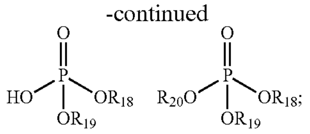

where groups $R_{18}$, $R_{19}$, and $R_{20}$ may each independently comprise or be alkyl groups having 1 to 18 carbon atoms and/or alkyl groups having 1 to 18 carbon atoms where the alkyl chain is interrupted by a thioether linkage, with the proviso that at least some from the set of all groups $R_{18}$, $R_{19}$, and $R_{20}$ in all structure (III) compounds, collectively, may comprise or be alkyl groups having 1 to 18 carbon atoms where the alkyl chain is interrupted by a thioether linkage. The mixture may comprise three or more, four or more, or five or more compounds of the structures (III).

In some embodiments, groups $R_{18}$, $R_{19}$, and $R_{20}$ may each independently comprise or be alkyl groups having 4 to 10 carbon atoms and/or alkyl groups having 4 to 10 carbon atoms where the alkyl chain is interrupted by a thioether linkage, with the proviso that at least some from the set of all groups $R_{18}$, $R_{19}$, and $R_{20}$ in all structure (III) compounds, collectively, may comprise or be alkyl groups having 4 to 10 carbon atoms where the alkyl chain is interrupted by a thioether linkage.

When groups $R_{18}$, $R_{19}$, and $R_{20}$ comprise alkyl groups (in which the alkyl chain is not interrupted by a thioether linkage), examples may include but are not limited to methyl, ethyl, propyl, and butyl, in particular including or being butyl.

When groups $R_{18}$, $R_{19}$, and $R_{20}$ comprise alkyl groups where the alkyl chain is interrupted by a thioether linkage, examples include groups of the structure —R'—S—R" where R' may be $—(CH_2)_n—$, in which n may be an integer from 2 to 4, and where R" may be $—(CH_2)_m—CH_3$, in which m may be an integer from 1 to 15, such as from 1 to 7.

In particular, in the mixture of compounds of structure (III) comprising component (i), at least 10% (e.g., at least 20%, at least 30%, or at least 40%) by mass of the mixture comprises compounds of structure (III) in which at least one of $R_{18}$, $R_{19}$, and $R_{20}$ comprises or is an alkyl group where the alkyl chain is interrupted by a thioether linkage, particularly having the structure —R'—S—R", where R' may be $—(CH_2)_n—$, in which n may be an integer from 2 to 4, and where R" may be $—(CH_2)_m—CH_3$, in which m may be an integer from 1 to 15, such as from 1 to 7.

Component (ii) may advantageously comprise one or more compounds of structures (IV):

(IV)

$$R_{21}—S—R_{22}—O—R_{24}$$

$$R_{21}—S—R_{22}—O—R_{23}—S—R_{24}$$

where groups $R_{21}$ and $R_{24}$ may each independently comprise or be alkyl groups having 1 to 12 carbon atoms, and where $R_{22}$ and $R_{23}$ may each independently comprise or be alkyl linkages having 2 to 12 carbon atoms. In particular, $R_{21}$ and $R_{24}$ may each independently comprise or be $—(CH_2)_m—CH_3$, where m is an integer from 1 to 15, such as from 1 to 7, and $R_{22}$ and $R_{23}$ (if present) may each independently comprise or be $—(CH_2)_n—$, where n is an integer from 2 to 4. The mixture may comprise two or more or three or more compounds of the structures (IV).

In some lubricant embodiments, compounds of structure (III) (Component (i)) and compounds of structure (IV) (Component (ii)) may each be present in the composition in an amount from 0.04 wt % to 1.0 wt %, based on the total weight of the composition, e.g., from 0.05 wt % to 0.8 wt %, from 0.05 wt % to 0.5 wt %, or from 0.07 wt % to 0.4 wt %. Additionally or alternatively, in certain lubricant embodiments, compounds of structure (III) (Component (i)) and compounds of structure (IV) (Component (ii)) may collectively provide the composition with from 80 to 800 parts per million by weight of phosphorous, based on the total weight of the composition, e.g., from 100 to 700 wppm, from 150 to 600 wppm, or from 200 to 500 wppm. Phosphorus content can be measured in accordance with ASTM D5185. Further additionally or alternatively, when present, a mass ratio of compounds of structure (III) (Component (i)) and compounds of structure (IV) (Component (ii)) may be from 2:1 to 1:2, from 5:3 to 3:5, from 3:2 to 2:3, or from 4:3 to 3:4.

Other, sulfur-free ashless antiwear components may include, for example, one or more dihydrocarbyl hydrogen phosphite compounds having the structure H—P(═O)—$(OR^*)_2$, which may be in equilibrium with the structure HO—P—$(OR^*)_2$, in which each R* may independently comprise or be straight, branched, and/or cyclic alkyl, alkenyl, alkynyl, alkadienyl, and/or alkatrienyl groups having 12 to 24 carbon atoms containing no thioether linkages (i.e., different from the phosphorus-containing structures (III) of component (i), in which at least some of the alkyl chains are interrupted by a thioether linkage). For example, each R* alkyl moiety may be the same or different and may each independently comprise straight and/or branched alkyl and/or alkenyl groups having from 14 to 22 carbon atoms (such as from 16 to 18 carbon atoms).

When present, the composition may comprise such sulfur-free dihydrocarbyl hydrogen phosphite compounds in a collective amount from 0.05 wt % to 2.0 wt %, based on the total weight of the composition, e.g., from 0.1 wt % to 1.4 wt %, from 0.2 wt % to 1.0 wt %, or from 0.25 wt % to 0.8 wt %. Additionally or alternatively, in particular, such sulfur-free dihydrocarbyl hydrogen phosphite compounds, when present, may collectively provide the transmission fluid composition with from 35 to 2200 parts per million by weight of phosphorous, based on the total weight of the composition, e.g., from 50 to 2000 wppm, from 100 to 1000 wppm, or from 300 to 750 wppm. Phosphorus content can be measured in accordance with ASTM D5185.

In some embodiments, the non-aqueous 3,4-oxypyridinone composition may comprise substantially no phosphorus-containing and/or sulfur-free ashless antiwear compounds (e.g., any one or more compound of structure (III) or a combination of at least one compound of structure (III) and structure (IV), but one or more compounds of structure (IV) alone is not considered an ashless antiwear compound herein).

In some embodiments, the non-aqueous 3,4-oxypyridinone composition may additionally or alternatively comprise one or more zinc-based phosphorus-containing compounds, such as one or more zinc dihydrocarbyl dithiophosphate compounds. Such compounds are known in the art and often referred to as ZDDP. In other embodiments, the non-aqueous 3,4-oxypyridinone composition may comprise substantially no zinc-based phosphorus-containing compounds or may comprise substantially no ZDDP (in which case other zinc-based phosphorus-containing compounds such as zinc dialkyldithiocarbamates or the like may nonetheless be present).

ZDDP compounds may be prepared in accordance with known techniques, such as by first forming a dihydrocarbyl dithiophosphoric acid (DDPA), usually by reaction of one or more alcohols or a phenol with $P_2S_5$, and then neutralizing the formed DDPA with a zinc compound. For example, a dithiophosphoric acid may be made by reacting mixtures of primary and secondary alcohols. Alternatively, dithiophosphoric acids can be prepared where the hydrocarbyl groups are entirely secondary in character or the hydrocarbyl groups are entirely primary in character. To make the zinc salt, any basic or neutral zinc compound may be used, but oxides, hydroxides, and carbonates are typically employed. Commercial additives, when used, may frequently contain an excess of zinc, due to the use of an excess of the basic zinc compound in the neutralization reaction.

Advantageous zinc dihydrocarbyl dithiophosphates may comprise or be oil-soluble salts of dihydrocarbyl dithiophosphoric acids, such as represented by the following formula:

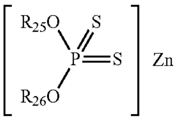

wherein $R_{25}$ and $R_{26}$ may be the same or different hydrocarbyl radicals containing from 1 to 18 (e.g., from 2 to 12 or from 2 to 8) carbon atoms, examples of which hydrocarbyl radicals may include one or more of alkyl, alkenyl, aryl, arylalkyl, alkaryl, and cycloaliphatic radicals. Exemplary hydrocarbyl radicals may comprise or be, but are not necessarily limited to, ethyl, n-propyl, i-propyl, n-butyl, i-butyl, sec-butyl, amyl, n-hexyl, i-hexyl, n-octyl, decyl, dodecyl, octadecyl, 2-ethylhexyl, phenyl, benzyl, butylphenyl, cyclohexyl, methylcyclopentyl, propenyl, butenyl, and combinations thereof. In order to obtain and/or maintain oil solubility, the total number of carbon atoms on each dihydrocarbyl dithiophosphoric acid ligand (i.e., a single $R_{25}$ and $R_{26}$ pair) may generally be at least about 5. In particular, the zinc dihydrocarbyl dithiophosphate can therefore comprise or be a zinc dialkyl dithiophosphate.

When desired, one or more ZDDP compounds may be present in the non-aqueous 3,4-oxypyridinone composition in an amount from 0.4 wt % to 5.0 wt %, based on the total weight of the composition, e.g., from 0.6 wt % to 3.5 wt %, from 1.0 wt % to 3.0 wt %, or from 1.2 wt % to 2.5 wt %. Additionally or alternatively, when present, ZDDP compounds may individually provide the composition with from 300 to 4000 parts per million by weight of phosphorous, based on the total weight of the composition, e.g., from 500 to 2500 wppm, from 750 to 2000 wppm, or from 800 to 1600 wppm. Further additionally or alternatively, when present, ZDDP compounds may individually provide the composition with from 400 to 4500 parts per million by weight of zinc, based on the total weight of the composition, e.g., from 500 to 3000 wppm, from 800 to 2600 wppm, or from 1000 to 2200 wppm. Zinc and phosphorus content can each be measured in accordance with ASTM D5185.

In some embodiments, the non-aqueous 3,4-oxypyridinone composition may further comprise one or more oil-soluble or oil-dispersible molybdenum-containing and/or tungsten-containing compounds, such as an oil-soluble or oil-dispersible organo-molybdenum compound and/or organotungsten compound. In other embodiments, the non-aqueous 3,4-dihydroxypyridinone composition may comprise substantially no oil-soluble or oil-dispersible molybdenum-containing or tungsten-containing compounds.

Non-limiting examples of such oil-soluble or oil-dispersible organo-molybdenum compound may include, but are not necessarily limited to, molybdenum dithiocarbamates, molybdenum dithiophosphates, molybdenum dithiophosphinates, molybdenum xanthates, molybdenum thioxanthates, molybdenum sulfides, and the like, and mixtures thereof, in particular one or more of molybdenum dialkyldithiocarbamates, molybdenum dialkyldithiophosphates, molybdenum alkyl xanthates, and molybdenum alkylthioxanthates. Representative molybdenum alkyl xanthate and molybdenum alkylthioxanthate compounds may be expressed using the formulae of $Mo(R_{27}OCS_2)_4$ and $Mo(R_{27}SCS_2)_4$, respectively, wherein each $R_{27}$ may independently be an organo group selected from the group consisting of alkyl, aryl, aralkyl, and alkoxyalkyl, generally having from 1 to 30 carbon atoms or from 2 to 12 carbon atoms, in particular each being an alkyl group having from 2 to 12 carbon atoms.

In some embodiments, the oil-soluble or oil-dispersible organo-molybdenum compound may comprise a molybdenum dithiocarbamate, such as a molybdenum dialkyldithiocarbamate, and/or may be substantially free from molybdenum dithiosphosphates, in particular from molybdenum dialkyldithiophosphates. In some embodiments, any oil-soluble or oil-dispersible molybdenum compounds may consist of a molybdenum dithiocarbamate, such as a molybdenum dialkyldithiocarbamate, and/or a molybdenum dithiophosphate, such as a molybdenum dialkyldithiophosphate, as the sole source(s) of molybdenum atoms in the composition. In either set of embodiments, when present, the oil-soluble or oil-dispersible molybdenum compound may consist essentially of a molybdenum dithiocarbamate, such as a molybdenum dialkyldithiocarbamate, as the sole source of molybdenum atoms in the composition.

The molybdenum compound, when present, may be mono-, di-, tri-, or tetra-nuclear, in particular comprising or being di-nuclear and/or tri-nuclear molybdenum compounds.

Suitable dinuclear or dimeric molybdenum dialkyldithiocarbamates, for example, can be represented by the following formula:

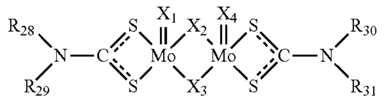

where $R_{28}$ through $R_{31}$ may each independently represent a straight chain, branched chain, or aromatic hydrocarbyl group having 1 to 24 carbon atoms, and where $X_1$ through $X_4$ may each independently represent an oxygen atom or a sulfur atom. The four hydrocarbyl groups, $R_{28}$ through $R_{31}$, may be identical to, or different from, each other.

Suitable tri-nuclear organo-molybdenum compounds may include those having the formula: $Mo_3S_kL_nQ_z$, and mixtures thereof. In such tri-nuclear formula, the three molybdenum atoms may be linked to multiple sulfur atoms (S), with k varying from 4 through 7. Additionally, each L may be an independently selected organic ligand having a sufficient number of carbon atoms to render the compound oil-soluble or oil-dispersible, with n being from 1 to 4. Further, when z is non-zero, Q may be selected from the group of neutral electron donating compounds such as water, amines, alcohols, phosphines, and/or ethers, with z ranging from 0 to 5 and including non-stoichiometric (non-integer) values.

In such tri-nuclear formula, at least 21 total carbon atoms (e.g., at least 25, at least 30, or at least 35) may typically be present among the combination of all ligands ($L_n$). Importantly, however, the organic groups of the ligands may advantageously collectively exhibit a sufficient number of carbon atoms to render the compound soluble or dispersible in the non-aqueous medium. For example, the number of carbon atoms within each ligand L may generally range from 1 to 100, e.g., from 1 to 30 or from 4 to 20.

Tri-nuclear molybdenum compounds having the formula $Mo_3S_kL_nQ_z$ may advantageously exhibit cationic cores surrounded by anionic ligands, such as represented by one or both of the following structures:

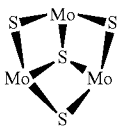 and 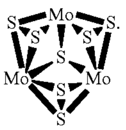

Such cationic cores may each have a net charge of +4 (e.g., due to the oxidation state of the Mo atoms each being+4). Consequently, in order to solubilize these cores, the total charge among all the ligands should correspond, in this case being −4. Four mono-anionic ligands may offer an advantageous core neutralization. Without wishing to be bound by any theory, it is believed that two or more tri-nuclear cores may be bound or interconnected by means of one or more ligands, and the ligands may be multidentate. This includes the case of a multidentate ligand having multiple connections to a single core. Oxygen and/or selenium may be substituted for some portion of the sulfur atoms in either of the cores.

As ligands for the tri-nuclear cores described above, non-limiting examples may include, but are not necessarily limited to, dithiophosphates such as dialkyldithiophosphate, xanthates such as alkylxanthate and/or alkylthioxanthate, dithiocarbamates such as dialkyldithiocarbamate, and combinations thereof, in particular each comprising or being dialkyldithiocarbamate. Additionally or alternatively, the ligands for the tri-nuclear molybdenum-containing cores may independently be one or more of the following:

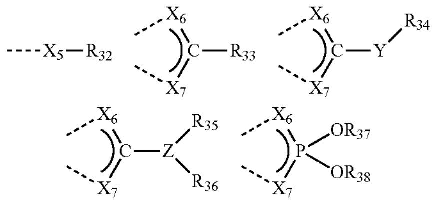

where $X_5$, $X_6$, $X_7$, and Y are each independently oxygen or sulfur, where Z is nitrogen or boron, and wherein $R_{32}$, $R_{33}$, $R_{34}$, $R_{35}$, $R_{36}$, $R_{37}$, and $R_{38}$ are each independently hydrogen or an organic (carbon-containing) moiety, such as a hydrocarbyl group, that may be the same or different from each other, in particular the same. Exemplary organic moieties may include or be alkyl (e.g., in which the carbon atom attached to the remainder of the ligand is primary or secondary), aryl, substituted aryl, alkaryl, substituted alkaryl, aralkyl, substituted aralkyl, an ether, a thioether, or a combination or reaction product thereof, in particular alkyl.

Oil-soluble or oil-dispersible tri-nuclear molybdenum compounds can be prepared by reacting in the appropriate liquid(s)/solvent(s) a molybdenum source such as $(NH_4)_2Mo_3S_{13}\cdot n(H_2O)$, where n varies from 0 to 2 including non-stoichiometric (non-integer) values, with a suitable ligand source, such as a tetralkylthiuram disulfide. Other oil-soluble or dispersible tri-nuclear molybdenum compounds can be formed during a reaction in the appropriate solvent(s) of a molybdenum source such as of $(NH_4)_2Mo_3S_{13}\cdot n(H_2O)$, a ligand source, such as tetralkylthiuram disulfide, a dialkyldithiocarbamate, or a dialkyldithiophosphate, and a sulfur abstracting agent, such as cyanide ions, sulfite ions, or substituted phosphines. Alternatively, a tri-nuclear molybdenum-sulfur halide salt such as $[M']_2[Mo_3S_7A_6]$, where M' is a counter ion and A is a halogen such as Cl, Br, or I, may be reacted with a ligand source such as a dialkyldithiocarbamate or a dialkyldithiophosphate in an appropriate liquid/solvent (system) to form an oil-soluble or oil-dispersible trinuclear molybdenum compound. The appropriate liquid/solvent (system) may be, for example, aqueous or organic.

Other molybdenum precursors may include acidic molybdenum compounds. Such compounds may react with a basic nitrogen compound, as measured by ASTM D-664 or D-2896 titration procedure, and may typically be hexavalent. Examples may include, but are not necessarily limited to, molybdic acid, ammonium molybdate, sodium molybdate, potassium molybdate, and other alkaline metal molybdates and other molybdenum salts, e.g., hydrogen sodium molybdate, $MoOCl_4$, $MoO_2Br_2$, $Mo_2O_3Cl_6$, molybdenum trioxide, or similar acidic molybdenum compounds, or combinations thereof. Thus, additionally or alternatively, the compositions of the present disclosure can be provided with molybdenum, when desired, by molybdenum/sulfur complexes of basic nitrogen compounds as described, for example, in U.S. Pat. Nos. 4,263,152, 4,285,822, 4,283,295, 4,272,387, 4,265,773, 4,261,843, 4,259,195, and 4,259,194, and/or in PCT Publication No. WO 94/06897.

Although molybdenum-containing (and/or tungsten-containing) compounds are described herein as antiwear agents, they may alternatively be characterized as friction modifiers.

When present, molybdenum-containing compounds may be used in the composition in an amount from 0.1 wt % to 2.0 wt %, based on the total weight of the composition, e.g., from 0.1 wt % to 1.5 wt %, from 0.2 wt % to 1.2 wt %, or from 0.2 wt % to 0.8 wt %. Additionally or alternatively, when present, molybdenum-containing compounds may provide the composition with from 50 to 1000 parts per million by weight of molybdenum, based on the total weight of the composition, e.g., from 50 to 800 wppm, from 100 to 650 wppm, or from 100 to 500 wppm. Molybdenum content can be measured in accordance with ASTM D5185.

Friction Modifiers

Although certain organometallic compounds containing molybdenum and/or tungsten may be characterized as antiwear agents or friction modifiers, most other friction modifiers are organic/ashless.

Ashless friction modifiers may include derivatives of polyethylene polyamines and/or ethoxylated long chain amines. The derivatives of polyethylene polyamines may advantageously include succinimides of a defined structure or may be simple amides.

Suitable succinimides derived from polyethylene polyamines may include those of the following structure:

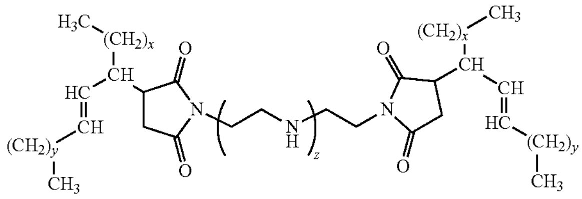

wherein x+y may be from 8 to 15 and z may be 0 or an integer from 1 to 5, in particular wherein x+y may be from 11 to 15 (e.g., 13) and z may be from 1 to 3. More broadly, such friction modifiers can be expressed using the following general structure:

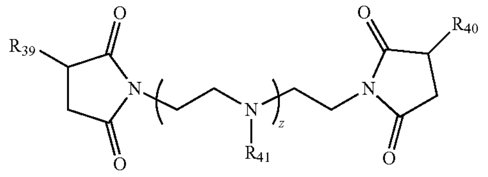

wherein each of $R_{39}$ and $R_{40}$ is independently:

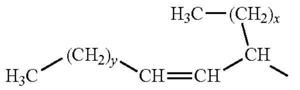

such that x+y is from 8 to 15 (in particular, from 11 to 15, e.g., 13) and z is 0 or an integer from 1 to 5 (in particular, an integer from 1 to 5 or an integer from 1 to 3); and wherein each $R_{41}$ is independently hydrogen, an acetyl moiety, or a moiety formed by reaction between ethylene carbonate and >N—$R_{41}$ (in particular, hydrogen or an acetyl moiety).

Preparation of such friction modifiers is described, for example, in U.S. Pat. No. 5,840,663.

The above succinimides may be post-reacted with acetic anhydride to form friction modifiers in which each $R_{41}$ is independently an acetyl group, as exemplified by the following structure (in which z=1):

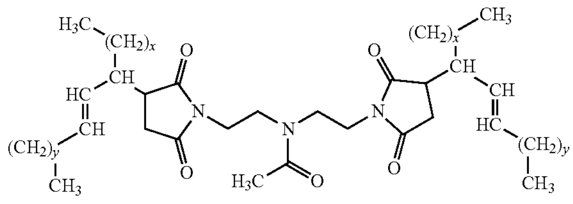

Preparation of this friction modifier, e.g., can be found in U.S. Patent Application Publication No. 2009/0005277. Post reaction with other reagents, e.g., borating agents, is also known in the art.

When present, such succinimide friction modifiers may be used in any effective amount. In lubricant embodiments, they may be used in amounts from 0.1 wt % to 10.0 wt %, based on the total weight of the composition, e.g., from 0.5 wt % to 6.0 wt % or from 2.0 wt % to 5.0 wt %.

An example of an alternative simple amide may have the following structure:

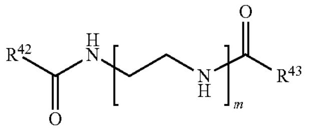

wherein $R^{42}$ and $R^{43}$ may be the same or different alkyl or alkenyl groups. For example, $R^{42}$ and $R^{43}$ may be $C_{14}$ to $C_{20}$ alkyl or alkenyl groups, which may be linear or branched, and m can be an integer from 1 to 5. In particular, $R^{42}$ and $R^{43}$ may both be derived from iso-stearic acid, and m may be 4. Other examples of simple amides may have the structure $R^{42}$—C(═O)—$NH_kR^{43}{}_{2-k}$, wherein k is 0, 1, or 2, and wherein $R^{42}$ and $R^{43}$ may be the same or different alkyl or alkenyl groups, e.g., $C_{14}$ to $C_{20}$ linear or branched alkyl or alkenyl groups; in particular, k can be 2 and $R^{42}$ can be derived from stearic, oleic, linoleic, and/or linolenic acid.

When present, such simple amide friction modifiers may be used in any effective amount. In lubricant embodiments, they may be used in amounts from 0.05 wt % to 5.0 wt %, based on the total weight of the composition, e.g., from 0.08 wt % to 3.0 wt % or from 0.1 wt % to 2.5 wt %.

Suitable ethoxylated amine friction modifiers may include or be reaction products of primary amines and/or diamines with ethylene oxide. The reaction with ethylene oxide may be suitably carried out using a stoichiometry such that substantially all primary and secondary amines may be converted to tertiary amines. Such amines may have the exemplary structures:

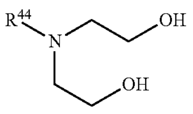

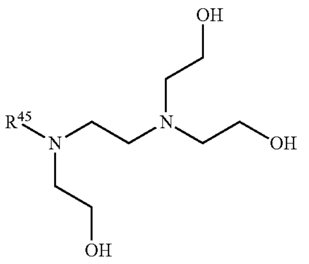

wherein $R^{44}$ and $R^{45}$ may be alkyl groups, or alkyl groups containing sulfur or oxygen linkages, containing from about 10 to 20 carbon atoms. Exemplary ethoxylated amine friction modifiers may include materials in which $R^{44}$ and/or $R^{45}$ may contain from 16 to 20 carbon atoms, e.g., from 16 to 18 carbon atoms. Materials of this type may be commercially available and sold under the tradenames of Ethomeen® and Ethoduomeen® by Akzo Nobel. Suitable materials from Akzo Nobel may include Ethomeen® T/12 and Ethoduomeen® T/13, inter alia.

When present, such ethoxylated amines may be used in any effective amount. In lubricant embodiments, they may be used in amounts from about 0.01 wt % to 1.0 wt %, based on the total weight of the composition, e.g., from 0.05 wt % to 0.5 wt %, or from 0.1 wt % to 0.3 wt %.

Other illustrative friction modifiers than may be used/useful in the compositions described herein include, for example, alkoxylated fatty acid esters, alkanolamides, polyol fatty acid esters, borated glycerol fatty acid esters, fatty alcohol ethers, and mixtures thereof.

Illustrative alkoxylated fatty acid esters include, for example, polyoxyethylene stearate, fatty acid polyglycol ester, and the like. These may include polyoxypropylene stearate, polyoxybutylene stearate, polyoxyethylene isostearate, polyoxypropylene isostearate, polyoxyethylene palmitate, and the like, as well as combinations thereof.

Illustrative alkanolamides include, for example, lauric acid diethylalkanolamide, palmic acid diethylalkanolamide, and the like. These may include oleic acid diethylalkanolamide, stearic acid diethylalkanolamide, oleic acid diethylalkanolamide, polyethoxylated hydrocarbylamides, polypropoxylated hydrocarbylamides, and the like, as well as combinations thereof.

Illustrative polyol fatty acid esters include, for example, glycerol mono-oleate, saturated mono-, di-, and tri-glyceride esters, glycerol mono-stearate, and the like, as well as combinations thereof. These may include polyol esters, hydroxyl-containing polyol esters, and the like.

Illustrative borated glycerol fatty acid esters include, for example, borated glycerol mono-oleate, borated saturated mono-, di-, and tri-glyceride esters, borated glycerol monostearate, and the like, as well as combinations thereof. In addition to glycerol polyols, these can include trimethylolpropane, pentaerythritol, and/or sorbitan. These esters can be polyol monocarboxylate esters, polyol dicarboxylate esters, and on occasion polyoltricarboxylate esters. In some embodiments, preferred can be the glycerol mono-oleates, glycerol dioleates, glycerol trioleates, glycerol monostearates, glycerol distearates, and glycerol tristearates and the corresponding glycerol monopalmitates, glycerol dipalmitates, and glycerol tripalmitates, and the respective isostearates, linoleates, and the like, as well as combinations thereof. Ethoxylated, propoxylated, butoxylated fatty acid esters of polyols, especially using glycerol as underlying polyol may be useful herein.

Illustrative fatty alcohol ethers include, for example, stearyl ether, myristyl ether, and the like. Alcohols, including those that have carbon numbers from $C_3$ to $C_{50}$, can be ethoxylated, propoxylated, or butoxylated to form the corresponding fatty alkyl ethers. The underlying alcohol portion can preferably be stearyl, myristyl, $C_{11}$-$C_{13}$ hydrocarbon, oleyl, isostearyl, and the like.

When present, the composition may comprise one or more friction modifiers collectively ranging from 0.01 wt % to 5 wt %, based on the total weight of the composition, e.g., from 0.1 wt % to 2.5 wt %, from 0.1 wt % to 1.5 wt %, or from 0.1 wt % to 1 wt %. However, in some embodiments, such as those in which the non-aqueous 3,4-oxypyridinone compositions may be used in conjunction with hybrid or fully electric engines, the compositions may optionally contain substantially no (e.g., less than 0.01 wt %, 0.005 wt % or less, no intentionally added, and/or absolutely no) friction modifiers, substantially no ashless friction modifiers, and/or substantially no friction modifiers of the type(s) described herein.

Other Additives

Other additives known in the art may optionally be added to the non-aqueous 3,4-oxypyridine compositions, such as antifoamants, demulsifiers, tackifiers, extreme pressure agents, seal compatibility agents, viscosity modifiers (VMs; a.k.a. viscosity index improvers, or VIIs), pour point depressants, and the like. They are typically disclosed in, for example, "Lubricant Additives" by C. V. Smallheer and R. Kennedy Smith, 1967, pp 1-11. Additionally or alternatively, whether fitting within these classes or those listed previously, the non-aqueous 3,4-oxypyridine compositions may contain ashless dihydrocarbyl dithiocarbamates (e.g., 4,4'-methylenebis(dibutyl-dithiocarbamate)s such as those commercially available under the tradename Vanlube® 7723 from Vanderbilt Chemicals of Norwalk, CT, USA), $C_8$-$C_{18}$ acrylates (e.g., lauryl acrylate), $C_2$-$C_6$ dialkylene glycol diesters (e.g., dipropylene glycol dibenzoate), $C_{12}$-$C_{24}$ alkenes (e.g., hexadecane), hydroxyalkylimidazolines (e.g., hydroxyethyl-imidazolines such as commercially available under the tradenames Imidazoline-12-OH™ and Imidazoline-18-OH™ from Lakeland Chemicals of Mumbai, India), and the like, as well as combinations thereof. Nevertheless, in some embodiments, the non-aqueous 3,4-oxypyridinone compositions may contain substantially none of (e.g., less than 0.001 wt % of, 0.0005 wt % or less of, no intentionally added, and/or absolutely none of) antifoamants, demulsifiers, extreme pressure agents, seal compatibility agents, viscosity modifiers, pour point depressants, and/or combinations of two, three, four, five, or all of these.

Lubricant/Coolant Compositions

As mentioned herein, lubricant and/or coolant compositions according to the present disclosure can comprise a 3,4-oxypyridone of structure (I) and a non-aqueous medium such as a Group I, Group II, Group III, Group IV, and/or Group V lubricating oil basestock, and optionally one or more (additional) additives, such as an antioxidant (e.g., an optionally substituted diaryl amine, a hindered phenol, or a combination thereof). Such lubricant and/or coolant compositions can advantageously exhibit an antioxidative synergy.

That antioxidative synergy can be manifest in any number of ways. One such way can involve performance in a CEC L-109(-14) oxidation test. The CEC L-109(14) oxidation test involves measurements of oxidation in the presence of an iron catalyst (Fe(III)Acac) and biofuel by analytical (e.g., FTIR) peak height according to DIN 51 453 and also of kinematic viscosities such as KV100 according to ASTM D445. Any deviations in sample testing from the CEC L-109-14 standard procedures is noted herein. A sample at 0 hours, or immediately before the CEC L-109 oxidation test begins, is considered an SOT (start of test) sample. A sample subject to the CEC L-109 oxidation test for ~216 hours at temperature is considered an EOT (end of test) sample, although in some cases the test is stopped at ~168 hours (which would be noted), at which point that value would be considered an EOT sample. Where there were at least two (or at least three) measurements of kinematic viscosity measurements in the CEC L-109(-14) tests herein (such as KV100), the reported values represent average values. All values are abbreviated as average values herein regardless of whether they are one value or multiples.

Another such way can involve performance in a TOC oxidation test according to standard test method D55 3099 (2016). This oxidation test involves measurement of oxidation in the presence of ~360 ppm of iron at ~170° C. in the presence of air flowing at ~10 L/h. A sample at 0 hours, or immediately before the TOC oxidation test begins, is considered an SOT (start of test) sample. Samples are also taken at ~16 hours, ~96 hours, optionally ~136 hours, and optionally ~168 hours. In some cases the test may be modified to be stopped after taking the ~96-hour sample. KV40 percent increase from start of test and KV100 percent increase from start of test can be of particular interest.

Still another such way can involve performance in an oxidation test in a heavy exhaust gas recycle (EGR) diesel engine with variable geometry turbocharging (VGT) for at least ~360 hours (and optionally for at least ~420 hours). This test is a fuel engine-dynamometer test which can evaluate the ability of a composition to minimize piston ring wear, cylinder liner wear, lead corrosion, "oil" consumption, oxidation and nitration. This test is a single phase, steady state test (constant speed and load), run with heavy EGR.

The test engine may be an in-line six-cylinder, four stroke Volvo D13 diesel or Mack MP8 engine with EGR and VGT, with electronically controlled fuel injection from six individual electronic pumps. A break-in may be conducted prior to each test according to the procedure since a new engine build is used for each test. In this case, oxidation performance can be inferred from measurements of KV40 at various intervals, as viscosity growth is believed to be significantly influenced (catalyzed) by oxidation phenomena.

| Parameter | | | |
|---|---|---|---|
| Time, h | 360 | Tailpipe Temp., ° C. | Record |
| Speed, r/min | 1500 | Main Gallery Oil Pressure kPa | Record |
| Fuel flow kg/h | 68 | Oil Sump Temp., ° C. | Record |
| Coolant Out Temp., ° C. | 110 | Oil Jet Temp., ° C. | Record |
| Oil Gallery Temp., ° C. | 130 | Oil Jet Pressure, kPa | Record |
| Inlet Air Temp., ° C. | 30 | Fuel Gallery Temp., ° C. | Record |
| Inlet Manifold Temp., ° C. | 78 | Fuel Gallery Pressure, kPa | Record |
| EGR Gas Out Temp., ° C. | 120 | Intercooler Out Temp., ° C. | Record |
| Fuel In Temp., ° C. | 35 | Intercooler Out Pressure, kPa | Record |
| Inlet Air Pressure, kPaA | 94 | Compressor Out Temp, ° C. | Record |
| Inlet Manifold Pressure, kPaG | 232 ± 5 | Compressor Out Pressure, kPa | Record |
| Intake $CO_2$ | 2.01 to 2.11 | Room Temp., ° C. | Record |
| Engine Coolant Blanket Pressure, kPaG | 99 to 107 | EGR Position, % | Record |
| EGR Coolant Blanket Pressure, kPaG | 99 to 140 | VGT Position, % | Record |
| Crankcase Pressure, kPa | −0.3 to 0.3 | Throttle Position, % | Record |
| Load, N-m | 2200 | Blowby, L/min | Record |
| Exhaust, CO2, % | Record | Inlet Air Dew Point, ° C. | Record |
| Coolant In Temp., ° C. | Record | | |
| Crankcase Pressure, kPa | Record | | |
| Pre-Turpine Temp. (F.), ° C. | Record | | |
| Pre-Turpine Temp. (R), ° C. | Record | | |

Although the base conditions delineated in the table above show a ~360-hour run time, it is contemplated that the test can be run for longer, e.g., ~420 hours as mentioned above.

In advantageous embodiments, when subject to a CEC L-109 oxidation test for at least ~168 hours at ~150° C. (e.g., for ~168 hours and/or ~216 hours at ~150° C.), or for at least ~200 hours at ~150° C. (e.g., for ~216 hours at ~150° C.), a lubricant and/or coolant formulation containing a 3,4-oxypyridone compound according to the present disclosure may exhibit an increase in a value of kinematic viscosity at ~100° C. (KV100) that is at most 60% above (e.g., at most 55% above, at most 50% above, at most 45% above, at most 40% above, at most 35% above, at most 30% above, at most 25% above, at most 20% above, at most 15% above, at most 10% above, at most 5% above, or equal to or less than; in particular, at most 50% above, at most 40% above, at most 30% above, or at most 10% above) a KV100 value from the same lubricant composition immediately before the CEC L-109 oxidation test began (0 hours; a.k.a. the SOT sample). In this context, KV100 decreases can be considered negative KV100 increases, such that, e.g., a KV100 decrease of ~10% should be understood as a ~−10% KV100 increase, which would thus be included in a range of KV100 increases that are at most 5%, for example.

Additionally or alternatively, in advantageous embodiments, when subject to a CEC L-109 oxidation test for at least ~168 hours at ~150° C. (e.g., for ~168 hours and/or ~216 hours at ~150° C.), or for at least ~200 hours at ~150° C. (e.g., for ~216 hours at ~150° C.), a lubricant and/or coolant formulation containing a 3,4-oxypyridone compound according to the present disclosure may exhibit an increase in a value of kinematic viscosity at ~100° C. (KV100) that is at least 10% below (e.g., at least 12% below, at least 13% below, at least 15% below, at least 20% below, at least 25% below, at least 30% below, at least 35% below, at least 40% below, at least 45% below, at least 50% below, at least 55% below, at least 60% below, at least 70% below, at least 80% below, or at least 90% below; in particular, at least 30% below, at least 35% below, at least 50% below, or at least 80% below) a KV100 value from a comparative composition that was subject to the CEC L-109 oxidation test for an identical time period. In this context, the KV100 increase of the 3,4-oxypyridone-containing ("inventive") composition at a specific time period is assessed in reference to its identical SOT sample (a.k.a. its $DKV_i^{100° C.}$, where subscript "i" is the specific time period), and the KV100 increase of the comparative composition at a specific time period is also assessed in reference to its identical SOT sample (its $DKV_i^{100° C.}$, at the same time period "i"), such that the KV100 increase in this expression is approximated by the difference between the inventive and comparative $DKV_i^{100° C.}$ values. Also in this context, the comparative composition: (a) comprises only either or both of the optionally substituted diaryl amine and hindered phenol antioxidants and not the 3,4-oxypyridinone of structure (I); and (b) comprises the optionally substituted diaryl amine and hindered phenol antioxidants in an identical weight ratio to the inventive composition, and comprises a collective amount of the optionally substituted diaryl amine and hindered phenol antioxidants that is identical to the sum of the amounts of optionally substituted diaryl amine antioxidant, hindered phenol antioxidant, and 3,4-oxypyridinone of structure (I) in the inventive composition.

Further additionally or alternatively, in advantageous embodiments, when subject to a CEC L-109 oxidation test for less than 175 hours at ~150° C. (e.g., for ~72 hours, ~144 hours and/or ~168 hours at ~150° C.), a lubricant and/or coolant formulation containing a 3,4-oxypyridone compound according to the present disclosure may exhibit an increase in a value of oxidation peak height (e.g., according to DIN 51 453, as specified in the CEC L-109-14 standards) that is at all points at most 70% above (e.g., at most 65% above, at most 60% above, at most 55% above, at most 50% above, at most 45% above, at most 40% above, at most 35% above, at most 30% above, at most 25% above, at most 15% above, or at most 5% above; in particular, at most 55% above, at most 45% above, at most 40% above, or at most 35% above) an oxidation peak height value from the same lubricant composition immediately before the CEC L-109 oxidation test began (0 hours; a.k.a. the SOT sample). In this context, oxidation peak height decreases can be considered negative oxidation peak height increases, such that, e.g., an oxidation peak height decrease of ~10% should be understood as about a −10% oxidation peak height increase.

Still further additionally or alternatively, in advantageous embodiments, when subject to a CEC L-109 oxidation test for less than 175 hours at ~150° C. (e.g., for ~72 hours, ~144 hours and/or ~168 hours at ~150° C.), a lubricant and/or coolant formulation containing a 3,4-oxypyridone compound according to the present disclosure may exhibit an increase in a value of oxidation peak height (e.g., according to DIN 51 453, as specified in the CEC L-109-14 standards) that is at all points at least 40% below (e.g., at least 45% below, at least 50% below, at least 55% below, at least 60% below, at least 65% below, at least 70% below, or at least 75% below; in particular, at least 45% below, at least 55% below, or at least 60% below) an oxidation peak height value from a comparative composition that was subject to the CEC L-109 oxidation test for an identical time period. In this context, the oxidation peak height increase of the 3,4-oxypyridone-containing ("inventive") composition at a specific time period is assessed in reference to its identical SOT sample (a.k.a. its $DOPH_i$, where subscript "i" is the specific time period), and the oxidation peak height increase of the comparative composition at a specific time period is also assessed in reference to its identical SOT sample (its $DOPH_i$, at the same time period "i"), such that the oxidation peak height increase in this expression is approximated by the difference between the inventive and comparative $DOPH_i$ values. Also in this context, the comparative composition: (a) comprises only the 3,4-oxypyridinone of structure (I) and neither of the optionally substituted diaryl amine and hindered phenol antioxidants; and (b) comprises an amount of the 3,4-oxypyridinone of structure (I) that is identical to the sum of the amounts of optionally substituted diaryl amine antioxidant, hindered phenol antioxidant, and 3,4-oxypyridinone of structure (I) in the inventive composition.

Even further additionally or alternatively, in advantageous embodiments, when subject to a TOC oxidation test according to standard test method D55 3099 for at least 4 days at ~170° C. (e.g., for at least ~96 hours), a lubricant and/or coolant formulation containing a 3,4-oxypyridone compound according to the present disclosure may exhibit an increase in a value of kinematic viscosity at ~40° C. (KV40) that is at most 15% above (e.g., at most 10% above, at most 5% above, about equal to or less than, at least 5% below, at least 10% below, at least 15% below, at least 20% below, at least 25% below, or at least 20% below; in particular, at most 5% above, at least 10% below, or at least 20% below) a KV40 value from the same lubricant composition immediately before the TOC oxidation test began (0 hours; a.k.a. the SOT sample). In this context, KV40 decreases can be considered negative KV40 increases, such that, e.g., a KV40 decrease of ~15% should be understood as a ~−15% KV40 increase, which would thus be included in a range of KV40 increases that are at most 10%, for example.

Yet further additionally or alternatively, in advantageous embodiments, when subject to a TOC oxidation test according to standard test method D55 3099 for at least 4 days at ~170° C. (e.g., for at least ~96 hours), a lubricant and/or coolant formulation containing a 3,4-oxypyridone compound according to the present disclosure may exhibit an increase in a value of kinematic viscosity at ~40° C. (KV40) that is at least 15% below (e.g., at least 20% below, at least 25% below, at least 30% below, at least 35% below, at least 40% below, at least 45% below, at least 50% below, at least 55% below, at least 60% below, at least 70% below, at least 80% below, or at least 90% below; in particular, at least 30% below, at least 35% below, at least 50% below, or at least 80% below) a KV40 value from a comparative composition that was subject to the TOC oxidation test for an identical time period. In this context, the KV40 increase of the 3,4-oxypyridone-containing ("inventive") composition at a specific time period is assessed in reference to its identical SOT sample, and the KV40 increase of the comparative composition at a specific time period is also assessed in reference to its identical SOT sample, such that the KV40 increase in this expression is approximated by the difference between the inventive and comparative KV40 differential values. Also in this context, the comparative composition: (a) comprises only either or both of the optionally substituted diaryl amine and hindered phenol antioxidants and not the 3,4-oxypyridinone of structure (I); and optionally (b) comprises the optionally substituted diaryl amine and hindered phenol antioxidants in an identical weight ratio to the inventive composition, and comprises a collective amount of the optionally substituted diaryl amine and hindered phenol antioxidants that is identical to the sum of the amounts of optionally substituted diaryl amine antioxidant, hindered phenol antioxidant, and 3,4-oxypyridinone of structure (I) in the inventive composition.

Even still further additionally or alternatively, in advantageous embodiments, when subject to a TOC oxidation test according to standard test method D55 3099 for at least 4 days at ~170° C. (e.g., for at least ~96 hours), a lubricant and/or coolant formulation containing a 3,4-oxypyridone compound according to the present disclosure may exhibit a decrease in a value of viscosity index (VI) that is at most 30% below (e.g., at most 25% below, at most 20% below, at most 15% below, or at most 10% below; in particular, at most 5% above, at least 10% below, or at least 20% below) a VI value from the same lubricant composition immediately before the TOC oxidation test began (0 hours; a.k.a. the SOT sample).

Yet still further additionally or alternatively, in advantageous embodiments, when subject to a TOC oxidation test according to standard test method D55 3099 for at least 4 days at ~170° C. (e.g., for at least ~96 hours), a lubricant and/or coolant formulation containing a 3,4-oxypyridone compound according to the present disclosure may exhibit an increase in a value of viscosity index (VI) that is at least 15% below (e.g., at least 20% below, at least 25% below, at least 30% below, at least 35% below, at least 40% below, at least 45% below, at least 50% below, at least 55% below, at least 60% below, at least 70% below, at least 80% below, or at least 90% below; in particular, at least 30% below, at least 35% below, at least 50% below, or at least 80% below) a VI value from a comparative composition that was subject to the TOC oxidation test for an identical time period. In this context, the VI increase of the 3,4-oxypyridone-containing ("inventive") composition at a specific time period is assessed in reference to its identical SOT sample, and the VI increase of the comparative composition at a specific time period is also assessed in reference to its identical SOT sample, such that the VI increase in this expression is approximated by the difference between the inventive and comparative VI differential values. Also in this context, the comparative composition: (a) comprises only either or both of the optionally substituted diaryl amine and hindered phenol antioxidants and not the 3,4-oxypyridinone of structure (I); and optionally (b) comprises the optionally substituted diaryl amine and hindered phenol antioxidants in an identical weight ratio to the inventive composition, and comprises a collective amount of the optionally substituted diaryl amine and hindered phenol antioxidants that is identical to the sum of the amounts of optionally substituted diaryl amine antioxidant, hindered phenol antioxidant, and 3,4-oxypyridinone of structure (I) in the inventive composition.

Yet even further additionally or alternatively, in advantageous embodiments, when subject to an oxidation test in a heavy exhaust gas recycle (EGR) diesel engine with variable geometry turbocharging (VGT) for up to ~420 hours, a lubricant and/or coolant formulation containing a 3,4-oxypyridone compound according to the present disclosure may exhibit an increase in a value of kinematic viscosity at ~40° C. (KV40) that is, after ~360 hours, at most 2 cSt above (e.g., at most 1.8 cSt above, at most 1.7 cSt above, at most 1.6 cSt above, at most 1.5 cSt above, at most 1.4 cSt above, at most 1.3 cSt above, or at most 1.2 cSt above; in particular, at most 1.7 cSt above, at most 1.5 cSt above, or at most 1.4 cSt above) a KV40 value from the same lubricant composition immediately before the diesel engine oxidation test began (0 hours; a.k.a. the SOT sample). In this context, KV40 decreases can be considered negative KV40 increases, such that, e.g., a KV40 decrease of ~1 cSt should be understood as a ~−1 cSt KV40 increase, which would thus be included in a range of KV40 increases that are at most 0.5 cSt, for example.

Yet even still further additionally or alternatively, in advantageous embodiments, when subject to an oxidation test in a heavy exhaust gas recycle (EGR) diesel engine with variable geometry turbocharging (VGT) (such as in a Volvo™ T13 engine) for up to ~420 hours, a lubricant and/or coolant formulation containing a 3,4-oxypyridone compound according to the present disclosure may exhibit an increase in a value of kinematic viscosity at ~40° C. (KV40) that is, after at least 336 hours, at least 5% below (e.g., at least 10% below, at least 12% below, at least 13% below, at least 15% below, at least 20% below, at least 25% below, or at least 30% below; in particular, at least 10% below, at least 12% below, or at least 13% below) a KV40 value from a comparative composition that was subject to the diesel engine oxidation test for an identical time period. In this context, the comparative composition: (a) comprises only either or both of the optionally substituted diaryl amine and hindered phenol antioxidants and not the 3,4-oxypyridinone of structure (I); and optionally (b) comprises the optionally substituted diaryl amine and hindered phenol antioxidants in an identical weight ratio to the inventive composition, and comprises a collective amount of the optionally substituted diaryl amine and hindered phenol antioxidants that is identical to the sum of the amounts of optionally substituted diaryl amine antioxidant, hindered phenol antioxidant, and 3,4-oxypyridinone of structure (I) in the inventive composition.

As mentioned herein, lubricant and/or coolant compositions according to the present disclosure can comprise a 3,4-oxypyridone of structure (I) and a non-aqueous medium such as comprising a Group I, Group II, Group III, Group IV, and/or Group V lubricating oil basestock (e.g., comprising a Group I, Group II, and/or Group III lubricating oil basestock), and optionally one or more (additional) additives, such as an antiwear compound (e.g., a zinc-based phosphorus-containing compound such as a ZDDP, an oil-soluble or oil-dispersible molybdenum-containing and/or tungsten-containing compound, a sulfur- and phosphorus-containing reaction product comprising both components (i) (two or more compounds of structures (III)) and (ii) (one or more compounds of structures (IV)), or a combination thereof), a friction modifier such as an organic friction modifier, or a combination thereof. Such lubricant and/or coolant compositions can advantageously exhibit an antiwear synergy. Closely related to antiwear performance is frictional performance. Therefore, such lubricant and/or coolant compositions may additionally or alternatively exhibit a frictional synergy. In some circumstances, desirable antiwear and/or desirable frictional performance can be achieved solely through compositions containing the 3,4-oxypyridone of structure (I) but containing substantially no antiwear component(s), substantially no friction modifier(s), and/or substantially no organic friction modifier(s).

That antiwear and/or frictional synergy can be manifest in any number of ways. One such way can involve performance in a high-frequency reciprocating rig (HFRR) antiwear/friction test. An HFRR device is commercially available from PCS Instruments, London, UK, and typically runs AUTOHFR software (v2.0 represents operation under PCS4 user manual). This device employs a ~6 mm diameter ball as an upper specimen which is reciprocated under an applied load against a lower specimen in the form of a ~10 mm diameter×~3 mm thick disc. The ball and disc are made of AISI 52100 polished steel (and must have their antirust coating removed before testing). Test conditions are as follows: reciprocating frequency ~40 Hz; stroke length ~1 mm; applied load ~400 g; and contact pressure ~1 GPa. Samples are analyzed at temperatures ranging from ~40° C. to ~140° C. Sample runs commence when a Sample is held at ~40° C. for ~1 min, subject to test conditions for ~5 mins, ramped at ~5-15° C./min up another ~20° C., held at that increased temperature for ~1 min, and the cycle repeated every ~20° C. up to ~140° C., after which the temperature is ramped down to room temperature (~20-25° C.). Under those conditions, wear scars were typically formed. The wear scars on the upper ball specimens were measured with the ball located in the holder using an optical microscope with a calibrated micrometer. This was reported herein as an average wear scar diameter (WSD, based on a simple average of longest and shortest lengths of the wear scar) in units of mm. The wear scars on the lower disc specimens were analyzed using a ZeScope™ 3D optical profilometer (commercially available from Zemetrics Inc. of Tucson, AZ, USA) using non-contact interferometric focal scanning. With proper calibration, profilometry techniques can enable measurement of the amount of wear by determining the material lost from the disc during the test. This was reported herein as a wear scar volume (WSV) in units of $mm^3$. The HFRR device can be (and the PCS device is) equipped with a piezoelectric transducer that can measure the average friction coefficient between the ball and the disc. Average wear scar diameter, average wear scar volume, and average friction coefficient reported herein represent an average of at least two or at least three (in particular, two or three) measurements from separate HFRR tests.

Another such way can involve performance in a motored friction B48 test. Motored friction B48 tests can be done over a range of temperatures and across a range of rpm rates, collectively simulating a variety of engine conditions. In these B48 tests, an electric motor provides a turning force to the engine crankshaft via a drive shaft and optional flywheel. The resultant torque can be measured and recorded at a number of steady state engine speed and fluid temperature setpoints by a torque meter mounted inline on the drive shaft. These torque measurements can then be compared to standard and/or control samples. Different arrays of operational setpoint conditions can be weighted, interpolated, and/or combined, based on desired or common features of different emission drive cycles, to approximate an overall fuel economy. Within each array of operational setpoints, lower measured torque values correlate to quantifiable increases in fuel economy, which may be expressed as percentage improvements or percentage declines, relative to a standard or control sample.

Yet another such way can involve performance in a Sequence X timing chain wear test. The Sequence X timing chain wear test is a fired engine dynamometer lubricant test, which can evaluate the ability of a test lubricant to inhibit (or reduce, with respect to a control or reference lubricant) timing chain wear. The test method is a cyclic test, with a total running duration of up to ~216 hours, but which can optionally run for longer, as desired. Sequence X can be run on a water-cooled, 4-cycle, in-line cylinder, 2.0-liter Ford EccoTech engine as the test apparatus. The Ford engine incorporates a dual overhead cam, four valves per cylinder (2 intake; 2 exhaust), and direct acting mechanical bucket lifter valve train design. The timing chain is replaced before each test. An ~8-hour break-in schedule is conducted prior to going on test conditions. ASTM D8279 provides a standard method, although modifications thereto are contemplated. The timing chain is measured prior to installation, after break-in and/or every ~24 hours, and at the end of test. The test sequence is typically repeated for 54 test cycles. Each cycle consists of two stages as outlined in the table below.

| Parameter | Units | Stage 1 | Stage 2 |
|---|---|---|---|
| Duration | min | 12 | 60 |
| Engine Speed | r/min | 1550 | 2500 |
| Engine Torque | N · m | 50 | 128 |
| Oil Gallery Temperature | ° C. | 50 | 100 |
| Coolant Out Temperature | ° C. | 45 | 85 |
| Coolant Flow | L/min | 40 | 70 |
| Intake Air Temperature | ° C. | 32 | 32 |
| Intake Air Pressure | kPa | 0.05 | 0.05 |
| Intake Air Humidity | g/kg | 11.4 | 11.4 |
| Coolant Pressure | kPa | 70 | 70 |
| Air Charge Temperature | ° C. | 30 | 30 |
| Air Fuel Ratio | λ | 0.78 | 1 |
| Exhaust Backpressure | kPa | 104 | 107 |
| Blowby Outlet Temperature | ° C. | 20 | 85 |

In advantageous embodiments, when subject to a high frequency reciprocating rig (HFRR) at temperatures from ~40° C. to ~140° C., a lubricant and/or coolant formulation containing a 3,4-oxypyridone compound according to the present disclosure may exhibit a decrease in average friction coefficient value at high temperatures (e.g., from ~80° C. to ~140° C., from ~85° C. to ~140° C., from ~90° C. to ~140° C., from ~95° C. to ~140° C., or from ~100° C. to ~140° C.; in particular from ~90° C. to ~140° C. or from ~100° C. to ~140° C.) that are at least 0.012 below (e.g., at least 0.014 below, at least 0.016 below, at least 0.018 below, or at least 0.020 below; in particular, at least 0.012 below, at least 0.014 below, or at least 0.018 below) an average friction coefficient value from a comparative composition that was subject to the HFRR at identical temperatures for an identical time period, wherein the comparative composition comprises only a zinc dialkyldithiophosphate antiwear agent and not the 3,4-oxypyridinone of structure (I) and/or only the 3,4-oxypyridinone of structure (I) and no zinc dialkyldithiophosphate antiwear agent.

Additionally or alternatively, when subject to a high frequency reciprocating rig (HFRR) at temperatures of ~140° C., a lubricant and/or coolant formulation containing a 3,4-oxypyridone compound according to the present disclosure may exhibit (i) a decrease in average wear scar void volume value that is at least 10% below (e.g., at least 15% below, at least 20% below, at least 25% below, at least 30% below, at least 35% below, at least 40% below, at least 45% below, at least 50% below, at least 55% below, at least 60% below, or at least 65% below; in particular, at least 15% below, at least 25% below, at least 50% below, or at least 60% below) a wear scar void volume value from a comparative composition that was subject to the HFRR at identical temperatures for an identical time period, and/or (ii) a decrease in average wear scar diameter value that is at least 9% below (e.g., at least 10% below, at least 12% below, at least 15% below, at least 18% below, at least 20% below, at least 22% below, or at least 25% below; in particular, at least 10% below, at least 12% below, at least 20% below, or at least 25% below) a wear scar diameter value from a comparative composition that was subject to the HFRR at identical temperatures for an identical time period, wherein the comparative composition comprises only a zinc dialkyldithiophosphate antiwear agent and not the 3,4-oxypyridinone of structure (I) and/or only the 3,4-oxypyridinone of structure (I) and no zinc dialkyldithiophosphate antiwear agent.

Further additionally or alternatively, when subject to a high frequency reciprocating rig (HFRR) at temperatures of ~140° C., a lubricant and/or coolant formulation containing a 3,4-oxypyridone compound according to the present disclosure may exhibit (i) a decrease in average wear scar void volume value that is at least 10% below (e.g., at least 12% below, at least 14% below, at least 15% below, at least 16% below, at least 18% below, at least 20% below, or at least 22% below; in particular, at least 12% below, at least 15% below, or at least 20% below) a wear scar void volume value from a comparative composition that was subject to the HFRR at identical temperatures for an identical time period, and/or (ii) a decrease in average wear scar diameter value that is at least 2.5% below (e.g., at least 3% below, at least 3.5% below, at least 5% below, at least 7.5% below, at least 10% below, at least 12.5% below, at least 15% below, or at least 17.5% below; in particular, at least 3% below, at least 3.5% below, at least 10% below, or at least 15% below) a wear scar diameter value from a comparative composition that was subject to the HFRR at identical temperatures for an identical time period, wherein the comparative composition comprises only an organic friction modifier and not the 3,4-oxypyridinone of structure (I) and/or only the 3,4-oxypyridinone of structure (I) and no organic friction modifier. In such embodiments, the lubricant and/or coolant formulation may exhibit a weight ratio of organic friction modifier to 3,4-oxypyridinone of structure (I) from 15:1 to 2.5:1, from 10:1 to 3:1, or from 9:1 to 4:1; in particular, from 10:1 to 3:1 or from 9:1 to 4:1.

Still further additionally or alternatively, when subject to a high frequency reciprocating rig (HFRR) at temperatures from ~40° C. to ~140° C., a lubricant and/or coolant formulation containing a 3,4-oxypyridone compound according to the present disclosure may exhibit an average friction coefficient value that is from 0.080 to 0.115 and lower than an average friction coefficient value from a comparative composition that was subject to the HFRR at identical temperatures for an identical time period, wherein the comparative composition comprises an amount of only organic friction modifier equal to the combined amount of organic friction modifier and the 3,4-oxypyridinone of structure (I) in the inventive composition. In such embodiments, the lubricant and/or coolant formulation may exhibit a weight ratio of organic friction modifier to 3,4-oxypyridinone of structure (I) from 9:1 to 1:1, from 8:1 to 4:3, or from 5:1 to 3:2; in particular, from 8:1 to 4:3 or from 5:1 to 3:2.

Yet further additionally or alternatively, when subject to a high frequency reciprocating rig (HFRR) at temperatures from ~40° C. to ~140° C., a lubricant and/or coolant formulation containing a 3,4-oxypyridone compound according to the present disclosure may exhibit a decrease in average friction coefficient value (i) at all temperatures that is at least 0.01 below (e.g., at least 0.015 below, at least 0.018 below, at least 0.02 below, at least 0.022 below, at least 0.025 below, or at least 0.03 below) an average friction coefficient value from a comparative composition that was subject to the HFRR at identical temperatures for an identical time period, and (ii) at moderate-to-high temperatures (e.g., from ~70° C. to ~140° C., from ~75° C. to ~140° C., from ~80° C. to ~140° C., from ~85° C. to ~140° C., or from ~90° C. to ~140° C.; in particular from ~80° C. to ~140° C. or from ~90° C. to ~140° C.) that is at least 0.05 below (e.g., at least 0.055 below, at least 0.06 below, at least 0.065 below, or at least 0.07 below; in particular, at least 0.0055 below, at least 0.06 below, or at least 0.07 below) an average friction coefficient value from a comparative composition that was subject to the HFRR at identical temperatures for an identical time period, wherein the comparative composition comprises substantially no 3,4-oxypyridinone of structure (I) and also substantially no friction modifier.

Even further additionally or alternatively, when subject to a motored friction B48 fuel economy test, a lubricant and/or coolant formulation containing a 3,4-oxypyridone compound according to the present disclosure may exhibit at least a 0.4% (e.g., at least a 0.5%, at least a 0.6%, at least a 0.7%, or at least a 0.8%; in particular at least a 0.5% or a 0.7%) fuel economy improvement over an identical composition comprising no 3,4-oxypyridinone compound of structure (I).

Even still further additionally or alternatively, when subject to a Sequence X timing chain wear test for at least 216 hours according to ASTM D8279, a lubricant and/or coolant formulation containing a 3,4-oxypyridone compound according to the present disclosure may exhibit (i) for times from ~72 hours to ~216 hours, a decrease in average timing chain elongation value of at least 15% below (e.g., at least 20% below, at least 25% below, at least 30% below, at least 35% below, at least 40% below, or at least 45% below; in particular, at least 25% below, at least 30% below, or at least 40% below) an average timing chain elongation value from a comparative composition that was subject to the Sequence X timing chain wear test for an identical time period, and/or (ii) at ~120 hours, a decrease in average timing chain elongation value of at least 30% below (e.g., at least 35% below, at least 40% below, at least 45% below, at least 50% below, or at least 55% below; in particular, at least 40% below, at least 45% below, or at least 55% below) an average timing chain elongation value from a comparative composition that was subject to the Sequence X timing chain wear test for an identical time period, wherein the comparative composition comprises only a zinc dialkyldithiophosphate antiwear agent and not the 3,4-oxypyridinone of structure (I).

As mentioned herein, lubricant and/or coolant compositions according to the present disclosure can comprise a 3,4-oxypyridone of structure (I) and a non-aqueous medium such as comprising a Group I, Group II, Group III, Group IV, and/or Group V lubricating oil basestock (e.g., comprising a Group I, Group II, and/or Group III lubricating oil basestock), and optionally one or more (additional) additives, such as a corrosion inhibitor (e.g., an optionally substituted triazole corrosion inhibitor, an optionally substituted benzotriazole corrosion inhibitor, an optionally substituted thiadiazole corrosion inhibitor, an ashless dihydrocarbyl dithiocarbamate, a $C_8$-$C_{18}$ acrylate, a $C_2$-$C_6$ dialkylene glycol diester, a tri-hydrocarbyl $C_1$-$C_8$ borate corrosion inhibitor, or a combination thereof). Such lubricant and/or coolant compositions can advantageously exhibit an anticorrosion synergy. Closely related to anticorrosion performance are increases in (or high absolute values of) total acid number (TAN) and/or decreases in (or low absolute values of) total base number (TBN). Therefore, such lubricant and/or coolant compositions may additionally or alternatively exhibit an anticorrosion synergy. Because 3,4-oxypyridinones of structure (I) may exacerbate certain types of corrosion (e.g., copper, lead, tin, and/or bronze; in particular, copper and/or lead) in certain situations, sometimes to a large degree, even relatively small increases in corrosion or significant mitigations of relatively large increases in corrosion can be viewed as a "synergy." In some circumstances, desirable (copper and/or lead) corrosion performance can be achieved solely through compositions containing the 3,4-oxypyridone of structure (I) but containing substantially no corrosion inhibitor component(s); however, more often, acceptable (copper and/or lead) corrosion performance can be achieved through particular combinations of the 3,4-oxypyridone of structure (I) with certain (or certain mixtures of) corrosion inhibitors, which may optionally include other components.

That anticorrosion synergy can be manifest in any number of ways. One such way can involve performance in a high temperature corrosion bench test (HTCBT). HTCBT can be done according to ASTM D6594 for at least copper and lead (and optionally also for tin), in which copper and lead (and optionally also tin) coupons are suspended in ~100 mL of a compositional liquid sample that is heated to ~135° C. Air is provided at ~5 L/min, and measurements are taken at various intervals for ~168 hours to determine copper and lead (and optionally also tin) concentrations in the liquid sample (expressed in ppm by mass), which measurements are corrected for evaporative losses during heating. Although performed under different conditions in ASTM D6594, the copper coupon subject to ~135° C. for ~168 hours can nonetheless be visually rated using the scale from ASTM D130. Although not believed to be specified in ASTM D6594, HTCBT may also be extended under the same conditions to include bronze coupons for evaluating bronze corrosion.

Another such way can involve performance in a Sequence VIII engine test. The Sequence VIII engine test evaluates compositions for their copper and lead corrosion control capabilities, along with shear stability under high temperature operating conditions, via exposure of the compositions to a copper or lead big end connecting rod bearing in a single cylinder CLR evaluation engine during steady state operation (e.g., at ~3150 rpm). After a 4-hour break-in and a ½-hour flush, the engine is operated under constant speed, air-fuel ratio and fuel flow conditions for an additional 40 hours. This engine test may advantageously be conducted according to conditions delineated in ASTM D6709. Bearing weight loss (as adjusted against a reference bearing) for a composition can be compared to a reference composition to achieve an adjusted bearing weight loss (in %), and composition(s) can be analyzed at various intervals and at end of test can be evaluated by measuring stripped viscosity at ~100° C.

Still another such way can involve performance in the oxidation test in a heavy exhaust gas recycle (EGR) diesel engine with variable geometry turbocharging (VGT) for at least 360 hours (and optionally for at least 420 hours), as mentioned above in the context of oxidation/viscosity increase. Under those procedures/conditions, at various relevant intervals, optional additional measurements of total acid number (TAN) and total base number (TBN) of the composition(s) subject to testing can be periodically done. In that way, the changes in TAN and TBN can be evaluated over time, and comparisons made to reference compositions.

Yet another such way can involve performance in the Sequence X timing chain wear test under conditions and procedures mentioned above in the context of antiwear/friction. Even under ASTM D8279 procedures/conditions, additional measurements of total acid number (TAN) and total base number (TBN) of the composition(s) subject to testing can be periodically done (e.g., at approximately the same intervals as the timing chain elongation is measured). In that way, the changes in TAN and TBN can be evaluated over time, and comparisons made to reference compositions.

Even another such way can involve performance in a Sequence IVB valve train wear test. The Sequence IVB engine valve train wear test is a fired engine dynamometer lubricant test which evaluates the ability of a test composition to reduce valve train wear. The test method is a low temperature cyclic test, with a total running duration of ~200 hours. The Sequence IVB test may use a Toyota 2NR-FE water cooled, 4 cycle, in-line cylinder, 1.5-liter engine as the test apparatus, which incorporates a dual overhead cam, four valves per cylinder (2 intake; 2 exhaust), and direct acting mechanical bucket lifter valve train design. The critical test parts (camshafts, direct acting mechanical bucket lifters) are replaced each test. A ~95-minute run-in schedule, followed by a 50-hour aging schedule, for Silicon (Si) pacification, is conducted whenever the long block or cylinder head are replaced with new components. The Sequence IVB valve train wear test is a flush-and-run type of lubricant test with one ~6-minute engine oil system flush and three ~38-minute engine oil system flushes conducted prior to the actual test start. The test sequence is repeated for ~24,000 test cycles. Each cycle consists of four stages as outlined in the table below.

| Parameter | Units | Stage 2 → 1 | Stage 1 | Stage 1→2 | Stage 2 |
|---|---|---|---|---|---|
| Duration | Sec | 8 | 7 | 8 | 7 |
| Engine Speed | r/min | 4300 to 800 | 800 ± 25 | 800 to 4300 | 4300 ± 25 |
| Engine Torque | N-m | 25 ± 1.5 | 25 ± 1.5 | 25 ± 1.5 | 25 ± 1.5 |
| Coolant Out Temperature | ° C. | | 51.5 ± 0.75 | | 52.5 ± 0.75 |
| Coolant Flow (Engine) | L/min | 80 ± 0.4 | 80 ± 0.4 | 80 ± 0.4 | 80 ± 0.4 |
| Coolant Flow (RAC) | L/min | 120 ± 0.75 | 120 ± 0.75 | 120 ± 0.75 | 120 ± 0.75 |
| Oil Gallery Temperature | ° C. | 54 ± 4 | 54 ± 4 | 54 ± 4 | 54 ± 4 |
| RAC Coolant Out Temperature | ° C. | 20 ± 0.75 | 20 ± 0.75 | 20 ± 0.75 | 20 ± 0.75 |
| Fuel Rail Temperature | ° C. | 24 ± 0.5 | 24 ± 0.5 | 24 ± 0.5 | 24 ± 0.5 |
| Load Cell Temperature | ° C. | 45 ± 4 | 45 ± 4 | 45 ± 4 | 45 ± 4 |
| Intake Air Temperature | ° C. | 32 ± 0.75 | 32 ± 0.75 | 32 ± 0.75 | 32 ± 0.75 |
| Blowby Gas Temperature | ° C. | 29 ± 0.5 | 29 ± 0.5 | 29 ± 0.5 | 29 ± 0.5 |
| Intake Air Pressure | kPa(g) | 0.25 ± 0.25 | 0.25 ± 0.25 | 0.25 ± 0.25 | 0.25 ± 0.25 |
| Intake Air Humidity | g/Kg | 11.5 ± 0.5 | 11.5 ± 0.5 | 11.5 ± 0.5 | 11.5 ± 0.5 |
| Exhaust Pressure | kPa(a) | | | | 104.5 ± 3 |
| Engine Coolant Pressure | kPa | 70 ± 10 | 70 ± 10 | 70 ± 10 | 70 ± 10 |
| Fuel to Rail Pressure | k(Pa) | 335 ± 10 | 335 ± 10 | 335 ± 10 | 335 ± 10 |
| Air to Fuel Ratio (not controlled) | :1 | Record | 4.5 ± 0.5 | Record | 14.5 ± 0.5 |

Also, at various relevant intervals, optional additional measurements of total acid number (TAN) and total base number (TBN) of the composition(s) subject to testing can be periodically done. In that way, the changes in TAN and TBN can be evaluated over time, and comparisons made to reference compositions, which can inform regarding relative likelihood of metallic (e.g., copper and/or lead) corrosion.

In advantageous embodiments, when subject to a high temperature corrosion bench test (HTCBT) at ~135° C. according to ASTM D6594, a lubricant and/or coolant formulation containing a 3,4-oxypyridone compound according to the present disclosure may exhibit a dissolved copper level after ~168 hours of no more than 40 ppm Cu (e.g., no more than 35 ppm Cu, no more than 30 ppm Cu, no more than 25 ppm Cu, no more than 23 ppm Cu, no more than 20 ppm Cu, no more than 18 ppm Cu, or no more than 15 ppm Cu; in particular, no more than 40 ppm Cu, no more than 25 ppm Cu, or no more than 20 ppm Cu) and a dissolved lead level after 168 hours of no more than 150 ppm Pb (e.g., no more than 140 ppm Pb, no more than 130 ppm Pb, no more than 120 ppm Pb, no more than 110 ppm Pb, no more than 100 ppm Pb, or no more than 90 ppm Pb; in particular, no more than 140 ppm Pb, no more than 130 ppm Pb, or no more than 100 ppm Pb). In some such embodiments, the lubricant and/or coolant formulation may also contain: (i) a tri-hydrocarbyl $C_1$-$C_8$ borate corrosion inhibitor; (ii) an optionally substituted triazole corrosion inhibitor and/or an optionally substituted benzotriazole corrosion inhibitor; (iii) one or more of an ashless dihydrocarbyl dithiocarbamate, a $C_8$-$C_{18}$ acrylate, and a $C_2$-$C_6$ dialkylene glycol diester; or (iv) any combination thereof. However, in other such embodiments, the lubricant and/or coolant formulation may contain substantially none of the following: an optionally substituted triazole corrosion inhibitor; an optionally substituted benzotriazole corrosion inhibitor; an optionally substituted thiadiazole corrosion inhibitor; an ashless dihydrocarbyl dithiocarbamate; a $C_8$-$C_{18}$ acrylate; a $C_2$-$C_6$ dialkylene glycol diester; and a tri-hydrocarbyl $C_1$-$C_8$ borate corrosion inhibitor.

Additionally or alternatively, when subject to a Sequence VIII engine test according to ASTM D6709 (e.g., involving a copper or lead bearing), a lubricant and/or coolant formulation containing a 3,4-oxypyridone compound according to the present disclosure containing two or more corrosion inhibitors (e.g., containing a tri-hydrocarbyl $C_1$-$C_8$ borate corrosion inhibitor and either an optionally substituted triazole corrosion inhibitor or an optionally substituted benzotriazole corrosion inhibitor) may exhibit: (a) an adjusted bearing weight loss from −7% to +70% below (e.g., from −7% to +60% below, from −7% to +55% below, from −7% to +50% below, from −7% to +45% below, from −7% to +40% below, from −5% to +70% below, from −5% to +60% below, from −5% to +55% below, from −5% to +50% below, from −5% to +45% below, from −5% to +40% below, from −3% to +70% below, from −3% to +60% below, from −3% to +55% below, from −3% to +50% below, from −3% to +45% below, or from −3% to +40% below; in particular, from −5% to +60% below, from −5% to +50% below, or from −3% to +50% below) an adjusted bearing weight loss from a comparative composition under identical test conditions; and/or (b) a stripped viscosity at ~100° C. of no more than 5% above (e.g., no more than 4.5% above, no more than 4% above, no more than 3.5% above, no more than 3% above, no more than 2.5% above, or no more than 2% above; in particular, no more than 3% above or no more than 2.5% above) a stripped viscosity at ~100° C. from a comparative composition under identical test conditions, wherein the comparative compositions contains substantially none of the 3,4-oxypyridinone compound of structure (I) and substantially none of the two or more corrosion inhibitors (e.g., substantially none of the tri-hydrocarbyl $C_1$-$C_8$ borate corrosion inhibitor and substantially none of either the optionally substituted triazole corrosion inhibitor or the optionally substituted benzotriazole corrosion inhibitor). It should be understood, in these contexts, that a negative bearing weight loss of a sample represents a bearing weight gain, relative to a comparative sample, and that a negative stripped viscosity increase of a sample represents a stripped viscosity decrease, relative to a comparative sample.

Further additionally or alternatively, when subject to an oxidation test in a heavy exhaust gas recycle (EGR) diesel engine with variable geometry turbocharging (VGT) for at least ~360 hours, a lubricant and/or coolant formulation containing a 3,4-oxypyridone compound according to the present disclosure may exhibit: (a) a decrease in TAN value, as measured according to ASTM D664, at end of test that is at least 20% below (e.g., at least 25% below, at least 30% below, at least 35% below, at least 40% below, at least 45% below, or at least 50% below; in particular, at least 25% below, at least 35% below, or at least 40% below) a TAN value from a comparative composition that was subject to the diesel engine oxidation test for an identical time period; and/or (b)(i) a difference in TBN value, as measured according to ASTM D4739, at end of test that is no more than 0.9 mg KOH/g above or below (e.g., no more than 0.8 mg KOH/g above or below, no more than 0.7 mg KOH/g above or below, no more than 0.6 mg KOH/g above or below, no more than 0.5 mg KOH/g above or below, no more than 0.4 mg KOH/g above or below, or no more than 0.3 mg KOH/g above or below; in particular, no more than 0.7 mg KOH/g above or below or no more than 0.5 mg KOH/g above or below) a TBN value from a comparative composition that was subject to the diesel engine oxidation test for an identical time period; (b)(ii) a difference in TBN value, as measured according to ASTM D4739, at any time during the test that is no more than 1.5 mg KOH/g above or below (e.g., no more than 1.3 mg KOH/g above or below, no more than 1.2 mg KOH/g above or below, no more than 1.1 mg KOH/g above or below, no more than 1.0 mg KOH/g above or below, no more than 0.9 mg KOH/g above or below, or no more than 0.8 mg KOH/g above or below; in particular, no more than 1.2 mg KOH/g above or below, no more than 1.0 mg KOH/g above or below, or no more than 0.9 mg KOH/g above or below) a TBN value from a comparative composition that was subject to the diesel engine oxidation test for an identical time period; or (b)(iii) both (b)(i) and (b)(ii), wherein the comparative composition contains substantially none the 3,4-oxypyridinone of structure (I) but is otherwise identical to the lubricant composition. In some such embodiments, the lubricant and/or coolant formulation may contain substantially none of the following: an optionally substituted triazole corrosion inhibitor; an optionally substituted benzotriazole corrosion inhibitor; an optionally substituted thiadiazole corrosion inhibitor; an ashless dihydrocarbyl dithiocarbamate; a $C_8$-$C_{18}$ acrylate; a $C_2$-$C_6$ dialkylene glycol diester; and a tri-hydrocarbyl $C_1$-$C_8$ borate corrosion inhibitor.

Yet further additionally or alternatively, when subject to a Sequence X timing chain wear test for at least ~216 hours according to ASTM D8279, a lubricant and/or coolant formulation containing a 3,4-oxypyridone compound according to the present disclosure may exhibit: (a) for times from ~120 hours to ~216 hours (or from ~144 hours to ~216 hours), a decrease in TAN value, as measured according to ASTM D664, of at least 0.8 mg KOH/g below (e.g., at least 0.9 mg KOH/g below, at least 1.0 mg KOH/g below, at least 1.1 mg KOH/g below, at least 1.2 mg KOH/g below, at least 1.3 mg KOH/g below, at least 1.4 mg KOH/g below, or at least 1.5 mg KOH/g below; in particular, at least 0.8 mg KOH/g below or at least 1.0 mg KOH/g below) a TAN value from a comparative composition that was subject to the Sequence X timing chain wear test for an identical time period; and/or (b)(i) a difference in TBN value, as measured according to ASTM D4739, at end of test that is no more than 0.9 mg KOH/g above or below (e.g., no more than 0.8 mg KOH/g above or below, no more than 0.7 mg KOH/g above or below, no more than 0.6 mg KOH/g above or below, no more than 0.5 mg KOH/g above or below, no more than 0.4 mg KOH/g above or below, or no more than 0.3 mg KOH/g above or below; in particular, no more than 0.7 mg KOH/g above or below or no more than 0.5 mg KOH/g above or below) a TBN value from a comparative composition that was subject to the Sequence X timing chain wear test for an identical time period; (b)(ii) a difference in TBN value, as measured according to ASTM D4739, at any time during the test that is no more than 1.5 mg KOH/g above or below (e.g., no more than 1.3 mg KOH/g above or below, no more than 1.2 mg KOH/g above or below, no more than 1.1 mg KOH/g above or below, no more than 1.0 mg KOH/g above or below, no more than 0.9 mg KOH/g above or below, or no more than 0.8 mg KOH/g above or below; in particular, no more than 1.2 mg KOH/g above or below, no more than 1.0 mg KOH/g above or below, or no more than 0.9 mg KOH/g above or below) a TBN value from a comparative composition that was subject to the Sequence X timing chain wear test for an identical time period; or (b)(iii) both (b)(i) and (b)(ii), wherein the comparative composition contains substantially none the 3,4-oxypyridinone of structure (I) but is otherwise identical to the lubricant composition. In some such embodiments, the lubricant and/or coolant formulation may contain substantially none of the following: an optionally substituted triazole corrosion inhibitor; an optionally substituted benzotriazole corrosion inhibitor; an optionally substituted thiadiazole corrosion inhibitor; an ashless dihydrocarbyl dithiocarbamate; a $C_8$-$C_{18}$ acrylate; a $C_2$-$C_6$ dialkylene glycol diester; and a tri-hydrocarbyl $C_1$-$C_8$ borate corrosion inhibitor.

Still further additionally or alternatively, when subject to a Sequence IVB valve train wear test for ~200 hours according to ASTM D8350, a lubricant and/or coolant formulation containing a 3,4-oxypyridone compound according to the present disclosure may exhibit: (a) for times of at least ~175 hours, a decrease in TAN value, as measured according to ASTM D664, of at least 0.9 mg KOH/g below (e.g., at least 1.0 mg KOH/g below, at least 1.1 mg KOH/g below, at least 1.2 mg KOH/g below, at least 1.3 mg KOH/g below, at least 1.4 mg KOH/g below, at least 1.5 mg KOH/g below, or at least 1.6 mg KOH/g below; in particular, at least 1.0 mg KOH/g below, at least 1.2 mg KOH/g below, or at least 1.4 mg KOH/g below) a TAN value from a comparative composition that was subject to the Sequence IVB valve train wear test for an identical time period; and/or (b)(i) a difference in TBN value, as measured according to ASTM D4739, at end of test that is no more than 0.9 mg KOH/g above or below (e.g., no more than 0.8 mg KOH/g above or below, no more than 0.7 mg KOH/g above or below, no more than 0.6 mg KOH/g above or below, no more than 0.5 mg KOH/g above or below, no more than 0.4 mg KOH/g above or below, or no more than 0.3 mg KOH/g above or below; in particular, no more than 0.7 mg KOH/g above or below or no more than 0.5 mg KOH/g above or below) a TBN value from a comparative composition that was subject to the Sequence IVB valve train wear test for an identical time period; (b)(ii) a difference in TBN value, as measured according to ASTM D4739, at any time during the test that is no more than 1.5 mg KOH/g above or below (e.g., no more than 1.3 mg KOH/g above or below, no more than 1.2 mg KOH/g above or below, no more than 1.1 mg KOH/g above or below, no more than 1.0 mg KOH/g above or below, no more than 0.9 mg KOH/g above or below, or no more than 0.8 mg KOH/g above or below; in particular, no more than 1.2 mg KOH/g above or below, no more than 1.0 mg KOH/g above or below, or no more than 0.9 mg KOH/g above or below) a TBN value from a comparative composition that was subject to the Sequence IVB valve train wear test for an identical time period; or (b)(iii) both (b)(i) and (b)(ii), wherein the comparative composition contains substantially none the 3,4-oxypyridinone of structure (I) but is otherwise identical to the lubricant composition. In some such embodiments, the lubricant and/or coolant formulation may contain substantially none of the following: an optionally substituted triazole corrosion inhibitor; an optionally substituted benzotriazole corrosion inhibitor; an optionally substituted thiadiazole corrosion inhibitor; an ashless dihydrocarbyl dithiocarbamate; a $C_8$-$C_{18}$ acrylate; a $C_2$-$C_6$ dialkylene glycol diester; and a tri-hydrocarbyl $C_1$-$C_8$ borate corrosion inhibitor.

Even further additionally or alternatively, when subject to one or more of (a) an oxidation test in a heavy exhaust gas recycle (EGR) diesel engine with variable geometry turbocharging (VGT) for at least ~360 hours (but for not longer than ~420 hours, (b) a Sequence X timing chain wear test for at least ~168 hours (in particular, at least ~216 hours; but not longer than ~240 hours) according to ASTM D8279, and/or (c) a Sequence IVB valve train wear test for ~200 hours according to ASTM D8350, a lubricant and/or coolant formulation containing a 3,4-oxypyridone compound according to the present disclosure may exhibit, at some time after TAN-TBN crossover and until end of test, a decrease in TAN value, as measured according to ASTM D664, that is at least 8% below (e.g., at least 9% below, at least 10% below, at least 12% below, at least 14% below, at least 15% below, at least 16% below, at least 18% below, or at least 20% below; in particular, at least 10% below or at least 12% below) and/or at least 0.5 mg KOH/g below (e.g., at least 0.6 mg KOH/g below, at least 0.7 mg KOH/g below, at least 0.8 mg KOH/g below, at least 0.9 mg KOH/g below, at least 1.0 mg KOH/g below, at least 1.1 mg KOH/g below, at least 1.2 mg KOH/g below, at least 1.3 mg KOH/g below, or at least 1.5 mg KOH/g below; in particular, at least 0.7 mg KOH/g below, at least 0.9 mg KOH/g below, or at least 1.0 mg KOH/g below) a TAN value from a comparative composition that was subject to the one or more tests for an identical time period, wherein the comparative composition contains substantially none the 3,4-oxypyridinone of structure (I) but is otherwise identical to the lubricant composition. In such embodiments, "TAN-TBN crossover" represents the time during the test at which TBN values of both lubricant composition and comparative composition, measured according to ASTM D4739, exceed TAN values of both lubricant composition and comparative composition, respectively, by at least 1% (e.g., at least 2%, at least 3%, at least 4%, or at least 5%; in particular, at least 3% or at least 5%), whereas both TAN values exceeded both TBN values by at least 1% (e.g., at least 2%, at least 3%, at least 4%, or at least 5%; in particular, at least 3% or at least 5%) at start of test (0 hours). In some such embodiments, the lubricant and/or coolant formulation may contain substantially none of the following: an optionally substituted triazole corrosion inhibitor; an optionally substituted benzotriazole corrosion inhibitor; an optionally substituted thiadiazole corrosion inhibitor; an ashless dihydrocarbyl dithiocarbamate; a $C_8$-$C_{18}$ acrylate; a $C_2$-$C_6$ dialkylene glycol diester; and a tri-hydrocarbyl $C_1$-$C_8$ borate corrosion inhibitor.

ADDITIONAL EMBODIMENTS

Additionally or alternatively, the present disclosure may include one or more of the following embodiments.

Embodiment A1. A composition comprising a non-aqueous medium and a 3,4-oxypyridinone compound of structure (I):

(I)

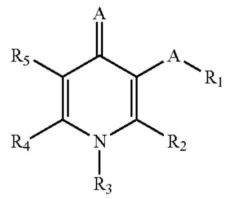

wherein:

each A is individually an oxygen atom, a sulfur atom, an oxymethyl (—$CH_2$—O—) moiety, or a thiomethyl (—$CH_2$—S—) moiety;

$R_1$ is hydrogen; an ammonium ion; a $C_1$-$C_6$ monoalkylammonium ion; a $C_1$-$C_6$ dialkylammonium ion; a $C_1$-$C_6$ trialkylammonium ion; a $C_1$-$C_6$ tetraalkylammonium ion; a $C_1$-$C_6$ monoalkylsilyl moiety; a $C_1$-$C_6$ dialkylsilyl moiety; a $C_1$-$C_6$ trialkylsilyl moiety; an optionally substituted aryl, alkyl, alkaryl, or aralkyl sulfonyl moiety; a linear, branched, and/or cyclic $C_1$-$C_{20}$ hydrocarbyl sulfide; a linear, branched, and/or cyclic $C_1$-$C_{20}$ hydrocarbyl moiety; an at least partially halogenated linear, branched, and/or cyclic $C_1$-$C_{20}$ moiety; an ether-containing linear, branched, and/or cyclic $C_1$-$C_{20}$ moiety; a thioether-containing linear, branched, and/or cyclic $C_1$-$C_{20}$ moiety; an ester-containing linear, branched, and/or cyclic $C_1$-$C_{20}$ moiety; a thioester-containing linear, branched, and/or cyclic $C_1$-$C_{20}$ moiety; a linear, branched, and/or cyclic $C_1$-$C_{20}$ acyl moiety; a linear, branched, and/or cyclic $C_1$-$C_{20}$ thioacyl moiety; a linear, branched, and/or cyclic $C_1$-$C_{20}$ hydrocarbyloxyacyl moiety; a linear, branched, and/or cyclic $C_1$-$C_{20}$ hydrocarbyloxythioacyl moiety; a linear, branched, and/or cyclic $C_1$-$C_{20}$ hydrocarbylthiocarbonyl moiety; a linear, branched, and/or cyclic $C_1$-$C_{20}$ hydrocarbylthio-thioacyl moiety; an amide-containing linear, branched, and/or cyclic $C_1$-$C_{20}$ moiety; a thioamide-containing linear, branched, and/or cyclic $C_1$-$C_{20}$ moiety; a ketone-containing linear, branched, and/or cyclic $C_1$-$C_{20}$ moiety; a thioketone-containing linear, branched, and/or cyclic $C_1$-$C_{20}$ moiety; an aldehyde-containing linear, branched, and/or cyclic $C_1$-$C_{20}$ moiety; a thioaldehyde-containing linear, branched, and/or cyclic $C_1$-$C_{20}$ moiety; a mercaptan-containing linear, branched, and/or cyclic $C_1$-$C_{20}$ moiety; a hydroxyl-containing linear, branched, and/or cyclic $C_1$-$C_{20}$ moiety; a nonionic linear, branched, and/or (hetero)cyclic moiety containing 1 to 20 carbon atoms at least one nitrogen atom, and optionally at least one sulfur and/or oxygen atom; another 3,4-oxypyridinone connected as an ether or thioether at a meta position to the ring nitrogen thereof; or a combination thereof;

$R_2$ is hydrogen; a halogen; a linear, branched, and/or cyclic $C_1$-$C_{12}$ hydrocarbyl moiety; an at least partially halogenated linear, branched, and/or cyclic $C_1$-$C_{12}$ moiety; an amine-containing linear, branched, and/or cyclic $C_1$-$C_{20}$ moiety; an ether-containing linear, branched, and/or cyclic $C_1$-$C_{20}$ moiety; a hydroxyl-containing linear, branched, and/or cyclic $C_1$-$C_{12}$ moiety; an aldehyde-containing linear, branched, and/or cyclic $C_1$-$C_{20}$ moiety; a nitrile-containing linear, branched, and/or cyclic $C_1$-$C_{20}$ moiety; or a combination thereof;

$R_3$ is hydrogen; a halogen; a linear, branched, and/or cyclic $C_6$-$C_{24}$ hydrocarbyl moiety; or a combination thereof;

$R_4$ is hydrogen; a halogen; a linear, branched, and/or cyclic $C_1$-$C_{12}$ hydrocarbyl moiety; an at least partially halogenated linear, branched, and/or cyclic $C_1$-$C_{12}$ moiety; an amine-containing linear, branched, and/or cyclic $C_1$-$C_{20}$ moiety; an ether-containing linear, branched, and/or cyclic $C_1$-$C_{20}$ moiety; a hydroxyl-containing linear, branched, and/or cyclic $C_1$-$C_{12}$ moiety; an aldehyde-containing linear, branched, and/or cyclic $C_1$-$C_{20}$ moiety; a nitrile-containing linear, branched, and/or cyclic $C_1$-$C_{20}$ moiety; or a combination thereof; and $R_5$ is hydrogen; a halogen; a linear, branched, and/or cyclic $C_1$-$C_{12}$ hydrocarbyl moiety; an at least partially halogenated linear, branched, and/or cyclic $C_1$-$C_{12}$ moiety; a hydroxylated linear, branched, and/or cyclic $C_1$-$C_6$ moiety; an $R_1$-A- moiety; or a combination thereof;

or alternatively one or more of $R_1$ and $R_2$, $R_2$ and $R_3$, $R_3$ and $R_4$, and $R_4$ and $R_5$ may together form one or more (hetero)cyclic rings;

with the proviso that $R_1$ and $R_3$ are not both hydrogen.

Embodiment A2. The composition of embodiment A1, wherein the non-aqueous medium comprises a Group I, Group II, Group III, Group IV, and/or Group V lubricating oil basestock.

Embodiment A3. The composition of embodiment A1 or embodiment A2, wherein:

all A's are oxygen atoms;

$R_1$ is hydrogen; a linear, branched, and/or cyclic $C_1$-$C_{12}$ hydrocarbyl moiety; an ether-containing linear, branched, and/or cyclic $C_1$-$C_{12}$ moiety; another 3,4-oxypyridinone connected as an ether at a meta position to the ring nitrogen thereof; or a combination thereof;

$R_2$ is hydrogen; a linear, branched, and/or cyclic $C_1$-$C_{12}$ hydrocarbyl moiety; an ether-containing linear, branched, and/or cyclic $C_1$-$C_{12}$ moiety; an aldehyde-containing linear, branched, and/or cyclic $C_1$-$C_{12}$ moiety; a nitrile-containing linear, branched, and/or cyclic $C_1$-$C_{12}$ moiety; or a combination thereof;

$R_3$ is a linear, branched, and/or cyclic $C_8$-$C_{20}$ hydrocarbyl moiety; an oligomeric and/or polymeric moiety containing repeat units comprising reacted olefins, hydrogenated conjugated dienes, or combinations thereof, at least one of which repeat units is attached to the ring nitrogen, optionally with a spacer, a number average molecular weight of which oligomeric and/or polymeric moiety is from 400 g/mol to 8000 g/mol; or a combination thereof;

$R_4$ is hydrogen; a linear, branched, and/or cyclic $C_1$-$C_{12}$ hydrocarbyl moiety; an ether-containing linear, branched, and/or cyclic $C_1$-$C_{12}$ moiety; an aldehyde-containing linear, branched, and/or cyclic $C_1$-$C_{12}$ moiety; a nitrile-containing linear, branched, and/or cyclic $C_1$-$C_{12}$ moiety; or a combination thereof; and $R_5$ is hydrogen; an $R_1$-A- moiety; or a combination thereof;

or $R_4$ and $R_5$ together comprise from 3 to 12 carbons and form a (hetero)cyclic ring structure.

Embodiment A4. A composition according to any of embodiments A1-A3, further comprising at least one lubricant additive selected from the group consisting of a calcium- and/or magnesium-containing detergent, an ashless dispersant, a corrosion inhibitor, an antioxidant, a friction modifier, an antiwear agent, an antifoamant, a viscosity modifier, a pour point depressant, a tackifier, a demulsifier, an extreme pressure agent, a seal swell agent, and a combination thereof.

Embodiment A5. The lubricant composition according to embodiment A4, wherein the at least one lubricant additive comprises an optionally substituted diaryl amine antioxidant, a hindered phenol antioxidant, or both.

Embodiment A6. The lubricant composition according to embodiment A5, wherein a weight ratio of the 3,4-oxypyridinone of structure (I) to a sum of the optionally substituted diaryl amine and hindered phenol antioxidants is from 10:1 to 1:10.

Embodiment A7. The lubricant composition according any one of embodiments A4-A6, wherein the at least one lubricant additive comprises one or more of: a zinc dialkyldithiophosphate antiwear agent; an organic friction modifier, a molybdenum-containing friction modifier, or a combination thereof; and an optionally substituted triazole corrosion inhibitor, an optionally substituted benzotriazole corrosion inhibitor, an optionally substituted thiadiazole corrosion inhibitor, an ashless dihydrocarbyl dithiocarbamate, a $C_8$-$C_{18}$ acrylate, a $C_2$-$C_6$ dialkylene glycol diester, a trihydrocarbyl $C_1$-$C_8$ borate corrosion inhibitor, or a combination thereof.

Embodiment A8. The lubricant composition according to any one of embodiments A4-A7, wherein the at least one lubricant additive comprises a multi-arm star viscosity modifier, an olefin copolymer viscosity modifier, a hydrogenated diene block copolymer viscosity modifier, a polystyrene copolymer viscosity modifier, a poly(meth)acrylate viscosity modifier, a poly(dialkyl fumarate)-based viscosity modifier, a poly(vinyl acyl ester)-based viscosity modifier such as poly(vinyl acetate), or a combination or copolymer thereof.

Embodiment A9. A method of inhibiting and/or mitigating viscosity increase in a composition comprising a non-aqueous medium by addition of the 3,4-oxypyridinone composition of any one of embodiments A1-A8, or via formation of a complex or reaction product thereof, in an amount that is effective in disrupting oxidation catalysis through iron chelation.

Embodiment A10. Use of the non-aqueous 3,4-oxypyridinone-containing composition according to any one of embodiments A1-A8, or a complex or reaction product thereof, to inhibit and/or mitigate viscosity increase in a lubricant composition containing said composition, e.g., through effective disruption of oxidation catalysis through iron chelation.

Embodiment A11. A method of improving oxidative stability and/or mitigating impact of oxidative degradation of a composition comprising a non-aqueous medium by addition of the 3,4-oxypyridinone composition of any one of embodiments A1-A18, or via formation of a complex or reaction product thereof, in an amount that is effective in disrupting oxidation catalysis through iron chelation:

Embodiment A12. Use of the non-aqueous 3,4-oxypyridinone-containing composition according to any one of embodiments A1-A8, or a complex or reaction product thereof, to improve oxidative degradation of and/or to mitigate viscosity increase in a lubricant composition containing said composition, e.g., through effective disruption of oxidation catalysis through iron chelation.

Embodiment A13. The lubricant composition according to any one of embodiments A5-A8, the method according to embodiment A9 or embodiment A11, or the use according to embodiment A10 or embodiment A12, wherein the lubricant composition comprising the 3,4-oxypyridinone of structure (I) and either or both of the optionally substituted diaryl amine and hindered phenol antioxidants, when subject to a CEC L-109 oxidation test for at least 200 hours (e.g., for ~216 hours and/or ~240 hours) at ~150° C., exhibits an increase in a value of kinematic viscosity at ~100° C. (KV100) that is:

at most 40% above a KV100 value from the same lubricant composition immediately before the CEC L-109 oxidation test began (0 hours); and at least 30% below a KV100 value from a comparative composition that was subject to the CEC L-109 oxidation test for an identical time period, wherein the comparative composition:

(a) comprises only either or both of the optionally substituted diaryl amine and hindered phenol antioxidants and not the 3,4-oxypyridinone of structure (I); and (b) comprises the optionally substituted diaryl amine and hindered phenol antioxidants in an identical weight ratio to the lubricant composition, and comprises a collective amount of the optionally substituted diaryl amine and hindered phenol antioxidants that is identical to the sum of the amounts of optionally substituted diaryl amine antioxidant, hindered phenol antioxidant, and 3,4-oxypyridinone of structure (I) in the lubricant composition.

Embodiment A14. The lubricant composition according to any one of embodiments A5-A8 and A13, the method according to any one of embodiments A9, A11, and A13, or the use according to any one of embodiments A10, A12, and A13, wherein the lubricant composition comprising the 3,4-oxypyridinone of structure (I) and either or both of the optionally substituted diaryl amine and hindered phenol antioxidants (and optionally also a magnesium detergent), when subject to a CEC L-109 oxidation test for at least 200 hours (e.g., for ~216 hours and/or ~240 hours) at ~150° C., exhibits an increase in a value of kinematic viscosity at ~100° C. (KV100) that is:

at most 30% above a KV100 value from the same lubricant composition immediately before the CEC L-109 oxidation test began (0 hours); and at least 12% below a KV100 value from a comparative composition that was subject to the CEC L-109 oxidation test for an identical time period, wherein the comparative composition:

(a) comprises only either or both of the optionally substituted diaryl amine and hindered phenol antioxidants and not the 3,4-oxypyridinone of structure (I); and (b) comprises the optionally substituted diaryl amine and hindered phenol antioxidants in an identical weight ratio to the lubricant composition, and comprises a collective amount of the optionally substituted diaryl amine and hindered phenol antioxidants that is identical to the sum of the amounts of optionally substituted diaryl amine antioxidant, hindered phenol antioxidant, and 3,4-oxypyridinone of structure (I) in the lubricant composition.

Embodiment A15. The lubricant composition according to any one of embodiments A6-A8 and A13-A14, the method according to any one of embodiments A9, A11, and A13-A14, or the use according to any one of embodiments A10 and A12-A14, wherein the lubricant composition comprising the 3,4-oxypyridinone of structure (I) (optionally in an amount from 0.25 wt % to 1.3 wt %, based on the weight of the lubricant composition) and either or both of the optionally substituted diaryl amine and hindered phenol antioxidants, when subject to an oxidation test in a heavy exhaust gas recycle (EGR) diesel engine with variable geometry turbocharging (VGT) for up to 420 hours, exhibits an increase in a value of kinematic viscosity at ~40° C. (KV40) that is:

after ~360 hours, at most 20 cSt above a KV40 value from the same lubricant composition immediately before the diesel engine oxidation test began (0 hours); and after at least 324 hours, at least 15% below a KV40 value from a comparative composition that was subject to the diesel engine oxidation test for an identical time period, wherein the comparative composition comprises only both the optionally substituted diaryl amine and hindered phenol antioxidants and not the 3,4-oxypyridinone of structure (I).

Embodiment A16. The lubricant composition, method, or use according to embodiment A15, wherein the lubricant composition comprising the 3,4-oxypyridinone of structure (I) and either or both of the optionally substituted diaryl amine and hindered phenol antioxidants, when subject to an oxidation test in a heavy exhaust gas recycle (EGR) diesel engine with variable geometry turbocharging (VGT) for up to 420 hours, further exhibits an increase in a value of kinematic viscosity at ~40° C. (KV40) that is:

after ~360 hours, at most 1.5 cSt above a KV40 value from the same lubricant composition immediately before the diesel engine oxidation test began (0 hours); and after at least 336 hours, at least 10% below a KV40 value from a comparative composition that was subject to the diesel engine oxidation test for an identical time period, wherein the comparative composition comprises only both the optionally substituted diaryl amine and hindered phenol antioxidants and not the 3,4-oxypyridinone of structure (I).

Embodiment B1. A composition comprising a non-aqueous medium and a 3,4-oxypyridinone compound of structure (I):

(I)

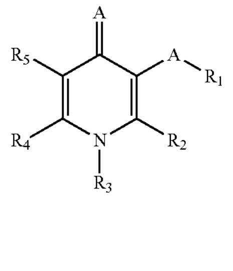

wherein:

each A is individually an oxygen atom, a sulfur atom, an oxymethyl (—$CH_2$—O—) moiety, or a thiomethyl (—$CH_2$—S—) moiety;

$R_1$ is hydrogen; an ammonium ion; a $C_1$-$C_6$ monoalkylammonium ion; a $C_1$-$C_6$ dialkylammonium ion; a $C_1$-$C_6$ trialkylammonium ion; a $C_1$-$C_6$ tetraalkylammonium ion; a $C_1$-$C_6$ monoalkylsilyl moiety; a $C_1$-$C_6$ dialkylsilyl moiety; a $C_1$-$C_6$ trialkylsilyl moiety; an optionally substituted aryl, alkyl, alkaryl, or aralkyl sulfonyl moiety; a linear, branched, and/or cyclic $C_1$-$C_{20}$ hydrocarbyl sulfide; a linear, branched, and/or cyclic $C_1$-$C_{20}$ hydrocarbyl moiety; an at least partially halogenated linear, branched, and/or cyclic $C_1$-$C_{20}$ moiety; an ether-containing linear, branched, and/or cyclic $C_1$-$C_{20}$ moiety; a thioether-containing linear, branched, and/or cyclic $C_1$-$C_{20}$ moiety; an ester-containing linear, branched, and/or cyclic $C_1$-$C_{20}$ moiety; a thioester-containing linear, branched, and/or cyclic $C_1$-$C_{20}$ moiety; a linear, branched, and/or cyclic $C_1$-$C_{20}$ acyl moiety; a linear, branched, and/or cyclic $C_1$-$C_{20}$ thioacyl moiety; a linear, branched, and/or cyclic $C_1$-$C_{20}$ hydrocarbyloxyacyl moiety; a linear, branched, and/or cyclic $C_1$-$C_{20}$ hydrocarbyloxythioacyl moiety; a linear, branched, and/or cyclic $C_1$-$C_{20}$ hydrocarbylthiocarbonyl moiety; a linear, branched, and/or cyclic $C_1$-$C_{20}$ hydrocarbylthio-thioacyl moiety; an amide-containing linear, branched, and/or cyclic $C_1$-$C_{20}$ moiety; a thioamide-containing linear, branched, and/or cyclic $C_1$-$C_{20}$ moiety; a ketone-containing linear, branched, and/or cyclic $C_1$-$C_{20}$ moiety; a thioketone-containing linear, branched, and/or cyclic $C_1$-$C_{20}$ moiety; an aldehyde-containing linear, branched, and/or cyclic $C_1$-$C_{20}$ moiety; a thioaldehyde-containing linear, branched, and/or cyclic $C_1$-$C_{20}$ moiety; a mercaptan-containing linear, branched, and/or cyclic $C_1$-$C_{20}$ moiety; a hydroxyl-containing linear, branched, and/or cyclic $C_1$-$C_{20}$ moiety; a nonionic linear, branched, and/or (hetero)cyclic moiety containing 1 to 20 carbon atoms at least one nitrogen atom, and optionally at least one sulfur and/or oxygen atom; another 3,4-oxypyridinone connected as an ether or thioether at a meta position to the ring nitrogen thereof; or a combination thereof;

$R_2$ is hydrogen; a halogen; a linear, branched, and/or cyclic $C_1$-$C_{12}$ hydrocarbyl moiety; an at least partially halogenated linear, branched, and/or cyclic $C_1$-$C_{12}$ moiety; an amine-containing linear, branched, and/or cyclic $C_1$-$C_{20}$ moiety; an ether-containing linear, branched, and/or cyclic $C_1$-$C_{20}$ moiety; a hydroxyl-containing linear, branched, and/or cyclic $C_1$-$C_{12}$ moiety; an aldehyde-containing linear, branched, and/or cyclic $C_1$-$C_{20}$ moiety; a nitrile-containing linear, branched, and/or cyclic $C_1$-$C_{20}$ moiety; or a combination thereof;

$R_3$ is an oligomeric and/or polymeric moiety pendant to one or more repeat units, optionally with a spacer, the oligomeric and/or polymeric moiety having a number average molecular weight from 400 g/mol to 300000 g/mol;

$R_4$ is hydrogen; a halogen; a linear, branched, and/or cyclic $C_1$-$C_{12}$ hydrocarbyl moiety; an at least partially halogenated linear, branched, and/or cyclic $C_1$-$C_{12}$ moiety; an amine-containing linear, branched, and/or cyclic $C_1$-$C_{20}$ moiety; an ether-containing linear, branched, and/or cyclic $C_1$-$C_{20}$ moiety; a hydroxyl-containing linear, branched, and/or cyclic $C_1$-$C_{12}$ moiety; an aldehyde-containing linear, branched, and/or cyclic $C_1$-$C_{20}$ moiety; a nitrile-containing linear, branched, and/or cyclic $C_1$-$C_{20}$ moiety; or a combination thereof; and $R_5$ is hydrogen; a halogen; a linear, branched, and/or cyclic $C_1$-$C_{12}$ hydrocarbyl moiety; an at least partially halogenated linear, branched, and/or cyclic $C_1$-$C_{12}$ moiety; a hydroxylated linear, branched, and/or cyclic $C_1$-$C_6$ moiety; an $R_1$-A- moiety; or a combination thereof;

or alternatively one or both of $R_1$ and $R_2$ and $R_4$ and $R_5$ may together form one or more (hetero)cyclic rings.

Embodiment B2. The composition of embodiment B1, wherein the non-aqueous medium comprises a Group I, Group II, Group III, Group IV, and/or Group V lubricating oil basestock.

Embodiment B3. The composition of embodiment B1 or embodiment B2, wherein:

all A's are oxygen atoms;

$R_1$ is hydrogen; a linear, branched, and/or cyclic $C_1$-$C_{12}$ hydrocarbyl moiety; an ether-containing linear, branched, and/or cyclic $C_1$-$C_{12}$ moiety; another 3,4-oxypyridinone connected as an ether at a meta position to the ring nitrogen thereof; or a combination thereof;

$R_2$ is hydrogen; a linear, branched, and/or cyclic $C_1$-$C_{12}$ hydrocarbyl moiety; an ether-containing linear, branched, and/or cyclic $C_1$-$C_{12}$ moiety; an aldehyde-containing linear, branched, and/or cyclic $C_1$-$C_{12}$ moiety; a nitrile-containing linear, branched, and/or cyclic $C_1$-$C_{12}$ moiety; or a combination thereof;

$R_3$ is an oligomeric and/or polymeric moiety containing repeat units comprising reacted olefins, hydrogenated conjugated dienes, or combinations thereof, at least one of which repeat units is attached to the ring nitrogen, optionally with a spacer, a number average molecular weight of which oligomeric and/or polymeric moiety is from 700 g/mol to 30000 g/mol;

$R_4$ is hydrogen; a linear, branched, and/or cyclic $C_1$-$C_{12}$ hydrocarbyl moiety; an ether-containing linear, branched, and/or cyclic $C_1$-$C_{12}$ moiety; an aldehyde-containing linear, branched, and/or cyclic $C_1$-$C_{12}$ moiety; a nitrile-containing linear, branched, and/or cyclic $C_1$-$C_{12}$ moiety; or a combination thereof; and $R_5$ is hydrogen; an $R_1$-A- moiety; or a combination thereof;

or $R_4$ and $R_5$ together comprise from 3 to 12 carbons and form a (hetero)cyclic ring structure.

Embodiment B4. A composition according to any one of embodiments B1-B3, further comprising at least one lubricant additive selected from the group consisting of a calcium- and/or magnesium-containing detergent, an ashless dispersant, a corrosion inhibitor, an antioxidant, a friction modifier, an antiwear agent, an antifoamant, a viscosity modifier, a pour point depressant, a tackifier, a demulsifier, an extreme pressure agent, a seal swell agent, and a combination thereof.

Embodiment B5. The lubricant composition according to embodiment B4, wherein the at least one lubricant additive comprises an optionally substituted diaryl amine antioxidant, a hindered phenol antioxidant, or both.

Embodiment B6. The lubricant composition according to embodiment B5, wherein a weight ratio of the 3,4-oxypyridinone of structure (I) (based on 3,4-oxypyridinone ring(s) plus optional spacer only, not including connected oligomer and/or polymer portion(s)) to a sum of the optionally substituted diaryl amine and hindered phenol antioxidants is from 10:1 to 1:10 or from 5:1 to 1:5.

Embodiment B7. The lubricant composition according to any one of embodiments B4-B6, wherein the at least one lubricant additive comprises:

a zinc dialkyldithiophosphate antiwear agent;

an organic friction modifier, a molybdenum-containing friction modifier, or a combination thereof;

an optionally substituted triazole corrosion inhibitor, an optionally substituted benzotriazole corrosion inhibitor, an optionally substituted thiadiazole corrosion inhibitor, an ashless dihydrocarbyl dithiocarbamate, a $C_8$-$C_{18}$ acrylate, a $C_2$-$C_6$ dialkylene glycol diester, a tri-hydrocarbyl $C_1$-$C_8$ borate corrosion inhibitor, or a combination thereof; and/or a multi-arm star viscosity modifier, an olefin copolymer viscosity modifier, a hydrogenated diene block copolymer viscosity modifier, a polystyrene copolymer viscosity modifier, a poly(meth)acrylate viscosity modifier, a poly(dialkyl fumarate)-based viscosity modifier, a poly(vinyl acyl ester)-based viscosity modifier, or a combination or copolymer thereof.

Embodiment B8. The lubricant composition according to any one of embodiments B4-B7, wherein the at least one lubricant additive comprises substantially no molybdenum-containing friction modifier.

Embodiment B9. A method of inhibiting and/or mitigating viscosity increase in a composition comprising a non-aqueous medium by addition of the 3,4-oxypyridinone composition of any one of embodiments B1-B8, or via formation of a complex or reaction product thereof, in an amount that is effective in disrupting oxidation catalysis through iron chelation.

Embodiment B10. Use of the non-aqueous 3,4-oxypyridinone-containing composition according to any one of embodiments B1-B8, or a complex or reaction product thereof, to inhibit and/or mitigate viscosity increase in a lubricant composition containing said composition, e.g., through effective disruption of oxidation catalysis through iron chelation.

Embodiment B11. A method of improving oxidative stability and/or mitigating impact of oxidative degradation of a composition comprising a non-aqueous medium by addition of the 3,4-oxypyridinone composition of any one of embodiments B1-B8, or via formation of a complex or reaction product thereof, in an amount that is effective in disrupting oxidation catalysis through iron chelation:

Embodiment B12. Use of the non-aqueous 3,4-oxypyridinone-containing composition according to any one of embodiments B1-B8, or a complex or reaction product thereof, to improve oxidative degradation of and/or to mitigate viscosity increase in a lubricant composition containing said composition, e.g., through effective disruption of oxidation catalysis through iron chelation.

Embodiment B13. The lubricant composition according to any one of embodiments B5-B8, the method according to embodiment B9 or embodiment B11, or the use according to embodiment B10 or embodiment B12, wherein the lubricant composition comprising the 3,4-oxypyridinone of structure (I) and either or both of the optionally substituted diaryl amine and hindered phenol antioxidants (and optionally also a magnesium detergent and/or a salicylate detergent), when subject to a CEC L-109 oxidation test for at least 200 hours (e.g., for ~216 hours and/or ~240 hours) at ~150° C., exhibits an increase in a value of kinematic viscosity at ~100° C. (KV100) that is:

at most 40% above a KV100 value from the same lubricant composition immediately before the CEC L-109 oxidation test began (0 hours); and at least 30% below a KV100 value from a comparative composition that was subject to the CEC L-109 oxidation test for an identical time period, wherein the comparative composition comprises only either or both of the optionally substituted diaryl amine and hindered phenol antioxidants and not the 3,4-oxypyridinone of structure (I).

Embodiment C1. A lubricant composition comprising:

a Group I, Group II, Group III, Group IV, and/or Group V lubricating oil basestock;

a 3,4-oxypyridinone compound of structure (I):

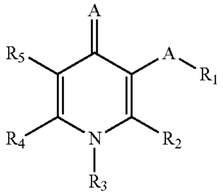

(I)

wherein:

each A is individually an oxygen atom, a sulfur atom, an oxymethyl (—$CH_2$—O—) moiety, or a thiomethyl (—$CH_2$—S—) moiety;

$R_1$ is hydrogen; an ammonium ion; a $C_1$-$C_6$ monoalkylammonium ion; a $C_1$-$C_6$ dialkylammonium ion; a $C_1$-$C_6$ trialkylammonium ion; a $C_1$-$C_6$ tetraalkylammonium ion; a $C_1$-$C_6$ monoalkylsilyl moiety; a $C_1$-$C_6$ dialkylsilyl moiety; a $C_1$-$C_6$ trialkylsilyl moiety; an optionally substituted aryl, alkyl, alkaryl, or aralkyl sulfonyl moiety; a linear, branched, and/or cyclic $C_1$-$C_{20}$ hydrocarbyl sulfide; a linear, branched, and/or cyclic $C_1$-$C_{20}$ hydrocarbyl moiety; an at least partially halogenated linear, branched, and/or cyclic $C_1$-$C_{20}$ moiety; an ether-containing linear, branched, and/or cyclic $C_1$-$C_{20}$ moiety; a thioether-containing linear, branched, and/or cyclic $C_1$-$C_{20}$ moiety; an ester-containing linear, branched, and/or cyclic $C_1$-$C_{20}$ moiety; a thioester-containing linear, branched, and/or cyclic $C_1$-$C_{20}$ moiety; a linear, branched, and/or cyclic $C_1$-$C_{20}$ acyl moiety; a linear, branched, and/or cyclic $C_1$-$C_{20}$ thioacyl moiety; a linear, branched, and/or cyclic $C_1$-$C_{20}$ hydrocarbyloxyacyl moiety; a linear, branched, and/or cyclic $C_1$-$C_{20}$ hydrocarbyloxythioacyl moiety; a linear, branched, and/or cyclic $C_1$-$C_{20}$ hydrocarbylthiocarbonyl moiety; a linear, branched, and/or cyclic $C_1$-$C_{20}$ hydrocarbylthio-thioacyl moiety; an amide-containing linear, branched, and/or cyclic $C_1$-$C_{20}$ moiety; a thioamide-containing linear, branched, and/or cyclic $C_1$-$C_{20}$ moiety; a ketone-containing linear, branched, and/or cyclic $C_1$-$C_{20}$ moiety; a thioketone-containing linear, branched, and/or cyclic $C_1$-$C_{20}$ moiety; an aldehyde-containing linear, branched, and/or cyclic $C_1$-$C_{20}$ moiety; a thioaldehyde-containing linear, branched, and/or cyclic $C_1$-$C_{20}$ moiety; a mercaptan-containing linear, branched, and/or cyclic $C_1$-$C_{20}$ moiety; a hydroxyl-containing linear, branched, and/or cyclic $C_1$-$C_{20}$ moiety; a nonionic linear, branched, and/or (hetero) cyclic moiety containing 1 to 20 carbon atoms at least one nitrogen atom, and optionally at least one sulfur and/or oxygen atom; another 3,4-oxypyridinone connected as an ether or thioether at a meta position to the ring nitrogen thereof; or a combination thereof;

$R_2$ is hydrogen; a halogen; a linear, branched, and/or cyclic $C_1$-$C_{12}$ hydrocarbyl moiety; an at least partially halogenated linear, branched, and/or cyclic $C_1$-$C_{12}$ moiety; an amine-containing linear, branched, and/or cyclic $C_1$-$C_{20}$ moiety; an ether-containing linear, branched, and/or cyclic $C_1$-$C_{20}$ moiety; a hydroxyl-containing linear, branched, and/or cyclic $C_1$-$C_{12}$ moiety; an aldehyde-containing linear, branched, and/or cyclic $C_1$-$C_{20}$ moiety; a nitrile-containing linear, branched, and/or cyclic $C_1$-$C_{20}$ moiety; or a combination thereof;

$R_3$ is hydrogen; a halogen; a linear, branched, and/or cyclic $C_6$-$C_{24}$ hydrocarbyl moiety; or a combination thereof;

$R_4$ is hydrogen; a halogen; a linear, branched, and/or cyclic $C_1$-$C_{12}$ hydrocarbyl moiety; an at least partially halogenated linear, branched, and/or cyclic $C_1$-$C_{12}$ moiety; an amine-containing linear, branched, and/or cyclic $C_1$-$C_{20}$ moiety; an ether-containing linear, branched, and/or cyclic $C_1$-$C_{20}$ moiety; a hydroxyl-containing linear, branched, and/or cyclic $C_1$-$C_{12}$ moiety; an aldehyde-containing linear, branched, and/or cyclic $C_1$-$C_{20}$ moiety; a nitrile-containing linear, branched, and/or cyclic $C_1$-$C_{20}$ moiety; or a combination thereof; and $R_5$ is hydrogen; a halogen; a linear, branched, and/or cyclic $C_1$-$C_{12}$ hydrocarbyl moiety; an at least partially halogenated linear, branched, and/or cyclic $C_1$-$C_{12}$ moiety; a hydroxylated linear, branched, and/or cyclic $C_1$-$C_6$ moiety; an $R_1$-A- moiety; or a combination thereof;

or alternatively one or more of $R_1$ and $R_2$, $R_2$ and $R_3$, $R_3$ and $R_4$, and $R_4$ and $R_5$ may together form one or more (hetero)cyclic rings;

with the proviso that $R_1$ and $R_3$ are not both hydrogen; and either:

a zinc dialkyldithiophosphate antiwear agent, an organic friction modifier, or both; or substantially no organic friction modifier (and optionally substantially no friction modifier).

Embodiment C2. The composition of embodiment C1, wherein the lubricating oil basestock comprises a Group I, Group II, and/or Group III lubricating oil basestock.

Embodiment C3. The composition of embodiment C1 or embodiment C2, wherein:

all A's are oxygen atoms;

$R_1$ is hydrogen; a linear, branched, and/or cyclic $C_1$-$C_{12}$ hydrocarbyl moiety; an ether-containing linear, branched, and/or cyclic $C_1$-$C_{12}$ moiety; another 3,4-oxypyridinone connected as an ether at a meta position to the ring nitrogen thereof; or a combination thereof;

$R_2$ is hydrogen; a linear, branched, and/or cyclic $C_1$-$C_{12}$ hydrocarbyl moiety; an ether-containing linear, branched, and/or cyclic $C_1$-$C_{12}$ moiety; an aldehyde-containing linear, branched, and/or cyclic $C_1$-$C_{12}$ moiety; a nitrile-containing linear, branched, and/or cyclic $C_1$-$C_{12}$ moiety; or a combination thereof;

$R_3$ is a linear, branched, and/or cyclic $C_8$-$C_{20}$ hydrocarbyl moiety;

$R_4$ is hydrogen; a linear, branched, and/or cyclic $C_1$-$C_{12}$ hydrocarbyl moiety; an ether-containing linear, branched, and/or cyclic $C_1$-$C_{12}$ moiety; an aldehyde-containing linear, branched, and/or cyclic $C_1$-$C_{12}$ moiety; a nitrile-containing linear, branched, and/or cyclic $C_1$-$C_{12}$ moiety; or a combination thereof; and $R_5$ is hydrogen; an $R_1$-A- moiety; or a combination thereof;

or $R_4$ and $R_5$ together comprise from 3 to 12 carbons and form a (hetero)cyclic ring structure.

Embodiment C4. The composition according to any one of embodiments C1-C3, further comprising at least one additional lubricant additive selected from the group consisting of a calcium- and/or magnesium-containing detergent, an ashless dispersant, a corrosion inhibitor, an antioxidant, an additional friction modifier, an additional antiwear agent, an antifoamant, a viscosity modifier, a pour point depressant, a tackifier, a demulsifier, an extreme pressure agent, a seal swell agent, and a combination thereof.

Embodiment C5. The lubricant composition according to embodiment C4, wherein the at least one lubricant additive comprises:

an optionally substituted diaryl amine antioxidant, a hindered phenol antioxidant, or both, wherein, when both are present, a weight ratio of the 3,4-oxypyridinone of structure (I) to a sum of the optionally substituted diaryl amine and hindered phenol antioxidants is from 10:1 to 1:10;

substantially no molybdenum-containing friction modifier;

an optionally substituted triazole corrosion inhibitor, an optionally substituted benzotriazole corrosion inhibitor, an optionally substituted thiadiazole corrosion inhibitor, an ashless dihydrocarbyl dithiocarbamate, a $C_8$-$C_{18}$ acrylate, a $C_2$-$C_6$ dialkylene glycol diester, a tri-hydrocarbyl $C_1$-$C_8$ borate corrosion inhibitor, or a combination thereof; and/or a multi-arm star viscosity modifier, an olefin copolymer viscosity modifier, a hydrogenated diene block copolymer viscosity modifier, a polystyrene copolymer viscosity modifier, a poly(meth)acrylate viscosity modifier, a poly(dialkyl fumarate)-based viscosity modifier, a poly(vinyl acyl ester)-based viscosity modifier, or a combination or copolymer thereof.

Embodiment C6. A method of reducing friction and/or wear on a powertrain surface exposed to a composition, the method comprising incorporation of an amount of a 3,4-oxypyridinone compound of structure (I), or via formation of an effective complex or reaction product thereof, to attain the composition of any one of embodiments C1-C5 and/or at the powertrain surface, wherein the composition comprises a zinc dialkyldithiophosphate antiwear agent, an organic friction modifier, or both.

Embodiment C7. Use of the non-aqueous 3,4-oxypyridinone-containing composition according to any one of embodiments C1-C5, or a complex or reaction product thereof, to reduce friction and/or wear on a powertrain surface exposed to said composition, wherein the composition comprises a zinc dialkyldithiophosphate antiwear agent, an organic friction modifier, or both.

Embodiment C8. A method of improving fuel economy of a powertrain exposed to a composition, the method comprising incorporation of an amount of a 3,4-oxypyridinone compound of structure (I), or via formation of an effective complex or reaction product thereof, to attain the composition of any one of embodiments C1-C5 and/or at or near the powertrain surface, wherein the composition comprises an organic friction modifier, and optionally wherein the fuel economy, when measured according to a motored friction B48 test, shows at least a 0.5% fuel economy improvement over an identical composition comprising no 3,4-oxypyridinone compound of structure (I).

Embodiment C9. Use of the non-aqueous 3,4-oxypyridinone-containing composition according to any one of embodiments C1-C5, or a complex or reaction product thereof, to improve fuel economy on a powertrain with a surface exposed to said composition, wherein the composition comprises an organic friction modifier, and optionally wherein the fuel economy, when measured according to a motored friction B48 test, shows at least a 0.5% fuel economy improvement over an identical composition comprising no 3,4-oxypyridinone compound of structure (I).

Embodiment C10. The lubricant composition according to any one of embodiments C1-C5, the method according to embodiment C6 or embodiment C8, or the use according to embodiment C7 or embodiment C9, wherein the lubricant composition comprising the 3,4-oxypyridinone of structure (I) and the zinc dialkyldithiophosphate antiwear agent (and optionally also a calcium detergent), when subject to a high frequency reciprocating rig (HFRR) at temperatures from ~40° C. to ~140° C., exhibits a decrease in average friction coefficient value at high temperatures that are at least 0.012 below average friction coefficient values from comparative compositions that were subject to the HFRR at identical temperatures for an identical time period, wherein the comparative compositions: (a) comprise only the zinc dialkyldithiophosphate antiwear agent and not the 3,4-oxypyridinone of structure (I); and (b) comprise only the 3,4-oxypyridinone of structure (I) and no zinc dialkyldithiophosphate antiwear agent, and wherein high temperatures are from ~90° C. to ~140° C.

Embodiment C11. The lubricant composition according to any one of embodiments C1-C5 and C10, the method according to any one of embodiments C6, C8, and C10, or the use according to any one of embodiments C7, C9, and C10, wherein the lubricant composition comprising the 3,4-oxypyridinone of structure (I) and the zinc dialkyldithiophosphate antiwear agent (and optionally also a calcium detergent), when subject to a high frequency reciprocating rig (HFRR) at a temperatures of ~140° C., exhibits:

- a decrease in average wear scar void volume value of at least 15% below average wear scar void volume values from comparative compositions that were subject to the HFRR at an identical temperature for an identical time period; and/or
- a decrease in average wear scar diameter value of at least 10% below average wear scar diameter values from comparative compositions that were subject to the HFRR at an identical temperature for an identical time period, wherein the comparative compositions:

- (a) comprise only the zinc dialkyldithiophosphate antiwear agent and not the 3,4-oxypyridinone of structure (I); and
- (b) comprise only the 3,4-oxypyridinone of structure (I) and no zinc dialkyldithiophosphate antiwear agent.

Embodiment C12. The lubricant composition according to any one of embodiments C1-C5 and C10-C11, the method according to any one of embodiments C6, C8, and C10-C11, or the use according to any one of embodiments C7, C9, and C10-C11, wherein the lubricant composition comprising the 3,4-oxypyridinone of structure (I) and the zinc dialkyldithiophosphate antiwear agent, when subject to a Sequence X timing chain wear test for at least 216 hours according to ASTM D8279, exhibits:

- for times from 72 hours to 216 hours, a decrease in average timing chain elongation value of at least 25% below an average timing chain elongation value from a comparative composition that was subject to the Sequence X timing chain wear test for an identical time period; and/or
- at ~120 hours, a decrease in average timing chain elongation value of at least 40% below an average timing chain elongation values from a comparative composition that was subject to the Sequence X timing chain wear test for an identical time period, wherein the comparative composition comprises only the zinc dialkyldithiophosphate antiwear agent and not the 3,4-oxypyridinone of structure (I).

Embodiment C13. The lubricant composition according to any one of embodiments C1-C5 and C10-C12, the method according to any one of embodiments C6, C8, and C10-C12, or the use according to any one of embodiments C7, C9, and C10-C12, wherein the lubricant composition comprising the 3,4-oxypyridinone of structure (I) and the organic friction modifier (optionally a weight ratio of organic friction modifier to 3,4-oxypyridinone of structure (I) can be from 10:1 to 3:1), when subject to a high frequency reciprocating rig (HFRR) at a temperature of ~140° C., exhibits:

- a decrease in average wear scar void volume value of at least 15% below average wear scar void volume values from comparative compositions that were subject to the HFRR at an identical temperature for an identical time period; and/or
- a decrease in average wear scar diameter value of at least 3.5% below average wear scar diameter values from comparative compositions that were subject to the HFRR at an identical temperature for an identical time period, wherein the comparative compositions:

- (a) comprise only the organic friction modifier and not the 3,4-oxypyridinone of structure (I); and
- (b) comprise only the 3,4-oxypyridinone of structure (I) and no organic friction modifier.

Embodiment C14. The lubricant composition according to any one of embodiments C1-C5 and C10-C13, the method according to any one of embodiments C6, C8, and C10-C13, or the use according to any one of embodiments C7, C9, and C10-C13, wherein the lubricant composition comprising the 3,4-oxypyridinone of structure (I) and the organic friction modifier (optionally a weight ratio of organic friction modifier to 3,4-oxypyridinone of structure (I) can be from 8:1 to 4:3), when subject to a high frequency reciprocating rig (HFRR) temperatures from ~40° C. to ~140° C., exhibits an average friction coefficient value from 0.080 to 0.115 and lower than an average friction coefficient value from a comparative composition that was subject to the HFRR at identical temperatures for an identical time period, wherein the comparative composition comprises an amount of only organic friction modifier equal to the combined amount of organic friction modifier and 3,4-oxypyridinone of structure (I).

Embodiment C15. A method of reducing friction and/or wear on a powertrain surface exposed to a composition, the method comprising incorporation of an amount of a 3,4-oxypyridinone compound of structure (I), or via formation of an effective complex or reaction product thereof, to attain the composition of any one of embodiments C1-C5 and/or at the powertrain surface, wherein the composition substantially no organic friction modifier (or substantially no friction modifier), and optionally, when subject to a high frequency reciprocating rig (HFRR) at temperatures from ~40° C. to ~140° C., the composition exhibits a decrease in average friction coefficient value:

at all temperatures that are at least 0.02 below an average friction coefficient value from a comparative composition that was subject to the HFRR at identical temperatures for an identical time period; and at moderate-to-high temperatures that are at least 0.06 below an average friction coefficient value from a comparative composition that was subject to the HFRR at identical temperatures for an identical time period, wherein moderate-to-high temperatures are from ~80° C. to ~140° C., wherein the comparative composition comprises substantially no 3,4-oxypyridinone of structure (I) and also substantially no friction modifier.

Embodiment D1. A lubricant composition comprising:

a Group I, Group II, Group III, Group IV, and/or Group V lubricating oil basestock;

a 3,4-oxypyridinone compound of structure (I):

(I)

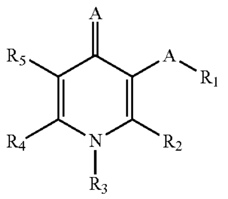

wherein:

each A is individually an oxygen atom, a sulfur atom, an oxymethyl (—$CH_2$—O—) moiety, or a methylthio (—$CH_2$—S—) moiety;

$R_1$ is hydrogen; an ammonium ion; a $C_1$-$C_6$ monoalkylammonium ion; a $C_1$-$C_6$ dialkylammonium ion; a $C_1$-$C_6$ trialkylammonium ion; a $C_1$-$C_6$ tetraalkylammonium ion; a $C_1$-$C_6$ monoalkylsilyl moiety; a $C_1$-$C_6$ dialkylsilyl moiety; a $C_1$-$C_6$ trialkylsilyl moiety; an optionally substituted aryl, alkyl, alkaryl, or aralkyl sulfonyl moiety; a linear, branched, and/or cyclic $C_1$-$C_{20}$ hydrocarbyl sulfide; a linear, branched, and/or cyclic $C_1$-$C_{20}$ hydrocarbyl moiety; an at least partially halogenated linear, branched, and/or cyclic $C_1$-$C_{20}$ moiety; an ether-containing linear, branched, and/or cyclic $C_1$-$C_{20}$ moiety; a thioether-containing linear, branched, and/or cyclic $C_1$-$C_{20}$ moiety; an ester-containing linear, branched, and/or cyclic $C_1$-$C_{20}$ moiety; a thioester-containing linear, branched, and/or cyclic $C_1$-$C_{20}$ moiety; a linear, branched, and/or cyclic $C_1$-$C_{20}$ acyl moiety; a linear, branched, and/or cyclic $C_1$-$C_{20}$ thioacyl moiety; a linear, branched, and/or cyclic $C_1$-$C_{20}$ hydrocarbyloxyacyl moiety; a linear, branched, and/or cyclic $C_1$-$C_{20}$ hydrocarbyloxythioacyl moiety; a linear, branched, and/or cyclic $C_1$-$C_{20}$ hydrocarbylthiocarbonyl moiety; a linear, branched, and/or cyclic $C_1$-$C_{20}$ hydrocarbylthio-thioacyl moiety; an amide-containing linear, branched, and/or cyclic $C_1$-$C_{20}$ moiety; a thioamide-containing linear, branched, and/or cyclic $C_1$-$C_{20}$ moiety; a ketone-containing linear, branched, and/or cyclic $C_1$-$C_{20}$ moiety; a thioketone-containing linear, branched, and/or cyclic $C_1$-$C_{20}$ moiety; an aldehyde-containing linear, branched, and/or cyclic $C_1$-$C_{20}$ moiety; a thioaldehyde-containing linear, branched, and/or cyclic $C_1$-$C_{20}$ moiety; a mercaptan-containing linear, branched, and/or cyclic $C_1$-$C_{20}$ moiety; a hydroxyl-containing linear, branched, and/or cyclic $C_1$-$C_{20}$ moiety; a nonionic linear, branched, and/or (hetero) cyclic moiety containing 1 to 20 carbon atoms at least one nitrogen atom, and optionally at least one sulfur and/or oxygen atom; another 3,4-oxypyridinone connected as an ether or thioether at a meta position to the ring nitrogen thereof; or a combination thereof;

$R_2$ is hydrogen; a halogen; a linear, branched, and/or cyclic $C_1$-$C_{12}$ hydrocarbyl moiety; an at least partially halogenated linear, branched, and/or cyclic $C_1$-$C_{12}$ moiety; an amine-containing linear, branched, and/or cyclic $C_1$-$C_{20}$ moiety; an ether-containing linear, branched, and/or cyclic $C_1$-$C_{20}$ moiety; a hydroxyl-containing linear, branched, and/or cyclic $C_1$-$C_{12}$ moiety; an aldehyde-containing linear, branched, and/or cyclic $C_1$-$C_{20}$ moiety; a nitrile-containing linear, branched, and/or cyclic $C_1$-$C_{20}$ moiety; or a combination thereof;

$R_3$ is hydrogen; a halogen; a linear, branched, and/or cyclic $C_6$-$C_{24}$ hydrocarbyl moiety; or a combination thereof;

$R_4$ is hydrogen; a halogen; a linear, branched, and/or cyclic $C_1$-$C_{12}$ hydrocarbyl moiety; an at least partially halogenated linear, branched, and/or cyclic $C_1$-$C_{12}$ moiety; an amine-containing linear, branched, and/or cyclic $C_1$-$C_{20}$ moiety; an ether-containing linear, branched, and/or cyclic $C_1$-$C_{20}$ moiety; a hydroxyl-containing linear, branched, and/or cyclic $C_1$-$C_{12}$ moiety; an aldehyde-containing linear, branched, and/or cyclic $C_1$-$C_{20}$ moiety; a nitrile-containing linear, branched, and/or cyclic $C_1$-$C_{20}$ moiety; or a combination thereof; and $R_5$ is hydrogen; a halogen; a linear, branched, and/or cyclic $C_1$-$C_{12}$ hydrocarbyl moiety; an at least partially halogenated linear, branched, and/or cyclic $C_1$-$C_{12}$ moiety; a hydroxylated linear, branched, and/or cyclic $C_1$-$C_6$ moiety; an $R_1$-A- moiety; or a combination thereof;

or alternatively one or more of $R_1$ and $R_2$, $R_2$ and $R_3$, $R_3$ and $R_4$, and $R_4$ and $R_5$ may together form one or more (hetero)cyclic rings;

with the proviso that $R_1$ and $R_3$ are not both hydrogen; and either:

an optionally substituted triazole corrosion inhibitor, an optionally substituted benzotriazole corrosion inhibitor, an optionally substituted thiadiazole, an optionally substituted thiadiazole corrosion inhibitor, an ashless dihydrocarbyl dithiocarbamate, a $C_8$-$C_{18}$ acrylate, a $C_2$-$C_6$ dialkylene glycol diester, a tri-hydrocarbyl $C_1$-$C_8$ borate corrosion inhibitor, or a combination thereof; or substantially none of the following: an optionally substituted triazole corrosion inhibitor; an optionally substituted benzotriazole corrosion inhibitor; an optionally substituted thiadiazole corrosion inhibitor; an ashless dihydrocarbyl dithiocarbamate; a $C_8$-$C_{18}$ acrylate; a $C_2$-$C_6$ dialkylene glycol diester; and a tri-hydrocarbyl $C_1$-$C_8$ borate corrosion inhibitor.

Embodiment D2. The composition of embodiment D1, wherein the lubricating oil basestock comprises a Group I, Group II, and/or Group III lubricating oil basestock.

Embodiment D3. The composition of embodiment D1 or embodiment D2, wherein:

all A's are oxygen atoms;

$R_1$ is hydrogen; a linear, branched, and/or cyclic $C_1$-$C_{12}$ hydrocarbyl moiety; an ether-containing linear, branched, and/or cyclic $C_1$-$C_{12}$ moiety; another 3,4-oxypyridinone connected as an ether at a meta position to the ring nitrogen thereof; or a combination thereof;

$R_2$ is hydrogen; a linear, branched, and/or cyclic $C_1$-$C_{12}$ hydrocarbyl moiety; an ether-containing linear, branched, and/or cyclic $C_1$-$C_{12}$ moiety; an aldehyde-containing linear, branched, and/or cyclic $C_1$-$C_{12}$ moiety; a nitrile-containing linear, branched, and/or cyclic $C_1$-$C_{12}$ moiety; or a combination thereof;

$R_3$ is a linear, branched, and/or cyclic $C_8$-$C_{20}$ hydrocarbyl moiety;

$R_4$ is hydrogen; a linear, branched, and/or cyclic $C_1$-$C_{12}$ hydrocarbyl moiety; an ether-containing linear, branched, and/or cyclic $C_1$-$C_{12}$ moiety; an aldehyde-containing linear, branched, and/or cyclic $C_1$-$C_{12}$ moiety; a nitrile-containing linear, branched, and/or cyclic $C_1$-$C_{12}$ moiety; or a combination thereof; and $R_5$ is hydrogen; an $R_1$-A- moiety; or a combination thereof;

or $R_4$ and $R_5$ together comprise from 3 to 12 carbons and form a (hetero)cyclic ring structure.

Embodiment D4. The composition according to any one of embodiments D1-D3, further comprising at least one additional lubricant additive selected from the group consisting of a calcium- and/or magnesium-containing detergent, an ashless dispersant, an additional corrosion inhibitor, an antioxidant, a friction modifier, an antiwear agent, an antifoamant, a viscosity modifier, a pour point depressant, a tackifier, a demulsifier, an extreme pressure agent, a seal swell agent, and a combination thereof.

Embodiment D5. The lubricant composition according to embodiment D4, wherein the at least one lubricant additive comprises:

an optionally substituted diaryl amine antioxidant, a hindered phenol antioxidant, or both, wherein, when both are present, a weight ratio of the 3,4-oxypyridinone of structure (I) to a sum of the optionally substituted diaryl amine and hindered phenol antioxidants is from 10:1 to 1:10;

a zinc dialkyldithiophosphate antiwear agent, an organic friction modifier, or both;

substantially no molybdenum-containing friction modifier;

an additional corrosion inhibitor comprising an optionally substituted triazole corrosion inhibitor, an optionally substituted benzotriazole corrosion inhibitor, an optionally substituted thiadiazole corrosion inhibitor, an ashless dihydrocarbyl dithiocarbamate, a $C_8$-$C_{18}$ acrylate, a $C_2$-$C_6$ dialkylene glycol diester, a tri-hydrocarbyl $C_1$-$C_8$ borate corrosion inhibitor, or a combination thereof; and/or a multi-arm star viscosity modifier, an olefin copolymer viscosity modifier, a hydrogenated diene block copolymer viscosity modifier, a polystyrene copolymer viscosity modifier, a poly(meth)acrylate viscosity modifier, a poly(dialkyl fumarate)-based viscosity modifier, a poly(vinyl acyl ester)-based viscosity modifier, or a combination or copolymer thereof.

Embodiment D6. The lubricant composition according to embodiment D4, wherein the at least one lubricant additive comprises a molybdenum-containing friction modifier.

Embodiment D7. A method of inhibiting and/or mitigating copper and/or lead corrosion on a powertrain surface exposed to a composition, the method comprising incorporation of an amount of a 3,4-oxypyridinone compound of structure (I), or via formation of an effective complex or reaction product thereof, to attain the composition of any one of embodiments D1-D6 and/or at the powertrain surface, wherein the composition comprises an optionally substituted triazole corrosion inhibitor, an optionally substituted benzotriazole corrosion inhibitor, an optionally substituted thiadiazole corrosion inhibitor, an ashless dihydrocarbyl dithiocarbamate, a $C_8$-$C_{18}$ acrylate, a $C_2$-$C_6$ dialkylene glycol diester, a tri-hydrocarbyl $C_1$-$C_8$ borate corrosion inhibitor, or a combination thereof.

Embodiment D8. Use of the non-aqueous 3,4-oxypyridinone-containing composition according to any one of embodiments D1-D6, or a complex or reaction product thereof, to inhibit and/or mitigate copper and/or lead corrosion on a powertrain surface exposed to said composition, wherein the composition comprises an optionally substituted triazole corrosion inhibitor, an optionally substituted benzotriazole corrosion inhibitor, an optionally substituted thiadiazole corrosion inhibitor, an ashless dihydrocarbyl dithiocarbamate, a $C_8$-$C_{18}$ acrylate, a $C_2$-$C_6$ dialkylene glycol diester, a tri-hydrocarbyl $C_1$-$C_8$ borate corrosion inhibitor, or a combination thereof.

Embodiment D9. A method of inhibiting and/or mitigating copper and/or lead corrosion on a powertrain surface exposed to a composition, the method comprising incorporation of an amount of a 3,4-oxypyridinone compound of structure (I), or via formation of an effective complex or reaction product thereof, to attain the composition of any one of embodiments D1-D6 and/or at the powertrain surface, wherein the composition comprises substantially none of the following: an optionally substituted triazole corrosion inhibitor; an optionally substituted benzotriazole corrosion inhibitor; an optionally substituted thiadiazole corrosion inhibitor; an ashless dihydrocarbyl dithiocarbamate; a $C_8$-$C_{18}$ acrylate; a $C_2$-$C_6$ dialkylene glycol diester; and a tri-hydrocarbyl $C_1$-$C_8$ borate corrosion inhibitor.

Embodiment D10. Use of the non-aqueous 3,4-oxypyridinone-containing composition according to any one of embodiments D1-D6, or a complex or reaction product thereof, to inhibit and/or mitigate copper and/or lead corrosion on a powertrain surface exposed to said composition, wherein the composition comprises substantially none of the following: an optionally substituted triazole corrosion inhibitor; an optionally substituted benzotriazole corrosion inhibitor; an optionally substituted thiadiazole corrosion inhibitor; an ashless dihydrocarbyl dithiocarbamate; a $C_8$-$C_{18}$ acrylate; a $C_2$-$C_6$ dialkylene glycol diester; and a tri-hydrocarbyl $C_1$-$C_8$ borate corrosion inhibitor.

Embodiment D11. The lubricant composition according to any one of embodiments D1-D6, the method according to embodiment D7, or the use according to embodiment D8, wherein the lubricant composition comprising the 3,4-oxypyridinone of structure (I) and a tri-hydrocarbyl $C_1$-$C_8$ borate corrosion inhibitor (and optionally also comprising: a calcium-containing detergent and substantially no magnesium-containing detergent; and/or a calcium salicylate detergent), when subject to a high temperature corrosion bench test (HTCBT) at ~135° C. according to ASTM D6594, exhibits a dissolved copper level after 168 hours of no more than 25 ppm Cu and a dissolved lead level after 168 hours of no more than 100 ppm Pb.

Embodiment D12. The lubricant composition according to any one of embodiments D1-D6 and D11, the method according to embodiment D7 or embodiment D11, or the use according to embodiment D8 or embodiment D11, wherein the lubricant composition comprising the 3,4-oxypyridinone of structure (I) and an optionally substituted triazole corrosion inhibitor and/or an optionally substituted benzotriazole corrosion inhibitor (and optionally also comprising: a calcium-containing detergent and substantially no magnesium-containing detergent; and/or a calcium salicylate detergent), when subject to a high temperature corrosion bench test (HTCBT) at ~135° C. according to ASTM D6594, exhibits a dissolved copper level after 168 hours of no more than 25 ppm Cu and a dissolved lead level after 168 hours of no more than 140 ppm Pb.

Embodiment D13. The lubricant composition according to any one of embodiments D1-D6 and D11-D12, the method according to any one of embodiments D7 and D11-D12, or the use according to any one of embodiments D8 and D11-D12, wherein the lubricant composition comprising the 3,4-oxypyridinone of structure (I) and one or more of an ashless dihydrocarbyl dithiocarbamate, a $C_8$-$C_{18}$ acrylate, and a $C_2$-$C_6$ dialkylene glycol diester (and optionally also comprising a calcium salicylate detergent), when subject to a high temperature corrosion bench test (HTCBT) at ~135° C. according to ASTM D6594, exhibits a dissolved copper level after 168 hours of no more than 25 ppm Cu and a dissolved lead level after 168 hours of no more than 140 ppm Pb.

Embodiment D14. The lubricant composition according to any one of embodiments D1-D6, the method according to embodiment D9, or the use according to embodiment D10, wherein the lubricant composition comprising the 3,4-oxypyridinone of structure (I) and substantially none of an optionally substituted triazole corrosion inhibitor, an optionally substituted benzotriazole corrosion inhibitor, an optionally substituted thiadiazole corrosion inhibitor, an ashless dihydrocarbyl dithiocarbamate, a $C_8$-$C_{18}$ acrylate, a $C_2$-$C_6$ dialkylene glycol diester, and a tri-hydrocarbyl $C_1$-$C_8$ borate corrosion inhibitor (and optionally further comprising one or more of a calcium salicylate detergent, a combination of magnesium- and calcium-containing detergents, substantially no sulfonate detergents, substantially no molybdenum friction modifier, a zinc dihydrocarbyl dithiophosphate antiwear agent in which the hydrocarbyl groups are connected to the dithiophosphate moiety via secondary carbon atoms, and at least one boron-containing compound), when subject to a high temperature corrosion bench test (HTCBT) at ~135° C. according to ASTM D6594, exhibits a dissolved copper level after 168 hours of no more than 25 ppm Cu and a dissolved lead level after 168 hours of no more than 140 ppm Pb.

Embodiment D15. The lubricant composition according to any one of embodiments D1-D6 and D11-D13, the method according to any one of embodiments D7 and D11-D13, or the use according to any one of embodiments D8 and D11-D13, wherein the lubricant composition comprising the 3,4-oxypyridinone of structure (I), a tri-hydrocarbyl $C_1$-$C_8$ borate corrosion inhibitor, and either an optionally substituted triazole corrosion inhibitor or an optionally substituted benzotriazole corrosion inhibitor, when subject to a Sequence VIII engine test according to ASTM D6709, exhibits:

an adjusted bearing weight loss from −3% to +50% below an adjusted bearing weight loss from a comparative composition under identical test conditions; and a stripped viscosity at ~100° C. of no more than 2.5% above a stripped viscosity at ~100° C. from a comparative composition under identical test conditions, wherein the comparative composition comprises substantially none of the 3,4-oxypyridinone compound of structure (I), substantially none of the tri-hydrocarbyl $C_1$-$C_8$ borate corrosion inhibitor, and substantially none of either the optionally substituted triazole corrosion inhibitor or the optionally substituted benzotriazole corrosion inhibitor.

Embodiment D16. A method of inhibiting and/or mitigating total acid number (TAN) increase over a time period, with substantially no (in this context, e.g., no more than 7%, no more than 5%, or no more than 3%; in particular, no more than 5% or no more than 3%) change in total base number (TBN) over the same time period, in a composition according to any of embodiments D1-D6 and D14, the method comprising incorporation of an amount of a 3,4-oxypyridinone compound of structure (I) to the composition, or formation of an effective complex or reaction product thereof in the composition, wherein the composition comprises substantially none of the following: an optionally substituted triazole corrosion inhibitor; an optionally substituted benzotriazole corrosion inhibitor; an optionally substituted thiadiazole corrosion inhibitor; an ashless dihydrocarbyl dithiocarbamate; a $C_8$-$C_{18}$ acrylate; a $C_2$-$C_6$ dialkylene glycol diester; and a tri-hydrocarbyl $C_1$-$C_8$ borate corrosion inhibitor.

Embodiment D17. The lubricating composition according to any one of embodiments D1-D6 and D14, the method according to any one of embodiments D9, D14, and D16, or the use according to embodiment D10 or embodiment D14, wherein the lubricant composition comprising the 3,4-oxypyridinone of structure (I) (and optionally also comprising a zinc dihydrocarbyl dithiophosphate antiwear agent, a molybdenum-containing friction modifier, and a salicylate detergent), when subject to a Sequence X timing chain wear test for at least 216 hours according to ASTM D8279, exhibits:

for times from 120 hours to 216 hours, a decrease in TAN value, as measured according to ASTM D664, of at least 1.0 mg KOH/g below a TAN value from a comparative composition that was subject to the Sequence X timing chain wear test for an identical time period; and (i) a difference in TBN value, as measured according to ASTM D4739, at end of test that is no more than 0.5 mg KOH/g above or below a TBN value from a comparative composition that was subject to the diesel engine oxidation test for an identical time period, and/or (ii) a difference in TBN value, as measured according to ASTM D4739, at any time during the test that is no more than 1.0 mg KOH/g above or below a TBN value from a comparative composition that was subject to the Sequence X timing chain wear test for an identical time period, wherein the comparative composition comprises substantially none the 3,4-oxypyridinone of structure (I) but is otherwise identical to the lubricant composition.

Embodiment D18. The lubricating composition according to any one of embodiments D1-D6, D14, and D17, the method according to any one of embodiments D9, D14, and D16-D17, or the use according to any one of embodiments D10, D14, and D17, wherein the lubricant composition comprising the 3,4-oxypyridinone of structure (I) (and optionally also comprising a zinc dihydrocarbyl dithiophosphate antiwear agent, a molybdenum-containing friction modifier, and a salicylate detergent), when subject to a Sequence IVB valve train wear test for ~200 hours according to ASTM D8350, exhibits:

for times of at least 175 hours, a decrease in TAN value, as measured according to ASTM D664, of at least 1.2 mg KOH/g below a TAN value from a comparative composition that was subject to the Sequence IVB valve train wear test for an identical time period; and/or (i) a difference in TBN value, as measured according to ASTM D4739, at end of test that is no more than 0.5 mg KOH/g above or below a TBN value from a comparative composition that was subject to the Sequence IVB valve train wear test for an identical time period, and/or (ii) a difference in TBN value, as measured according to ASTM D4739, at times of at least 25 hours that are each no more than 1.0 mg KOH/g above or below a TBN value from a comparative composition that was subject to the Sequence IVB valve train wear test for an identical time period, wherein the comparative composition comprises substantially none the 3,4-oxypyridinone of structure (I) but is otherwise identical to the lubricant composition.

Embodiment D19. The lubricating composition according to any one of embodiments D1-D6, D14, and D17-D18, the method according to any one of embodiments D9, D14, and D16-D18, or the use according to any one of embodiments D10, D14, and D17-D18, wherein the lubricant composition comprising the 3,4-oxypyridinone of structure (I), when subject to one or more of (a) an oxidation test in a heavy exhaust gas recycle (EGR) diesel engine with variable geometry turbocharging (VGT) for at least 360 hours, (b) a Sequence X timing chain wear test for at least 216 hours according to ASTM D8279, and/or (c) a Sequence IVB valve train wear test for ~200 hours according to ASTM D8350, exhibits, at some time after TAN-TBN crossover and until end of test, a decrease in TAN value, as measured according to ASTM D664, that is at least 10% and/or at least 0.7 mg KOH/g below a TAN value from a comparative composition that was subject to the one or more tests for an identical time period, wherein:

TAN-TBN crossover represents the time during the test at which TBN values of both lubricant composition and comparative composition, measured according to ASTM D4739, exceed TAN values of both lubricant composition and comparative composition, respectively, by at least 3%, whereas both TAN values exceeded both TBN values by at least 3% at start of test (0 hours); and the comparative composition comprises substantially none the 3,4-oxypyridinone of structure (I) but is otherwise identical to the lubricant composition.

Embodiment E1. A lubricating composition, method, or use comprising any combination of lubricating compositions, methods, or uses according to any one of embodiments A1-A16, any one of embodiments B1-B13, any one of embodiments C1-C15, and/or any one of embodiments D1-D19.

The invention will now be described by way of non-limiting examples only.

EXAMPLES

Throughout these Examples, several exemplary lubricant formulations were used to illustrate performance characteristics, both as a baseline and in tandem with 3,4-oxypyridinones according to the disclosure and sometimes other ligands for comparison. In some cases, variations on these formulations were used—those variations are noted herein. Below are the exemplary lubricant formulations.

Lubricant Formulation V is made from a ~12 wt % additive package containing: a mixture of a neutral calcium salicylate detergent (TBN ~60-65) and an overbased calcium salicylate detergent (TBN above 200) in a weight ratio of ~1:~4; a ZDDP antiwear agent whose alkyl phosphate esters are a mixture of primary and secondary alkyl groups with an average carbon-to-zinc atomic ratio of less than 10; a combination of PIBSA-PAM dispersants whose polyisobutylene arms are lower molecular weight (e.g., ~800-1200 g/mol) and higher molecular weight (e.g., ~1800-2500 g/mol), respectively, with the dispersants being present in a weight ratio of ~1:~10; a polysiloxane antifoamant; a diaryl amine antioxidant; a tackifier; and a minor amount of Group II and/or Group III lubricating oil basestock. In addition to the additive package, Lubricant Formulation V contains a pour point depressant; a star copolymer viscosity modifier with triblock copolymer arms whose middle block is polystyrene and whose inner and outer blocks are hydrogenated diene; and more than 75 wt % of Group II and/or Group III lubricating oil basestock/diluent.

Lubricant Formulation W is made from a ~13 wt % additive package containing: an overbased magnesium salicylate detergent (TBN above 300); a ZDDP antiwear agent whose alkyl phosphate esters are secondary alkyl groups with an average carbon-to-zinc atomic ratio of less than 10; a combination of PIBSA-PAM dispersants whose polyisobutylene arms are lower molecular weight (e.g., ~800-1200 g/mol) and higher molecular weight (e.g., ~1800-2500 g/mol), respectively, with the dispersants being present in a weight ratio of ~1:~14; a glycerol monooleate organic friction modifier; a polysiloxane antifoamant; a diaryl amine antioxidant; a tackifier; and a minor amount of Group II and/or Group III lubricating oil basestock. In addition to the additive package, Lubricant Formulation W contains a pour point depressant; a star copolymer viscosity modifier with triblock copolymer arms whose middle block is polystyrene and whose inner and outer blocks are hydrogenated diene; and at least 80 wt % of Group II and/or Group III lubricating oil basestock/diluent.

Lubricant Formulation X is made from an ~11 wt % additive package containing: a mixture of an overbased calcium sulfonate detergent (TBN above 275) and an overbased magnesium sulfonate detergent (TBN above 375) in a weight ratio of ~3:~4; a ZDDP antiwear agent whose alkyl phosphate esters are a mixture of primary and secondary alkyl groups with an average carbon-to-zinc atomic ratio of less than 10; a combination of PIBSA-PAM dispersants whose polyisobutylene arms are lower molecular weight (e.g., ~800-1200 g/mol) and higher molecular weight (e.g., ~1800-2500 g/mol), respectively, with the LMW and HIW dispersants being present in a weight ratio of ~1:~4; a trimeric molybdenum dithiocarbamate friction modifier; a polysiloxane antifoamant; a diaryl amine antioxidant; a tackifier; and a minor amount of Group II and/or Group III lubricating oil basestock. In addition to the additive package, Lubricant Formulation X contains a pour point depressant; a star copolymer viscosity modifier with triblock copolymer arms whose middle block is polystyrene and whose inner and outer blocks are hydrogenated diene; and at least 80 wt % of Group II and/or Group III lubricating oil basestock/diluent.

Lubricant Formulation Y is made from an ~13-14 wt % additive package containing: a mixture of an overbased calcium salicylate detergent (TBN above 200) and an overbased magnesium salicylate detergent (TBN above 300) in a weight ratio of ~5:~3; a mixture of ZDDP antiwear agents, one of whose alkyl phosphate esters are a mixture of primary and secondary alkyl groups and the other of whose alkyl phosphate esters are all primary alkyl groups, in a weight ratio of one to the other of ~10:~3; a dispersant comprising the reaction product of an isobutylene oligomer with a pendant succinic anhydride and an alkylene-bridged hydroxyalkoxyaromatic compound; a combination of PIBSA-PAM dispersants whose polyisobutylene arms are lower molecular weight (e.g., ~800-1200 g/mol) and higher molecular weight (e.g., ~1800-2500 g/mol), respectively, with the dispersants being present in a weight ratio of ~2:~11, so as to provide a combination of borated and unborated PIBSA-PAM dispersants in a weight ratio of ~1:~14; a trimeric molybdenum dithiocarbamate friction modifier; a polysiloxane antifoamant; a diaryl amine antioxidant; a tackifier; and a minor amount of Group II and/or Group III lubricating oil basestock. In addition to the additive package, Lubricant Formulation Y contains a pour point depressant; a star copolymer viscosity modifier with triblock copolymer arms whose middle block is polystyrene and whose inner and outer blocks are hydrogenated diene; and more than 70 wt % of Group II and/or Group III lubricating oil basestock/diluent.

Lubricant Formulation Z is made from an ~12 wt % additive package containing: a mixture of an overbased calcium sulfonate detergent (TBN above 275) and an overbased magnesium sulfonate detergent (TBN above 375) in a weight ratio of ~3:~4; a ZDDP antiwear agent whose alkyl phosphate esters are a mixture of primary and secondary alkyl groups with an average carbon-to-zinc atomic ratio of less than 10; a PIBSA-PAM dispersant with polyisobutylene arms of relatively higher molecular weight (e.g., ~1800-2500 g/mol); a trimeric molybdenum dithiocarbamate friction modifier; a polysiloxane antifoamant; a diaryl amine antioxidant; and a minor amount of Group I, Group II, and/or Group III lubricating oil basestock. In addition to the additive package, Lubricant Formulation Z contains a pour point depressant; a star copolymer viscosity modifier with triblock copolymer arms whose middle block is polystyrene and whose inner and outer blocks are hydrogenated diene; and at least 80 wt % of Group I, Group II, and/or Group III lubricating oil basestock/diluent.

Examples 1-2—Cyclic Voltammetry and UV-Vis Spectroscopy

In Example 1, cyclic voltammetry experiments were conducted to evaluate the potential ability of a variety of ligands to affect the $Fe^{3+}/Fe^{2+}$ redox. Without being bound by theory, the more negative the reduction potential (voltage, measured as E in volts), as compared to the flow of current (amperage, measured in μA) at the working electrode, the more difficult it is for the trivalent iron species to be reduced to the divalent iron species, which is believed to relate to the stability of the Fe(III) complex. Therefore, theoretically, a lower reduction potential (more negative voltage) should be an indicator of complex stability, which is more desirable for inhibiting oxidation processes mediated by iron. Because it may be desirable to concatenate these results to a CEC L-109 oxidation test, and as some trivalent iron compound is useful as a benchmark, $Fe(Acac)_3$ was identified for comparison, with Ag/AgCl reduction potential representing "normalization" to 0 Volts. In each experiment (except for Example 1P), 0.1 mM $Fe(Acac)_3$ was added in addition to the approximately 3 molar equivalents of each ligand (except for Example 1D where 1 molar equivalent of ligand was added, and 1K where 2 molar equivalents of ligand were added), relative to the iron compound (in Example 1P, only the iron compound was present and no other). In Table 1 below, more than one distinct reduction potential was observed for some ligands. Nevertheless, as can be seen from Table 1 below, it should also be noted that the 1,2-dimethyl-3-hydroxypyridin-4-one ligand of Example 1A showed the most negative singular distinct reduction potential of those ligands that were tested.

TABLE 1

| Example | Ligand | Reduction Potential |
|---|---|---|
| 1A | 1,2-dimethyl-3-hydroxypyridin-4-one | −0.93 |
| 1B | 2-methylpyridine-3,4-diol | −0.89 |
| 1C | pyridine-3,4-diol | −0.85 |
| 1D | deferoxamine mesylate | −0.83 |
| 1E | 3-methylcatechol | −0.82, −1.02 |
| 1F | 4-methylcatechol | −0.77, −1.06 |
| 1G | Catechol | −0.74, −1.09 |
| 1H | 1-methyl-3-hydroxypyridin-2-one | −0.62 |
| 1J | Pyridine-2,3-diol | −0.55 |
| 1K | Deferasirox | −0.53, −0.87 |
| 1L | Benzhydroxamic acid | −0.51 |
| 1M | Maltol | −0.50 |
| 1N | Kojic acid | −0.38 |
| 1P | $Fe(Acac)_3$ (no additional ligand) | −0.38 |
| 1Q | 1-hydroxypyridin-2-one | −0.37 |
| 1R | 1-hydroxypyridine-2-thione | −0.34 |
| 1S | Hydroxynicotinic acid | −0.18 |
| 1T | Salicylic acid | −0.11 |

Binding affinity is believed to play a role in the effectiveness of a potential ligand in disrupting iron-based catalytic oxidation. Thus, in Example 2, UV-Vis spectroscopy was performed on mixtures of 0.1 mM $Fe(Acac)_3$ and approximately 3 molar equivalents of 1,2-dimethyl-3-hydroxypyridin-4-one (Example 2A) and catechol ligands (Example 2G). Samples of 0.1 mM $Fe(Acac)_3$ alone in water and of ~3 equivalents of each respective ligand alone in water (without any $Fe(Acac)_3$) were also analyzed for comparison.

Because catechol (from Example 1G) exhibited the largest reduction potential in cyclic voltammetry experiments, the UV-Vis spectroscopy was utilized to probe binding affinity for iron, via complexes that can absorb UV-Vis wavelengths (~300-900 nm). The 1,2-dimethyl-3-hydroxypyridin-4-one ligand (example 2A; at ~3 equivalents with 0.1 mM $Fe(Acac)_3$) showed a moderately broad peak centered at ~450 nm with a small shoulder near 400 nm but extending out only to ~630 nm (not shown), whereas the catechol ligand (example 2G; at ~3 equivalents with 0.1 mM $Fe(Acac)_3$) showed an extremely broad major peak centered at ~650 nm and extending past ~900 nm, with a minor overlapping peak at lower wavelengths (also not shown). Without being bound by theory, it is believed that the extremely broad UV-Vis peak for catechol indicates binding with iron(III) to give a mixture of species, whereas the moderate peak breadth for 1,2-dimethyl-3-hydroxypyridin-4-one is believed to indicate binding to give essentially a single multi-ligand, probably tris-chelated, iron(III) complex. The latter 1,2-dimethyl-3-hydroxypyridin-4-one ligand is believed, therefore, to have a higher binding efficiency for the iron in $Fe(Acac)_3$ than catechol (and, by extension, the other ligands having dihydroxyl functionality at neighboring ring locations). Confirmation of the hypothesis regarding high reduction potential and high binding efficiency and its collective effect(s) on iron-catalyzed oxidation processes was therefore sought.

Examples 3-93—CEC L-109 Oxidation/KV100 Increase

The CEC L-109(-14) oxidation test involves measurements of oxidation in the presence of an iron catalyst (Fe(III)Acac) and biofuel by analytical (e.g., FTIR) peak height according to DIN 51 453 and also of kinematic viscosities such as KV100 according to ASTM D445. Any deviations in sample testing from the CEC L-109-14 standard procedures is noted herein. A sample at 0 hours, or immediately before the CEC L-109 oxidation test begins, is considered an SOT (start of test) sample. A sample subject to the CEC L-109 oxidation test for ~216 hours at temperature is considered an EOT (end of test) sample, although in some cases the test is stopped at ~168 hours (which would be noted), at which point that value would be considered an EOT sample. Where there were at least two (or at least three) measurements of kinematic viscosity measurements in the CEC L-109(-14) tests herein (such as KV100), the reported values represent average values. All values are abbreviated as average values herein regardless of whether they are one value or multiples.

Table 2 below shows change in oxidation peak height from SOT (in units of Absorbance per cm), kinematic viscosity at ~100° C. (KV100; in units of $mm^2/s$), and KV100 change from SOT (unitless, as %) for a variety of formulations. The potential iron-chelating ligand compounds are identified by the following alphanumeric nomenclature. They are listed in Table 2 below as [Formulation] "plus" an amount of ligand—however, where specifically noted herein with an "s" superscript, the amount of ligand is more accurately substituted for an equal amount of diluent (basestock) in the composition (optionally in the additive package, before being further diluted, although it is contemplated, though less preferable in most circumstances, that the 3,4-oxypyridinone components could be added separately, such as around the addition of the pour point depressant(s) and/or the viscosity modifier(s) or before or after that).

AA=N-hexadecyl-2-methyl-3-hydroxypyridin-4-one
AB=N-hexadecyl-2-methyl-3-(4-methoxybenzyloxy)-pyridin-4-one
AC=N-hexadecyl-2-methyl-3-t-butylcarbonyloxypyridin-4-one
AD=2-hexadecyl-5-hydroxypyran-4-one
AE=Vanlube® 7723
AF=N-hexadecyl-2-methyl-3-benzyloxypyridin-4-one
AG=N-(2-ethylhexyl)-2-methyl-3-hydroxypyridin-4-one
AH=N-(2-ethylhexyl)-2-ethyl-3-hydroxypyridin-4-one
AI=N-oleyl-2-methyl-3-hydroxypyridin-4-one
AJ=N-oleyl-2-ethyl-3-hydroxypyridin-4-one
AK=N-hexadecyl-2-methyl-3-(2-propenyl-1-oxy)-pyridin-4-one
AL=N-(2-ethylhexyl)-2-ethyl-3-benzyloxypyridin-4-one
AM=N-hexadecyl-2-ethyl-3-benzyloxypyridin-4-one
AN=N-hexadecyl-2-ethyl-3-(2-propenyl-1-oxy)-pyridin-4-one
AO=N-oleyl-2-ethyl-3-benzyloxypyridin-4-one
AP=N-hydrogenated-tallow-2-ethyl-3-benzyloxypyridin-4-one AQ=N-hexadecyl-2-methyl-3-hydroxymethyl-pyridin-4-one
AR=N-hexadecyl-3-methoxypyridin-4-one
AS=N-decyl-2-methyl-3-hydroxypyridin-4-one
AT=N-hexyl-2-methyl-3-hydroxypyridin-4-one
AU=2-hexadecyl-5-hydroxypyridin-4-one
AV=N-methyl-2-hexadecyl-5-hydroxypyridin-4-one
AW=N-hexadecyl-3-hydroxypyridin-4-one
AX=N-hexadecylpyridin-4-one
CA=N-hexadecyl-3-hydroxypyridin-2-one
CB=4-hexadecyl-1-hydroxypyridin-2-one
PA=reaction product of N-aminoethyl-2-methyl-3-hydroxypyridin-4-one and a ~950 Mn polyisobutylene having ~1 succinic anhydride per chain (mono-PIBSA)
PB=reaction product of N-hydroxyethyl-2-ethyl-3-hydroxypyridin-4-one and a ~950 Mn polyisobutylene made via chloro maleation and having ~1 succinic anhydride per chain (mono-PIBSA)
PC=reaction product of N-hydroxyethyl-2-ethyl-3-hydroxypyridin-4-one and a ~950 Mn polyisobutylene made via thermal maleation and having ~1 succinic anhydride per chain (mono-PIBSA)
PD=reaction product of N-aminoethyl-2-ethyl-3-hydroxypyridin-4-one and a ~950 Mn polyisobutylene made via chloro maleation and having ~1 succinic anhydride per chain (mono-PIBSA)
PE=reaction product of N-aminoethyl-2-ethyl-3-hydroxypyridin-4-one and a ~950 Mn polyisobutylene made via thermal maleation and having ~1 succinic anhydride per chain (mono-PIBSA)
PF=copolymerization product of maleic anhydride (MA) and an α-olefin comonomer (OL) having 26-28 carbon atoms, in a weight ratio of ~1:~1 MA:OL (Mn ~10 kDa)
PG=esterification reaction product of N-hydroxyethyl-2-ethyl-3-benzyloxy-pyridin-4-one and PF (~1:~1 molar ratio of pyridinone to anhydride)
PH=esterification reaction product of N-hydroxyethyl-2-ethyl-3-benzyloxy-pyridin-4-one and PF (~1:~5 molar ratio of pyridinone to anhydride)
PI=copolymerisation product of 2-(2-ethyl-3-benzyloxy-pyridin-4-one)ethyl acrylate and 2-ethylhexyl acrylate (~1:~9 molar ratio of pyridinone to 2-ethylhexyl acrylate)
PJ=copolymerisation product of 2-(2-ethyl-3-benzyloxy-pyridin-4-one)ethyl acrylate and 2-ethylhexyl acrylate (~1:~25 molar ratio of pyridinone to 2-ethylhexyl acrylate)
PK=copolymerisation product of N-(2-(2-ethyl-3-benzyloxypyridin-4-one)ethyl) acrylamide and 2-ethylhexyl acrylate (~1:~9 molar ratio of pyridinone to 2-ethylhexyl acrylate)
PL=copolymerisation product of N-(2-(2-ethyl-3-benzyloxypyridin-4-one)ethyl) acrylamide and 2-ethylhexyl acrylate (~1:~50 molar ratio of pyridinone to 2-ethylhexyl acrylate)

TABLE 2

| | | Change in Oxidation Peak Height | | | | | KV100 | | | | | KV100 change | | | | |
|---|---|---|---|---|---|---|---|---|---|---|---|---|---|---|---|---|
| Example | Description | 0 | 72 | 144 | 168 | 216 | 0 | 72 | 144 | 168 | 216 | 0 | 72 | 144 | 168 | 216 |
| 3 (Comp) | V Baseline | 0.0 | 22.2 | 35.1 | 37.5 | 41.4 | 12.0 | 10.6 | 11.2 | 11.6 | 12.9 | 0.0% | −11% | −6.7% | 3.5% | 7.1% |
| 4 | V + 9 eq AA | 0.0 | 14.3 | 24.0 | 26.2 | 30.0 | 11.8 | 11.3 | 11.2 | 11.3 | 11.7 | 0.0% | −4.5% | −5.0% | −4.2% | −1.2% |
| 5 (Comp) | V + 9 eq CB | 0.0 | 21.3 | 52.2 | 64.4 | 84.2 | 11.8 | 10.4 | 10.6 | 11.3 | 15.5 | 0.0% | −12% | −10% | −4.2% | 32% |
| 6 (Comp) | V + 9 eq CA | 0.0 | 21.5 | 37.0 | 40.2 | 45.5 | 11.9 | 11.0 | 11.6 | 12.1 | 13.6 | 0.0% | −7.4% | −2.1% | 1.7% | 15% |
| 7 | V + 9 eq AB | 0.0 | 13.5 | 24.9 | 27.5 | 31.8 | 11.9 | 11.3 | 10.9 | 10.9 | 11.2 | 0.0% | −5.1% | −8.3% | −8.0% | −5.4% |

TABLE 2-continued

| | | Change in Oxidation Peak Height | | | | | KV100 | | | | | KV100 change | | | | |
|---|---|---|---|---|---|---|---|---|---|---|---|---|---|---|---|---|
| Example | Description | 0 | 72 | 144 | 168 | 216 | 0 | 72 | 144 | 168 | 216 | 0 | 72 | 144 | 168 | 216 |
| 8 | V + 9 eq AC | 0.0 | 13.4 | 22.6 | 24.6 | 28.2 | 11.8 | 11.3 | 11.2 | 11.3 | 11.7 | 0.0% | −4.6% | −5.2% | −4.3% | −1.4% |
| 9 | V + 9 eq AD | 0.0 | 26.9 | 40.8 | 43.2 | 47.1 | 1.9 | 10.5 | 11.2 | 11.6 | 13.3 | 0.0% | −11% | −5.6% | −2.1% | 12% |
| 10 | V + 0.5 wt % AE | 0.0 | 20.4 | 31.2 | 33.2 | 36.6 | 12.0 | 11.0 | 11.9 | 12.4 | 14.3 | 0.0% | −8.3% | −0.5% | 3.5% | 19% |
| 11 | V + 9 eq AF | 0.0 | 12.8 | 22.0 | 24.6 | 29.4 | 12.0 | 11.3 | 10.9 | 10.9 | 11.1 | 0.0% | −5.2% | −8.6% | −8.8% | −7.4% |
| 12 | V + 9 eq AG$^{S}$ | 0.0 | 16.6 | 21.1 | 23.0 | 26.2 | 12.0 | 11.3 | 11.4 | 11.5 | 11.9 | 0.0% | −5.5% | −4.6% | −3.7% | −0.8% |
| 13 | V + 9 eq AH | 0.0 | 17.0 | 26.8 | 29.3 | 33.0 | 12.0 | 11.2 | 11.2 | 11.3 | 11.7 | 0.0% | −6.5% | −6.2% | 5.3% | −2.4% |
| 14 | V + 9 eq AI$^{S}$ | 0.0 | 16.0 | 19.7 | 21.5 | 24.9 | 12.0 | 11.6 | 12.0 | 12.2 | 12.8 | 0.0% | 2.9% | 0.1% | 1.9% | 6.9% |
| 15 | V + 9 eq AJ$^{S}$ | 0.0 | 15.9 | 25.2 | 27.1 | 30.7 | 12.0 | 11.5 | 11.8 | 12.0 | 12.5 | 0.0% | 4.5% | −2.4% | 0.7% | 3.4% |
| 16 | V + 9 eq AK | 0.0 | 13.8 | 23.2 | 25.5 | 30.2 | 12.0 | 11.6 | 11.4 | 11.5 | 11.6 | 0.0% | −3.3% | −4.4% | −4.1% | −3.3% |
| 17 | V + 9 eq AL | 0.0 | 16.1 | 27.4 | 30.5 | 36.2 | 12.0 | 11.2 | 11.0 | 11.0 | 11.1 | 0.0% | −6.3% | −8.4% | −8.4% | 7.5% |
| 20 | V + 9 eq AM | 0.0 | 14.2 | 24.2 | 26.9 | 32.0 | 11.9 | 11.2 | 10.8 | 10.8 | 10.9 | 0.0% | −6.5% | −9.9% | −9.9% | −8.4% |
| 21 | V + 9 eq AN | 0.0 | 14.3 | 23.8 | 26.3 | 31.1 | 11.9 | 11.3 | 11.0 | 11.1 | 11.3 | 0.0% | −5.1% | 7.4% | −7.1% | −5.5% |
| 22 | V + 9 eq AO | 0.0 | 13.4 | 22.5 | 24.6 | 28.9 | 12.0 | 11.5 | 11.4 | 11.6 | 11.8 | 0.0% | −4.5% | −5.0% | −4.1% | −1.8% |
| 23 | V + 9 eq AP | 0.0 | 14.9 | 25.6 | 28.4 | 33.9 | 12.0 | 11.2 | 10.9 | 10.8 | 10.9 | 0.0% | −6.7% | −9.8% | −10% | −9.1% |
| 24 | V + 9 eq AQ | 0.0 | 17.9 | 30.6 | 33.4 | 39.1 | 11.8 | 11.2 | 11.7 | 12.2 | 13.2 | 0.0% | −5.3% | −0.5% | 3.1% | 12% |
| 25 | V + 9 eq AR | 0.0 | 10.4 | 23.8 | 39.6 | 79.0 | 11.9 | 11.6 | 10.6 | 9.7 | 9.9 | 0.0% | −0.3% | −1.4% | −2.2% | −2.0% |
| 26 | V + 9 eq AS | 0.0 | 15.4 | 25.5 | 27.8 | 33.0 | 11.8 | 11.3 | 11.3 | 11.3 | 11.6 | 0.0% | −4.2% | −4.7% | −4.1% | −2.1% |
| 27 | V + 9 eq AT | 0.0 | 14.5 | 23.8 | 25.8 | 29.0 | 12.0 | 11.5 | 11.6 | 11.7 | 12.0 | 0.0% | −4.0% | 3.3% | 2.5% | −0.1% |
| 28 | V + 9 eq AU | 0.0 | 12.6 | 20.0 | 21.6 | 24.2 | 12.1 | 11.7 | 11.7 | 11.9 | 12.4 | 0.0% | −3.3% | −2.6% | −1.3% | 2.8% |
| 29 | V + 9 eq AW | 0.0 | 17.1 | 26.5 | 28.3 | 31.9 | 11.8 | 11.0 | 11.4 | 11.6 | 12.1 | 0.0% | −7.0% | −3.6% | −1.5% | 2.4% |
| 30 | V + 9 eq AX | 0.0 | 17.0 | 30.0 | 33.2 | 37.7 | 11.8 | 11.1 | 12.0 | 12.7 | 14.3 | 0.0% | −5.4% | 2.3% | 7.7% | 22% |
| 31 (Comp) | W Baseline | 0.0 | 25.4 | 73.5 | 93.4 | 120 | 8.8 | 8.7 | 9.7 | 12.4 | 56.0 | 0.0% | −1.3% | 4.7% | 19% | 530% |
| 32 | W + 9 eq AA$^{S}$ | 0.0 | 16.4 | 23.5 | 26.2 | 47.3 | 8.8 | 8.9 | 9.0 | 9.0 | 8.7 | 0.0% | 1.2% | 2.6% | 2.4% | −0.6% |
| 33 (Comp) | W + 9 eq CB | 0.0 | 20.8 | 78.9 | 99.7 | 138 | 8.9 | 8.6 | 8.8 | 9.8 | 14.2 | 0.0% | −3.4% | −0.9% | 10% | 60% |
| 34 (Comp) | W + 9 eq CA | 0.0 | 22.2 | 55.4 | 73.2 | 106 | 8.7 | 8.9 | 9.2 | 9.7 | 18.1 | 0.0% | 2.1% | 3.1% | 11.8% | 110% |
| 35 | W + 9 eq AB | 0.0 | 16.9 | 36.4 | 50.5 | 85.6 | 8.8 | 8.6 | 8.2 | 8.2 | 9.6 | 0.0% | −1.9% | −6.0% | −5.9% | 9.7% |
| 36 | W + 9 eq AC | 0.0 | 11.2 | 17.7 | 20.6 | 50.4 | 8.8 | 8.9 | 9.0 | 9.0 | 8.5 | 0.0% | 1.5% | 2.6% | 2.3% | 2.7% |
| 37 | W + 9 eq AD | 0.0 | 28.4 | 85.3 | 103 | 136 | 8.9 | 8.5 | 9.3 | 10.8 | 31.8 | 0.0% | −5.2% | 3.8% | 21% | 260% |
| 38 | W+ 0.5 wt % AE | 0.0 | 22.3 | 35.0 | 39.8 | 50.1 | 8.8 | 8.8 | 9.4 | 10.0 | 15.6 | 0.0% | −0.6% | 6.6% | 14% | 77% |
| 39 | W + 9 eq AF | 0.0 | 15.4 | 30.5 | 45.3 | 86.0 | 8.7 | 8.7 | 8.4 | 8.3 | 9.3 | 0.0% | −0.6% | −4.3% | −5.6% | 6.4% |
| 40 | W + 9 eq AG$^{S}$ | 0.0 | 16.2 | 18.4 | 21.4 | 48.5 | 8.9 | 8.9 | 9.0 | 9.0 | 8.6 | 0.0% | 0.5% | 1.5% | 1.2% | −3.1% |
| 41 | W + 9 eq AH | 0.0 | 17.3 | 34.6 | 60.1 | 103 | 8.8 | 8.8 | 8.4 | 8.3 | 10.1 | 0.0% | −0.2% | −4.6% | −6.1% | 15% |
| 42 | W + 9 eq AI$^{S}$ | 0.0 | 16.3 | 18.5 | 21.6 | 40.0 | 8.8 | 9.0 | 9.2 | 9.3 | 9.2 | 0.0% | 2.2% | 4.9% | 5.6% | 4.8% |
| 43 | W + 9 eq AJ$^{S}$ | 0.0 | 17.5 | 27.4 | 41.5 | 89.2 | 8.8 | 8.9 | 9.1 | 8.8 | 10.2 | 0.0% | 1.1% | 2.6% | −0.4% | 15% |
| 44 | W + 9 eq AK | 0.0 | 14.9 | 25.0 | 39.3 | 85.9 | 8.7 | 8.8 | 8.8 | 8.3 | 8.8 | 0.0% | 0.5% | 1.1% | −4.8% | 0.7% |
| 45 | W + 9 eq AL | 0.0 | 17.7 | 29.9 | 45.2 | 83.9 | 8.7 | 8.6 | 8.4 | 8.2 | 9.0 | 0.0% | −1.3% | −3.2% | −6.3% | 3.8% |
| 46 | W + 9 eq AM | 0.0 | 15.6 | 29.6 | 49.5 | 59.3 | 8.8 | 8.7 | 8.3 | 8.1 | 8.0 | 0.0% | −0.9% | −4.7% | −7.4% | 8.1% |
| 47 | W + 9 eq AN | 0.0 | 14.8 | 31.3 | 55.4 | 97.4 | 8.7 | 8.7 | 8.3 | 8.1 | 9.5 | 0.0% | 0.2% | −5.1% | −7.2% | 8.5% |
| 48 | W + 9 eq AO | 0.0 | 16.3 | 29.5 | 42.5 | 85.2 | 8.8 | 8.7 | 8.6 | 8.6 | 10.0 | 0.0% | −0.2% | −1.3% | −1.9% | 14% |
| 49 | W + 9 eq AP | 0.0 | 17.7 | 42.3 | 63.4 | 102 | 8.8 | 8.6 | 8.2 | 8.4 | 10.3 | 0.0% | −1.5% | −6.4% | −4.7% | 18% |
| 50 | W + 9 eq AQ | 0.0 | 18.9 | 27.6 | 34.0 | 62.7 | 8.7 | 9.0 | 9.3 | 9.4 | 10.3 | 0.0% | 3.3% | 7.3% | 8.8% | 19% |
| 51 | W + 9 eq AR | 0.0 | 19.1 | 79.7 | 99.6 | 138 | 8.6 | 8.6 | 8.2 | 9.0 | 12.0 | 0.0% | 0.0% | −0.5% | 0.4% | 3.3% |
| 52 | W + 9 eq AS | 0.0 | 16.5 | 22.9 | 25.2 | 33.7 | 8.8 | 8.9 | 9.0 | 9.1 | 8.9 | 0.0% | 1.7% | 2.8% | 3.0% | 1.7% |
| 53 | W + 9 eq AT | 0.0 | 14.6 | 20.8 | 22.7 | 33.2 | 8.8 | 8.9 | 9.0 | 9.0 | 8.9 | 0.0% | 1.3% | 2.8% | 3.0% | 1.3% |
| 54 | W + 9 eq AU | 0.0 | 11.3 | 16.2 | 17.2 | 18.9 | 8.7 | 8.9 | 9.2 | 9.4 | 9.6 | 0.0% | 2.5% | 5.8% | 7.4% | 10% |
| 55 | W + 9 eq AV | 0.0 | 17.2 | 23.8 | 26.4 | 35.6 | 8.7 | 8.9 | 9.3 | 9.4 | 9.6 | 0.0% | 2.4% | 6.6% | 7.7% | 10% |
| 56 | W + 9 eq AW | 0.0 | 17.2 | 23.8 | 26.1 | 33.3 | 8.7 | 8.8 | 9.1 | 9.2 | 9.2 | 0.0% | 1.0% | 4.9% | 5.7% | 6.2% |
| 57 | W + 9 eq AX | 0.0 | 19.1 | 26.0 | 29.1 | 41.3 | 8.6 | 9.2 | 10.1 | 10.5 | 11.9 | 0.0% | 6.2% | 16% | 22% | 38% |
| 58 | W + 9 eq PA | 0.0 | 14.2 | 25.1 | 45.6 | 94.8 | 9.1 | 9.1 | 8.9 | 8.5 | 9.7 | 0.0% | 0.0% | 2.1% | −6.4% | 6.0% |
| 59 | W + 9 eq PB | 0.0 | 9.8 | 16.2 | 17.7 | 20.9 | 9.4 | 10.0 | 9.5 | 9.5 | 9.6 | 0.0% | 1.4% | 1.1% | 1.3% | 1.5% |
| 60 | W + 9 eq PC | 0.0 | 10.4 | 16.7 | 18.4 | 21.8 | 9.4 | 10.0 | 9.5 | 9.6 | 9.6 | 0.0% | 1.3% | 1.7% | 1.8% | 1.8% |
| 61 | W + 9 eq PD | 0.0 | 13.1 | 19.8 | 23.8 | 43.8 | 9.5 | 9.4 | 9.4 | 9.3 | 9.2 | 0.0% | −1.4% | −1.5% | 2.1% | −2.7% |
| 62 | W + 9 eq PE | 0.0 | 13.1 | 20.0 | 24.1 | 46.7 | 9.4 | 9.3 | 9.3 | 9.3 | 9.1 | 0.0% | −0.5% | −0.4% | −1.1% | −2.9% |
| 63 | W + 4 eq PG | 0.0 | 12.5 | 20.1 | 23.1 | 34.1 | 9.3 | 9.4 | 9.5 | 9.5 | 9.4 | 0.0% | 1.1% | 2.1% | 2.2% | 1.0% |
| 64 | W + 4 eq PH | 0.0 | 11.8 | 18.7 | 20.9 | 27.1 | 10.8 | 10.9 | 11.0 | 11.1 | 11.0 | 0.0% | 1.4% | 2.1% | 2.7% | 2.6% |
| 65 | W + 4 eq PI | 0.0 | 18.5 | 37.5 | 50.5 | 80.7 | 9.2 | 9.2 | 9.1 | 9.3 | 12.0 | 0.0% | 0.1% | −0.7% | 1.5% | 31% |
| 66 | W + 4 eq PJ | 0.0 | 23.1 | 49.5 | 61.4 | 85.4 | 10.0 | 9.9 | 10.0 | 10.6 | 13.8 | 0.0% | −0.5% | 0.6% | 6.1% | 39% |
| 67 | W + 4 eq PK | 0.0 | 16.9 | 35.9 | 51.9 | 85.7 | 9.1 | 9.0 | 8.7 | 8.8 | 10.8 | 0.0% | −1.3% | −4.1% | −3.0% | 19% |
| 68 | W + 4 eq PL | 0.0 | 19.7 | 38.8 | 47.7 | 65.2 | 10.4 | 11.0 | 10.7 | 11.0 | 12.6 | 0.0% | 2.8% | 3.0% | 5.9% | 21% |
| 69 (Comp) | X Baseline | 0.0 | 24.0 | 36.8 | 42.7 | 59.4 | 10.5 | 11.6 | 13.5 | 14.5 | 21.4 | 0.0% | 10% | 28% | 38% | 100% |
| 70 | X + 9 eq AA | 0.0 | 19.1 | 27.4 | 30.2 | 38.5 | 10.4 | 11.4 | 12.7 | 13.1 | 13.8 | 0.0% | 9.2% | 22% | 26% | 33% |
| 71 (Comp) | X + 9 eq CB | 0.0 | 23.6 | 37.7 | 43.5 | 59.4 | 10.4 | 11.6 | 13.7 | 14.7 | 20.0 | 0.0% | 11% | 32% | 41% | 91% |
| 72 (Comp) | X + 9 eq CA | 0.0 | 23.7 | 37.9 | 45.4 | 65.4 | 10.3 | 11.5 | 13.2 | 14.0 | 19.3 | 0.0% | 12% | 28% | 35% | 87% |
| 73 | X + 9 eq AB | 0.0 | 17.9 | 27.4 | 30.8 | 40.2 | 10.4 | 10.9 | 11.6 | 11.7 | 12.2 | 0.0% | 4.8% | 11% | 13% | 17% |
| 74 | X + 9 eq AC | 0.0 | 18.0 | 25.4 | 27.8 | 34.2 | 10.4 | 11.1 | 12.1 | 12.4 | 12.8 | 0.0% | 7.6% | 17% | 19% | 24% |
| 75 | X + 0.5 wt % AE | 0.0 | 21.8 | 31.5 | 34.5 | 42.6 | 10.4 | 11.2 | 13.0 | 13.7 | 16.4 | 0.0% | 8.0% | 25% | 31% | 57% |
| 76 | X + 9 eq AF | 0.0 | 17.2 | 25.1 | 27.9 | 35.6 | 10.4 | 11.0 | 11.7 | 11.8 | 12.2 | 0.0% | 5.6% | 13% | 14% | 17% |
| 77 | X + 9 eq AG$^{S}$ | 0.0 | 19.7 | 22.3 | 24.4 | 30.1 | 10.4 | 11.0 | 11.5 | 11.7 | 11.9 | 0.0% | 5.6% | 11% | 12% | 14% |
| 78 | X + 9 eq AH | 0.0 | 20.1 | 27.8 | 30.6 | 38.3 | 10.4 | 10.9 | 11.5 | 11.6 | 11.8 | 0.0% | 4.7% | 10% | 11% | 13% |
| 79 | X + 9 eq AI$^{S}$ | 0.0 | 20.1 | 22.8 | 25.2 | 31.6 | 10.4 | 11.5 | 12.7 | 13.0 | 14.1 | 0.0% | 11% | 22% | 26% | 36% |
| 80 | X + 9 eq AJ$^{S}$ | 0.0 | 20.0 | 28.1 | 30.5 | 37.1 | 10.4 | 11.3 | 12.5 | 12.9 | 13.7 | 0.0% | 9.2% | 20% | 24% | 32% |
| 81 | X + 9 eq AK | 0.0 | 18.5 | 27.6 | 30.5 | 38.3 | 10.4 | 11.2 | 12.4 | 12.6 | 13.1 | 0.0% | 7.3% | 19% | 21% | 25% |

TABLE 2-continued

| Example | Description | Change in Oxidation Peak Height 0 | 72 | 144 | 168 | 216 | KV100 0 | 72 | 144 | 168 | 216 | KV100 change 0 | 72 | 144 | 168 | 216 |
|---|---|---|---|---|---|---|---|---|---|---|---|---|---|---|---|---|
| 82 | X + 9 eq AL | 0.0 | 19.4 | 29.1 | 32.6 | 44.8 | 10.4 | 10.9 | 11.3 | 11.3 | 11.4 | 0.0% | 4.8% | 8.4% | 8.6% | 8.9% |
| 83 | X + 9 eq AM | 0.0 | 18.2 | 27.7 | 31.3 | 40.5 | 10.5 | 11.0 | 11.8 | 11.9 | 12.3 | 0.0% | 5.3% | 13% | 14% | 18% |
| 84 | X + 9 eq AN | 0.0 | 18.1 | 27.3 | 30.5 | 40.7 | 10.5 | 11.1 | 12.0 | 12.2 | 12.5 | 0.0% | 5.9% | 15% | 16% | 20% |
| 85 | X + 9 eq AO | 0.0 | 18.8 | 28.0 | 31.1 | 39.9 | 10.4 | 11.2 | 12.2 | 12.5 | 13.5 | 0.0% | 7.8% | 17% | 20% | 29% |
| 86 | X + 9 eq AP | 0.0 | 21.4 | 31.6 | 35.9 | 48.8 | 10.4 | 11.1 | 11.9 | 12.1 | 12.8 | 0.0% | 6.5% | 14% | 16% | 23% |
| 87 | X + 9 eq AQ | 0.0 | 18.7 | 26.2 | 28.8 | 35.9 | 10.3 | 12.2 | 14.4 | 15.3 | 17.1 | 0.0% | 18% | 39% | 48% | 66% |
| 88 | X + 9 eq AR | 0.0 | 16.7 | 25.5 | 29.3 | 45.5 | 10.3 | 11.0 | 11.7 | 11.7 | 11.4 | 0.0% | 6.2% | 13% | 13% | 11% |
| 89 | X + 9 eq AS | 0.0 | 20.5 | 28.1 | 30.2 | 35.8 | 10.4 | 11.2 | 11.9 | 12.1 | 12.4 | 0.0% | 7.4% | 15% | 17% | 20% |
| 90 | X + 9 eq AT | 0.0 | 18.7 | 26.3 | 28.8 | 36.4 | 10.4 | 11.0 | 11.5 | 11.6 | 11.7 | 0.0% | 5.9% | 11% | 12% | 13% |
| 91 | X + 9 eq AU | 0.0 | 16.4 | 22.1 | 23.5 | 26.0 | 10.3 | 11.0 | 12.1 | 12.5 | 13.4 | 0.0% | 6.8% | 17% | 21% | 30% |
| 92 | X + 9 eq AW | 0.0 | 19.6 | 26.1 | 28.1 | 32.4 | 10.3 | 11.1 | 12.3 | 12.6 | 13.1 | 0.0% | 7.5% | 19% | 22% | 27% |
| 93 | X + 9 eq AX | 0.0 | 18.1 | 24.9 | 27.0 | 31.9 | 10.3 | 12.1 | 14.9 | 16.0 | 18.7 | 0.0% | 18% | 45% | 55% | 82% |

In Table 2, the amounts of ligands were calculated to approximately ~9 equivalents of 3,4-oxypyridinone (or the like), relative to what was taken as ~1 equivalent molar amount of Fe(III) in the CEC L-109 testing regimen.

From the entirety of the data, addition of 3,4-oxypryidinones according to the disclosure to existing formulations radically improved (in this case, reduced) the KV100 increase at longer CEC L-109 oxidation times (e.g., at least 168 hours and/or at least 216 hours). Even where oxidation peak height seemed to indicate significant oxidation, that oxidation did not seem to correlate (as it usually does) to corresponding drastic increases in KV100 over time. This supports both the hypothesis of 3,4-oxypyridinones according to the disclosure disrupting Fe(III) catalytic oxidation mechanisms (e.g., by chelation) and that the disruption seems to be specific to the physico-chemical structure of these 3,4-oxypyridinones. Decreases in KV100 are reflected as negative numbers—in several examples, KV100 actually decreased over time.

These results are believed to show a powerful antioxidant character to these 3,4-oxypyridinones, and perhaps a synergistic effect when used in tandem with one or more other antioxidant additives (e.g., diaryl amines and/or hindered phenols) that are already contained within the baseline formulations. This potential antioxidative synergy was ripe for further exploration.

Examples 94-117—Antioxidant Synergy

In these Examples, the baseline formulations W and X were modified and tested according to CEC L-109(-14). Comparative Examples 31 and 69 from Table 2 were reproduced for context regarding the baselines for Formulation W and X, respectively. In Comparative Examples 94 and 106 the diaryl amine antioxidant (DAA) was removed entirely. In Comparative Examples 95 and 107 the diaryl amine antioxidant was increased by ~40% in Formulation W and by ~50% in Formulation X. In the increased antioxidant formulations ("Hi W" or "Hi X"), 3,4-oxypyridinones according to the disclosure (identified as ligand AA in the previous Examples) were substituted for portions of the diaryl amine antioxidants, such that the total content of diaryl amine antioxidant+3,4-oxypyridine ligand remained at the increased levels, at differing weight ratios. A "1:0" weight ratio in these Examples corresponds to all diaryl amine antioxidant (no 3,4-oxypyridinone ligand) at the increased levels; a "0:1" weight ratio in these Examples corresponds to all 3,4-oxypyridinone ligand (no diaryl amine antioxidant) at the increased levels; a "0:0" weight ratio refers to no diaryl amine antioxidant and no 3,4-oxypyridinone ligand; other weight ratios should be self-explanatory. In other increased antioxidant formulations, a 2,6-di-t-butyl-4-substituted hindered phenol antioxidant (TPA) was substituted for the diaryl amine antioxidant (DAA). Then, the hindered phenol antioxidant was replaced by portions of 3,4-oxypyridinones according to the disclosure (identified as ligand AA in the previous Examples), such that the total content of hindered phenol antioxidant+3,4-oxypyridine ligand remained at the increased levels, at differing weight ratios. Same "1:0" weight ratio for the hindered phenol/3,4-oxypyridinones, and the other weight ratios should be self-explanatory. But the "0:1" weight ratio involving the hindered phenol antioxidant is identical to the diaryl amine antioxidant (zero antioxidant; only ligand), so it was not repeated. See Table 3 below for CEC L-109 results.

TABLE 3

| Example | Description | Change in Oxidation Peak Height 0 | 72 | 144 | 168 | 216 | KV100 0 | 72 | 144 | 168 | 216 | KV100 change 0 | 72 | 144 | 168 | 216 |
|---|---|---|---|---|---|---|---|---|---|---|---|---|---|---|---|---|
| 31 (Comp) | W Baseline | 0.0 | 25.4 | 73.5 | 93.4 | 120 | 8.8 | 8.7 | 9.7 | 12.4 | 56.0 | 0.0% | 1.3% | 4.7% | 19% | 530% |
| 94 (Comp) | W minus DAA | 0.0 | 55.2 | 104 | 121 | 148 | 8.8 | 8.0 | 10.9 | 13.3 | 34.1 | 0.0% | −11% | 24% | 51% | 290% |
| 95 (Comp) | Hi W 1:0 DAA:Lig | 0.0 | 22.9 | 41.8 | 54.3 | 84.4 | 8.8 | 8.9 | 9.1 | 9.5 | 14.3 | 0.0% | 1.0% | 2.9% | 7.5% | 62% |
| 96 | Hi W 5:1 DAA:Lig | 0.0 | 21.0 | 36.9 | 48.5 | 78.9 | 8.8 | 9.1 | 9.2 | 9.5 | 12.6 | 0.0% | 2.8% | 4.9% | 7.4% | 43% |
| 97 | Hi W 5:2 DAA:Lig | 0.0 | 18.7 | 29.8 | 42.7 | 87.7 | 8.8 | 8.9 | 8.9 | 8.6 | 9.6 | 0.0% | 0.8% | 0.7% | 1.9% | 8.8% |
| 98 | Hi W 1:1 DAA:Lig | 0.0 | 16.2 | 24.0 | 28.5 | 77.4 | 8.8 | 8.9 | 8.9 | 8.8 | 8.6 | 0.0% | 0.8% | 0.7% | −0.3% | −3.2% |
| 99 | Hi W 2:5 DAA:Lig | 0.0 | 16.2 | 27.3 | 51.9 | 102 | 8.9 | 8.9 | 8.7 | 8.2 | 9.2 | 0.0% | −0.1% | −2.1% | −8.0% | 3.7% |
| 100 | Hi W 1:5 DAA:Lig | 0.0 | 19.5 | 74.0 | 87.6 | 123 | 9.7 | 8.6 | 9.0 | 10.0 | 14.7 | 0.0% | −11% | −6.6% | 3.8% | 52% |
| 101 | Hi W 0:1 DAA:Lig | 0.0 | 57.0 | 109 | 124 | 150 | 9.8 | 8.1 | 11.0 | 13.2 | 27.8 | 0.0% | −17% | 12% | 34% | 180% |
| 102 | Hi W 1:0 HPA:Lig | 0.0 | 51.0 | 110 | 126 | — | 8.8 | 8.0 | 11.6 | 15.1 | — | 0.0% | −8.7% | 32% | 72% | N/A |

TABLE 3-continued

| Example | Description | Change in Oxidation Peak Height 0 | 72 | 144 | 168 | 216 | KV100 0 | 72 | 144 | 168 | 216 | KV100 change 0 | 72 | 144 | 168 | 216 |
|---|---|---|---|---|---|---|---|---|---|---|---|---|---|---|---|---|
| 103 | Hi W 5:1 HPA:Lig | 0.0 | 50.5 | 115 | 131 | — | 8.8 | 7.9 | 11.5 | 15.1 | — | 0.0% | −10% | 32% | 72% | N/A |
| 104 | Hi W 1:1 HPA:Lig | 0.0 | 45.7 | 108 | 125 | 149 | 8.9 | 7.9 | 10.8 | 13.2 | 37.9 | 0.0% | −11% | 21% | 49% | 330% |
| 105 | Hi W 1:5 HPA:Lig | 0.0 | 55.4 | 118 | 135 | — | 9.8 | 8.1 | 11.5 | 14.7 | 60.9 | 0.0% | −18% | 17% | 50% | 520% |
| 69 (Comp) | X Baseline | 0.0 | 24.0 | 36.8 | 42.7 | 59.4 | 10.5 | 11.6 | 13.5 | 14.5 | 21.4 | 0.0% | 10% | 28% | 38% | 100% |
| 106 (Comp) | X minus DAA | 0.0 | 42.3 | 84.6 | 97.0 | 118 | 10.4 | 9.3 | 13.0 | 16.2 | 45.3 | 0.0% | −10% | 25% | 56% | 330% |
| 107 (Comp) | Hi X 1:0 DAA:Lig | 0.0 | 23.9 | 32.2 | 35.4 | 43.4 | 10.4 | 11.8 | 13.5 | 14.3 | 16.9 | 0.0% | 13% | 30% | 37% | 62% |
| 108 | Hi X 5:1 DAA:Lig | 0.0 | 22.2 | 30.0 | 32.7 | 42.1 | 10.4 | 11.8 | 13.3 | 13.9 | 15.5 | 0.0% | 13% | 28% | 33% | 48% |
| 109 | Hi X 2:1 DAA:Lig | 0.0 | 21.6 | 31.2 | 35.3 | 47.5 | 10.4 | 11.6 | 12.8 | 13.2 | 14.3 | 0.0% | 12% | 23% | 27% | 37% |
| 110 | Hi X 1:1 DAA:Lig | 0.0 | 20.1 | 28.4 | 32.0 | 43.7 | 10.4 | 11.5 | 12.7 | 13.0 | 13.5 | 0.0% | 9.9% | 22% | 24% | 30% |
| 111 | Hi X 1:2 DAA:Lig | 0.0 | 20.6 | 33.3 | 40.0 | 59.6 | 10.5 | 11.3 | 12.2 | 12.3 | 13.2 | 0.0% | 7.6% | 16% | 17% | 26% |
| 112 | Hi X 1:5 DAA:Lig | 0.0 | 23.2 | 48.4 | 61.4 | 84.3 | 10.6 | 11.0 | 11.6 | 12.2 | 15.6 | 0.0% | 4.4% | 9.7% | 15% | 48% |
| 113 | Hi X 0:1 DAA:Lig | 0.0 | 47.0 | 89.4 | 101 | 122 | 11.0 | 9.4 | 12.2 | 14.6 | 29.0 | 0.0% | −15% | 12% | 33% | 160% |
| 114 | Hi X 1:0 HPA:Lig | 0.0 | 37.9 | 80.9 | 93.6 | 115 | 10.4 | 9.9 | 13.9 | 18.2 | 72.6 | 0.0% | −4.4% | 34% | 75% | 600% |
| 115 | Hi X 5:1 HPA:Lig | 0.0 | 40.1 | 87.2 | 101 | 122 | 10.4 | 9.8 | 13.7 | 17.7 | 63.2 | 0.0% | −5.3% | 32% | 70% | 510% |
| 116 | Hi X 1:1 HPA:Lig | 0.0 | 34.0 | 77.5 | 90.5 | 113 | 10.4 | 9.8 | 12.3 | 14.7 | 31.4 | 0.0% | −5.9% | 19% | 41% | 200% |
| 117 | Hi X 1:5 HPA:Lig | 0.0 | 46.1 | 95.8 | 108 | 128 | 10.7 | 9.4 | 12.6 | 14.6 | 37.7 | 0.0% | −12% | 18% | 37% | 250% |

In Table 3, cells with two dashes (or "N/A") represent values that were not measured or were not measurable, e.g., because the samples were too viscous for measurement.

Examples 118-142—Oxidation Induction (PDSC)

In these Examples, a pressure differential scanning calorimetry (PDSC) oxidation test is used to measure the oxidation induction time according to ASTM D6186. Any deviations in sample testing from the ASTM D6186 is noted herein. The test involves exposure of ~3 mg±~0.2 mg of sample optionally containing ~100 ppm of iron (as $Fe(AcAc)_3$, added as ~50 mM solution in chloroform) to an oxygen containing gas. The test was run under steady state conditions at ~200° C. The onset oxidation time represents the intersection of an extrapolated baseline and a tangent line (leading edge) of the (exothermal) PDSC curve, representing oxidation.

In these Examples, all ligands were added to the Formulation W baseline composition (or using a noted modification of the Formulation W baseline), and oxidation induction times ("INDT," in units of minutes) were measured/reported in Table 4 below (using the same alphanumeric nomenclature as in Table 2, involving Examples 3-93), both with and without the 100 ppm of Fe(III). The "% Change" refers to the percent difference from baseline Formulation W with no ligand present (Comparative Example 118 below).

TABLE 4

| Example | Description | Without $Fe(acac)_3$ INDT | % Change | With $Fe(acac)_3$ INDT | % Change |
|---|---|---|---|---|---|
| 118 (Comp) | W Baseline | 44 mins | 0 | 12 mins | 0 |
| 119 | W + 0.56 wt % AA | 43 mins | −2 | 22 mins | 83 |
| 120 | W + 0.43 wt % AS | 44 mins | 0 | 21 mins | 75 |
| 121 | W + 0.34 wt % AT | 42 mins | −5 | 21 mins | 75 |
| 122 (Comp) | W + 0.54 wt % CB | 46 mins | 5 | 21 mins | 75 |
| 123 (Comp) | W + 0.54 wt % CA | 60 mins | 36 | 19 mins | 58 |
| 124 | W + 0.54 wt % AW | 47 mins | 7 | 17 mins | 42 |

TABLE 4-continued

| Example | Description | Without $Fe(acac)_3$ INDT | % Change | With $Fe(acac)_3$ INDT | % Change |
|---|---|---|---|---|---|
| 125 | W + 0.54 wt % AU | 52 mins | 18 | 32 mins | 170 |
| 126 | W + 0.56 wt % AV | 50 mins | 14 | 18 mins | 50 |
| 127 | W + 0.59 wt % AR | 50 mins | 14 | 18 mins | 50 |
| 128 | W + 0.59 wt % AQ | 47 mins | 7 | 14 mins | 17 |
| 129 | W + 0.38 wt % AG | 43 mins | −2 | 20 mins | 67 |
| 130 | W + 0.60 wt % AI | 40 mins | −9 | 20 mins | 67 |
| 131 | W + 0.40 wt % AH | 39 mins | −11 | 20 mins | 67 |
| 132 | W + 0.63 wt % AJ | 36 mins | −18 | 18 mins | 50 |
| 133 | W + 0.71 wt % AF | 49 mins | 11 | 17 mins | 42 |
| 134 | W + 0.76 wt % AB | 44 mins | 0 | 19 mins | 58 |
| 135 | W + 0.72 wt % AC | 47 mins | 7 | 22 mins | 83 |
| 136 | W + 0.63 wt % AK | 45 mins | 2 | 18 mins | 50 |
| 137 | W + 0.55 wt % AL | 41 mins | −7 | 15 mins | 25 |
| 138 (Comp) | Hi W | 48 mins | 9 | 15 mins | 25 |
| 139 | Hi W 5:2 DAA:Ligand | 43 mins | −2 | 19 mins | 58 |
| 140 | Hi W 1:1 DAA:Ligand | 41 mins | −7 | 21 mins | 75 |
| 141 | Hi W 2:5 DAA:Ligand | 34 mins | −23 | 18 mins | 50 |
| 142 | Hi W 0:1 DAA:Ligand | <10 mins | −77 | <10 mins | −17 |

Examples 143-148—TOC Oxidation Testing

In these Examples, a TOC oxidation test according to standard test method D55 3099 (2016) was done to complement the other oxidation testing. This oxidation test involved measurement of oxidation in the presence of ~360 ppm of iron at ~170° C. in the presence of air flowing at ~10 L/h. A sample at 0 hours, or immediately before the TOC oxidation test begins, is considered an SOT (start of test)

sample. Samples were also taken at ~16 hours, ~96 hours, optionally ~136 hours, and optionally ~168 hours. In some cases the test may be modified to be stopped after taking the ~96-hour sample. KV40 percent increase from start of test and KV 100 percent increase from start of test can be of particular interest. TOC oxidation testing can also involve calculating an oxidation peak area, which is not reported.

Formulations V and X were used as baselines for comparison (Comparative Examples 143 and 146), and ligands AA and AF were added as exemplars to probe viscosity changes—for brevity, only changes in measured KV40 and KV100, from SOT to end of test (in this case, ~168 hours) are reported below.

TABLE 5

| Example | Description | KV40 Change | KV100 Change |
|---|---|---|---|
| 143 (Comp) | V Baseline | 22% | −7% |
| 144 | V + 0.56 wt % AA | −30% | −31% |
| 145 | V + 0.71 wt % AF | −30% | −32% |
| 146 (Comp) | X Baseline | 94% | 28% |
| 147 | X + 0.56 wt % AA | −21% | −23% |
| 148 | X + 0.71 wt % AF | −21% | −23% |

Examples 149-166—HFRR Antiwear/Friction Testing

Antiwear and/or frictional behavior was probed using a high-frequency reciprocating rig (HFRR) test. The HFRR device used is commercially available from PCS Instruments, London, UK, and typically runs AUTOHFR software (v2.0 represents operation under PCS4 user manual). This device employs a ~6 mm diameter ball as an upper specimen which is reciprocated under an applied load against a lower specimen in the form of a ~10 mm diameter×~3 mm thick disc. The ball and disc are made of AISI 52100 polished steel (and must have their antirust coating removed before testing). Test conditions were as follows: reciprocating frequency ~40 Hz; stroke length ~1 mm; applied load ~400 g; and contact pressure ~1 GPa. Samples were analyzed at temperatures ranging from ~40° C. to ~140° C. Sample runs commenced when a Sample was held at ~40° C. for ~1 min, subject to test conditions for ~5 mins, ramped at ~5-15° C./min up another ~20° C., held at that increased temperature for ~1 min, and the cycle repeated every ~20° C. up to ~140° C., after which the temperature was ramped down to room temperature (~20-25° C.). Under those conditions, wear scars were typically formed. The wear scars on the upper ball specimens were measured with the ball located in the holder using an optical microscope with a calibrated micrometer. This was reported herein as an average wear scar diameter (WSD, based on a simple average of longest and shortest lengths of the wear scar) in units of mm. The wear scars on the lower disc specimens were analyzed using a ZeScope™ 3D optical profilometer (commercially available from Zemetrics Inc. of Tucson, AZ, USA) using non-contact interferometric focal scanning. With proper calibration, profilometry techniques can enable measurement of the amount of wear by determining the material lost from the disc during the test. This was reported herein as a wear scar volume (WSV) in units of $mm^3$. The HFRR device was equipped with a piezoelectric transducer to measure the average friction coefficient between the ball and the disc. Average wear scar diameter, average wear scar volume, and average friction coefficient reported herein represent an average of at least two or at least three (in particular, two or three) measurements from separate HFRR tests.

In these Examples, 0.73 wt % (approximately 9 molar equivalents, relative to the amount of Fe(III) present in the CEC L-109(-14) test conditions) of ligand AM and/or 0.56 wt % (approximately 9 molar equivalents, relative to the amount of Fe(III) present in the CEC L-109(-14) test conditions) of ligand AA were added as an additional component (effectively as a top-treat) to baseline Formulations V, W, and X at various enumerated temperatures (identified as "+[A?] Lig" for brevity). In addition, samples containing baseline Formulations alone (no ligand—identified as "Baseline" in Comparative Examples 149, 155, and 161), samples containing baseline Formulations with basestock/diluent substituted for all the ZDDP component (identified as "−P" for brevity), and samples containing ligand but no ZDDP component (identified as "−P+[A?] Lig" for brevity) were tested for comparison. Frictional coefficients, wear scar diameter (in mm), and wear scar volume (in $mm^3$; all averages) for each composition were calculated at each temperature and are reported in Table 6 below.

TABLE 6

| | | Frictional Coefficient | | | | | | Wear Scar | Void |
|---|---|---|---|---|---|---|---|---|---|
| Example | Description | @40° C. | @60° C. | @80° C. | @100° C. | @120° C. | @140° C. | Diameter | Volume |
| 149 (Comp) | V Baseline | 0.111 | 0.118 | 0.135 | 0.142 | 0.150 | 0.154 | 0.23 | 1.6E−4 |
| 150 | V + AM Lig | 0.124 | 0.126 | 0.124 | 0.121 | 0.125 | 0.125 | 0.17 | 5.4E−5 |
| 151 | V − P | 0.129 | 0.140 | 0.148 | 0.162 | 0.165 | 0.164 | 0.26 | 2.9E−4 |
| 152 | V − P + AM Lig | 0.133 | 0.139 | 0.147 | 0.146 | 0.146 | 0.148 | 0.26 | 3.4E−4 |
| 153 | V + AA Lig | 0.110 | 0.110 | 0.115 | 0.122 | 0.133 | 0.140 | 0.20 | 1.2E−4 |
| 154 | V − P + AA Lig | 0.130 | 0.139 | 0.144 | 0.155 | 0.163 | 0.157 | 0.27 | 3.4E−4 |
| 155 (Comp) | W Baseline | 0.127 | 0.133 | 0.135 | 0.153 | 0.172 | 0.178 | 0.17 | 9.0E−5 |
| 156 | W + AM Lig | 0.138 | 0.138 | 0.132 | 0.133 | 0.141 | 0.146 | 0.18 | 1.1E−4 |
| 157 | W − P | 0.130 | 0.139 | 0.147 | 0.156 | 0.162 | 0.166 | 0.19 | 1.5E−4 |
| 158 | W − P + AM Lig | 0.133 | 0.141 | 0.139 | 0.137 | 0.131 | 0.130 | 0.22 | 2.4E−4 |
| 159 | W + AA Lig | 0.128 | 0.134 | 0.132 | 0.131 | 0.131 | 0.150 | 0.19 | 1.7E−4 |
| 160 | W − P + AA Lig | 0.129 | 0.139 | 0.140 | 0.141 | 0.141 | 0.138 | 0.19 | 1.5E−4 |
| 161 (Comp) | X Baseline | 0.123 | 0.140 | 0.141 | 0.147 | 0.159 | 0.168 | 0.18 | 5.5E−5 |
| 162 | X + AM Lig | 0.124 | 0.131 | 0.133 | 0.137 | 0.141 | 0.141 | 0.18 | 5.2E−5 |
| 163 | X − P | 0.136 | 0.149 | 0.158 | 0.166 | 0.164 | 0.130 | 0.21 | 1.4E−4 |
| 164 | X − P + AM Lig | 0.131 | 0.142 | 0.136 | 0.139 | 0.137 | 0.130 | 0.23 | 2.6E−4 |

TABLE 6-continued

| Example | Description | Frictional Coefficient @40° C. | @60° C. | @80° C. | @100° C. | @120° C. | @140° C. | Wear Scar Diameter | Void Volume |
|---|---|---|---|---|---|---|---|---|---|
| 165 | X + AA Lig | 0.118 | 0.127 | 0.123 | 0.131 | 0.135 | 0.139 | 0.19 | 8.4E−5 |
| 166 | X − P + AA Lig | 0.134 | 0.146 | 0.148 | 0.147 | 0.140 | 0.137 | 0.23 | 2.5E−4 |

In almost all situations, addition of either 3,4-oxypyridinone ligand seemed to reduce the higher temperature average frictional coefficients. This appeared to be more pronounced when both the ligand and ZDDP were present in the formulations. It also appears that the capped ligand (AM) tended to even out the change in average frictional coefficient across temperatures, although it is believed (without being bound by theory) that the capping of the 3-hydroxyl group likely uncaps under testing/lubricating conditions, making the differential results between uncapped (AA) and capped (AM) ligands quite interesting and non-intuitive. However, as noted during oxidation testing, the antiwear capacity (like antioxidative capacity) of the ligands alone do not appear to be large without an existing functional agent—they seem to provide synergistic results when used in tandem with existing functional agents (in this case, such as a ZDDP).

Regarding average wear scar, the capped ligand (AM) seemed to universally lead to the lower wear scar diameter/volume, relative to the uncapped ligand (AA), and sometimes (when in tandem with the existing antiwear agent ZDDP) improved from the baseline formulation itself.

Examples 167-179—HFRR Synergy with Friction Modifiers

Using the same HFRR device and test methods, these Examples were done to test the relative capability of 3,4-oxypyridinones according to the disclosure as friction modifiers, either alone or in tandem with one or more existing friction modifiers. In these experiments, tested samples were not based on complete formulations—the baseline was 100 wt % of a Group II and/or Group III basestock/diluent (in this case, Yubase™ 4, which is commercially available from SK Lubricants of Seoul, South Korea—abbreviated as "D" and identified as Comparative Example 167 in the Table), and disclosed amounts of ligand AM, glycerol monooleate (GMO) organic friction modifier, or both, in various weight ratios relative to each other, were substituted for identical amounts of basestock/diluent (abbreviated in the Table as "+[amt] AM", "+[amt] GMO", or "+[?]:[?] AM:GMO", even though substituted, not added). Where both ligand and friction modifier are present, the total amount of both is ~1 wt % in the diluent. A "0:1" weight ratio in these Examples corresponds to all organic friction modifier (no 3,4-oxypyridinone ligand), and a "1:0" weight ratio in these Examples corresponds to all 3,4-oxypyridinone ligand (no organic friction modifier); other weight ratios should be self-explanatory. Table 7 below shows results as frictional coefficients, wear scar diameter (in mm), and wear scar volume (in $mm^3$; all averages) for each Example.

TABLE 7

| Example | Description | Frictional Coefficient @40° C. | @60° C. | @80° C. | @100° C. | @120° C. | @140° C. | Wear Scar Diameter | Void Volume |
|---|---|---|---|---|---|---|---|---|---|
| 167 (Comp) | D only | 0.160 | 0.191 | 0.221 | 0.245 | 0.282 | 0.316 | 0.31 | 2.3E−4 |
| 168 | D + 0.5 wt % AM | 0.137 | 0.147 | 0.147 | 0.146 | 0.143 | 0.140 | 0.29 | 4.0E−4 |
| 169 (Comp) | D + 0.5 wt % GMO | 0.112 | 0.116 | 0.128 | 0.127 | 0.119 | 0.124 | 0.15 | 5.5E−5 |
| 170 (Comp) | D + 0.2 wt % GMO | 0.124 | 0.131 | 0.130 | 0.136 | 0.141 | 0.140 | 0.21 | 1.3E−4 |
| 171 | D + 0:1 AM:GMO | 0.107 | 0.115 | 0.115 | 0.107 | 0.100 | 0.095 | 0.19 | 1.4E−4 |
| 172 | D + 1:9 AM:GMO | 0.115 | 0.126 | 0.128 | 0.129 | 0.120 | 0.110 | 0.18 | 1.2E−4 |
| 173 | D + 1:4 AM:GMO | 0.117 | 0.127 | 0.125 | 0.124 | 0.100 | 0.088 | 0.16 | 1.1E−4 |
| 174 | D + 2:3 AM:GMO | 0.124 | 0.136 | 0.134 | 0.130 | 0.096 | 0.092 | 0.20 | 1.6E−4 |
| 175 | D + 1:1 AM:GMO | 0.126 | 0.138 | 0.137 | 0.127 | 0.127 | 0.112 | 0.19 | 1.9E−4 |
| 176 | D + 3:2 AM:GMO | 0.132 | 0.140 | 0.137 | 0.132 | 0.135 | 0.136 | 0.19 | 1.8E−4 |
| 177 | D + 4:1 AM:GMO | 0.135 | 0.141 | 0.138 | 0.125 | 0.117 | 0.120 | 0.17 | 2.2E−4 |
| 178 | D + 9:1 AM:GMO | 0.136 | 0.144 | 0.138 | 0.132 | 0.128 | 0.130 | 0.22 | 2.5E−4 |
| 179 | D + 1:0 AM:GMO | 0.137 | 0.146 | 0.146 | 0.142 | 0.138 | 0.134 | 0.32 | 5.0E−4 |

While these values may not be comparable on an absolute basis with HFRR results on full formulations, it is believed that the trends, including the percentage difference, from the isolated 3,4-oxypyridinone and organic friction modifier components would qualitatively (and possible also quantitatively) follow from these experiments. While these experiments indicate that 3,4-oxypyridinones are not as efficient at modifying frictional and/or antiwear properties by themselves, these experiments do appear to show a synergy at certain ratios between organic friction modifier (GMO, in this case) and 3,4-oxypyridinone ligand, when both are present.

Examples 180-221—Corrosion Testing

In these Examples, a high temperature corrosion bench test (HTCBT) was conducted to evaluate corrosion behavior of baseline formulations and the effect of 3,4-oxypyridinone ligands thereon. HTCBT can be done according to ASTM D6594 for copper and lead, in which copper and lead coupons are suspended in ~100 mL of a compositional liquid sample that is heated to ~135° C. Air is provided at ~5 L/min, and measurements are taken at various intervals for ~168 hours to determine copper and lead concentrations in the liquid sample (expressed in ppm by mass), which measurements are corrected for evaporative losses during heating. Although performed under different conditions in ASTM D6594, the copper coupon subject to ~135° C. for ~168 hours can nonetheless be visually rated using the scale from ASTM D130.

In these Examples, as in previous examples, a certain number of molar equivalents (~3, ~6, or ~9) of 3,4-oxypyridinone ligands were used, relative to the Fe(III) concentration in the CEC L-109(-14) test method. Formulations V, W, X, and Y were used as baselines (Comparative Examples 180, 192, 203, and 215, respectively), and, as in previous Examples, the amount of the various 3,4-oxypyridinones in ligand-containing Examples is identified in Table 8 as the alphanumeric Formulation "plus" an amount of each ligand (even though in some situations, specifically noted with an "s" superscript, the amount of ligand is more accurately substituted for an equal amount of diluent/basestock). In Table 8 below, the average amount (in ppm by weight) of dissolved copper after ~168 hours of testing, the average amount (also in ppm by weight) of dissolved lead after ~168 hours of testing, and the copper corrosion ratings after ~168 hours of testing (according to ASTM D6594) are reported for each Example.

TABLE 8

| Example | Description | Dissolved Cu | Dissolved Pb | Cu Rating |
|---|---|---|---|---|
| 180 (Comp) | V Baseline | 6 | 8 | 1A |
| 181 | V + 9 eq AA | 23 | 370 | 3A |
| 182 | V + 9 eq AI$^S$ | 16 | 210 | 1A |
| 183 | V + 9 eq AF | 9 | 130 | 1A |
| 184 | V + 9 eq AC | 12 | 190 | 1A |
| 185 | V + 9 eq AB | 9 | 170 | 1A |
| 186 | V + 9 eq AK | 5 | 120 | 1A |
| 187 | V + 9 eq AM | 9 | 230 | 1A |
| 188 | V + 9 eq AN | 7 | 190 | 1A |
| 189 | V + 9 eq AL | 15 | 330 | 1A |
| 190 | V + 9 eq AO | 8 | 190 | 1A |
| 191 | V + 9 eq AP | 7 | 170 | 1A |
| 192 (Comp) | W Baseline | 7 | 52 | 1A |
| 193 | W + 9 eq AA | 20 | 210 | 1A |
| 194 | W + 9 eq AF | 190 | 330 | 2B |
| 195 | W + 9 eq AC | 130 | 440 | 4A |
| 196 | W + 9 eq AB | 160 | 340 | 2B |
| 197 | W + 9 eq AK | 110 | 250 | 2C |
| 198 | W + 9 eq AM | 160 | 430 | 2C |
| 199 | W + 9 eq AN | 210 | 430 | 2C |
| 200 | W + 9 eq AL | 190 | 570 | 4A |
| 201 | W + 9 eq AO | 190 | 400 | 2C/4A |
| 202 | W + 9 eq AP | 190 | 430 | 2C/4A |
| 203 (Comp) | X Baseline | 35 | 5 | 4A |
| 204 | X + 9 eq AA | 65 | 370 | 4A |
| 205 | X + 9 eq AI$^S$ | 45 | 110 | 4A |
| 206 | X + 9 eq AF | 53 | 190 | 4A |
| 207 | X + 9 eq AC | 40 | 72 | 4A |
| 208 | X + 9 eq AB | 63 | 370 | 4A |
| 209 | X + 9 eq AK | 300 | 96 | 4B |
| 210 | X + 9 eq AM | 32 | 300 | 4A |
| 211 | X + 9 eq AN | 190 | 260 | 4A |
| 212 | X + 9 eq AL | 39 | 440 | 4A |
| 213 | X + 9 eq AO | 110 | 380 | 4A |
| 214 | X + 9 eq AP | 39 | 350 | 4A |
| 215 (Comp) | Y Baseline | 7 | 4 | 1A |
| 216 | Y + 3 eq AO | 6 | 4 | 1A |
| 217 | Y + 6 eq AO | 6 | 6 | 1A |
| 218 | Y + 9 eq AO | 9 | 82 | 1A |
| 219 | Y + 3 eq AP | 8 | 3 | 1A |
| 220 | Y + 6 eq AP | 83 | 4 | 4A |
| 221 | Y + 9 eq AP | 160 | 80 | 4A |

In several cases, addition of a 3,4-oxypyridinone ligand according to the disclosure to a formulation can worsen corrosion involving copper and/or lead. While, in some cases, the corrosion levels including a ligand could be deemed acceptable, further experiments were conducted to determine whether such copper and/or lead corrosion issues could be mitigated, and to what extent.

Examples 222-326—Corrosion Mitigation in HTCBT

In these Examples, building off the HTCBT experiments in Examples 180-221 (using the same method), certain amounts of various compounds/components (mostly corrosion inhibitors) were added to the existing 3,4-oxypyridinone-containing formulations. As in previous Examples, the amounts of the various compounds/components are each identified in the Table as being "plus" an amount of each compound/component. Compounds/Components added may be neat, or may be diluted with Group I, II, and/or III basestock, as well as synthesis by-products and/or separation artifacts, to some active ingredient (AI) content typical for lubricant additives. Identifications/Descriptions in the Table that contain a bare number are meant to refer to that Example, either as-is or with the modifications identified. The results from baseline Formulations V, W, X, and Y alone (Comparative Examples 180, 192, 203, and 215, respectively) are repeated for comparison only. In Table 9 below, the average amount (in ppm by weight) of dissolved copper after ~168 hours of testing and the average amount (also in ppm by weight) of dissolved lead after ~168 hours of testing are reported for each Example.

Compounds/Components tested as corrosion inhibitors in these Examples are abbreviated as follows:

TDZ=optionally substituted thiadiazole
TB=tri-hydrocarbyl $C_1$-$C_8$ borate
IR39=Irgamet™ 39
SLO=sulfurized lard oil and palm oil fatty acid methyl ester
IR30=Irgamet™ 30
BDis=highly borated PIBSA-PAM dispersant whose PIB arms have ~1000 Mn
HDE=1-hexadecene
AE=Vanlube® 7723
TTZ=10 wt % tolyltriazole active ingredient
IDZ=optionally substituted hydroxyethyl imidazoline
LA=lauryl acrylate
OA=oleamide

TABLE 9

| Example | Description | Dissolved Cu | Dissolved Pb | Cu Rating |
|---|---|---|---|---|
| 180 (Comp) | V Baseline | 6 | 8 | 1A |
| 222 | 180 + 0.5 wt % TDZ | 350 | 160 | 4B |
| 223 | 181 + 0.5 wt % TDZ | 420 | 220 | 4B |
| 224 | 183 + 0.5 wt % TDZ | 17 | 500 | 1A |
| 225 | 180 + 0.5 wt % TB | 4 | 5 | 1A |
| 226 | 181 + 0.5 wt % TB | 8 | 37 | 1A |
| 227 | 183 + 0.5 wt % TB | 5 | 57 | 1A |
| 228 | 187 + 0.5 wt % TB | 7 | 46 | 1A |
| 229 | 188 + 0.5 wt % TB | 6 | 38 | 1A |
| 230 | 180 + 0.5 wt % IR39 | 28 | 380 | 1B |
| 231 | 181 + 0.5 wt % IR39 | 91 | 720 | 3A |
| 232 | 183 + 0.5 wt % IR39 | 16 | 420 | 1B |
| 233 | 180 + 0.25 wt % IR39 + 0.25 wt % TDZ | 59 | 300 | 4A |

TABLE 9-continued

| Example | Description | Dissolved Cu | Dissolved Pb | Cu Rating |
|---|---|---|---|---|
| 234 | 181 + 0.25 wt % IR39 + 0.25 wt % TDZ | 110 | 750 | 4A |
| 235 | 183 + 0.25 wt % IR39 + 0.25 wt % TDZ | 130 | 490 | 4A |
| 236 | 180 + 0.25 wt % IR39 + 0.25 wt % TB | 11 | 140 | 1B |
| 237 | 181 + 0.25 wt % IR39 + 0.25 wt % TB | 24 | 230 | 1B |
| 238 | 183 + 0.25 wt % IR39 + 0.25 wt % TB | 10 | 140 | 1A |
| 239 | 180 + 0.25 wt % IR39 + 0.5 wt % SLO | 11 | 370 | 1B |
| 240 | 181 + 0.25 wt % IR39 + 0.5 wt % SLO | 21 | 670 | 1B |
| 241 | 183 + 0.25 wt % IR39 + 0.5 wt % SLO | 24 | 420 | 3A |
| 192 (Comp) | W Baseline | 7 | 52 | 1A |
| 242 | 192 + 0.5 wt % TDZ | 150 | 8 | 4A |
| 243 | 193 + 0.5 wt % TDZ | 180 | 15 | 4A |
| 244 | 192 + 0.5 wt % TB | 7 | 3 | 1A |
| 245 | 193 + 0.5 wt % TB | 17 | 220 | 1B |
| 246 | 198 + 0.5 wt % TB | 110 | 16 | 3B |
| 247 | 199 + 0.5 wt % TB | 110 | 56 | 4A |
| 248 | 192 + 0.5 wt % IR39 | 71 | 470 | 2C |
| 249 | 193 + 0.5 wt % IR39 | 97 | 770 | 3B |
| 250 | 192 + 0.25 wt % IR39 + 0.25 wt % TDZ | 140 | 340 | 4A |
| 251 | 193 + 0.25 wt % IR39 + 0.25 wt % TDZ | 100 | 430 | 3A |
| 252 | 192 + 0.25 wt % IR39 + 0.25 wt % TB | 34 | 210 | 1B |
| 253 | 193 + 0.25 wt % IR39 + 0.25 wt % TB | 50 | 590 | 1B |
| 254 | 192 + 0.25 wt % IR39 + 0.5 wt % SLO | 16 | 320 | 1B |
| 255 | 193 + 0.25 wt % IR39 + 0.5 wt % SLO | 54 | 590 | 2C |
| 203 (Comp) | X Baseline | 35 | 5 | 4A |
| 256 | 203 + 0.5 wt % TDZ | 190 | 390 | 4A |
| 257 | 204 + 0.5 wt % TDZ | 400 | 450 | 4B |
| 258 | 206 + 0.5 wt % TDZ | 330 | 370 | 4B |
| 259 | 210 + 0.1 wt % TDZ | 38 | 520 | 4A |
| 260 | 213 + 0.1 wt % TDZ | 88 | 500 | 4A |
| 261 | 203 + 0.5 wt % TB | 68 | 1 | 4A |
| 262 | 204 + 0.5 wt % TB | 91 | 7 | 4A |
| 263 | 206 + 0.5 wt % TB | 100 | 240 | 4A |
| 264 | 210 + 0.5 wt % TB | 130 | 45 | 4A |
| 265 | 211 + 0.5 wt % TB | 410 | 47 | 4A |
| 266 | 210 + 0.1 wt % TB | 37 | 280 | 4A |
| 267 | 213 + 0.1 wt % TB | 110 | 330 | 4A |
| 268 | 210 + 0.5 wt % BDis | 51 | 200 | 4A |
| 269 | 213 + 0.5 wt % BDis | 88 | 290 | 4A |
| 270 | 203 + 0.5 wt % IR39 | 17 | 160 | 1B |
| 271 | 204 + 0.5 wt % IR39 | 53 | 260 | 4A |
| 272 | 206 + 0.5 wt % IR39 | 24 | 410 | 3A |
| 273 | 203 + 0.25 wt % IR39 + 0.25 wt % TDZ | 140 | 590 | 4A |
| 274 | 204 + 0.25 wt % IR39 + 0.25 wt % TDZ | 170 | 460 | 4A |
| 275 | 206 + 0.25 wt % IR39 + 0.25 wt % TDZ | 100 | 470 | 4A |
| 276 | 203 + 0.25 wt % IR39 + 0.25 wt % TB | 16 | 15 | 1A |
| 277 | 204 + 0.25 wt % IR39 + 0.25 wt % TB | 48 | 230 | 4A |
| 278 | 206 + 0.25 wt % IR39 + 0.25 wt % TB | 38 | 370 | 4A |
| 279 | 210 + 0.1 wt % IR39 + 0.1 wt % TB | 34 | 370 | 4A |
| 280 | 213 + 0.1 wt % IR39 + 0.1 wt % TB | 51 | 440 | 4A |
| 281 | 210 + 0.1 wt % IR30 + 0.1 wt % TB | 28 | 340 | 4A |
| 282 | 213 + 0.1 wt % IR30 + 0.1 wt % TB | 43 | 340 | 4A |
| 283 | 203 + 0.25 wt % IR39 + 0.5 wt % SLO | 16 | 18 | 1B |
| 284 | 204 + 0.25 wt % IR39 + 0.5 wt % SLO | 45 | 200 | 4A |
| 285 | 206 + 0.25 wt % IR39 + 0.5 wt % SLO | 39 | 470 | 3A |
| 286 | 210 + 0.35 wt % HDE | 56 | 380 | 4A |
| 287 | 213 + 0.35 wt % HDE | 95 | 480 | 4A |
| 215 (Comp) | Y Baseline | 7 | 4 | 1A |
| 288 | 215 + 0.125% IR30 | 7 | 4 | 1B |
| 289 | 218 + 0.125% IR30 | 5 | 58 | 1A |
| 290 | 221 + 0.125% IR30 | 5 | 130 | 1A |
| 291 | 215 + 0.25% IR30 | 12 | 5 | 4A |
| 292 | 218 + 0.25% IR30 | 5 | 110 | 1A |
| 293 | 221 + 0.25% IR30 | 5 | 120 | 1A |
| 294 | 215 + 0.125% IR39 | 20 | 13 | 4A |
| 295 | 218 + 0.125% IR39 | 11 | 160 | 1A |
| 296 | 221 + 0.125% IR39 | 11 | 200 | 1B |
| 297 | 215 + 0.25% IR39 | 24 | 25 | 4A |
| 298 | 218 + 0.25% IR39 | 12 | 210 | 1B |
| 299 | 221 + 0.25% IR39 | 20 | 250 | 1B |
| 300 | 215 + 0.125% TB | 8 | 2 | 4A |
| 301 | 218 + 0.125% TB | 6 | 53 | 1A |
| 302 | 221 + 0.125% TB | 91 | 31 | 4A |
| 303 | 215 + 0.25% TB | 10 | 5 | 1B |
| 304 | 218 + 0.25% TB | 4 | 16 | 1A |
| 305 | 221 + 0.25% TB | 100 | 10 | 4A |
| 306 | 215 + 0.36% HDE | 6 | 5 | 1A |
| 307 | 218 + 0.36% HDE | 11 | 95 | 1A |
| 308 | 221 + 0.36% HDE | 71 | 120 | 4A |
| 309 | 215 + 0.125% IR30 + 0.125% TB | 12 | 3 | 1A |
| 310 | 218 + 0.125% IR30 + 0.125% TB | 5 | 52 | 1A |
| 311 | 221 + 0.125% IR30 + 0.125% TB | 8 | 3 | 1A |
| 312 | 215 + 0.25% AE | 7 | 5 | 1A |
| 313 | 218 + 0.25% AE | 7 | 76 | 1A |
| 314 | 221 + 0.25% AE | 50 | 80 | 4A |
| 315 | 215 + 0.25% TTZ | 9 | 29 | 1B |
| 316 | 218 + 0.25% TTZ | 12 | 110 | 1A |
| 317 | 221 + 0.25% TTZ | 11 | 170 | 1A |
| 318 | 215 + 0.25% IDZ | 7 | 28 | 1A |
| 319 | 218 + 0.25% IDZ | 48 | 290 | 4A |
| 320 | 221 + 0.25% IDZ | 52 | 300 | 4A |
| 321 | 215 + 0.39% LA | 5 | 7 | 1A |
| 322 | 218 + 0.39% LA | 10 | 100 | 1A |
| 323 | 221 + 0.39% LA | 44 | 110 | 4A |
| 324 | 215 + 0.45% OA | 5 | 15 | 1A |
| 325 | 218 + 0.45% OA | 40 | 200 | 4A |
| 326 | 221 + 0.45% OA | 48 | 240 | 4A |

Although there may not be universal trends in this data, it does appear that copper and/or lead dissolution in HTCBT testing (and, by extension, in the operation of a lubricated engine, transmission, etc.) can be mitigated by addition of certain (combinations of) corrosion inhibiting compounds/components, in tandem with addition of 3,4-oxypyridinones according to the disclosure.

All documents described herein are incorporated by reference herein, including any priority documents and/or testing procedures, to the extent they are not inconsistent with this text. As should be apparent from the foregoing general description and the specific embodiments, while forms of the invention have been illustrated and described, various modifications can be made without departing from the spirit and scope of the invention. Accordingly, it is not intended that the invention be limited thereby. The term "comprising" specifies the presence of stated features, steps, integers, or components, but does not preclude the presence or addition of one or more other features, steps, integers, components, or groups thereof. Likewise, the term "comprising" is considered synonymous with the term "including." Similarly, whenever a composition, an element, or a group of elements is preceded with the transitional phrase "comprising," it should be understood that the same composition or group of elements is contemplated with transitional phrases "consisting essentially of," "consisting of," "selected from the group of consisting of," or "can be"/"may be"/"is" preceding the recitation of the composition, element, or elements, and vice versa. In juxtaposition to the well-known terms "comprising" meaning "including what follows and anything else" [open] and "consisting of" meaning "including only what follows" [closed], the term "consisting essentially of" should be understood to be semi-inclusive and to mean, in accordance with US judicial interpretation, including that which follows and other things that do not materially affect the basic and novel properties.

What is claimed is:

1. A composition comprising a non-aqueous medium and a 3,4-oxypyridinone compound of structure (I):

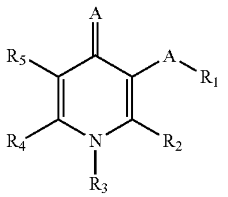

(I)

wherein:

all A's are oxygen atoms;

$R_1$ is hydrogen; a linear, branched, and/or cyclic $C_1$-$C_{12}$ hydrocarbyl moiety; an ether-containing linear, branched, and/or cyclic $C_1$-$C_{12}$ moiety; another 3,4-oxypyridinone connected as an ether at a meta position to the ring nitrogen thereof, or a combination thereof;

$R_2$ is hydrogen; a linear, branched, and/or cyclic $C_1$-$C_{12}$ hydrocarbyl moiety; an ether-containing linear, branched, and/or cyclic $C_1$-$C_{12}$ moiety; an aldehyde-containing linear, branched, and/or cyclic $C_1$-$C_{12}$ moiety; a nitrile-containing linear, branched, and/or cyclic $C_1$-$C_{12}$ moiety; or a combination thereof;

$R_3$ is an oligomeric and/or polymeric moiety containing repeat units comprising reacted pendant to one or more repeat units, optionally olefins, hydrogenated conjugated dienes, or combinations thereof, at least one of which repeat units is attached to the ring nitrogen, optionally with a spacer, a number average molecular weight of which oligomeric and/or polymeric moiety is from 700 g/mol to 30000 g/mol;

$R_4$ is hydrogen; a linear, branched, and/or cyclic $C_1$-$C_{12}$ hydrocarbyl moiety; an ether-containing linear, branched, and/or cyclic $C_1$-$C_{12}$ moiety; an aldehyde-containing linear, branched, and/or cyclic $C_1$-$C_{12}$ moiety; a nitrile-containing linear, branched, and/or cyclic $C_1$-$C_{12}$ moiety; or a combination thereof; and $R_5$ is hydrogen; an $R_1$-A- moiety; or a combination thereof;

or $R_4$ and $R_5$ may together comprise from 3 to 12 carbons and form a (hetero)cyclic ring structure, wherein:

all A's are oxygen atoms;

$R_1$ is hydrogen; a linear, branched, and/or cyclic $C_1$-$C_{12}$ hydrocarbyl moiety; an ether-containing linear, branched, and/or cyclic $C_1$-$C_{12}$ moiety; another 3,4-oxypyridinone connected as an ether at a meta position to the ring nitrogen thereof, or a combination thereof;

$R_2$ is hydrogen; a linear, branched, and/or cyclic $C_1$-$C_{12}$ hydrocarbyl moiety; an ether-containing linear, branched, and/or cyclic $C_1$-$C_{12}$ moiety; an aldehyde-containing linear, branched, and/or cyclic $C_1$-$C_{12}$ moiety; a nitrile-containing linear, branched, and/or cyclic $C_1$-$C_{12}$ moiety; or a combination thereof;

$R_3$ is an oligomeric and/or polymeric moiety containing repeat units comprising reacted pendant to one or more repeat units, optionally olefins, hydrogenated conjugated dienes, or combinations thereof, at least one of which repeat units is attached to the ring nitrogen, optionally with a spacer, a number average molecular weight of which oligomeric and/or polymeric moiety is from 700 g/mol to 30000 g/mol;

$R_4$ is hydrogen; a linear, branched, and/or cyclic $C_1$-$C_{12}$ hydrocarbyl moiety; an ether-containing linear, branched, and/or cyclic $C_1$-$C_{12}$ moiety; an aldehyde-containing linear, branched, and/or cyclic $C_1$-$C_{12}$ moiety; a nitrile-containing linear, branched, and/or cyclic $C_1$-$C_{12}$ moiety; or a combination thereof; and $R_5$ is hydrogen; an $R_1$-A- moiety; or a combination thereof;

or $R_4$ and $R_5$ may together comprise from 3 to 12 carbons and form a (hetero)cyclic ring structure.

2. The composition of claim 1, wherein the non-aqueous medium comprises a Group I, Group II, Group III, Group IV, and/or Group V lubricating oil basestock.

3. The composition of claim 1, further comprising at least one lubricant additive selected from the group consisting of a calcium- and/or magnesium-containing detergent, an ashless dispersant, a corrosion inhibitor, an antioxidant, a friction modifier, an antiwear agent, an antifoamant, a viscosity modifier, a pour point depressant, a tackifier, a demulsifier, an extreme pressure agent, a seal swell agent, and a combination thereof.

4. The composition of claim 3, wherein the at least one lubricant additive comprises an optionally substituted diaryl amine antioxidant, a hindered phenol antioxidant, or both.

5. The composition of claim 4, wherein a weight ratio of the 3,4-oxypyridinone of structure (I) (based on 3,4-oxypyridinone ring(s) plus optional spacer only, not including connected oligomer and/or polymer portion(s)) to a sum of the optionally substituted diaryl amine and hindered phenol antioxidants is from 10:1 to 1:10 or from 5:1 to 1:5.

6. The composition of claim 3, wherein the at least one lubricant additive comprises:

a zinc dialkyldithiophosphate antiwear agent;

an organic friction modifier, a molybdenum-containing friction modifier, or a combination thereof;

an optionally substituted triazole corrosion inhibitor, an optionally substituted benzotriazole corrosion inhibitor, an optionally substituted thiadiazole corrosion inhibitor, an ashless dihydrocarbyl dithiocarbamate, a $C_8$-$C_{18}$ acrylate, a $C_2$-$C_6$ dialkylene glycol diester, a tri-hydrocarbyl $C_1$-$C_8$ borate corrosion inhibitor, or a combination thereof; and/or a multi-arm star viscosity modifier, an olefin copolymer viscosity modifier, a hydrogenated diene block copolymer viscosity modifier, a polystyrene copolymer viscosity modifier, a poly(meth)acrylate viscosity modifier, a poly(dialkyl fumarate)-based viscosity modifier, a poly(vinyl acyl ester)-based viscosity modifier, or a combination or copolymer thereof.

7. The composition of claim 4, wherein the at least one lubricant additive comprises:

a zinc dialkyldithiophosphate antiwear agent;

an organic friction modifier, a molybdenum-containing friction modifier, or a combination thereof;

an optionally substituted triazole corrosion inhibitor, an optionally substituted benzotriazole corrosion inhibitor, an optionally substituted thiadiazole corrosion inhibitor, an ashless dihydrocarbyl dithiocarbamate, a $C_8$-$C_{18}$ acrylate, a $C_2$-$C_6$ dialkylene glycol diester, a tri-hydrocarbyl $C_1$-$C_8$ borate corrosion inhibitor, or a combination thereof; and/or a multi-arm star viscosity modifier, an olefin copolymer viscosity modifier, a hydrogenated diene block copolymer viscosity modifier, a polystyrene copolymer viscosity modifier, a poly(meth)acrylate viscosity modifier, a poly(dialkyl fumarate)-based viscosity modifier, a poly(vinyl acyl ester)-based viscosity modifier, or a combination or copolymer thereof.

8. The composition of claim 3, wherein the at least one lubricant additive comprises substantially no molybdenum-containing friction modifier.

9. The composition of claim 4, wherein the at least one lubricant additive comprises substantially no molybdenum-containing friction modifier.

10. A lubricant composition comprising the composition of claim 1.

11. A lubricant composition comprising the composition of claim 3.

12. A lubricant composition comprising the composition of claim 4.

13. A lubricant composition comprising the composition of claim 5.

14. A lubricant composition comprising the composition of claim 6.

15. A lubricant composition comprising the composition of claim 7.

16. A lubricant composition comprising the composition of claim 8.

17. A lubricant composition comprising the composition of claim 9.

18. A method of inhibiting and/or mitigating viscosity increase in a composition comprising a non-aqueous medium by addition of the 3,4-oxypyridinone composition of claim 1, or via formation of a complex or reaction product thereof, in an amount that is effective in disrupting oxidation catalysis through iron chelation.

19. A method to inhibit and/or mitigate viscosity increase in a lubricant composition through effective disruption of oxidation catalysis through iron chelation comprising combining the non-aqueous 3,4-oxypyridinone-containing composition of claim 1, or a complex or reaction product thereof, with a lubricant composition.

20. A method of improving oxidative stability and/or mitigating impact of oxidative degradation of a composition comprising a non-aqueous medium comprising addition of the 3,4-oxypyridinone composition of claim 1, or via formation of a complex or reaction product thereof, in an amount that is effective in disrupting oxidation catalysis through iron chelation.

21. A method of improving oxidative degradation of and/or mitigating impact of oxidative degradation of a lubricant composition comprising addition of the 3,4-oxypyridinone containing composition of claim 1, or via formation of a complex or reaction product thereof, in an amount that is effective in disrupting oxidation catalysis through iron chelation.

22. A lubricant composition comprising the composition of claim 4, wherein the lubricant composition comprising the 3,4-oxypyridinone of structure (I) and either or both of the optionally substituted diaryl amine and hindered phenol antioxidants (and optionally also a magnesium detergent and/or a salicylate detergent), when subject to a CEC L-109 oxidation test for at least 200 hours at ~150° C., exhibits an increase in a value of kinematic viscosity at ~100° C. (KV100) that is:

at most 40% above a KV100 value from the same lubricant composition immediately before the CEC L-109 oxidation test began (0 hours); and at least 30% below a KV100 value from a comparative composition that was subject to the CEC L-109 oxidation test for an identical time period, wherein the comparative composition comprises only either or both of the optionally substituted diaryl amine and hindered phenol antioxidants and not the 3,4-oxypyridinone of structure (I).

* * * * *